US008729114B2

(12) United States Patent
Burke et al.

(10) Patent No.: US 8,729,114 B2
(45) Date of Patent: May 20, 2014

(54) HETEROARYL NITRILE COMPOUNDS USEFUL AS INHIBITORS OF CATHEPSIN-S

(75) Inventors: Michael J. Burke, Cheshire, CT (US); Derek Cogan, Sandy Hook, CT (US); Donghong Amy Gao, Ridgefield, CT (US); Alexander Heim-Riether, Biberach an de Riss (DE); Eugene Richard Hickey, Danbury, CT (US); Matthew Russell Netherton, Danbury, CT (US); Philip Dean Ramsden, Woodbury, CT (US); David Charles Thompson, White Plains, NY (US); Zhaoming Xiong, Brookfield, CT (US)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 13/581,829

(22) PCT Filed: Mar. 2, 2011

(86) PCT No.: PCT/US2011/026905
§ 371 (c)(1),
(2), (4) Date: Oct. 8, 2012

(87) PCT Pub. No.: WO2011/109470
PCT Pub. Date: Sep. 9, 2011

(65) Prior Publication Data
US 2013/0158018 A1    Jun. 20, 2013

Related U.S. Application Data

(60) Provisional application No. 61/310,827, filed on Mar. 5, 2010.

(51) Int. Cl.
| A61K 31/4164 | (2006.01) |
| A61K 31/4192 | (2006.01) |
| C07D 249/04 | (2006.01) |
| C07D 247/02 | (2006.01) |
| C07D 257/04 | (2006.01) |

(52) U.S. Cl.
USPC ........... 514/381; 514/396; 548/251; 548/255; 548/335.1

(58) Field of Classification Search
USPC .......................................... 514/359; 548/255
See application file for complete search history.

(56) References Cited

FOREIGN PATENT DOCUMENTS

| WO | 2004083182 A1 | 9/2004 |
| WO | 2011109470 A1 | 9/2011 |

OTHER PUBLICATIONS

Ahmed, 2009, Chem Biol Drug Des, vol. 74, p. 129-141.*
Porter, 1991, Pure & Appl. Chem, vol. 63, No. 8, p. 1119-1122.*
International Search Report and Written Opinon for PCT/US2011/026805 mailed Apr. 8, 2011.
Patterson, A.W. et al., "Identification of Selective, Nonpeptidic Nitrile Inhibitors of Cathepsin S Using the Substrate Activity Screening Method." Journal of Medicinal Chemistry, vol. 49, No. 21, Oct. 2006, pp. 6298-6307.

\* cited by examiner

*Primary Examiner* — Rebecca Anderson
*Assistant Examiner* — Karen Cheng
(74) *Attorney, Agent, or Firm* — Michael P. Morris; Anthony P. Bottino

(57) ABSTRACT

Disclosed are Cathepsin-S reversible inhibitor compounds of the formula (I) which are useful in the treatment of autoimmune and other diseases. Also disclosed are pharmaceutical compositions containing the same, and methods of making and using the same.

(I)

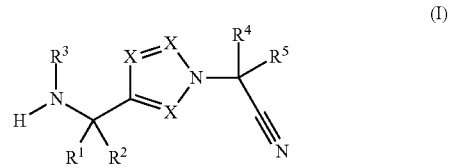

15 Claims, No Drawings

HETEROARYL NITRILE COMPOUNDS USEFUL AS INHIBITORS OF CATHEPSIN-S

APPLICATION DATA

This application claims benefit to U.S. provisional application Ser. No. 61/310,827 filed Mar. 5, 2010.

BACKGROUND OF THE INVENTION

1. Technical Field

This invention relates reversible inhibitors of the Cathepsin-S which are useful in the treatment of autoimmune and other diseases.

2. Background Information

Cathepsin-S, and compounds active as inhibitors of the Cathepsin-S have been described elsewhere. See for example WO2004083182. A step thought to be critical in autoimmune diseases is the display of self-antigen on the surface of antigen presenting cells (e.g. B-cells) by MHCII. Before presenting antigens to the CD4$^+$ T cells, the antigen binding groove of MCHII is occupied by a protein called P10. Apparently critical to allowing the self-antigen to be displayed on the B-cell surface, the protease Cathepsin-S is involved in cleaving P10 to a lower affinity peptide called CLIP, which can be displaced by the antigenic peptides. Thus by blocking Cathepsin-S with a small-molecule inhibitor may prevent the display of self-antigen, and ameliorate the disease or symptoms of autoimmune or inflammatory diseases. There is presently a large unmet medical need for treatments of autoimmune diseases such as multiple sclerosis, rheumatoid arthritis, psoriasis, atherosclerosis, and inflammatory diseases such as chronic obstructive pulmonary disease.

BRIEF SUMMARY OF THE INVENTION

The work cited above supports the principle that by blocking Cathepsin-S, a small-molecule inhibitor can ameliorate the disease or symptoms of autoimmune diseases.

It is therefore an object of the invention to provide a novel class of potent inhibitors of Cathepsin-S for treatments of autoimmune diseases, and their pharmaceutical compositions.

It is a further object of the invention to provide methods of making and methods of using such compounds.

DETAILED DESCRIPTION OF THE INVENTION

In the broadest generic embodiment, there is provided a compound of the formula (I):

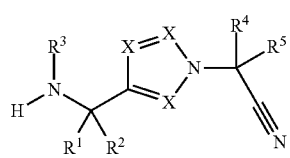

(I)

wherein the

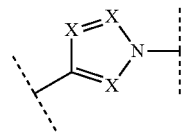

ring is chosen from:

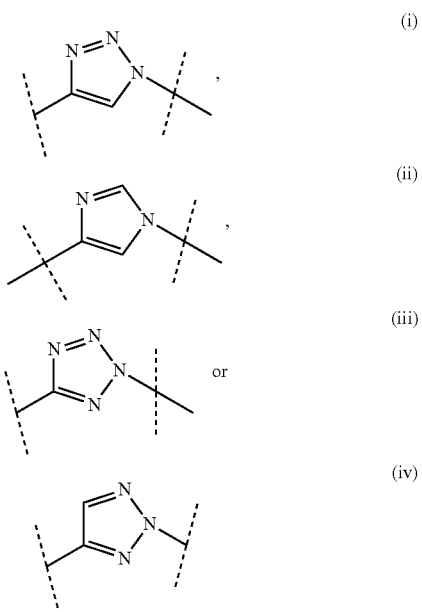

each optionally substituted by $C_{1-3}$ alkyl;

$R^1$ is $C_{3-7}$ alkyl, $C_{3-7}$cycloalkyl, aryl, heterocyclyl or heteroaryl each optionally substituted by one or more $R^c$;

$R^2$ is hydrogen or $C_{1-7}$alkyl;

or $R^1$ and $R^2$ taken together form a $C_{3-7}$cycloalkyl or $C_{3-7}$heterocyclyl ring optionally substituted by one or more halogen or $C_{1-7}$alkyl;

$R^3$ is —C(O)$C_{1-7}$alkyl, —C(O)$C_{3-7}$cycloalkyl, —C(O)aryl, —C(O)heteroaryl, —C(O)heterocyclyl, —C(O)NR$^a$R$^b$, —C(O)OR$^a$, —CH(R$_f$)-heteroaryl, —CH(R$_f$)-aryl, —CH(R$_f$)— heterocyclyl, aryl, $C_{3-7}$cycloalkyl or heteroaryl, each ring is optionally substituted by one or more $R^d$;

$R^4$ and $R^5$ are each independently hydrogen, $C_{1-7}$alkyl, aryl, or heteroaryl, or $R^4$ and $R^5$ taken together may form a $C_{3-7}$cycloalkyl or $C_{3-7}$ heterocyclyl ring each ring being optionally substituted by $C_{1-5}$ alkyl;

$R^a$, $R^b$ each independently are hydrogen, $C_{1-7}$alkyl, aryl or heteroaryl, or may be taken together to form a saturated or unsaturated $C_{3-7}$cycloalkyl or $C_{3-7}$ heterocyclyl ring;

$R^c$ is $C_{1-7}$alkyl, $C_{1-7}$alkoxy, $C_{3-7}$cycloalkyl, aryl, benzyl, halogen or —C(O)—O-benzyl;

$R^d$ each is independently chosen from $C_{1-7}$alkyl, $C_{1-7}$alkoxy, $C_{1-7}$ acyl, —C(O)NR$^a$R$^b$, —NH—C(O)—C$_{1-7}$alkyl, halogen, —CN, —S(O)$_m$—R$_e$, —NH—S(O)$_m$—R$_e$;

$R_e$ is chosen from $C_{1-7}$alkyl and amino;

$R^f$ each is independently chosen from hydrogen or $C_{1-7}$alkyl;

m is 0-2;

wherein one or more hydrogens on any one or more of $R^1$, $R^2$, $R^3$, $R^2$, $R^4$, $R^5$, $R^a$, $R^b$ $R^c$, $R^d$, $R^e$, $R^f$ or

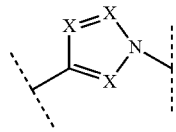

may be replaced by a halogen or deuterium atom;

with the proviso that when

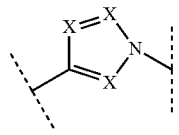

is (i), and neither $R^1$ nor $R^2$ is hydrogen, and $R^3$ is —C(O)$C_{1-7}$alkyl, —C(O)$C_{3-7}$cycloalkyl, —C(O)aryl, —C(O)heteroaryl, —C(O)heterocyclyl, —CH($R^f$)-heteroaryl, —CH($R^f$)-aryl, —CH($R^f$)-heterocyclyl, aryl, $C_{3-7}$cycloalkyl or heteroaryl then $R^4$ and $R^5$ must either both be hydrogen or they must form a ring.

or a pharmaceutically acceptable salt thereof.

In another embodiment of the invention there is provided a compound of the formula (I) according the embodiments immediately above and wherein $R^2$=hydrogen or $C_{1-7}$alkyl if a)

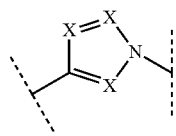

is (i), or b) $R^4$ and $R^5$ are hydrogen, or c) $R^4$ and $R^5$ form a ring, or d) $R^3$ is —C(O)NR$^a$R$^b$ or —C(O)OR$^a$, or a pharmaceutically acceptable salt thereof.

In another embodiment of the invention there is provided a compound of the formula (I) according any of the embodiments above and wherein $R^1$ is $C_{1-7}$alkyl, $C_{3-7}$cycloalkyl, cyclohexyl-D11, phenyl, oxiranyl, azepanyl, diazepanyl, azetidinyl, pyrrolidinyl, pyrrolinyl, thiomorpholinyl, dioxalanyl, piperazinyl, 1,3-dioxolanone, 1,3-dioxanone, 1,4-dioxanyl, piperidinonyl, tetrahydropyrimidonyl, piperidinyl, tetrahydrofuranyl, tetrahydropyranyl, tetrahydrothiopyranyl, 1,1-dioxo-hexahydro-1λ6-thiopyranyl, 1-oxo-hexahydro-1λ4-thiopyranyl, aziridinyl, thiadiazolyl, tetrazolyl, pyrrolyl, pyrimidinyl, pyrazinyl, pyridazinyl, pyranyl, quinoxalinyl, indolyl, benzimidazolyl, benzoxazolyl, benzothiazolyl, benzothienyl, quinolinyl, quinazolinyl, naphthyridinyl, indazolyl, triazolyl, purinyl, benzofuranyl, thiazolyl, isothiazolyl, imidazolyl, oxazolyl, isoxazolyl, thienyl, furanyl, pyrazolyl and pyridinyl, each optionally substituted by an $R^c$;

$R^2$ is hydrogen or $C_{1-5}$alkyl;

or $R^1$ and $R^2$ taken together form a $C_{3-7}$cycloalkyl;

$R^3$=—C(O)$C_{1-7}$alkyl, —C(O)$C_{3-6}$cycloalkyl, —C(O)phenyl, —C(O)heterocyclyl wherein the heterocyclyl is chosen from oxiranyl, azepanyl, diazepanyl, azetidinyl, pyrrolidinyl, pyrrolinyl, thiomorpholinyl, dioxalanyl, piperazinyl, 1,3-dioxolanone, 1,3-dioxanone, 1,4-dioxanyl, piperidinonyl, tetrahydropyrimidonyl, piperidinyl, tetrahydrothiopyranyl, morpholinyl, piperidinyl, tetrahydrofuranyl and tetrahydropyranyl, —C(O)heteroaryl wherein the heteroaryl is chosen from benzofuranyl, imidazo[2,1-b]thiazolyl, imidazo[1,2-a]pyrazinyl, pyrazolo[1,5-a]pyridinyl, imidazo[1,2-a]pyridinyl, thiazolyl, isothiazolyl, imidazolyl, oxazolyl, isoxazolyl, thienyl, furanyl, pyrazolyl and pyridinyl, —C(O)NH-phenyl, heterocyclyl chosen from oxiranyl, azepanyl, diazepanyl, azetidinyl, pyrrolidinyl, pyrrolinyl, thiomorpholinyl, dioxalanyl, piperazinyl, 1,3-dioxolanone, 1,3-dioxanone, 1,4-dioxanyl, piperidinonyl, tetrahydropyrimidonyl, piperidinyl, tetrahydrothiopyranyl, morpholinyl, piperidinyl, tetrahydropyranyl 1,1-Dioxo-1λ6-thiomorpholine, tetrahydrofuranyl, 1,1-dioxo-hexahydro-1λ6-thiopyranyl, piperidinyl and 2-oxo-imidazolidinyl, phenyl, $C_{3-7}$cycloalkyl, —CH$_2$-2-oxo-imidazolidinyl and —CH($R_f$)-heteroaryl wherein the heteroaryl is chosen from thiazolyl, isothiazolyl, imidazolyl, oxazolyl, isoxazolyl, thienyl, furanyl, pyrazolyl and pyridinyl, each ring is optionally substituted by one or more $R^d$;

$R^4$ and $R^5$ are each independently hydrogen or $C_{1-7}$alkyl, or $R^4$ and $R^5$ taken together may form a $C_{3-6}$cycloalkyl, oxiranyl, azepanyl, diazepanyl, azetidinyl, pyrrolidinyl, pyrrolinyl, thiomorpholinyl, dioxalanyl, piperazinyl, 1,3-dioxolanone, 1,3-dioxanone, 1,4-dioxanyl, piperidinonyl, tetrahydropyrimidonyl, piperidinyl, tetrahydrothiopyranyl, morpholinyl, piperidinyl or tetrahydropyranyl each ring being optionally substituted by $C_{1-3}$alkyl;

$R^a$, $R^b$ are each independently hydrogen, $C_{1-5}$alkyl or phenyl;

$R^c$ is $C_{1-5}$alkyl, $C_{1-5}$alkoxy, $C_{3-6}$cycloalkyl, phenyl, benzyl, fluoro or —C(O)—O-benzyl;

$R^d$ is independently chosen from $C_{1-5}$ alkyl, $C_{1-5}$ alkoxy, $C_{1-5}$acyl, —C(O)NR$^a$R$^b$, —NH—C(O)—$C_{1-5}$alkyl, halogen, —CN, —S(O)$_2$—R$_e$, —NH—S(O)$_2$—R$_e$;

$R_e$ is chosen from $C_{1-5}$alkyl and amino;

$R^f$ is independently chosen from hydrogen and $C_{1-5}$alkyl;

wherein one or more hydrogens on any one or more of $R^1$, $R^2$, $R^3$, $R^2$, $R^4$, $R^5$, $R^a$, $R^b$, $R^c$, $R^d$, $R^e$, $R^f$ or

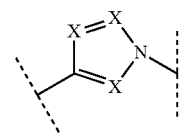

may be replaced by a halogen or deuterium atom;

or a pharmaceutically acceptable salt thereof.

In another embodiment of the invention there is provided a compound of the formula (I) according to any of the embodiments above and wherein $R^1$ is t-butyl, sec-butyl, 3-pentyl, cyclohexyl, —CH$_2$-cyclohexyl, cyclopentyl, cyclopropyl, phenyl, cyclohexyl-D11, piperidinyl, tetrahydropyranyl, tetrahydrothiopyranyl, 1,1-dioxo-hexahydro-1λ6-thiopyranyl or 1-oxo-hexahydro-1λ4-thiopyranyl, each optionally substituted by an $R^c$;

R² is hydrogen or methyl;

or R¹ and R² taken together form a cyclohexyl;

R³ is —C(O)C$_{1-7}$alkyl, —C(O)cyclopropyl, —C(O)cyclopentyl, —C(O)phenyl, —C(O)heterocyclyl wherein the heterocyclyl is chosen from morpholinyl, piperidinyl, tetrahydrofuranyl and tetrahydropyranyl, —C(O)heteroaryl wherein the heteroaryl is chosen from benzofuranyl, imidazo[2,1-b]thiazolyl, imidazo[1,2-a]pyrazinyl, pyrazolo[1,5-a]pyridinyl, imidazo[1,2-a]pyridinyl, thiazolyl, isothiazolyl, imidazolyl, oxazolyl, isoxazolyl, thienyl, furanyl, pyrazolyl and pyridinyl, C(O)NH-phenyl, heterocyclyl chosen from 1,1-Dioxo-1λ6-thiomorpholine, tetrahydrofuranyl, 1,1-dioxo-hexahydro-1λ6-thiopyranyl, piperidinyl and 2-oxo-imidazolidinyl, phenyl, cyclohexyl and —CH$_2$-thienyl;

R⁴ and R⁵ are each independently hydrogen, methyl or n-butyl or

R⁴ and R⁵ taken together may form cyclopropyl, piperidinyl, tetrahydropyranyl or 1-methyl-piperidinyl;

R$^a$, R$^b$ are each independently hydrogen, methyl or phenyl;

R$^c$ is methyl, methoxy, cyclohexyl, phenyl, benzyl, fluoro or —C(O)—O-benzyl;

R$^d$ is independently chosen from methyl, —CF$_3$, —CH$_2$CF$_3$, methoxy, acetyl, —C(O)NH$_2$, —C(O)NHCH$_3$, —C(O)N(CH$_3$)$_2$, —NH—C(O)-methyl, —S(O)$_2$—CH$_3$, —S(O)$_2$—NH$_2$, —NH—S(O)$_2$—CH$_3$, F, Cl and —CN;

R$^f$ is independently chosen from hydrogen, methyl and CF$_3$;

or a pharmaceutically acceptable salt thereof.

In another embodiment of the invention there is provided a compound of the formula (I) according to any of the embodiments above and wherein wherein the

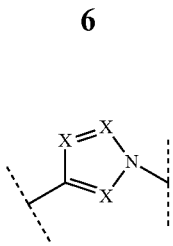

ring is chosen from:

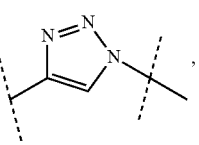   (i)

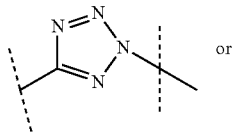   (iii)   or

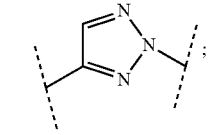   (iv) ;

or a pharmaceutically acceptable salt thereof.

In another embodiment of the invention there is provided a compound of the formula (I) according to any of the embodiments above and wherein wherein the

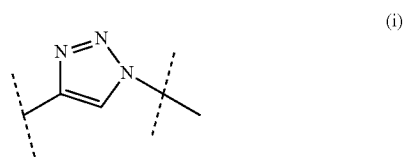

ring is

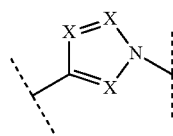   (i)

or a pharmaceutically acceptable salt thereof.

In another embodiment of the invention there is provided a compound of the formula (I) according to any of the embodiments above and wherein wherein the

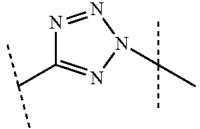

ring is

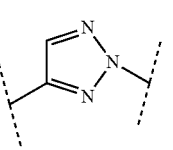   (iii)

or a pharmaceutically acceptable salt thereof.

In another embodiment of the invention there is provided a compound of the formula (I) according to any of the embodiments above and wherein wherein the ring is:

(iv)

or a pharmaceutically acceptable salt thereof.

In another embodiment of the invention there is provided a compound of the formula (I) according to any of the embodiments above and wherein R¹ is cyclohexyl, —CH₂-cyclohexyl, 4,4-difluorocyclohexyl, 3-methoxycyclohexyl, 4-methylcyclohexyl, 4-trifluoromethylcyclohexyl, cyclohexyl-D11, cyclopentyl, 3-pentyl, sec-butyl, tetrahydropyranyl, or tetrahydrothiopyranyl.

In another embodiment of the invention there is provided a compound of the formula (I) according to any of the embodiments above and wherein R² is hydrogen or methyl;

or R¹ and R² taken together form a cyclohexyl.

In another embodiment of the invention there is provided a compound of the formula (I) according to any of the embodiments above and wherein R³ is —C(O)cyclopropyl, —C(O)phenyl, —C(O)heterocyclyl wherein the heterocyclyl is chosen from morpholinyl and piperidinyl, —C(O)heteroaryl wherein the heteroaryl is chosen from imidazo[2,1-b]thiazolyl, thiazolyl, isothiazolyl, oxazolyl, isoxazolyl, thienyl, furanyl, pyrazolyl and pyridinyl, or R³ is

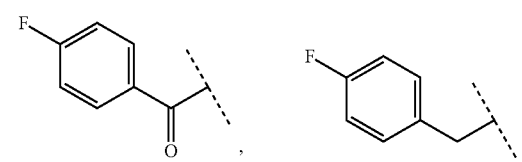

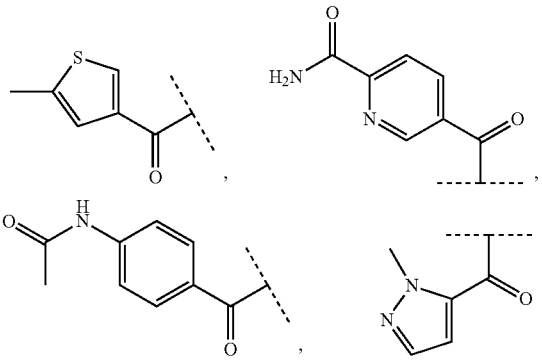

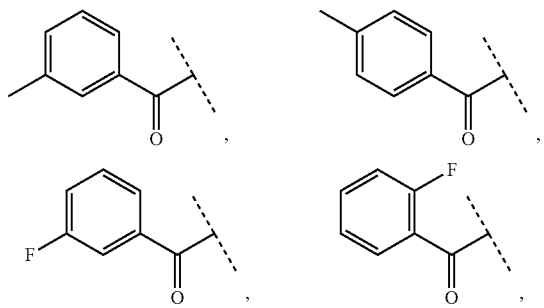

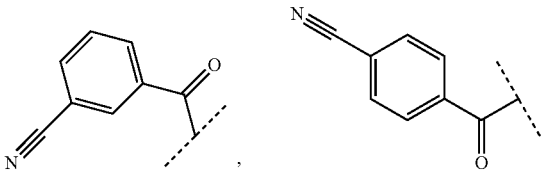

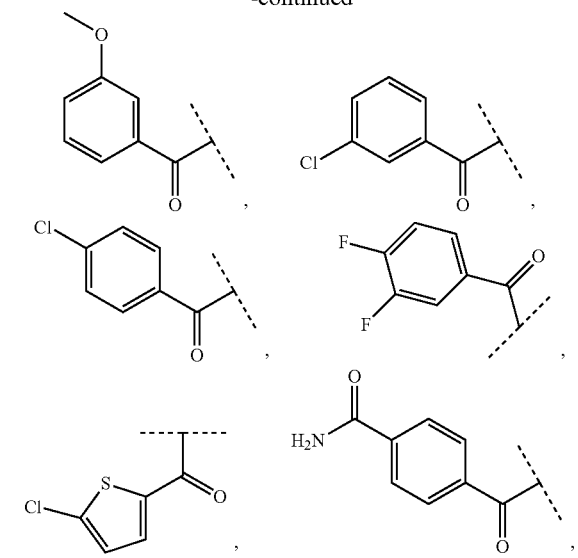

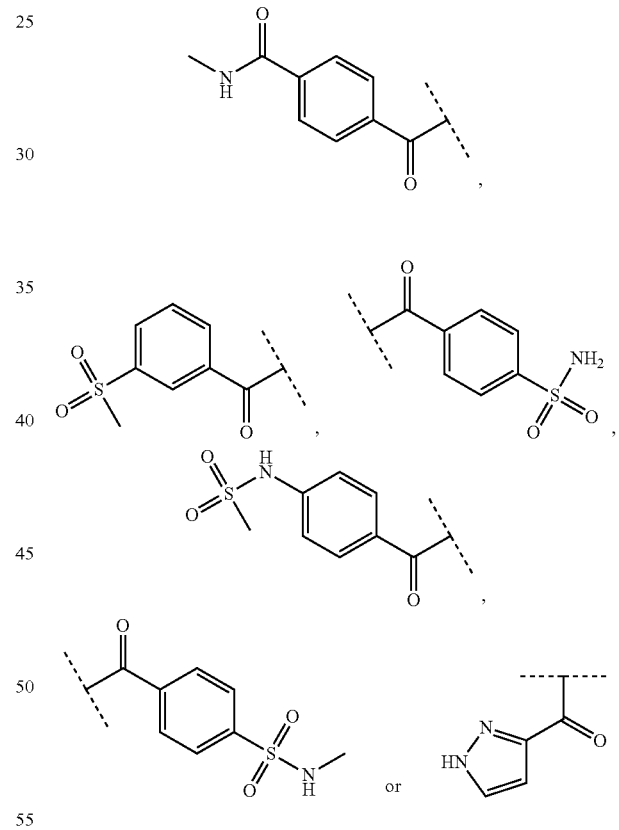

In another embodiment of the invention there is provided a compound of the formula (I) according to any of the embodiments above and wherein R⁴ and R⁵ are each independently hydrogen, methyl or n-butyl or R⁴ and R⁵ taken together may form cyclopropyl, piperidinyl, or tetrahydropyranyl.

In another embodiment, the invention provides compounds in Table I which can be made in view of the general schemes, examples and methods known in the art.

| Compound | Structure | Name | LCMS Method, RT (min), [M + H]+ |
|---|---|---|---|
| 1 | 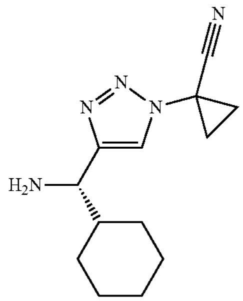 [SMILES: N#CC1(n2cc([C@@H](N)C3CCCCC3)nn2)CC1] | 1-[4-((S)-Amino-cyclohexyl-methyl)-[1,2,3]triazol-1-yl]-cyclopropanecarbonitrile | E<br>0.51<br>246.1 |
| 2 | 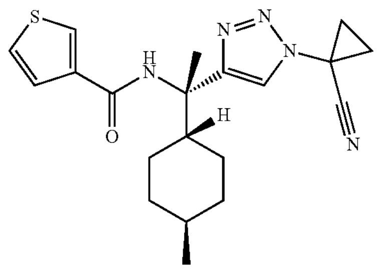 [SMILES: C[C@@](NC(=O)c1ccsc1)(c1cn(C2(C#N)CC2)nn1)[C@H]1CC[C@H](C)CC1] | Thiophene-3-carboxylic acid [(S)-1-[1-(1-cyano-cyclopropyl)-1H-[1,2,3]triazol-4-yl]-1-(4-methyl-cyclohexyl)-ethyl]-amide | A<br>1.75<br>384.8 |
| 3 | 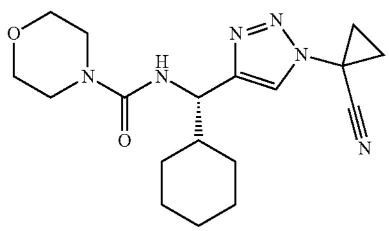 [SMILES: N#CC1(n2cc([C@@H](NC(=O)N3CCOCC3)C3CCCCC3)nn2)CC1] | Morpholine-4-carboxylic acid {(S)-[1-(1-cyano-cyclopropyl)-1H-[1,2,3]triazol-4-yl]-cyclohexyl-methyl}-amide | A<br>1.35<br>359.4 |
| 4 | 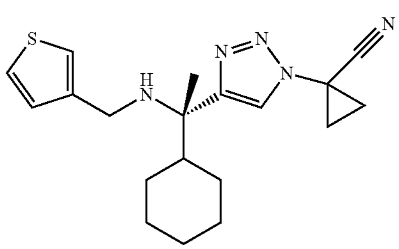 [SMILES: C[C@@](NCc1ccsc1)(c1cn(C2(C#N)CC2)nn1)C1CCCCC1] | 1-(4-{(S)-1-Cyclohexyl-1-[(thiophen-3-ylmethyl)-amino]-ethyl}-[1,2,3]triazol-1-yl)-cyclopropanecarbonitrile | E<br>0.67<br>356.5 |
| 5 | 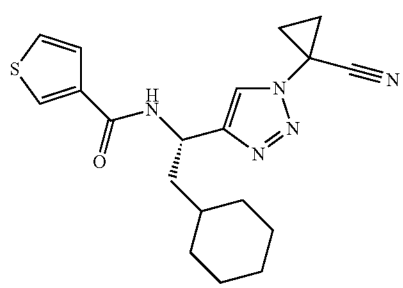 [SMILES: N#CC1(n2cc([C@H](CC3CCCCC3)NC(=O)c3ccsc3)nn2)CC1] | Thiophene-3-carboxylic acid {(S)-1-[1-(1-cyano-cyclopropyl)-1H-[1,2,3]triazol-4-yl]-2-cyclohexyl-ethyl}-amide | F<br>2.24<br>370.3 |

-continued

| Compound | Structure | Name | LCMS Method, RT (min), [M + H]+ |
|---|---|---|---|
| 6 | 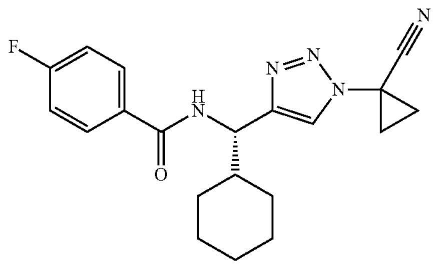 [SMILES: N#CC1(n2cc([C@@H](NC(=O)c3ccc(F)cc3)C3CCCCC3)nn2)CC1] | N-{(S)-[1-(1-Cyano-cyclopropyl)-1H-[1,2,3]triazol-4-yl]-cyclohexyl-methyl}-4-fluoro-benzamide | A 1.65 368.6 |
| 7 | 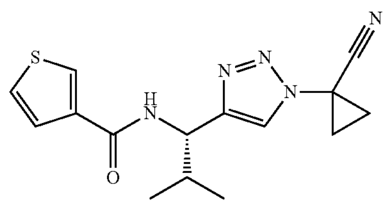 [SMILES: CC(C)[C@H](NC(=O)c1ccsc1)c1cn(C2(C#N)CC2)nn1] | Thiophene-3-carboxylic acid {(S)-1-[1-(1-cyano-cyclopropyl)-1H-[1,2,3]triazol-4-yl]-2-methyl-propyl}-amide | F 1.38 316.3 |
| 8 | 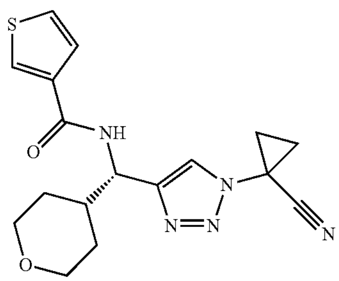 [SMILES: N#CC1(n2cc([C@@H](NC(=O)c3ccsc3)C3CCOCC3)nn2)CC1] | Thiophene-3-carboxylic acid [(S)-[1-(1-cyano-cyclopropyl)-1H-[1,2,3]triazol-4-yl]-(tetrahydro-pyran-4-yl)-methyl]-amide | F 1.05 358.2 |
| 9 | 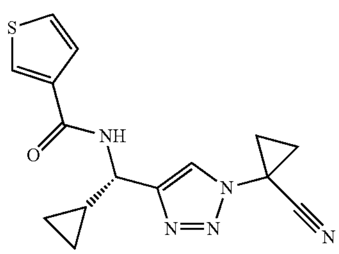 [SMILES: N#CC1(n2cc([C@@H](NC(=O)c3ccsc3)C3CC3)nn2)CC1] | Thiophene-3-carboxylic acid {(S)-[1-(1-cyano-cyclopropyl)-1H-[1,2,3]triazol-4-yl]-cyclopropyl-methyl}-amide | F 1.18 314.2 |
| 10 | 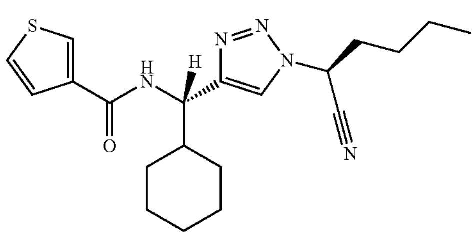 [SMILES: CCCC[C@@H](C#N)n1cc([C@@H](NC(=O)c2ccsc2)C2CCCCC2)nn1] | Thiophene-3-carboxylic acid {(S)-[1-((S)-1-cyano-pentyl)-1H-[1,2,3]triazol-4-yl]-cyclohexyl-methyl}-amide | C 1.49 386.2 |
| 11 | 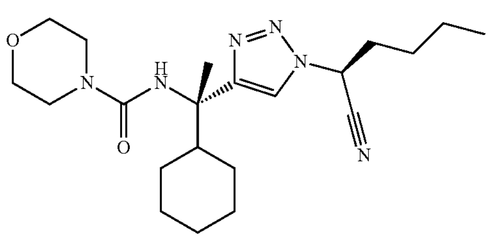 [SMILES: CCCC[C@@H](C#N)n1cc([C@@](C)(NC(=O)N2CCOCC2)C2CCCCC2)nn1] | Morpholine-4-carboxylic acid {(S)-1-[1-((S)-1-cyano-pentyl)-1H-[1,2,3]triazol-4-yl]-1-cyclohexyl-ethyl}-amide | A 1.65 403.8 |

| Compound | Structure | Name | LCMS Method, RT (min), [M + H]+ |
|---|---|---|---|
| 12 | 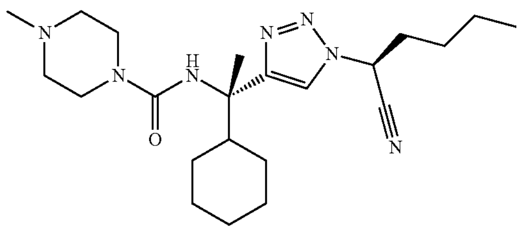 [SMILES: CCCC[C@@H](C#N)n1cc([C@@](C)(NC(=O)N2CCN(C)CC2)C2CCCCC2)nn1] | 4-Methyl-piperazine-1-carboxylic acid {(S)-1-[1-((S)-1-cyano-pentyl)-1H-[1,2,3]triazol-4-yl]-1-cyclohexyl-ethyl}-amide | A 1.41 416.8 |
| 13 | 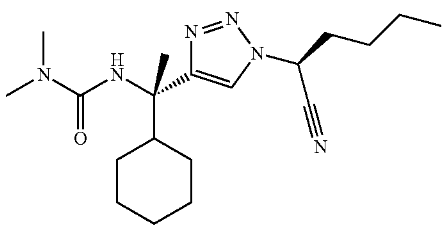 [SMILES: CCCC[C@@H](C#N)n1cc([C@@](C)(NC(=O)N(C)C)C2CCCCC2)nn1] | 3-{(S)-1-[1-((S)-1-Cyano-pentyl)-1H-[1,2,3]triazol-4-yl]-1-cyclohexyl-ethyl}-1,1-dimethyl-urea | A 1.69 361.7 |
| 14 | 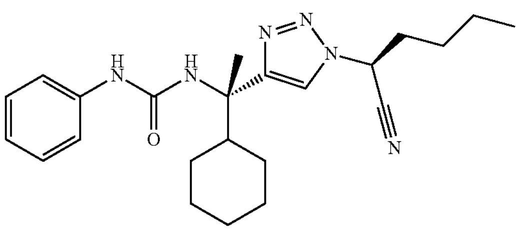 [SMILES: CCCC[C@@H](C#N)n1cc([C@@](C)(NC(=O)Nc2ccccc2)C2CCCCC2)nn1] | 1-{(S)-1-[1-((S)-1-Cyano-pentyl)-1H-[1,2,3]triazol-4-yl]-1-cyclohexyl-ethyl}-3-phenyl-urea | A 1.88 409.8 |
| 15 | 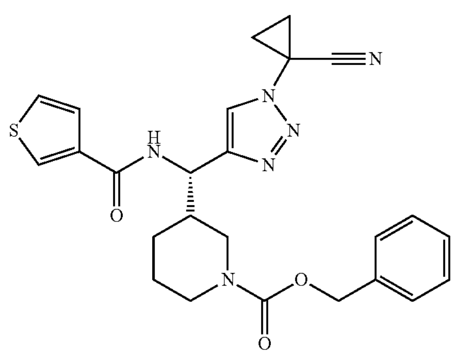 [SMILES: N#CC1(n2cc([C@@H](NC(=O)c3ccsc3)C3CCCN(C(=O)OCc4ccccc4)C3)nn2)CC1] | 3-{(S)-[1-(1-Cyano-cyclopropyl)-1H-[1,2,3]triazol-4-yl]-[(thiophene-3-carbonyl)-amino]-methyl}-piperidine-1-carboxylic acid benzyl ester | B 6.17 491.7 |
| 16 | 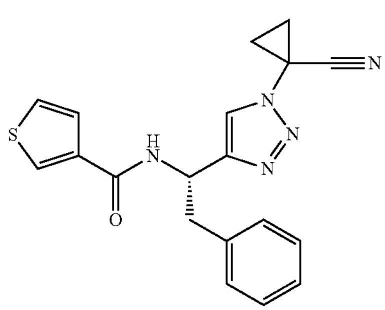 [SMILES: N#CC1(n2cc([C@H](Cc3ccccc3)NC(=O)c3ccsc3)nn2)CC1] | Thiophene-3-carboxylic acid {(S)-1-[1-(1-cyano-cyclopropyl)-1H-[1,2,3]triazol-4-yl]-2-phenyl-ethyl}-amide | B 5.8 364.5 |

-continued

| Compound | Structure | Name | LCMS Method, RT (min), [M + H]+ |
|---|---|---|---|
| 17 | 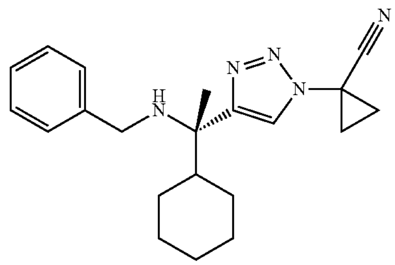 [SMILES: C[C@@](NCc1ccccc1)(c1cn(C2(C#N)CC2)nn1)C1CCCCC1] | 1-[4-((S)-1-Benzylamino-1-cyclohexyl-ethyl)-[1,2,3]triazol-1-yl]-cyclopropanecarbonitrile | E 0.59 350.3 |
| 18 | 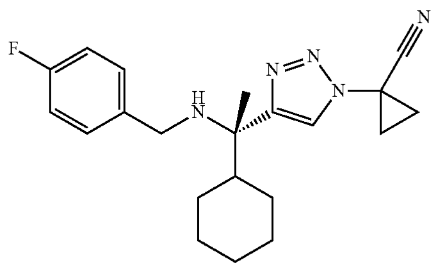 [SMILES: C[C@@](NCc1ccc(F)cc1)(c1cn(C2(C#N)CC2)nn1)C1CCCCC1] | 1-{4-[(S)-1-Cyclohexyl-1-(4-fluoro-benzylamino)-ethyl]-[1,2,3]triazol-1-yl}-cyclopropanecarbonitrile | E 0.7 368.5 |
| 19 | 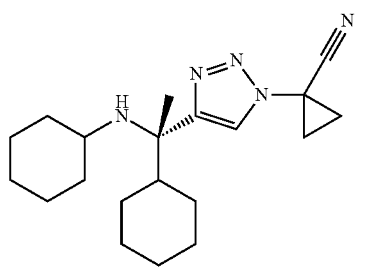 [SMILES: C[C@@](NC1CCCCC1)(c1cn(C2(C#N)CC2)nn1)C1CCCCC1] | 1-[4-((S)-1-Cyclohexyl-1-cyclohexylamino-ethyl)-[1,2,3]triazol-1-yl]-cyclopropanecarbonitrile | E 0.71 342.3 |
| 20 | 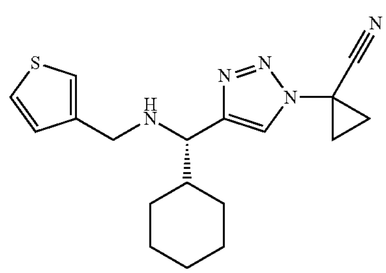 [SMILES: N#CC1(n2cc([C@@H](NCc3ccsc3)C3CCCCC3)nn2)CC1] | 1-(4-{(S)-Cyclohexyl-[(thiophen-3-ylmethyl)-amino]-methyl}-[1,2,3]triazol-1-yl)-cyclopropanecarbonitrile | E 0.64 342.2 |
| 21 | 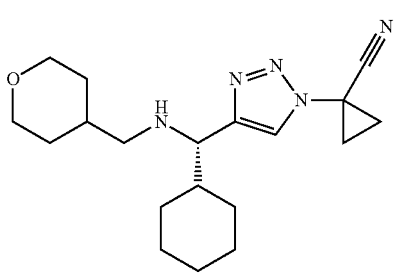 [SMILES: N#CC1(n2cc([C@@H](NCC3CCOCC3)C3CCCCC3)nn2)CC1] | 1-(4-{(S)-Cyclohexyl-[(tetrahydro-pyran-4-ylmethyl)-amino]-methyl}-[1,2,3]triazol-1-yl)-cyclopropanecarbonitrile | E 0.57 344.2 |

-continued

| Compound | Structure | Name | LCMS Method, RT (min), [M + H]⁺ |
|---|---|---|---|
| 22 | 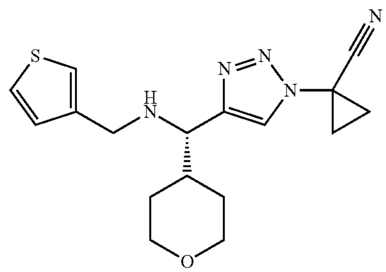 [SMILES: N#CC1(n2cc([C@@H](NCc3ccsc3)C3CCOCC3)nn2)CC1] | 1-(4-{(S)-(Tetrahydro-pyran-4-yl)-[(thiophen-3-ylmethyl)-amino]-methyl}-[1,2,3]triazol-1-yl)-cyclopropanecarbonitrile | E 0.47 344.1 |
| 23 | 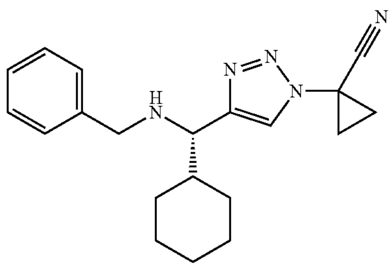 [SMILES: N#CC1(n2cc([C@@H](NCc3ccccc3)C3CCCCC3)nn2)CC1] | 1-[4-((S)-Benzylamino-cyclohexyl-methyl)-[1,2,3]triazol-1-yl]-cyclopropanecarbonitrile | E 0.65 336.2 |
| 24 | 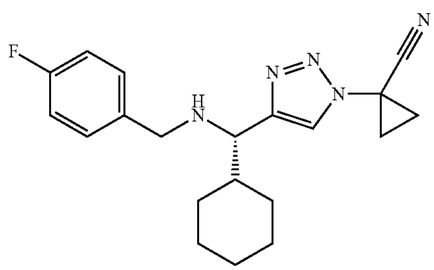 [SMILES: N#CC1(n2cc([C@@H](NCc3ccc(F)cc3)C3CCCCC3)nn2)CC1] | 1-{4-[(S)-Cyclohexyl-(4-fluoro-benzylamino)-methyl]-[1,2,3]triazol-1-yl}-cyclopropanecarbonitrile | E 0.68 354.1 |
| 25 | 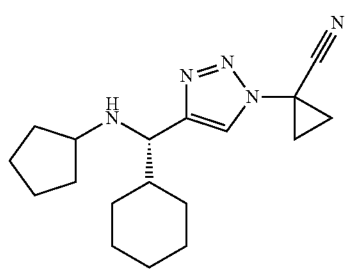 [SMILES: N#CC1(n2cc([C@@H](NC3CCCC3)C3CCCCC3)nn2)CC1] | 1-[4-((S)-Cyclohexyl-cyclopentylamino-methyl)-[1,2,3]triazol-1-yl]-cyclopropanecarbonitrile | E 0.65 314.1 |
| 26 | 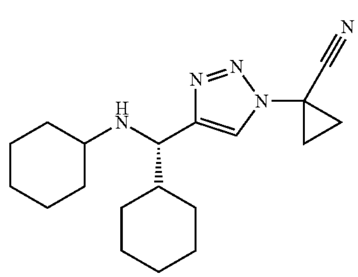 [SMILES: N#CC1(n2cc([C@@H](NC3CCCCC3)C3CCCCC3)nn2)CC1] | 1-[4-((S)-Cyclohexyl-cyclohexylamino-methyl)-[1,2,3]triazol-1-yl]-cyclopropanecarbonitrile | E 0.70 328.2 |

-continued

| Compound | Structure | Name | LCMS Method, RT (min), [M + H]+ |
|---|---|---|---|
| 27 | 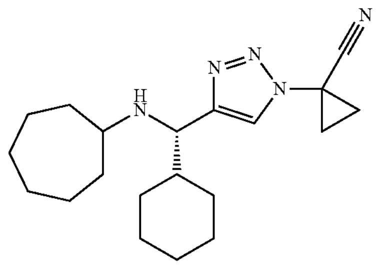 [SMILES: N#CC1(n2cc([C@@H](NC3CCCCCC3)C3CCCCC3)nn2)CC1] | 1-[4-((S)-Cycloheptylamino-cyclohexyl-methyl)-[1,2,3]triazol-1-yl]-cyclopropanecarbonitrile | E 0.71 342.2 |
| 28 | 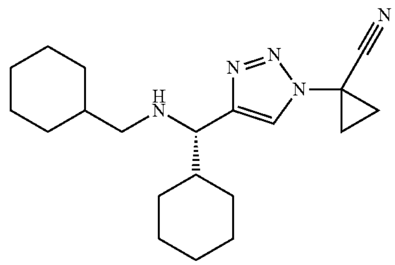 [SMILES: N#CC1(n2cc([C@@H](NCC3CCCCC3)C3CCCCC3)nn2)CC1] | 1-{4-[(S)-Cyclohexyl-(cyclohexylmethyl-amino)-methyl]-[1,2,3]triazol-1-yl}-cyclopropanecarbonitrile | E 0.73 342.2 |
| 29 | 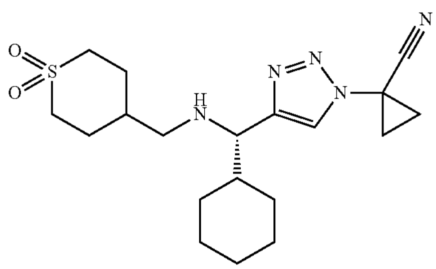 [SMILES: N#CC1(n2cc([C@@H](NCC3CCS(=O)(=O)CC3)C3CCCCC3)nn2)CC1] | 1-(4-{(S)-Cyclohexyl-[(1,1-dioxo-hexahydro-1l6-thiopyran-4-ylmethyl)-amino]-methyl}-[1,2,3]triazol-1-yl)-cyclopropanecarbonitrile | E 0.53 392.2 |
| 30 | 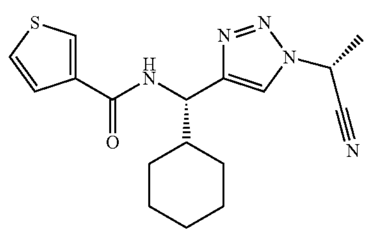 [SMILES: C[C@H](C#N)n1cc([C@@H](NC(=O)c2ccsc2)C2CCCCC2)nn1] | Thiophene-3-carboxylic acid {(S)-[1-((R)-cyano-methyl-methyl)-1H-[1,2,3]triazol-4-yl]-cyclohexyl-methyl}-amide | A 1.87 344.1 |
| 31 | 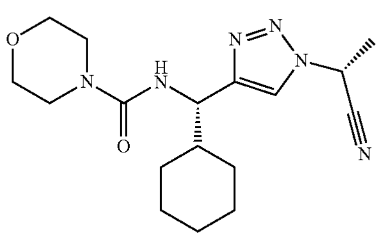 [SMILES: C[C@H](C#N)n1cc([C@@H](NC(=O)N2CCOCC2)C2CCCCC2)nn1] | Morpholine-4-carboxylic acid {(S)-[1-((R)-cyano-methyl-methyl)-1H-[1,2,3]triazol-4-yl]-cyclohexyl-methyl}-amide | F 1.37 347.2 |
| 32 | 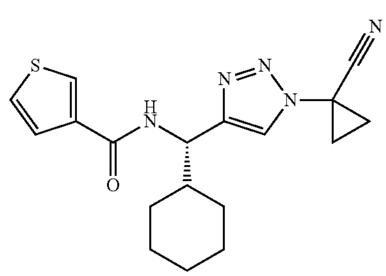 [SMILES: N#CC1(n2cc([C@@H](NC(=O)c3ccsc3)C3CCCCC3)nn2)CC1] | Thiophene-3-carboxylic acid {(S)-[1-(1-cyano-cyclopropyl)-1H-[1,2,3]triazol-4-yl]-cyclohexyl-methyl}-amide | A 1.58 356.6 |

| Compound | Structure | Name | LCMS Method, RT (min), [M + H]+ |
|---|---|---|---|
| 33 | 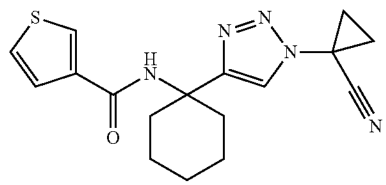 [SMILES: N#CC1(n2cc(C3(NC(=O)c4ccsc4)CCCCC3)nn2)CC1] | Thiophene-3-carboxylic acid {1-[1-(1-cyano-cyclopropyl)-1H-[1,2,3]triazol-4-yl]-cyclohexyl}-amide | A 1.47 342.3 |
| 34 | 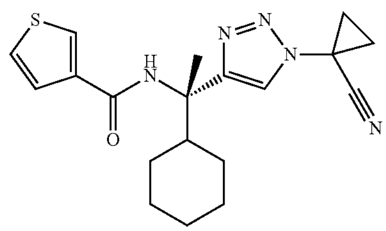 [SMILES: C[C@@](NC(=O)c1ccsc1)(c1cn(C2(C#N)CC2)nn1)C1CCCCC1] | Thiophene-3-carboxylic acid {(S)-1-[1-(1-cyano-cyclopropyl)-1H-[1,2,3]triazol-4-yl]-1-cyclohexyl-ethyl}-amide | F 2.11 370.2 |
| 35 | 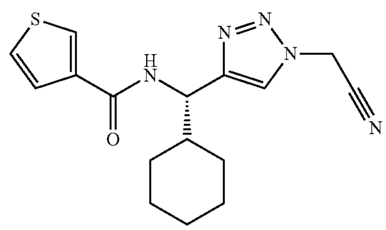 [SMILES: N#CCn1cc([C@@H](NC(=O)c2ccsc2)C2CCCCC2)nn1] | Thiophene-3-carboxylic acid [(S)-(1-cyanomethyl-1H-[1,2,3]triazol-4-yl)-cyclohexyl-methyl]-amide | F 1.78 330.1 |
| 36 | 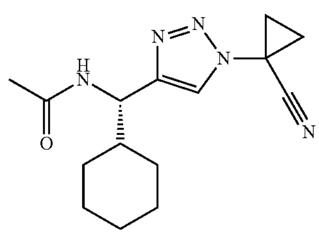 [SMILES: CC(=O)N[C@H](c1cn(C2(C#N)CC2)nn1)C1CCCCC1] | N-{(S)-[1-(1-Cyano-cyclopropyl)-1H-[1,2,3]triazol-4-yl]-cyclohexyl-methyl}-acetamide | F 1.33 288.1 |
| 37 | 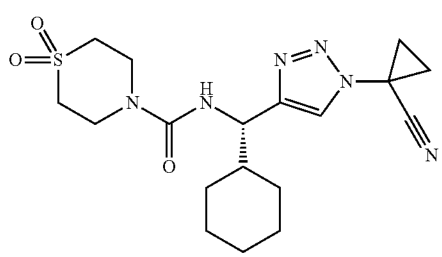 [SMILES: N#CC1(n2cc([C@@H](NC(=O)N3CCS(=O)(=O)CC3)C3CCCCC3)nn2)CC1] | 1,1-Dioxo-1l6-thiomorpholine-4-carboxylic acid {(S)-[1-(1-cyano-cyclopropyl)-1H-[1,2,3]triazol-4-yl]-cyclohexyl-methyl}-amide | A 1.34 407.3 |
| 38 | 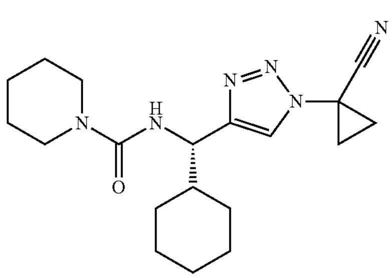 [SMILES: N#CC1(n2cc([C@@H](NC(=O)N3CCCCC3)C3CCCCC3)nn2)CC1] | Piperidine-1-carboxylic acid {(S)-[1-(1-cyano-cyclopropyl)-1H-[1,2,3]triazol-4-yl]-cyclohexyl-methyl}-amide | A 1.57 357.3 |

| Compound | Structure | Name | LCMS Method, RT (min), [M + H]+ |
|---|---|---|---|
| 39 | 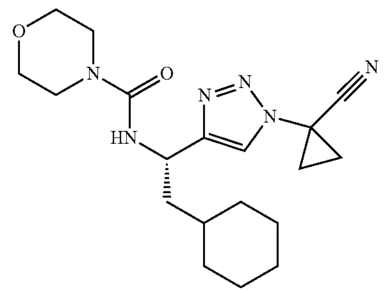 [SMILES: N#CC1(n2cc([C@H](CC3CCCCC3)NC(=O)N3CCOCC3)nn2)CC1] | Morpholine-4-carboxylic acid {(S)-1-[1-(1-cyano-cyclopropyl)-1H-[1,2,3]triazol-4-yl]-2-cyclohexyl-ethyl}-amide | F 1.74 373.2 |
| 40 | 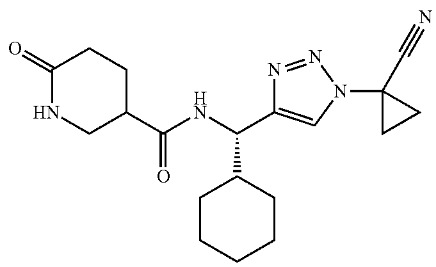 [SMILES: N#CC1(n2cc([C@@H](NC(=O)C3CCC(=O)NC3)C3CCCCC3)nn2)CC1] | 6-Oxo-piperidine-3-carboxylic acid {(S)-[1-(1-cyano-cyclopropyl)-1H-[1,2,3]triazol-4-yl]-cyclohexyl-methyl}-amide | E 0.72 371.2 |
| 41 | 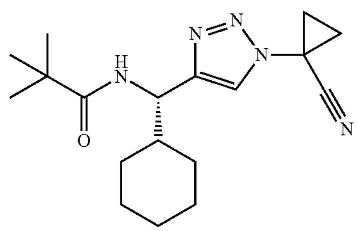 [SMILES: CC(C)(C)C(=O)N[C@H](c1cn(C2(C#N)CC2)nn1)C1CCCCC1] | N-{(S)-[1-(1-Cyano-cyclopropyl)-1H-[1,2,3]triazol-4-yl]-cyclohexyl-methyl}-2,2-dimethyl-propionamide | F 2.07 330.2 |
| 42 | 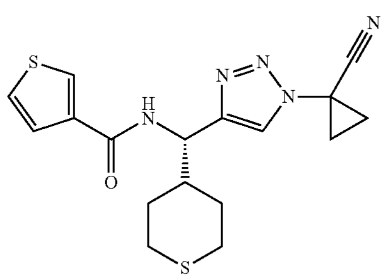 [SMILES: N#CC1(n2cc([C@@H](NC(=O)c3ccsc3)C3CCSCC3)nn2)CC1] | Thiophene-3-carboxylic acid [(S)-[1-(1-cyano-cyclopropyl)-1H-[1,2,3]triazol-4-yl]-(tetrahydro-thiopyran-4-yl)-methyl]-amide | A 1.43 374.3 |
| 43 | 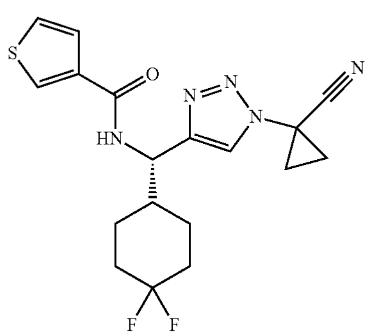 [SMILES: N#CC1(n2cc([C@@H](NC(=O)c3ccsc3)C3CCC(F)(F)CC3)nn2)CC1] | Thiophene-3-carboxylic acid [(S)-[1-(1-cyano-cyclopropyl)-1H-[1,2,3]triazol-4-yl]-(4,4-difluoro-cyclohexyl)-methyl]-amide | F 1.72 392.1 |

-continued

| Compound | Structure | Name | LCMS Method, RT (min), [M + H]+ |
|---|---|---|---|
| 44 | 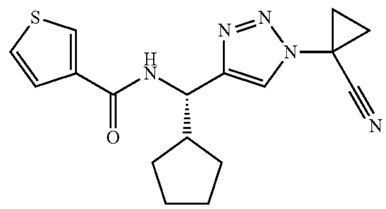 [SMILES: N#CC1(n2cc([C@@H](NC(=O)c3ccsc3)C3CCCC3)nn2)CC1] | Thiophene-3-carboxylic acid {(S)-[1-(1-cyano-cylcopropyl)-1H-[1,2,3]triazol-4-yl]-cyclopentyl-methyl}-amide | F 1.72 342.3 |
| 45 | 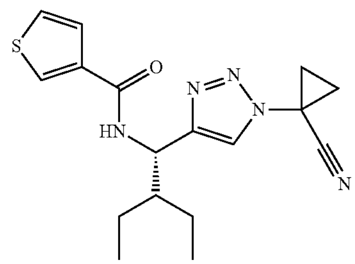 [SMILES: CCC(CC)[C@H](NC(=O)c1ccsc1)c1cn(C2(C#N)CC2)nn1] | Thiophene-3-carboxylic acid {(S)-1-[1-(1-cyano-cyclopropyl)-1H-[1,2,3]triazol-4-yl]-2-ethyl-butyl}-amide | F 1.93 344.1 |
| 46 | 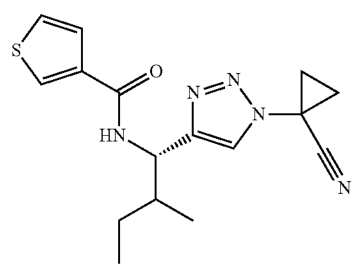 [SMILES: CCC(C)[C@H](NC(=O)c1ccsc1)c1cn(C2(C#N)CC2)nn1] | Thiophene-3-carboxylic acid {(S)-1-[1-(1-cyano-cyclopropyl)-1H-[1,2,3]triazol-4-yl]-2-methyl-butyl}-amide | F 1.71 330.1 |
| (R,R)-47 | 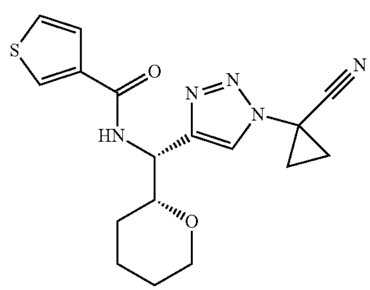 [SMILES: N#CC1(n2cc([C@@H](NC(=O)c3ccsc3)[C@H]3CCCCO3)nn2)CC1] | Thiophene-3-carboxylic acid {(R)-[1-(1-cyano-cyclopropyl)-1H-[1,2,3]triazol-4-yl]-(R)-tetrahydro-pyran-2-yl-methyl}-amide | F 1.48 358.1 |
| (R,S)-47 | 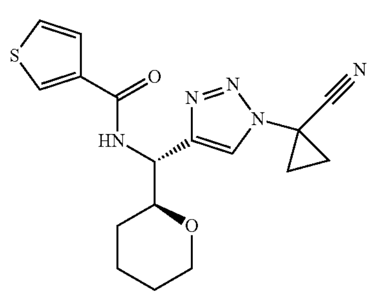 [SMILES: N#CC1(n2cc([C@@H](NC(=O)c3ccsc3)[C@@H]3CCCCO3)nn2)CC1] | Thiophene-3-carboxylic acid {(R)-[1-(1-cyano-cyclopropyl)-1H-[1,2,3]triazol-4-yl]-(S)-tetrahydro-pyran-2-yl-methyl}-amide | F 1.51 358.1 |

-continued

| Compound | Structure | Name | LCMS Method, RT (min), [M + H]+ |
|---|---|---|---|
| 48 | 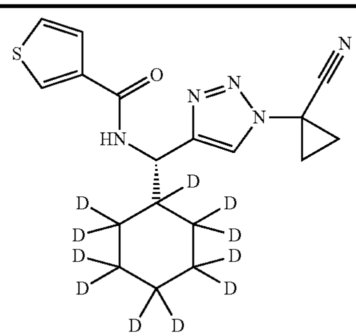 | Thiophene-3-carboxylic acid {(S)-[1-(1-cyano-cyclopropyl)-1H-[1,2,3]triazol-4-yl]-cyclohexyl-D11-methyl}-amide | C<br>1.26<br>367.2 |
| 49 | 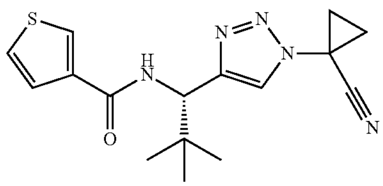 [SMILES: CC(C)(C)[C@H](NC(=O)c1ccsc1)c1cn(C2(C#N)CC2)nn1] | Thiophene-3-carboxylic acid {(S)-1-[1-(1-cyano-cyclopropyl)-1H-[1,2,3]triazol-4-yl]-2,2-dimethyl-propyl}-amide | F<br>1.65<br>330.3 |
| 50 | 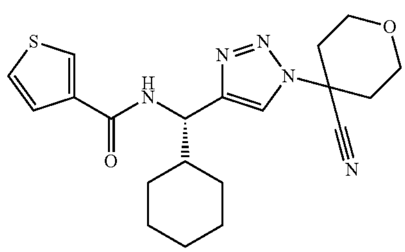 [SMILES: N#CC1(n2cc([C@@H](NC(=O)c3ccsc3)C3CCCCC3)nn2)CCOCC1] | Thiophene-3-carboxylic acid {(S)-[1-(4-cyano-tetrahydro-pyran-4-yl)-1H-[1,2,3]triazol-4-yl]-cyclohexyl-methyl}-amide | F<br>1.94<br>400.1 |
| 51 | 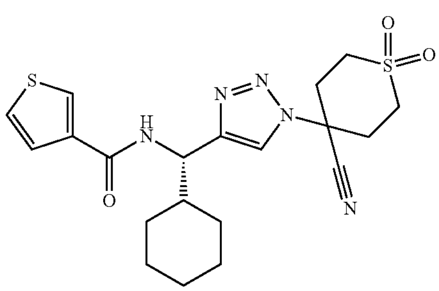 [SMILES: N#CC1(n2cc([C@@H](NC(=O)c3ccsc3)C3CCCCC3)nn2)CCS(=O)(=O)CC1] | Thiophene-3-carboxylic acid {(S)-[1-(4-cyano-1,1-dioxo-hexahydro-1l6-thiopyran-4-yl)-1H-[1,2,3]triazol-4-yl]-cyclohexyl-methyl}-amide | F<br>1.96<br>448.1 |
| 52 | 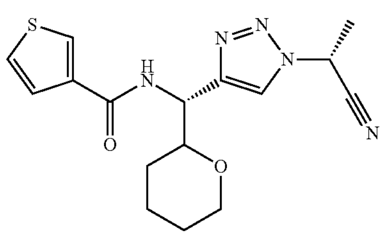 [SMILES: C[C@H](C#N)n1cc([C@@H](NC(=O)c2ccsc2)C2CCCCO2)nn1] | Thiophene-3-carboxylic acid [(R)-[1-((R)-cyano-methyl-methyl)-1H-[1,2,3]triazol-4-yl]-(tetrahydro-pyran-2-yl)-methyl]-amide | F<br>1.31<br>346.1 |
| 53 | 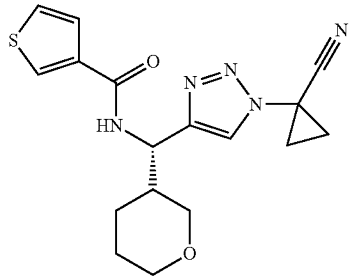 [SMILES: N#CC1(n2cc([C@@H](NC(=O)c3ccsc3)C3CCCOC3)nn2)CC1] | Thiophene-3-carboxylic acid [(S)-[1-(1-cyano-cyclopropyl)-1H-[1,2,3]triazol-4-yl]-(tetrahydro-pyran-3-yl)-methyl]-amide | F<br>1.12<br>358.1 |

-continued

| Compound | Structure | Name | LCMS Method, RT (min), [M + H]+ |
|---|---|---|---|
| 54 | 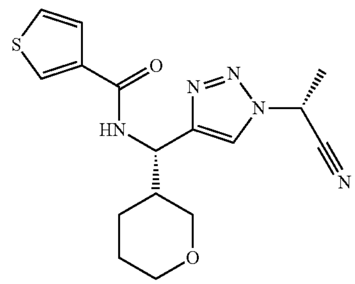 [SMILES: C[C@H](C#N)n1cc([C@@H](NC(=O)c2ccsc2)C2CCCOC2)nn1] | Thiophene-3-carboxylic acid [(S)-[1-((R)-cyano-methyl-methyl)-1H-[1,2,3]triazol-4-yl]-(tetrahydro-pyran-3-yl)-methyl]-amide | E<br>1.03 & 1.09<br>346.0 & 346.0 |
| 55 | 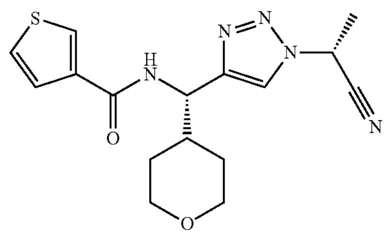 [SMILES: C[C@H](C#N)n1cc([C@@H](NC(=O)c2ccsc2)C2CCOCC2)nn1] | Thiophene-3-carboxylic acid [(S)-[1-((R)-cyano-methyl-methyl)-1H-[1,2,3]triazol-4-yl]-(tetrahydro-pyran-4-yl)-methyl]-amide | F<br>1.05<br>346.1 |
| 56 | 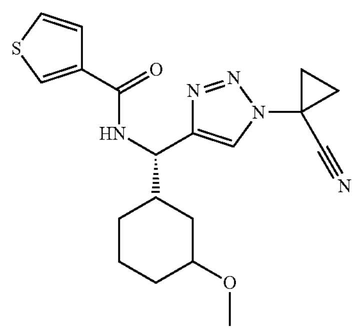 [SMILES: COC1CCCC([C@H](NC(=O)c2ccsc2)c2cn(C3(C#N)CC3)nn2)C1] | Thiophene-3-carboxylic acid [(S)-[1-(1-cyano-cyclopropyl)-1H-[1,2,3]triazol-4-yl]-(3-methoxy-cyclohexyl)-methyl]-amide | F<br>1.44 & 1.46<br>3.86.1 & 386.1 |
| 57 | 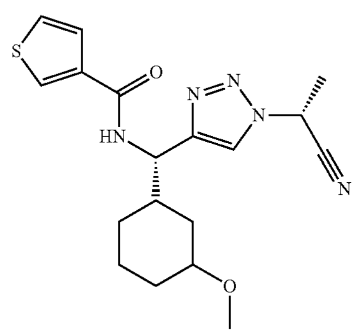 [SMILES: COC1CCCC([C@H](NC(=O)c2ccsc2)c2cn([C@H](C)C#N)nn2)C1] | Thiophene-3-carboxylic acid [(S)-[1-((R)-cyano-methyl-methyl)-1H-[1,2,3]triazol-4-yl]-(3-methoxy-cyclohexyl)-methyl]-amide | F<br>1.40/1.47<br>374.1/374.1 |
| 58 | 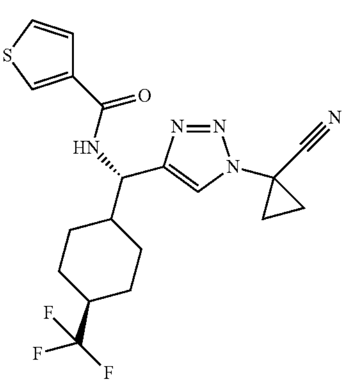 | Thiophene-3-carboxylic acid [(S)-[1-(1-cyano-cyclopropyl)-1H-[1,2,3]triazol-4-yl]-(4-trifluoromethyl-cyclohexyl)-methyl]-amide | D<br>1.31<br>424.2 |

| Compound | Structure | Name | LCMS Method, RT (min), [M + H]+ |
|---|---|---|---|
| 59 | 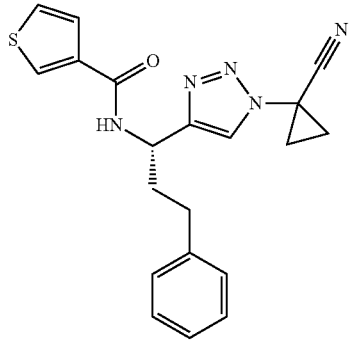 [SMILES: N#CC1(n2cc([C@H](CCc3ccccc3)NC(=O)c3ccsc3)nn2)CC1] | Thiophene-3-carboxylic acid {(S)-1-[1-(1-cyano-cyclopropyl)-1H-[1,2,3]triazol-4-yl]-3-phenyl-propyl}-amide | F 1.93 378.2 |
| 60 | 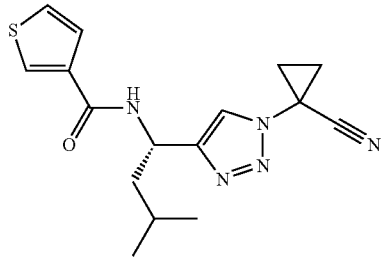 [SMILES: CC(C)C[C@H](NC(=O)c1ccsc1)c1cn(C2(C#N)CC2)nn1] | Thiophene-3-carboxylic acid {(S)-1-[1-(1-cyano-cyclopropyl)-1H-[1,2,3]triazol-4-yl]-3-methyl-butyl}-amide | F 1.57 330.2 |
| 61 | 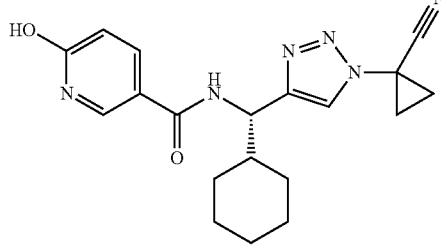 | N-{(S)-[1-(1-Cyano-cyclopropyl)-1H-[1,2,3]triazol-4-yl]-cyclohexyl-methyl}-6-hydroxy-nicotinamide | E 0.74 367.0 |
| 62 | 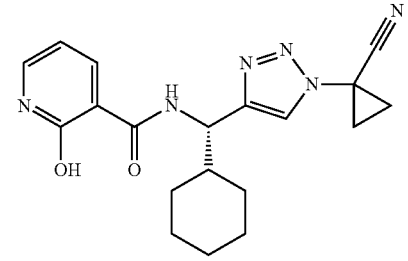 [SMILES: N#CC1(n2cc([C@@H](NC(=O)c3cccnc3O)C3CCCCC3)nn2)CC1] | N-{(S)-[1-(1-Cyano-cyclopropyl)-1H-[1,2,3]triazol-4-yl]-cyclohexyl-methyl}-2-hydroxy-nicotinamide | E 0.78 367.1 |
| 64 | 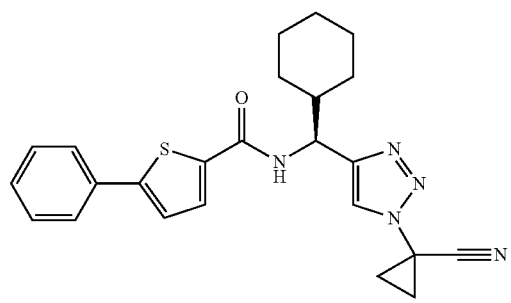 [SMILES: N#CC1(n2cc([C@@H](NC(=O)c3ccc(-c4ccccc4)s3)C3CCCCC3)nn2)CC1] | 5-Phenyl-thiophene-2-carboxylic acid {(S)-[1-(1-cyano-cyclopropyl)-1H-[1,2,3]triazol-4-yl]-cyclohexyl-methyl}-amide | F 2.73 432.2 |

-continued

| Compound | Structure | Name | LCMS Method, RT (min), [M + H]+ |
|---|---|---|---|
| 65 | 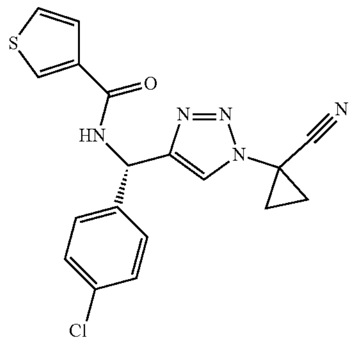 [SMILES: N#CC1(n2cc([C@@H](NC(=O)c3ccsc3)c3ccc(Cl)cc3)nn2)CC1] | Thiophene-3-carboxylic acid {(S)-(4-chloro-phenyl)-[1-(1-cyano-cyclopropyl)-1H-[1,2,3]triazol-4-yl]-methyl}-amide | C 1.25 384.2 |
| 66 | 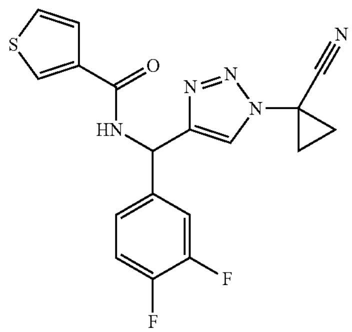 [SMILES: N#CC1(n2cc(C(NC(=O)c3ccsc3)c3ccc(F)c(F)c3)nn2)CC1] | Thiophene-3-carboxylic acid [[1-(1-cyano-cyclopropyl)-1H-[1,2,3]triazol-4-yl]-(3,4-difluoro-phenyl)-methyl]-amide | C 1.55 386.2 |
| 67 | 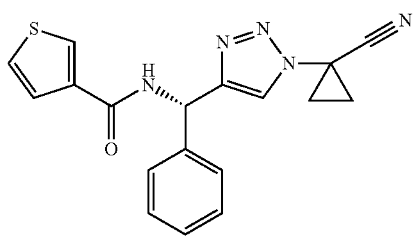 [SMILES: N#CC1(n2cc([C@@H](NC(=O)c3ccsc3)c3ccccc3)nn2)CC1] | Thiophene-3-carboxylic acid {(S)-[1-(1-cyano-cyclopropyl)-1H-[1,2,3]triazol-4-yl]-phenyl-methyl}-amide | C 1.15 350.2 |
| 68 | 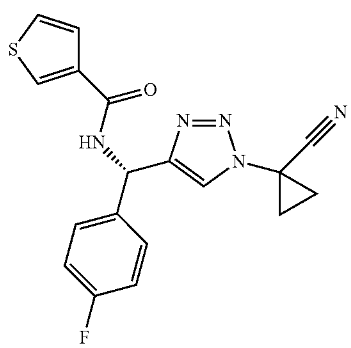 [SMILES: N#CC1(n2cc([C@@H](NC(=O)c3ccsc3)c3ccc(F)cc3)nn2)CC1] | Thiophene-3-carboxylic acid [(S)-[1-(1-cyano-cyclopropyl)-1H-[1,2,3]triazol-4-yl]-(4-fluoro-phenyl)-methyl]-amide | C 1.17 368.2 |
| 69 | 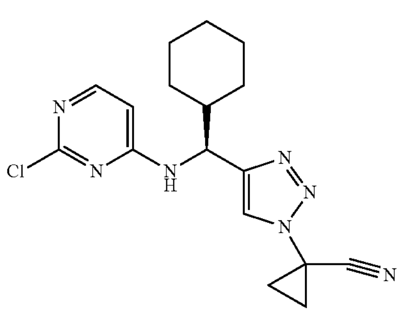 [SMILES: N#CC1(n2cc([C@@H](Nc3ccnc(Cl)n3)C3CCCCC3)nn2)CC1] | 1-{4-[(S)-(2-Chloro-pyrimidin-4-ylamino)-cyclohexyl-methyl]-[1,2,3]triazol-1-yl}-cyclopropanecarbonitrile | F 1.97 358.1 |

-continued

| Compound | Structure | Name | LCMS Method, RT (min), [M + H]+ |
|---|---|---|---|
| 70 | 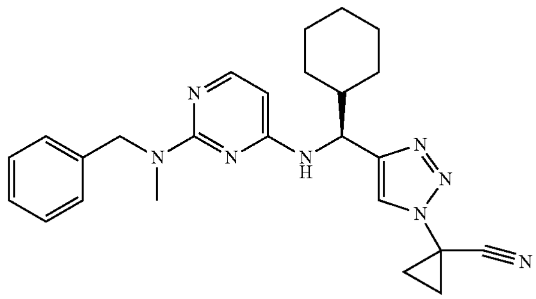 [SMILES: CN(Cc1ccccc1)c1nccc(N[C@H](c2cn(C3(C#N)CC3)nn2)C2CCCCC2)n1] | 1-(4-{(S)-[2-(Benzyl-methyl-amino)-pyrimidin-4-ylamino]-cyclohexyl-methyl}-[1,2,3]triazol-1-yl)-cyclopropanecarbonitrile | F 1.39 461.0 |
| 71 | 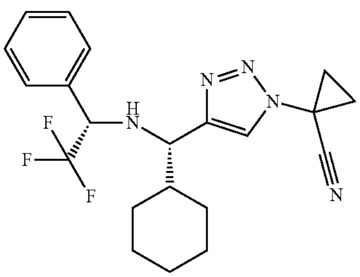 [SMILES: N#CC1(n2cc([C@@H](N[C@@H](c3ccccc3)C(F)(F)F)C3CCCCC3)nn2)CC1] | 1-{4-[(S)-Cyclohexyl-((S)-2,2,2-trifluoro-1-phenyl-ethylamino)-methyl]-[1,2,3]triazol-1-yl}-cyclopropanecarbonitrile | A 1.97 404.4 |
| 72 | 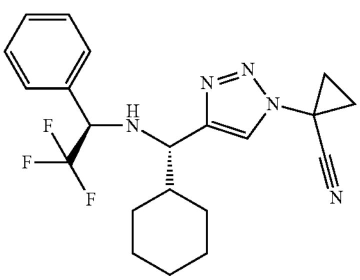 [SMILES: N#CC1(n2cc([C@@H](N[C@H](c3ccccc3)C(F)(F)F)C3CCCCC3)nn2)CC1] | 1-{4-[(S)-Cyclohexyl-((R)-2,2,2-trifluoro-1-phenyl-ethylamino)-methyl]-[1,2,3]triazol-1-yl}-cyclopropanecarbonitrile | A 2 404.4 |
| 73 | 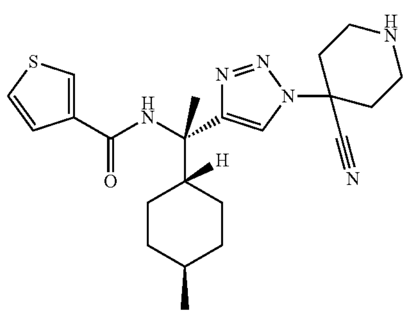 [SMILES: C[C@@](NC(=O)c1ccsc1)(c1cn(C2(C#N)CCNCC2)nn1)[C@H]1CC[C@H](C)CC1] | Thiophene-3-carboxylic acid [(S)-1-[1-(4-cyano-piperidin-4-yl)-1H-[1,2,3]triazol-4-yl]-1-(4-methyl-cyclohexyl)-ethyl]-amide | F 1.43 427.7 |
| 74 | 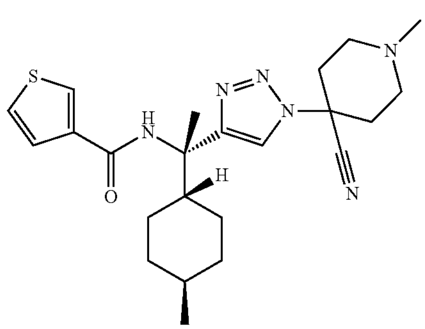 [SMILES: CN1CCC(C#N)(n2cc([C@@](C)(NC(=O)c3ccsc3)[C@H]3CC[C@H](C)CC3)nn2)CC1] | Thiophene-3-carboxylic acid [(S)-1-[1-(4-cyano-1-methyl-piperidin-4-yl)-1H-[1,2,3]triazol-4-yl]-1-(4-methyl-cyclohexyl)-ethyl]-amide | F 1.43 441.4 |

| Compound | Structure | Name | LCMS Method, RT (min), [M + H]+ |
|---|---|---|---|
| 75 | 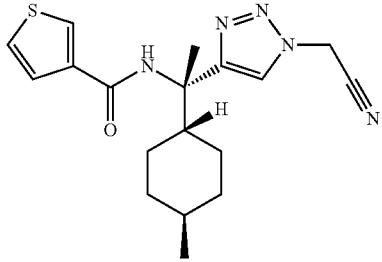 [SMILES: C[C@@](NC(=O)c1ccsc1)(c1cn(CC#N)nn1)[C@H]1CC[C@H](C)CC1] | Thiophene-3-carboxylic acid [(S)-1-(1-cyanomethyl-1H-[1,2,3]triazol-4-yl)-1-(4-methyl-cyclohexyl)-ethyl]-amide | A 1.61 358.2 |
| 76 | 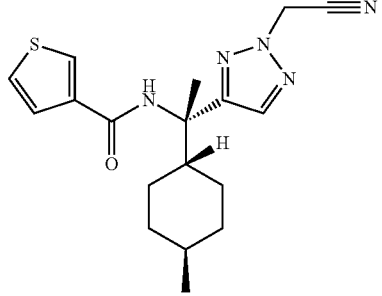 [SMILES: C[C@@](NC(=O)c1ccsc1)(c1cnn(CC#N)n1)[C@H]1CC[C@H](C)CC1] | Thiophene-3-carboxylic acid [(S)-1-(2-cyanomethyl-2H-[1,2,3]triazol-4-yl)-1-(4-methyl-cyclohexyl)-ethyl]-amide | A 1.71 358.2 |
| 77 | 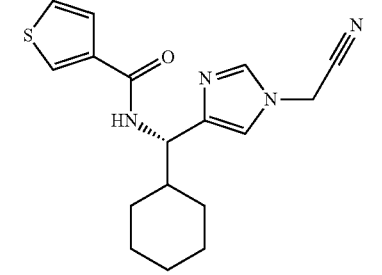 [SMILES: N#CCn1cnc([C@@H](NC(=O)c2ccsc2)C2CCCCC2)c1] | Thiophene-3-carboxylic acid [(S)-(1-cyanomethyl-1H-imidazol-4-yl)-cyclohexyl-methyl]-amide | C 1.3 329.6 |
| 78 | 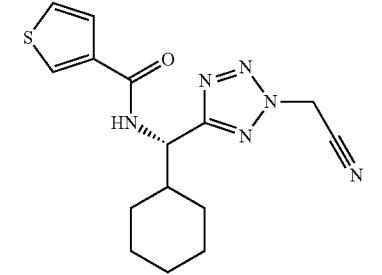 [SMILES: N#CCn1nnc([C@@H](NC(=O)c2ccsc2)C2CCCCC2)n1] | Thiophene-3-carboxylic acid [(S)-(2-cyanomethyl-2H-tetrazol-5-yl)-cyclohexyl-methyl]-amide | D 2.32 331.2 |
| 79 | 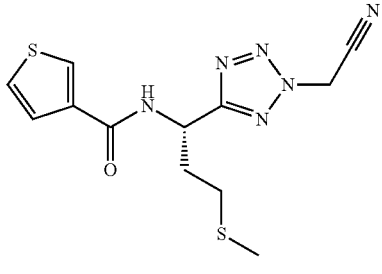 [SMILES: CSCC[C@H](NC(=O)c1ccsc1)c1nnn(CC#N)n1] | Thiophene-3-carboxylic acid [(S)-1-(2-cyanomethyl-2H-tetrazol-5-yl)-3-methylsulfanyl-propyl]-amide | |

| Compound | Structure | Name | LCMS Method, RT (min), [M + H]+ |
|---|---|---|---|
| 80 | 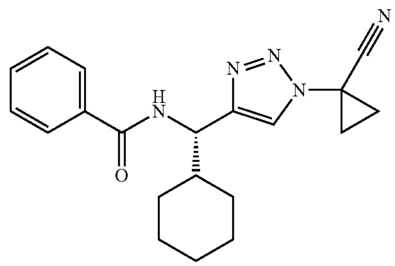 [SMILES: N#CC1(n2cc([C@@H](NC(=O)c3ccccc3)C3CCCCC3)nn2)CC1] | N-{(S)-[1-(1-Cyano-cyclopropyl)-1H-[1,2,3]triazol-4-yl]-cyclohexyl-methyl}-benzamide | E 0.98 350.2 |
| 81 | 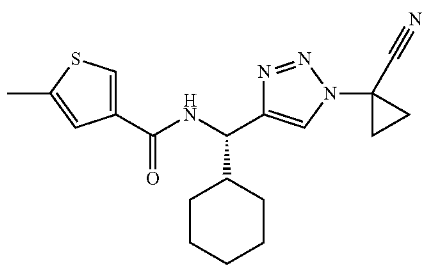 [SMILES: Cc1cc(C(=O)N[C@H](c2cn(C3(C#N)CC3)nn2)C2CCCCC2)cs1] | 5-Methyl-thiophene-3-carboxylic acid {(S)-[1-(1-cyano-cyclopropyl)-1H-[1,2,3]triazol-4-yl]-cyclohexyl-methyl}-amide | E 1.02 370.1 |
| 82 | 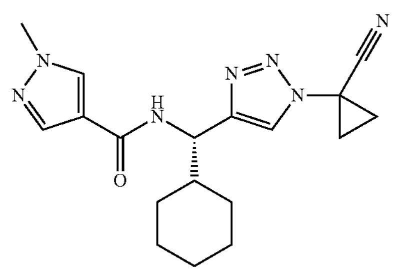 [SMILES: Cn1cc(C(=O)N[C@H](c2cn(C3(C#N)CC3)nn2)C2CCCCC2)cn1] | 1-Methyl-1H-pyrazole-4-carboxylic acid {(S)-[1-(1-cyano-cyclopropyl)-1H-[1,2,3]triazol-4-yl]-cyclohexyl-methyl}-amide | E 0.72 354.4 |
| 83 | 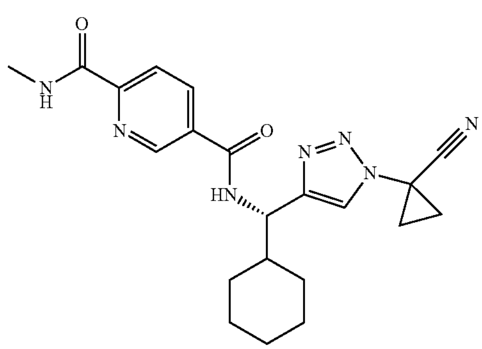 [SMILES: CNC(=O)c1ccc(C(=O)N[C@H](c2cn(C3(C#N)CC3)nn2)C2CCCCC2)cn1] | Pyridine-2,5-dicarboxylic acid 5-({(S)-[1-(1-cyano-cyclopropyl)-1H-[1,2,3]triazol-4-yl]-cyclohexyl-methyl}-amide) 2-methylamide | C 1.4 408.3 |
| 84 | 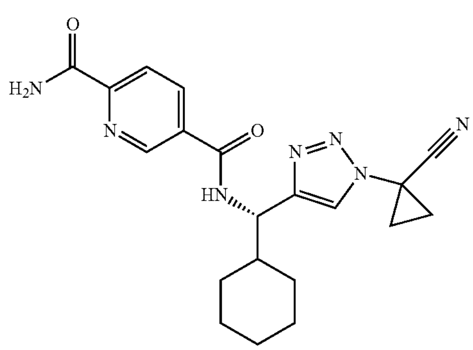 [SMILES: N#CC1(n2cc([C@@H](NC(=O)c3ccc(C(N)=O)nc3)C3CCCCC3)nn2)CC1] | Pyridine-2,5-dicarboxylic acid 2-amide 5-({(S)-[1-(1-cyano-cyclopropyl)-1H-[1,2,3]triazol-4-yl]-cyclohexyl-methyl}-amide) | C 1.09 394.2 |

| Compound | Structure | Name | LCMS Method, RT (min), [M + H]+ |
|---|---|---|---|
| 85 | 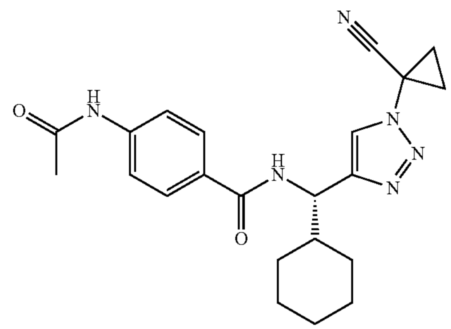 [SMILES: CC(=O)Nc1ccc(C(=O)N[C@H](c2cn(C3(C#N)CC3)nn2)C2CCCCC2)cc1] | 4-Acetylamino-N-{(S)-[1-(1-cyano-cyclopropyl)-1H-[1,2,3]triazol-4-yl]-cyclohexyl-methyl}-benzamide | E 0.77 407.21 |
| 86 | 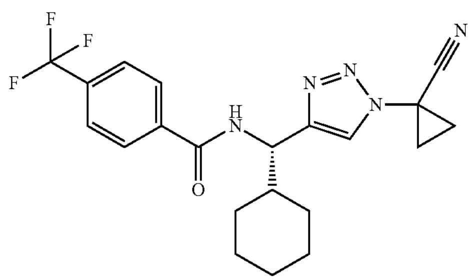 [SMILES: N#CC1(n2cc([C@@H](NC(=O)c3ccc(C(F)(F)F)cc3)C3CCCCC3)nn2)CC1] | N-{(S)-[1-(1-Cyano-cyclopropyl)-1H-[1,2,3]triazol-4-yl]-cyclohexyl-methyl}-4-trifluoromethyl-benzamide | E 1.12 418.2 |
| 87 | 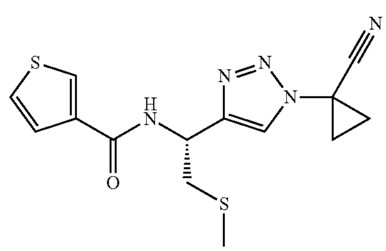 [SMILES: CSC[C@H](NC(=O)c1ccsc1)c1cn(C2(C#N)CC2)nn1] | Thiophene-3-carboxylic acid {(R)-1-[1-(1-cyano-cyclopropyl)-1H-[1,2,3]triazol-4-yl]-2-methylsulfanyl-ethyl}-amide | F 1.33 334.2 |
| 88 | 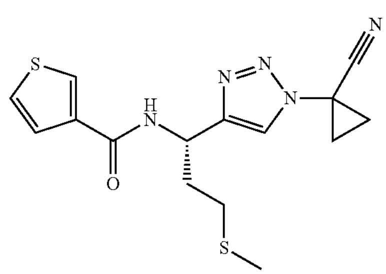 [SMILES: CSCC[C@H](NC(=O)c1ccsc1)c1cn(C2(C#N)CC2)nn1] | Thiophene-3-carboxylic acid {(S)-1-[1-(1-cyano-cyclopropyl)-1H-[1,2,3]triazol-4-yl]-3-methylsulfanyl-propyl}-amide | F 1.36 348.3 |
| 89 | 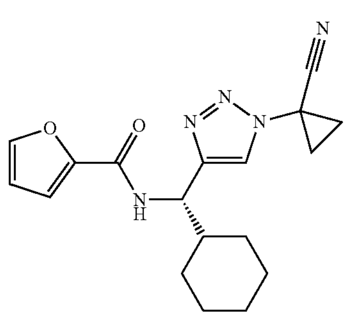 [SMILES: N#CC1(n2cc([C@@H](NC(=O)c3ccco3)C3CCCCC3)nn2)CC1] | Furan-2-carboxylic acid {(S)-[1-(1-cyano-cyclopropyl)-1H-[1,2,3]triazol-4-yl]-cyclohexyl-methyl}-amide | F 1.62 340.1 |

-continued

| Compound | Structure | Name | LCMS Method, RT (min), [M + H]⁺ |
|---|---|---|---|
| 90 | 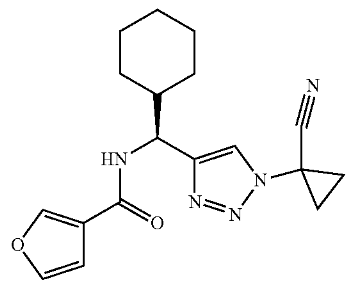 [SMILES: N#CC1(n2cc([C@@H](NC(=O)c3ccoc3)C3CCCCC3)nn2)CC1] | Furan-3-carboxylic acid {(S)-[1-(1-cyano-cyclopropyl)-1H-[1,2,3]triazol-4-yl]-cyclohexyl-methyl}-amide | E 0.83 340.19 |
| 91 | 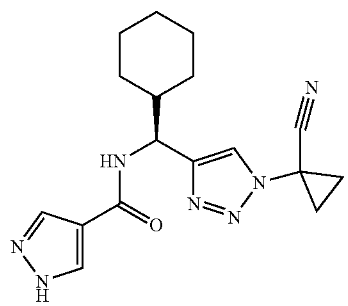 [SMILES: N#CC1(n2cc([C@@H](NC(=O)c3cn[nH]c3)C3CCCCC3)nn2)CC1] | 1H-Pyrazole-4-carboxylic acid {(S)-[1-(1-cyano-cyclopropyl)-1H-[1,2,3]triazol-4-yl]-cyclohexyl-methyl}-amide | E 0.67 340.18 |
| 92 | 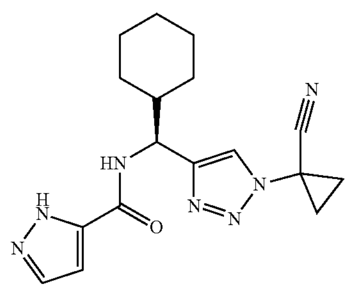 [SMILES: N#CC1(n2cc([C@@H](NC(=O)c3ccn[nH]3)C3CCCCC3)nn2)CC1] | 2H-Pyrazole-3-carboxylic acid {(S)-[1-(1-cyano-cyclopropyl)-1H-[1,2,3]triazol-4-yl]-cyclohexyl-methyl}-amide | E 0.72 340.18 |
| 93 | 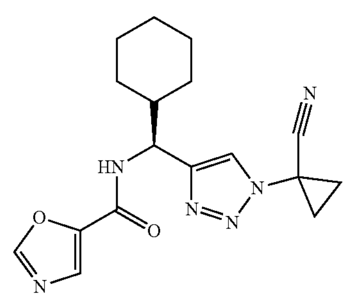 [SMILES: N#CC1(n2cc([C@@H](NC(=O)c3cnco3)C3CCCCC3)nn2)CC1] | Oxazole-5-carboxylic acid {(S)-[1-(1-cyano-cyclopropyl)-1H-[1,2,3]triazol-4-yl]-cyclohexyl-methyl}-amide | E 0.73 341.15 |
| 94 | 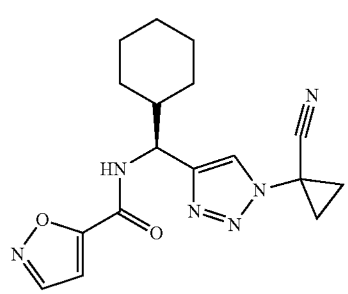 [SMILES: N#CC1(n2cc([C@@H](NC(=O)c3ccno3)C3CCCCC3)nn2)CC1] | Isoxazole-5-carboxylic acid {(S)-[1-(1-cyano-cyclopropyl)-1H-[1,2,3]triazol-4-yl]-cyclohexyl-methyl}-amide | E 0.8 341.17 |

| Compound | Structure | Name | LCMS Method, RT (min), [M + H]⁺ |
|---|---|---|---|
| 95 | 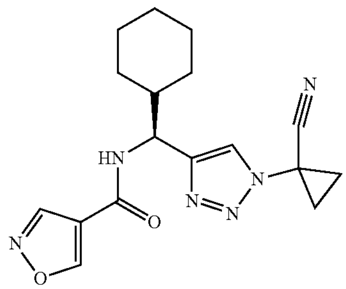 [SMILES: N#CC1(n2cc([C@@H](NC(=O)c3cnoc3)C3CCCCC3)nn2)CC1] | Isoxazole-4-carboxylic acid {(S)-[1-(1-cyano-cyclopropyl)-1H-[1,2,3]triazol-4-yl]-cyclohexyl-methyl}-amide | E 0.79 341.16 |
| 96 | 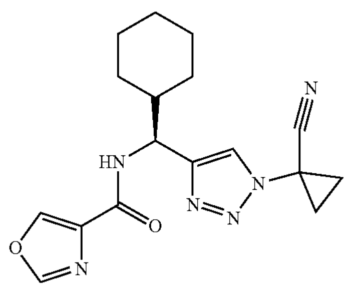 [SMILES: N#CC1(n2cc([C@@H](NC(=O)c3cocn3)C3CCCCC3)nn2)CC1] | Oxazole-4-carboxylic acid {(S)-[1-(1-cyano-cyclopropyl)-1H-[1,2,3]triazol-4-yl]-cyclohexyl-methyl}-amide | E 0.78 341.17 |
| 97 | 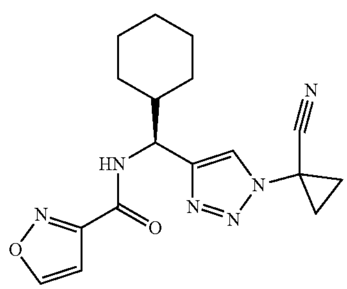 [SMILES: N#CC1(n2cc([C@@H](NC(=O)c3ccon3)C3CCCCC3)nn2)CC1] | Isoxazole-3-carboxylic acid {(S)-[1-(1-cyano-cyclopropyl)-1H-[1,2,3]triazol-4-yl]-cyclohexyl-methyl}-amide | E 0.84 341.19 |
| 98 | 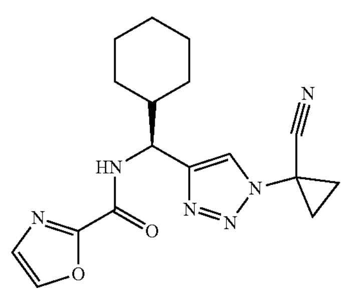 [SMILES: N#CC1(n2cc([C@@H](NC(=O)c3ncco3)C3CCCCC3)nn2)CC1] | Oxazole-2-carboxylic acid {(S)-[1-(1-cyano-cyclopropyl)-1H-[1,2,3]triazol-4-yl]-cyclohexyl-methyl}-amide | E 0.8 341.19 |
| 99 | 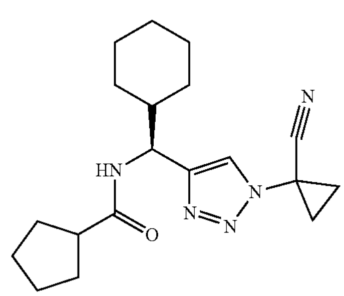 [SMILES: N#CC1(n2cc([C@@H](NC(=O)C3CCCC3)C3CCCCC3)nn2)CC1] | Cyclopentanecarboxylic acid {(S)-[1-(1-cyano-cyclopropyl)-1H-[1,2,3]triazol-4-yl]-cyclohexyl-methyl}-amide | E 0.92 342.26 |

-continued

| Compound | Structure | Name | LCMS Method, RT (min), [M + H]+ |
|---|---|---|---|
| 100 | 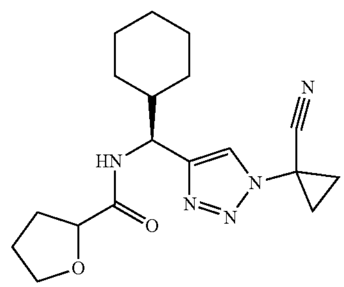 [SMILES: N#CC1(n2cc([C@@H](NC(=O)C3CCCO3)C3CCCCC3)nn2)CC1] | Tetrahydro-furan-2-carboxylic acid {(S)-[1-(1-cyano-cyclopropyl)-1H-[1,2,3]triazol-4-yl]-cyclohexyl-methyl}-amide | E 0.82 344.21 |
| 101 | 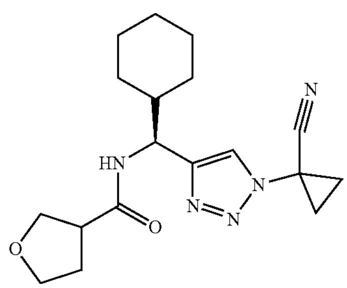 [SMILES: N#CC1(n2cc([C@@H](NC(=O)C3CCOC3)C3CCCCC3)nn2)CC1] | Tetrahydro-furan-3-carboxylic acid {(S)-[1-(1-cyano-cyclopropyl)-1H-[1,2,3]triazol-4-yl]-cyclohexyl-methyl}-amide | E 0.73 344.19 |
| 102 | 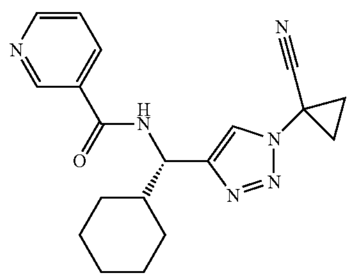 [SMILES: N#CC1(n2cc([C@@H](NC(=O)c3cccnc3)C3CCCCC3)nn2)CC1] | N-{(S)-[1-(1-Cyano-cyclopropyl)-1H-[1,2,3]triazol-4-yl]-cyclohexyl-methyl}-nicotinamide | E 0.72 351.72 |
| 103 | 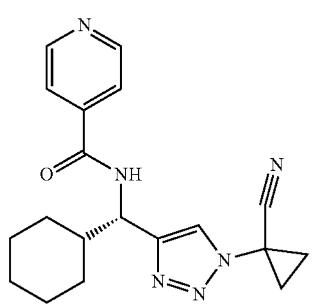 [SMILES: N#CC1(n2cc([C@@H](NC(=O)c3ccncc3)C3CCCCC3)nn2)CC1] | N-{(S)-[1-(1-Cyano-cyclopropyl)-1H-[1,2,3]triazol-4-yl]-cyclohexyl-methyl}-isonicotinamide | E 0.7 351.94 |
| 104 | 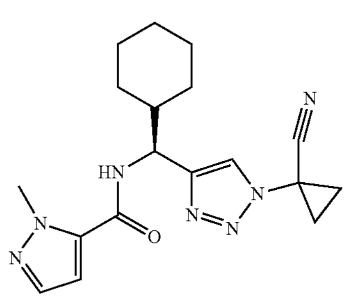 [SMILES: Cn1nccc1C(=O)N[C@H](c1cn(C2(C#N)CC2)nn1)C1CCCCC1] | 2-Methyl-2H-pyrazole-3-carboxylic acid {(S)-[1-(1-cyano-cyclopropyl)-1H-[1,2,3]triazol-4-yl]-cyclohexyl-methyl}-amide | E 0.81 354.26 |

-continued

| Compound | Structure | Name | LCMS Method, RT (min), [M + H]+ |
|---|---|---|---|
| 105 | 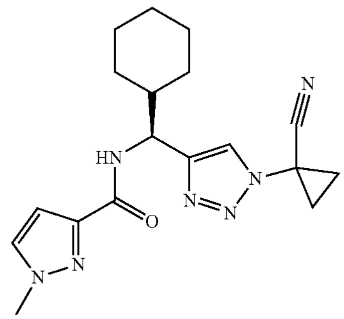 [SMILES: Cn1ccc(C(=O)N[C@H](c2cn(C3(C#N)CC3)nn2)C2CCCCC2)n1] | 1-Methyl-1H-pyrazole-3-carboxylic acid {(S)-[1-(1-cyano-cyclopropyl)-1H-[1,2,3]triazol-4-yl]-cyclohexyl-methyl}-amide | E 0.8 354.21 |
| 106 | 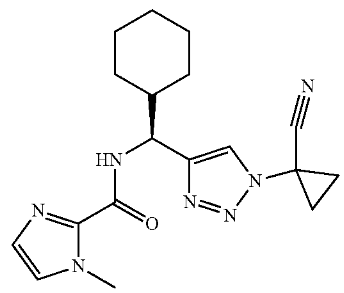 [SMILES: Cn1ccnc1C(=O)N[C@H](c1cn(C2(C#N)CC2)nn1)C1CCCCC1] | 1-Methyl-1H-imidazole-2-carboxylic acid {(S)-[1-(1-cyano-cyclopropyl)-1H-[1,2,3]triazol-4-yl]-cyclohexyl-methyl}-amide | E 0.81 354.96 |
| 107 | 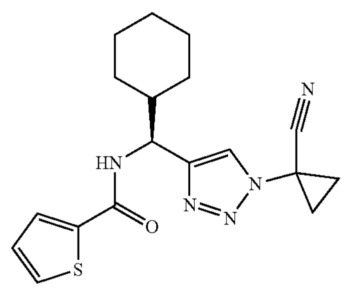 [SMILES: N#CC1(n2cc([C@@H](NC(=O)c3cccs3)C3CCCCC3)nn2)CC1] | Thiophene-2-carboxylic acid {(S)-[1-(1-cyano-cyclopropyl)-1H-[1,2,3]triazol-4-yl]-cyclohexyl-methyl}-amide | E 0.9 356.16 |
| 108 | 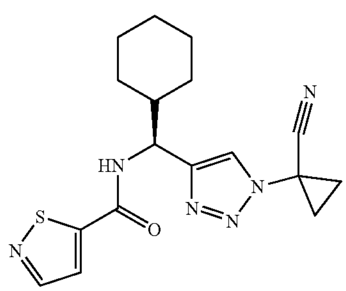 [SMILES: N#CC1(n2cc([C@@H](NC(=O)c3ccns3)C3CCCCC3)nn2)CC1] | Isothiazole-5-carboxylic acid {(S)-[1-(1-cyano-cyclopropyl)-1H-[1,2,3]triazol-4-yl]-cyclohexyl-methyl}-amide | E 0.85 357.13 |
| 109 | 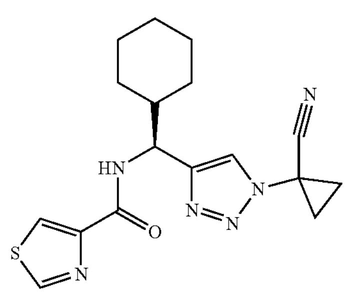 [SMILES: N#CC1(n2cc([C@@H](NC(=O)c3cscn3)C3CCCCC3)nn2)CC1] | Thiazole-4-carboxylic acid {(S)-[1-(1-cyano-cyclopropyl)-1H-[1,2,3]triazol-4-yl]-cyclohexyl-methyl}-amide | E 0.84 357.16 |

-continued

| Compound | Structure | Name | LCMS Method, RT (min), [M + H]+ |
|---|---|---|---|
| 110 | 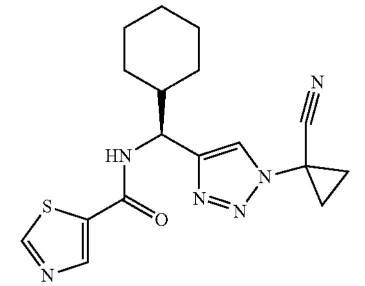 [SMILES: N#CC1(n2cc([C@@H](NC(=O)c3cncs3)C3CCCCC3)nn2)CC1] | Thiazole-5-carboxylic acid {(S)-[1-(1-cyano-cyclopropyl)-1H-[1,2,3]triazol-4-yl]-cyclohexyl-methyl}-amide | E 0.78 357.17 |
| 111 | 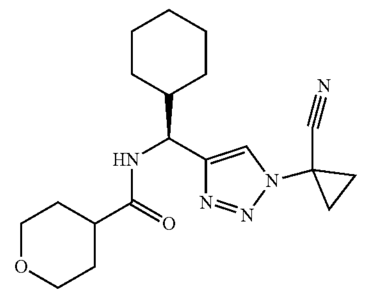 [SMILES: N#CC1(n2cc([C@@H](NC(=O)C3CCOCC3)C3CCCCC3)nn2)CC1] | Tetrahydro-pyran-4-carboxylic acid {(S)-[1-(1-cyano-cyclopropyl)-1H-[1,2,3]triazol-4-yl]-cyclohexyl-methyl}-amide | E 0.75 358.21 |
| 112 | 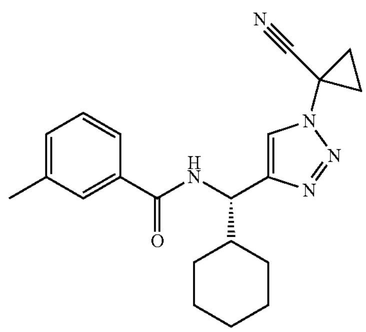 [SMILES: Cc1cccc(C(=O)N[C@H](c2cn(C3(C#N)CC3)nn2)C2CCCCC2)c1] | N-{(S)-[1-(1-Cyano-cyclopropyl)-1H-[1,2,3]triazol-4-yl]-cyclohexyl-methyl}-3-methyl-benzamide | E 0.98 364.26 |
| 113 | 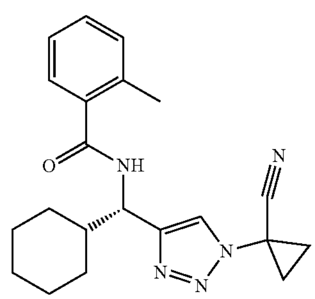 [SMILES: Cc1ccccc1C(=O)N[C@H](c1cn(C2(C#N)CC2)nn1)C1CCCCC1] | N-{(S)-[1-(1-Cyano-cyclopropyl)-1H-[1,2,3]triazol-4-yl]-cyclohexyl-methyl}-2-methyl-benzamide | E 0.94 364.07 |
| 114 | 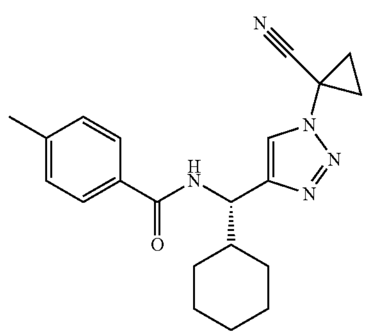 [SMILES: Cc1ccc(C(=O)N[C@H](c2cn(C3(C#N)CC3)nn2)C2CCCCC2)cc1] | N-{(S)-[1-(1-Cyano-cyclopropyl)-1H-[1,2,3]triazol-4-yl]-cyclohexyl-methyl}-4-methyl-benzamide | E 0.98 364.24 |

-continued

| Compound | Structure | Name | LCMS Method, RT (min), [M + H]+ |
|---|---|---|---|
| 115 | 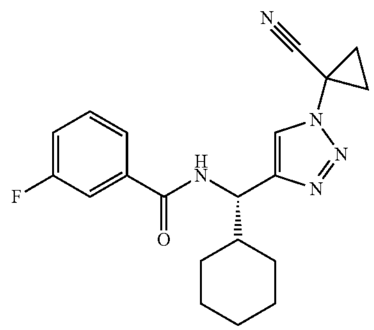 [SMILES: N#CC1(n2cc([C@@H](NC(=O)c3cccc(F)c3)C3CCCCC3)nn2)CC1] | N-{(S)-[1-(1-Cyano-cyclopropyl)-1H-[1,2,3]triazol-4-yl]-cyclohexyl-methyl}-3-fluoro-benzamide | E 0.96 368.93 |
| 116 | 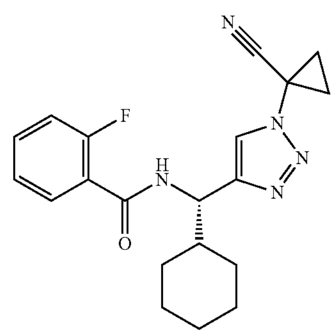 [SMILES: N#CC1(n2cc([C@@H](NC(=O)c3ccccc3F)C3CCCCC3)nn2)CC1] | N-{(S)-[1-(1-Cyano-cyclopropyl)-1H-[1,2,3]triazol-4-yl]-cyclohexyl-methyl}-2-fluoro-benzamide | E 0.95 368.19 |
| 117 | 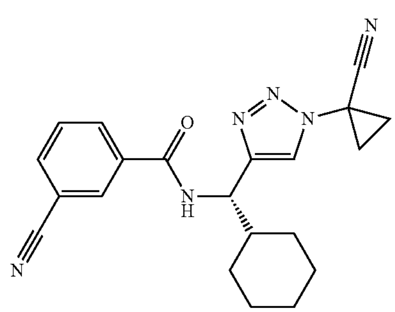 [SMILES: N#Cc1cccc(C(=O)N[C@H](c2cn(C3(C#N)CC3)nn2)C2CCCCC2)c1] | 3-Cyano-N-{(S)-[1-(1-cyano-cyclopropyl)-1H-[1,2,3]triazol-4-yl]-cyclohexyl-methyl}-benzamide | E 0.91 375.18 |
| 118 | 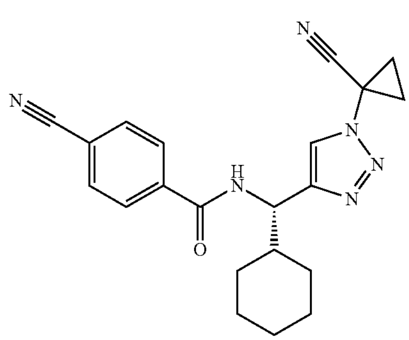 [SMILES: N#Cc1ccc(C(=O)N[C@H](c2cn(C3(C#N)CC3)nn2)C2CCCCC2)cc1] | 4-Cyano-N-{(S)-[1-(1-cyano-cyclopropyl)-1H-[1,2,3]triazol-4-yl]-cyclohexyl-methyl}-benzamide | E 0.9 375.19 |

| Compound | Structure | Name | LCMS Method, RT (min), [M + H]+ |
|---|---|---|---|
| 119 | 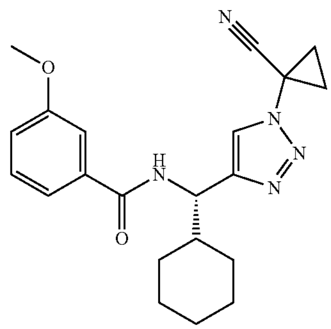 [SMILES: COc1cccc(C(=O)N[C@H](c2cn(C3(C#N)CC3)nn2)C2CCCCC2)c1] | N-{(S)-[1-(1-Cyano-cyclopropyl)-1H-[1,2,3]triazol-4-yl]-cyclohexyl-methyl}-3-methoxy-benzamide | E 0.94 380.21 |
| 120 | 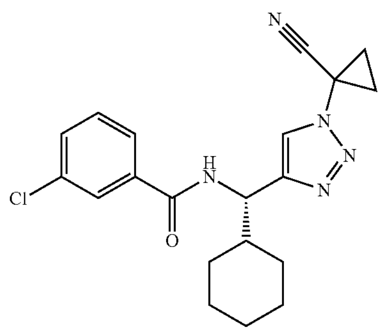 [SMILES: N#CC1(n2cc([C@@H](NC(=O)c3cccc(Cl)c3)C3CCCCC3)nn2)CC1] | 3-Chloro-N-{(S)-[1-(1-cyano-cyclopropyl)-1H-[1,2,3]triazol-4-yl]-cyclohexyl-methyl}-benzamide | E 1.02 384.18 |
| 121 | 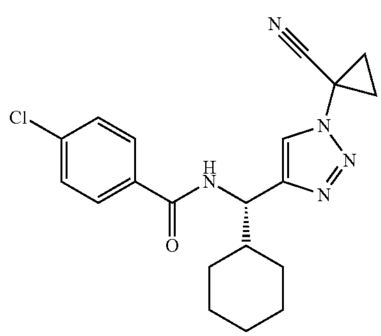 [SMILES: N#CC1(n2cc([C@@H](NC(=O)c3ccc(Cl)cc3)C3CCCCC3)nn2)CC1] | 4-Chloro-N-{(S)-[1-(1-cyano-cyclopropyl)-1H-[1,2,3]triazol-4-yl]-cyclohexyl-methyl}-benzamide | E 1.01 384.13 |
| 122 | 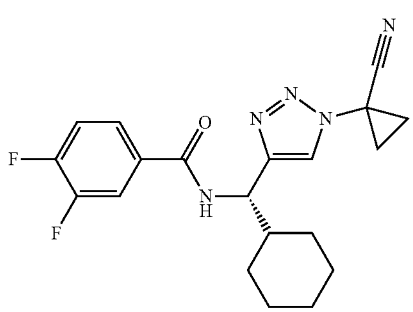 [SMILES: N#CC1(n2cc([C@@H](NC(=O)c3ccc(F)c(F)c3)C3CCCCC3)nn2)CC1] | N-{(S)-[1-(1-Cyano-cyclopropyl)-1H-[1,2,3]triazol-4-yl]-cyclohexyl-methyl}-3,4-difluoro-benzamide | F 1.47 386.2 |

| Compound | Structure | Name | LCMS Method, RT (min), [M + H]+ |
|---|---|---|---|
| 123 | 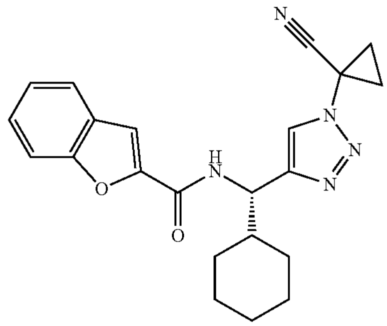 [SMILES: N#CC1(n2cc([C@@H](NC(=O)c3cc4ccccc4o3)C3CCCCC3)nn2)CC1] | Benzofuran-2-carboxylic acid {(S)-[1-(1-cyano-cyclopropyl)-1H-[1,2,3]triazol-4-yl]-cyclohexyl-methyl}-amide | E 1.02 390.2 |
| 124 | 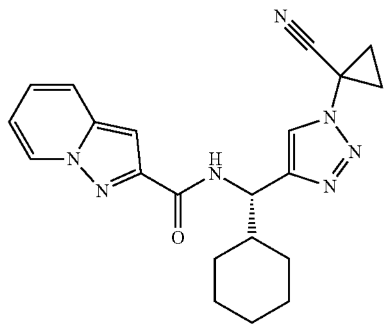 [SMILES: N#CC1(n2cc([C@@H](NC(=O)c3cc4ccccn4n3)C3CCCCC3)nn2)CC1] | Pyrazolo[1,5-a]pyridine-2-carboxylic acid {(S)-[1-(1-cyano-cyclopropyl)-1H-[1,2,3]triazol-4-yl]-cyclohexyl-methyl}-amide | E 0.92 390.22 |
| 125 | 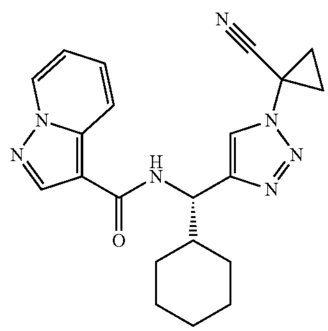 [SMILES: N#CC1(n2cc([C@@H](NC(=O)c3cnn4ccccc34)C3CCCCC3)nn2)CC1] | Pyrazolo[1,5-a]pyridine-3-carboxylic acid {(S)-[1-(1-cyano-cyclopropyl)-1H-[1,2,3]triazol-4-yl]-cyclohexyl-methyl}-amide | E 0.84 390.2 |
| 126 | 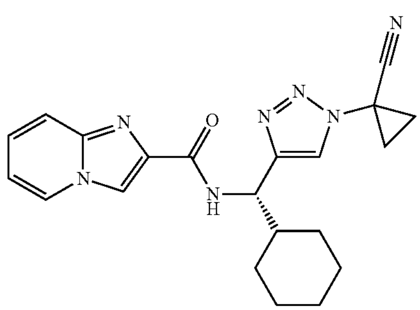 [SMILES: N#CC1(n2cc([C@@H](NC(=O)c3cn4ccccc4n3)C3CCCCC3)nn2)CC1] | Imidazo[1,2-a]pyridine-2-carboxylic acid {(S)-[1-(1-cyano-cyclopropyl)-1H-[1,2,3]triazol-4-yl]-cyclohexyl-methyl}-amide | F 1.47 390.2 |
| 127 | 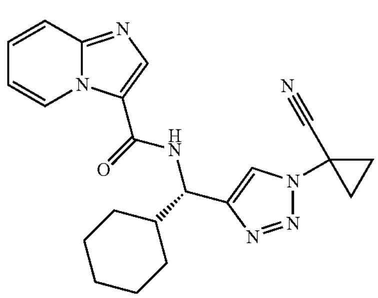 [SMILES: N#CC1(n2cc([C@@H](NC(=O)c3cnc4ccccn34)C3CCCCC3)nn2)CC1] | Imidazo[1,2-a]pyridine-3-carboxylic acid {(S)-[1-(1-cyano-cyclopropyl)-1H-[1,2,3]triazol-4-yl]-cyclohexyl-methyl}-amide | E 0.68 390.01 |

-continued

| Compound | Structure | Name | LCMS Method, RT (min), [M + H]+ |
|---|---|---|---|
| 128 | 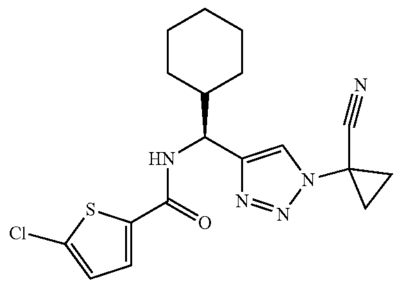 [SMILES: N#CC1(n2cc([C@@H](NC(=O)c3ccc(Cl)s3)C3CCCCC3)nn2)CC1] | 5-Chloro-thiophene-2-carboxylic acid {(S)-[1-(1-cyano-cyclopropyl)-1H-[1,2,3]triazol-4-yl]-cyclohexyl-methyl}-amide | E 1.03 390.11 |
| 129 | 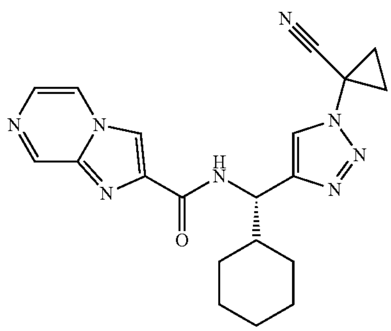 [SMILES: N#CC1(n2cc([C@@H](NC(=O)c3cn4ccncc4n3)C3CCCCC3)nn2)CC1] | Imidazo[1,2-a]pyrazine-2-carboxylic acid {(S)-[1-(1-cyano-cyclopropyl)-1H-[1,2,3]triazol-4-yl]-cyclohexyl-methyl}-amide | E 0.76 391.56 |
| 130 | 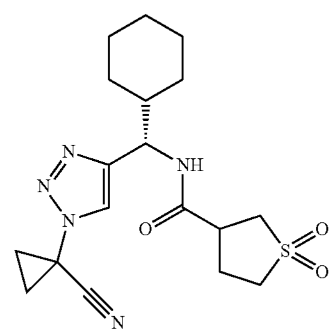 [SMILES: N#CC1(n2cc([C@@H](NC(=O)C3CCS(=O)(=O)C3)C3CCCCC3)nn2)CC1] | 1,1-Dioxo-tetrahydro-1lambda*6*-thiophene-3-carboxylic acid {(S)-[1-(1-cyano-cyclopropyl)-1H-[1,2,3]triazol-4-yl]-cyclohexyl-methyl}-amide | E 0.71 392.16 |
| 131 | 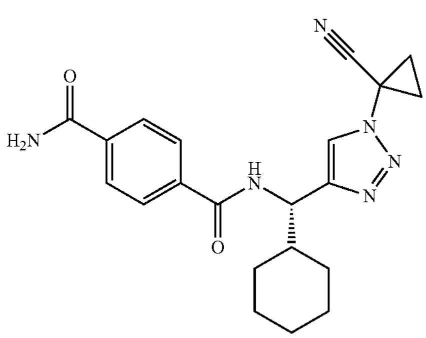 [SMILES: N#CC1(n2cc([C@@H](NC(=O)c3ccc(C(N)=O)cc3)C3CCCCC3)nn2)CC1] | N-{(S)-[1-(1-Cyano-cyclopropyl)-1H-[1,2,3]triazol-4-yl]-cyclohexyl-methyl}-terephthalamide | E 0.71 393.18 |

| Compound | Structure | Name | LCMS Method, RT (min), [M + H]+ |
|---|---|---|---|
| 132 | 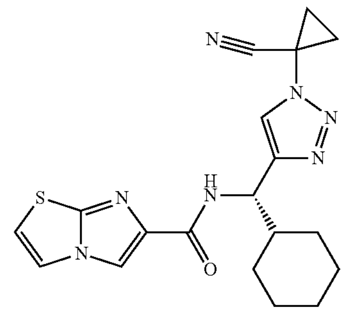 [SMILES: N#CC1(n2cc([C@@H](NC(=O)c3cn4ccsc4n3)C3CCCCC3)nn2)CC1] | Imidazo[2,1-b]thiazole-6-carboxylic acid {(S)-[1-(1-cyano-cyclopropyl)-1H-[1,2,3]triazol-4-yl]-cyclohexyl-methyl}-amide | E 0.84 396.11 |
| 133 | 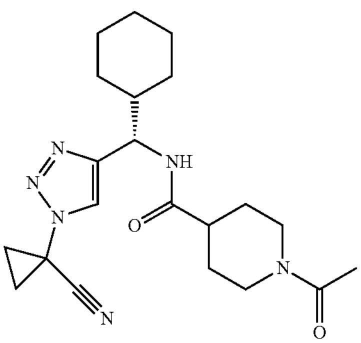 [SMILES: CC(=O)N1CCC(C(=O)N[C@H](c2cn(C3(C#N)CC3)nn2)C2CCCCC2)CC1] | 1-Acetyl-piperidine-4-carboxylic acid {(S)-[1-(1-cyano-cyclopropyl)-1H-[1,2,3]triazol-4-yl]-cyclohexyl-methyl}-amide | E 0.7 399.25 |
| 134 | 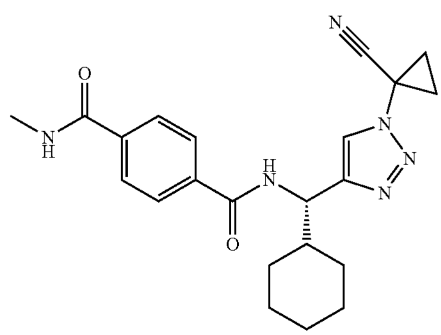 [SMILES: CNC(=O)c1ccc(C(=O)N[C@H](c2cn(C3(C#N)CC3)nn2)C2CCCCC2)cc1] | N-{(S)-[1-(1-Cyano-cyclopropyl)-1H-[1,2,3]triazol-4-yl]-cyclohexyl-methyl}-N'-methyl-terephthalamide | E 0.75 407.21 |
| 135 | 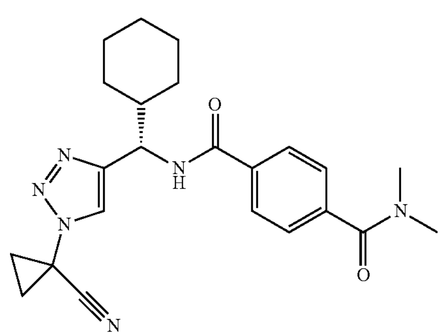 [SMILES: CN(C)C(=O)c1ccc(C(=O)N[C@H](c2cn(C3(C#N)CC3)nn2)C2CCCCC2)cc1] | N-{(S)-[1-(1-Cyano-cyclopropyl)-1H-[1,2,3]triazol-4-yl]-cyclohexyl-methyl}-N',N'-dimethyl-terephthalamide | E 0.8 421.24 |

-continued

| Compound | Structure | Name | LCMS Method, RT (min), [M + H]+ |
|---|---|---|---|
| 136 | 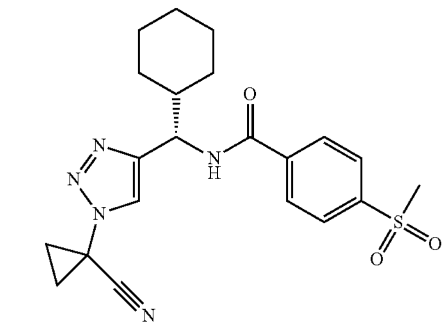 [SMILES: CS(=O)(=O)c1ccc(C(=O)N[C@H](c2cn(C3(C#N)CC3)nn2)C2CCCCC2)cc1] | N-{(S)-[1-(1-Cyano-cyclopropyl)-1H-[1,2,3]triazol-4-yl]-cyclohexyl-methyl}-4-methanesulfonyl-benzamide | E 0.81 428.17 |
| 137 | 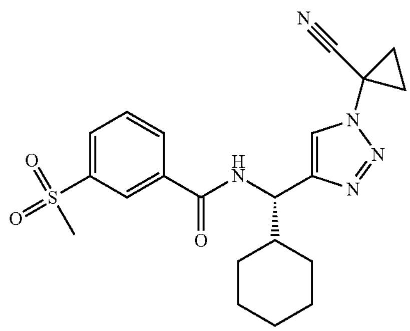 [SMILES: CS(=O)(=O)c1cccc(C(=O)N[C@H](c2cn(C3(C#N)CC3)nn2)C2CCCCC2)c1] | N-{(S)-[1-(1-Cyano-cyclopropyl)-1H-[1,2,3]triazol-4-yl]-cyclohexyl-methyl}-3-methanesulfonyl-benzamide | E 0.83 428.19 |
| 138 | 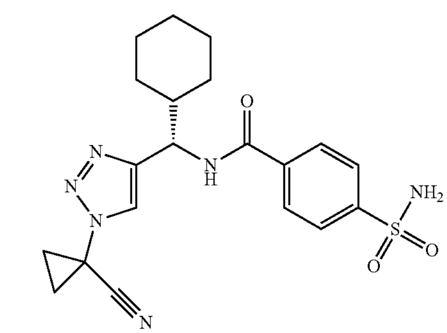 [SMILES: N#CC1(n2cc([C@@H](NC(=O)c3ccc(S(N)(=O)=O)cc3)C3CCCCC3)nn2)CC1] | N-{(S)-[1-(1-Cyano-cyclopropyl)-1H-[1,2,3]triazol-4-yl]-cyclohexyl-methyl}-4-sulfamoyl-benzamide | E 0.75 429.18 |
| 139 | 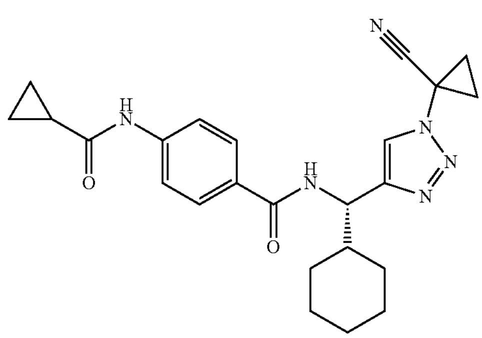 [SMILES: N#CC1(n2cc([C@@H](NC(=O)c3ccc(NC(=O)C4CC4)cc3)C3CCCCC3)nn2)CC1] | N-{(S)-[1-(1-Cyano-cyclopropyl)-1H-[1,2,3]triazol-4-yl]-cyclohexyl-methyl}-4-(cyclopropanecarbonyl-amino)-benzamide | E 0.87 433.23 |

| Compound | Structure | Name | LCMS Method, RT (min), [M + H]+ |
|---|---|---|---|
| 140 | 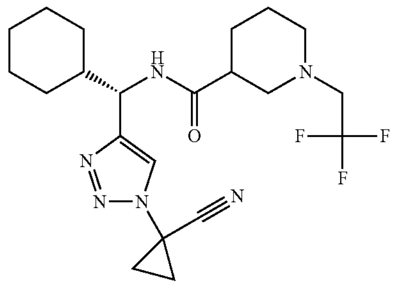 [SMILES: N#CC1(n2cc([C@@H](NC(=O)C3CCCN(CC(F)(F)F)C3)C3CCCCC3)nn2)CC1] | 1-(2,2,2-Trifluoro-ethyl)-piperidine-3-carboxylic acid {(S)-[1-(1-cyano-cyclopropyl)-1H-[1,2,3]triazol-4-yl]-cyclohexyl-methyl}-amide | E 0.96 439.59 |
| 141 | 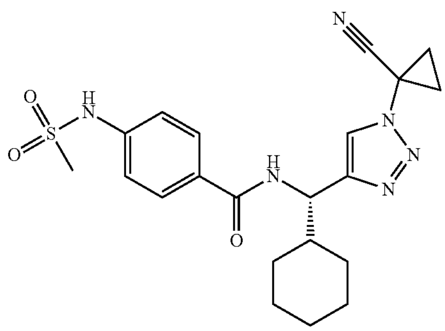 [SMILES: CS(=O)(=O)Nc1ccc(C(=O)N[C@H](c2cn(C3(C#N)CC3)nn2)C2CCCCC2)cc1] | N-[(S)-[1-(1-Cyano-cyclopropyl)-1H-[1,2,3]triazol-4-yl]-cyclohexyl-methyl]-4-methanesulfonylamino-benzamide | E 0.8 443.21 |
| 142 | 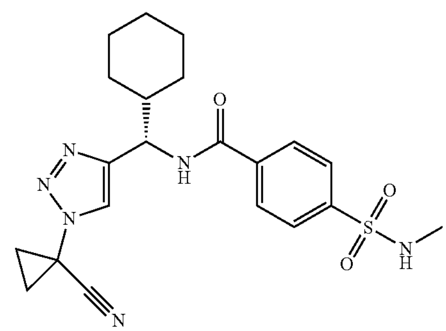 [SMILES: CNS(=O)(=O)c1ccc(C(=O)N[C@H](c2cn(C3(C#N)CC3)nn2)C2CCCCC2)cc1] | N-{(S)-[1-(1-Cyano-cyclopropyl)-1H-[1,2,3]triazol-4-yl]-cyclohexyl-methyl}-4-methylsulfamoyl-benzamide | E 0.83 443.18 |
| 143 | 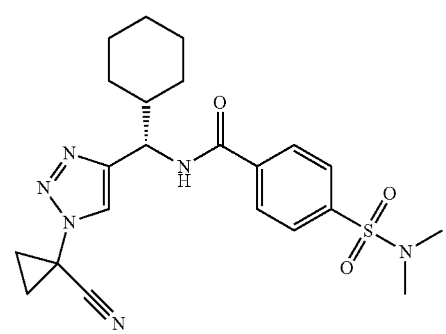 [SMILES: CN(C)S(=O)(=O)c1ccc(C(=O)N[C@H](c2cn(C3(C#N)CC3)nn2)C2CCCCC2)cc1] | N-{(S)-[1-(1-Cyano-cyclopropyl)-1H-[1,2,3]triazol-4-yl]-cyclohexyl-methyl}-4-dimethylsulfamoyl-benzamide | E 0.9 457.22 |

-continued

| Compound | Structure | Name | LCMS Method, RT (min), [M + H]+ |
|---|---|---|---|
| 144 | 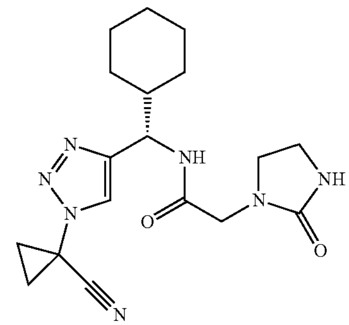 [SMILES: N#CC1(n2cc([C@@H](NC(=O)CN3CCNC3=O)C3CCCCC3)nn2)CC1] | N-{(S)-[1-(1-Cyano-cyclopropyl)-1H-[1,2,3]triazol-4-yl]-cyclohexyl-methyl}-2-(2-oxo-imidazolidin-1-yl)-acetamide | E 0.64 372.21 |
| 145 | 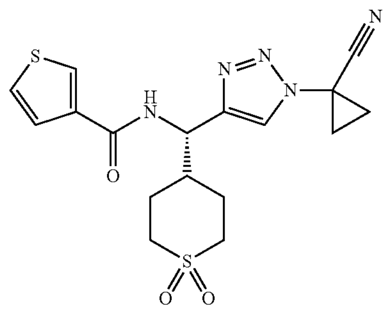 [SMILES: N#CC1(n2cc([C@@H](NC(=O)c3ccsc3)C3CCS(=O)(=O)CC3)nn2)CC1] | Thiophene-3-carboxylic acid [(S)-[1-(1-cyano-cyclopropyl)-1H-[1,2,3]triazol-4-yl]-(1,1-dioxo-hexahydro-1λ6-thiopyran-4-yl)-methyl]-amide | A 1.19 406.2 |
| 146 | 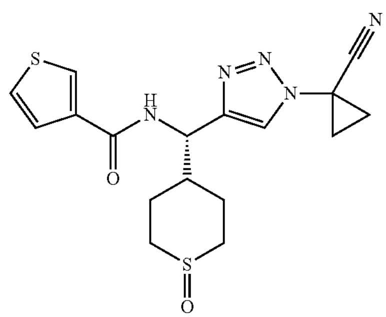 [SMILES: N#CC1(n2cc([C@@H](NC(=O)c3ccsc3)C3CCS(=O)CC3)nn2)CC1] | Thiophene-3-carboxylic acid [(S)-[1-(1-cyano-cyclopropyl)-1H-[1,2,3]triazol-4-yl]-(1-oxo-hexahydro-1λ4-thiopyran-4-yl)-methyl]-amide | B 4.01 390.2 |
| 147 | 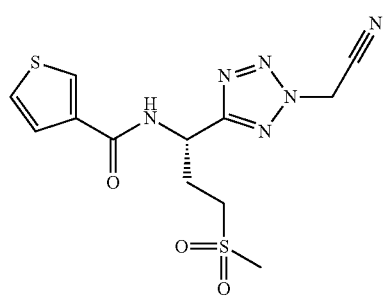 [SMILES: CS(=O)(=O)CC[C@H](NC(=O)c1ccsc1)c1nnn(CC#N)n1] | Thiophene-3-carboxylic acid [(S)-1-(2-cyanomethyl-2H-tetrazol-5-yl)-3-methanesulfonyl-propyl]-amide | C 1.12 355.2 |
| 148 | 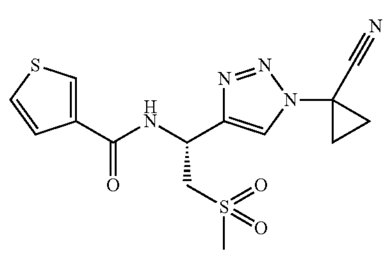 [SMILES: CS(=O)(=O)C[C@H](NC(=O)c1ccsc1)c1cn(C2(C#N)CC2)nn1] | Thiophene-3-carboxylic acid {(R)-1-[1-(1-cyano-cyclopropyl)-1H-[1,2,3]triazol-4-yl]-2-methanesulfonyl-ethyl}-amide | F 1.14 366.3 |

| Compound | Structure | Name | LCMS Method, RT (min), [M + H]+ |
|---|---|---|---|
| 149 | 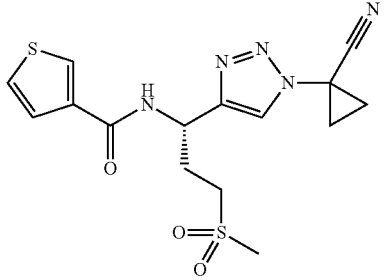 [SMILES: CS(=O)(=O)CC[C@H](NC(=O)c1ccsc1)c1cn(C2(C#N)CC2)nn1] | Thiophene-3-carboxylic acid {(S)-1-[1-(1-cyano-cyclopropyl)-1H-[1,2,3]triazol-4-yl]-3-methanesulfonyl-propyl}-amide | F 1.16 380.2 | or the pharmaceutically acceptable salts thereof.

In another aspect the invention relates to compounds—or the pharmaceutically acceptable salts—of the formula (I) as medicaments.

In another aspect the invention relates to pharmaceutical preparations, containing as active ingredient one or more compounds of the formula (I) or the pharmacologically acceptable salts thereof, optionally in combination with conventional excipients and/or carriers.

In another aspect the invention relates to the use of compounds of the formula (I) for preparing a pharmaceutical composition for the treatment of autoimmune diseases.

In another aspect the invention relates to the a method of treating autoimmune diseases by administering a therapeutically effective amount of a compound of the formula (I).

In another aspect the invention relates to a pharmaceutical preparation comprising a compound of the formula (I), while the formula (I) compounds are optionally also in the form of the tautomers, the racemates, the enantiomers, the diastereomers, the mixtures thereof, or as pharmaceutically acceptable salts of all the above-mentioned forms.

In another aspect the invention relates to compounds of the invention which also include their isotopically-labelled forms. An isotopically-labelled form of an active agent of a combination of the present invention is identical to said active agent but for the fact that one or more atoms of said active agent have been replaced by an atom or atoms having an atomic mass or mass number different from the atomic mass or mass number of said atom which is usually found in nature. Examples of isotopes which are readily available commercially and which can be incorporated into an active agent of a combination of the present invention in accordance with well established procedures, include isotopes of hydrogen, carbon, nitrogen, oxygen, phosphorous, fluorine and chlorine, e.g., $^2$H, $^3$H, $^{13}$C, $^{14}$C, $^{15}$N, $^{18}$O, $^{17}$O, $^{31}$P, $^{32}$P, $^{35}$S, $^{18}$F, and $^{36}$Cl, respectively.

In another aspect the invention relates to the compounds of the formula (I) which may be used in combination with other active substances which are used in the treatments of autoimmune diseases such as multiple sclerosis, rheumatoid arthritis, psoriasis, atherosclerosis, and chronic obstructive pulmonary disease. Such combinations can be administered either separately or in combination in a pharmaceutical composition.

DEFINITIONS

All terms as used herein in this specification, unless otherwise stated, shall be understood in their ordinary meaning as known in the art. Other more specific definitions are as follows:

The phrase "pharmaceutically acceptable" is employed herein to refer to those compounds, materials, compositions, and/or dosage forms which are, within the scope of sound medical judgment, suitable for use in contact with the tissues of human beings without excessive toxicity, irritation, allergic response, or other problem or complication, and commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. For example, such salts include acetates, ascorbates, benzenesulfonates, benzoates, besylates, bicarbonates, bitartrates, bromides/hydrobromides, Ca-edetates/edetates, camsylates, carbonates, chlorides/hydrochlorides, citrates, edisylates, ethane disulfonates, estolates esylates, fumarates, gluceptates, gluconates, glutamates, glycolates, glycollylarsnilates, hexylresorcinates, hydrabamines, hydroxymaleates, hydroxynaphthoates, iodides, isothionates, lactates, lactobionates, malates, maleates, mandelates, methanesulfonates, mesylates, methylbromides, methylnitrates, methylsulfates, mucates, napsylates, nitrates, oxalates, pamoates, pantothenates, phenylacetates, phosphates/diphosphates, polygalacturonates, propionates, salicylates, stearates subacetates, succinates, sulfamides, sulfates, tannates, tartrates, teoclates, toluenesulfonates, triethiodides, ammonium, benzathines, chloroprocaines, cholines, diethanolamines, ethylenediamines, meglumines and procaines. Further pharmaceutically acceptable salts can be formed with cations from metals like aluminium, calcium, lithium, magnesium, potassium, sodium, zinc and the like.

The pharmaceutically acceptable salts of the present invention can be synthesized from the parent compound which contains a basic or acidic moiety by conventional chemical methods. Generally, such salts can be prepared by reacting the free acid or base forms of these compounds with a sufficient amount of the appropriate base or acid in water or in an organic diluent like ether, ethyl acetate, ethanol, isopropanol, or acetonitrile, or a mixture thereof.

The term "$C_{1-n}$-alkyl", wherein n is an integer from 2 to n, either alone or in combination with another radical denotes an acyclic, saturated, branched or linear hydrocarbon radical with 1 to n C atoms. For example the term $C_{1-5}$-alkyl embraces the radicals H$_3$C—, H$_3$C—CH$_2$—, H$_3$C—CH$_2$—CH$_2$—, H$_3$C—CH(CH$_3$)—, H$_3$C—CH$_2$—CH$_2$—CH$_2$—, H$_3$C—CH$_2$—CH(CH$_3$)—, H$_3$C—CH(CH$_3$)—CH$_2$—, H₃C—C(CH₃)₂—, H₃C—CH₂—CH₂—CH₂—CH₂—, H₃C—CH₂—CH₂—CH(CH₃)—, H₃C—CH₂—CH(CH₃)—CH₂—, H₃C—CH(CH₃)—CH₂—CH₂—, H₃C—CH₂—C(CH₃)₂—, H₃C—C(CH₃)₂—CH₂—, H₃C—CH(CH₃)—CH(CH₃)— and H₃C—CH₂—CH(CH₂CH₃)—.

Alkoxy shall be understood to be a $C_{1-n}$-alkyl with an oxygen atom wherein the point of attachment is via the oxygen, for example methoxy: H₃CO—.

Acyl shall be understood to be a $C_{1-n}$-alkyl with an carbonyl group wherein the point of attachment is via the carbonyl, for example acetyl: H₃CC(O)—.

The term "$C_{3-n}$-cycloalkyl", wherein n is an integer 4 to n, either alone or in combination with another radical denotes a cyclic, saturated hydrocarbon radical with 3 to n C atoms. For example the term $C_{3-7}$-cycloalkyl includes cyclopropyl, cyclobutyl, cyclopentyl, cyclohexyl and cycloheptyl.

The structures of the above will be apparent to one skilled in the art, other specific examples include the deuterated form of cyclohexyl: cyclohexyl-D11

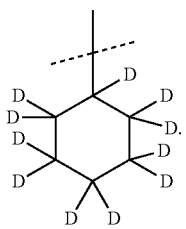

The term "aryl" as used herein, either alone or in combination with another radical, denotes a carbocyclic aromatic monocyclic group containing 6 carbon atoms which may be further fused to a second 5- or 6-membered carbocyclic group which may be aromatic, saturated or unsaturated. Aryl includes, but is not limited to, phenyl, indanyl, indenyl, naphthyl, anthracenyl, phenanthrenyl, tetrahydronaphthyl and dihydronaphthyl. The term "aryl" is intended to include all the possible hydrogenated forms.

The term "heterocyclyl" means a saturated or unsaturated mono- or polycyclic-ring systems including aromatic ring system containing one or more heteroatoms selected from N, O or $S(O)_r$ with r=0, 1 or 2 wherein none of the heteroatoms is part of the aromatic ring. The term "heterocycle" is intended to include all the possible isomeric forms. Unless otherwise stated, heterocycles include but are not limited to, for example oxiranyl, azepanyl, diazepanyl, azetidinyl, pyrrolidinyl, pyrrolinyl, thiomorpholinyl, dioxalanyl, piperazinyl, 1,3-dioxolanone, 1,3-dioxanone, 1,4-dioxanyl, piperidinonyl, tetrahydropyrimidonyl. The structures of the above will be apparent to one skilled in the art, other specific examples include morpholinyl

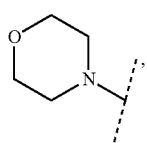

1,1-Dioxo-1λ6-thiomorpholine

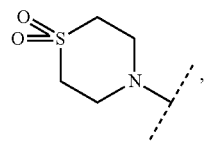

2-oxo-imidazolidinyl

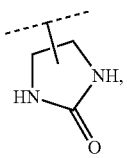

piperidinyl

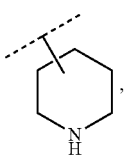

tetrahydropyranyl

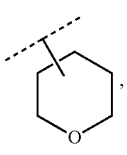

tetrahydrofuranyl

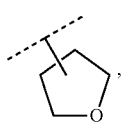

tetrahydrothiopyranyl

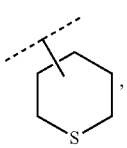

1,1-dioxo-hexahydro-1λ6-thiopyranyl

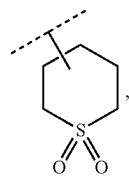

1-oxo-hexahydro-1λ4-thiopyranyl

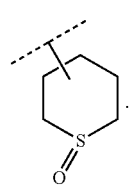

The term "heteroaryl" means a mono- or polycyclic-ring systems containing one or more heteroatoms selected from N, O or S(O)$_r$ with r=0, 1 or 2 wherein the heteroatom(s) is part of aromatic ring. The term "heteroaryl" is intended to include all the possible isomeric and hydrogenated forms. Unless otherwise stated, such heteroaryls include but are not limited to, for example: aziridinyl, thiadiazolyl, tetrazolyl, pyrrolyl, pyrimidinyl, pyrazinyl, pyridazinyl, pyranyl, quinoxalinyl, indolyl, benzimidazolyl, benzoxazolyl, benzothiazolyl, benzothienyl, quinolinyl, quinazolinyl, naphthyridinyl, indazolyl, triazolyl and purinyl. The structures of the above will be apparent to one skilled in the art, other specific examples include:

benzofuranyl

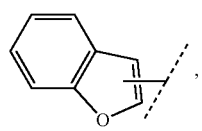

imidazo[2,1-b]thiazolyl

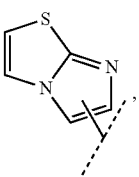

imidazo[1,2-a]pyrazinyl

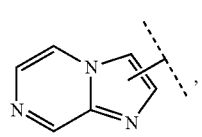

pyrazolo[1,5-a]pyridinyl

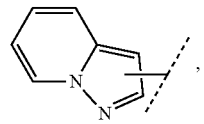

imidazo[1,2-a]pyridinyl

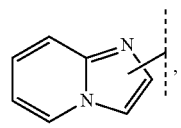

thiazolyl

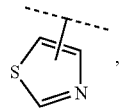

isothiazolyl

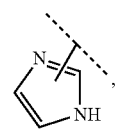

imidazolyl

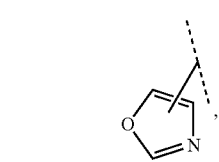

oxazolyl

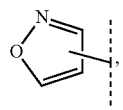

isoxazolyl

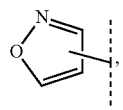

thienyl

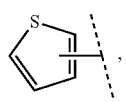

furanyl

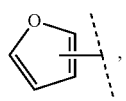

pyrazolyl

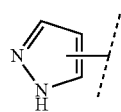

and pyridinyl

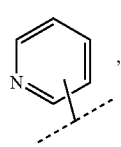

and all the possible hydrogenated forms thereof.

Halogen encompasses fluorine, chlorine, bromine and/or iodine atoms.

Each of the above alkyl, cycloalkyl, aryl, heteroalkyl, heterocyclyl or heteroaryl, or any other substituent recited in this application, shall be understood to be optionally fully or partially halogenated where possible, preferably by Cl, F or Br.

Any ring structure which has shown this bond

such bond shall be understood to be covalently attached to another moiety at the dashed line and covalently attached at any point in the ring (floating) that will replace a hydrogen atom and result in a stable bond, for example

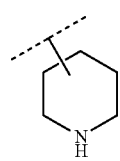

represent piperidinyl attached at the 1, 2, 3 or 4 position.

Features and advantages of the present invention will become apparent from the following detailed Examples, which illustrate the fundamentals of the invention by way of example, without restricting its scope.

General Synthetic Methods

The invention also provides processes for making compounds of Formula (I). In all methods, unless specified otherwise, $R^1$, $R^2$, $R^3$, $R^4$, $R^5$ and X in the formulas below shall have the meaning of $R^1$, $R^2$, $R^3$, $R^4$, $R^5$ and X in Formula (I) of the invention described herein above.

Optimum reaction conditions and reaction times may vary depending on the particular reactants used. Unless otherwise specified, solvents, temperatures, pressures, and other reaction conditions may be readily selected by one of ordinary skill in the art. Specific procedures are provided in the Synthetic Examples section. Typically, reaction progress may be monitored by thin layer chromatography (TLC), if desired, and intermediates and products may be purified by chromatography on silica gel and/or by recrystallization.

The examples which follow are illustrative and, as recognized by one skilled in the art, particular reagents or conditions could be modified as needed for individual compounds without undue experimentation. Starting materials and intermediates used, in the methods below, are either commercially available or easily prepared from commercially available materials by those skilled in the art.

Compounds of Formula (I) may be synthesized by the method illustrated in Scheme 1

Scheme 1

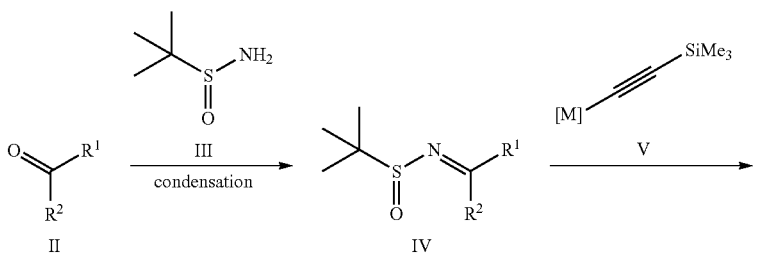

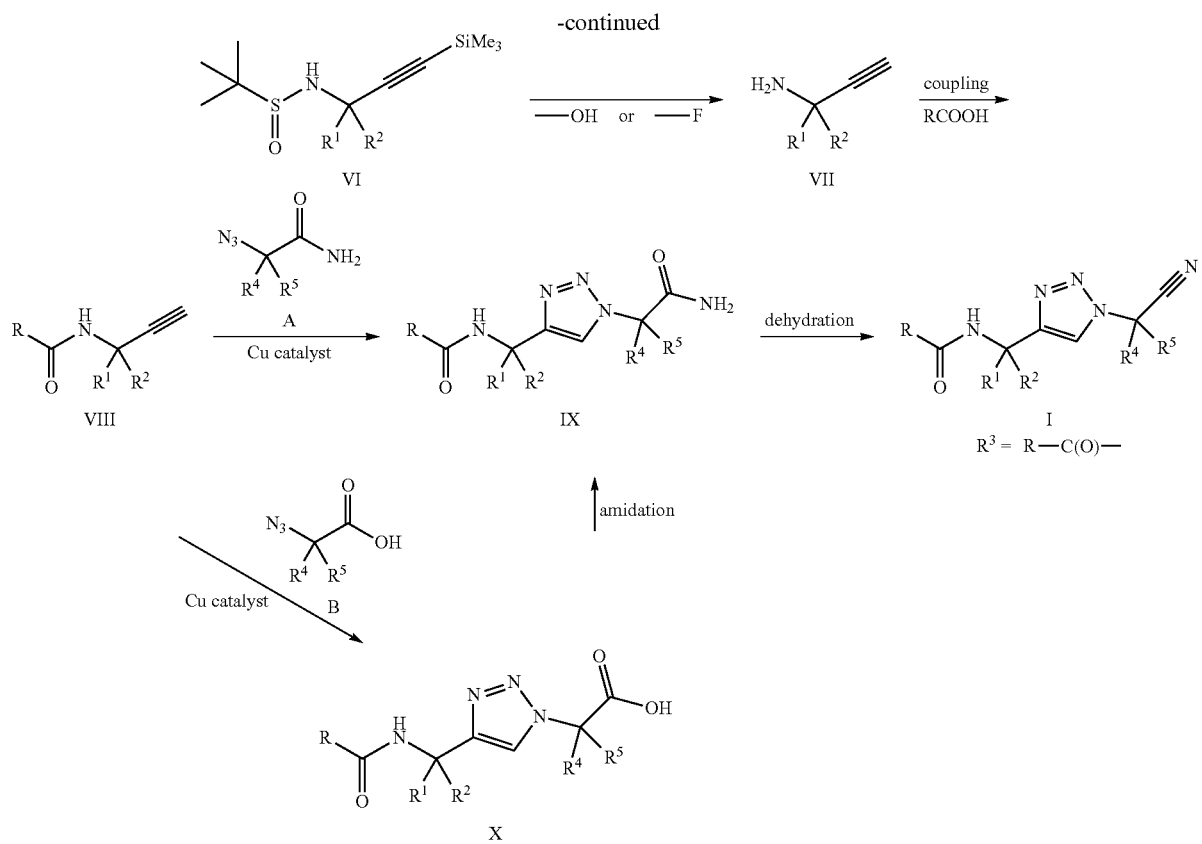

As illustrated in scheme 1, reaction of a carbonyl compound of formula II with sulfinamide of formula III, in a suitable solvent, provides an imine of formula IV. Reaction of the compound of formula IV with a trimethylsilyl alkyne of formula V, in a suitable solvent, in the presence of a suitable base, provides an alkyne of formula VI. Removal of the silyl group, under standard conditions, provides an alkyne and deprotection of the amine nitrogen provides an amino compound of the formula VII. Coupling of the free amino group in compound VII with an acid RCOOH, under standard coupling conditions, provides an amide of formula VIII. Standard peptide coupling reactions known in the art (see for example M. Bodanszky, 1984, The Practice of Peptide Synthesis, Springer-Verlag) may be employed in these syntheses. An example of suitable coupling conditions is treatment of a solution of the carboxylic acid in a suitable solvent such as DMF with EDC, HOBT, and a base such as diisopropylethylamine, followed by the desired amine. Alternatively, the acid may be converted to its corresponding acid chloride by reaction with reagents such as thionyl chloride or oxalyl chloride, the acid chloride is then reacted with a suitable amine, in a suitable solvent to provide the corresponding amide. Reaction of the alkyne of formula VIII with an azide A, in the presence of a copper catalyst, provides a triazole of formula IX. Dehydration of the triazole of formula IX under standard conditions, using standard reagents such as cyanuric chloride, provides a compound of formula (I).

Alternatively reaction of the alkyne of formula VIII with an azide B, in the presence of a copper catalyst, provides a triazole of formula X. Amidation of the acid of formula X, under standard conditions, provides a compound of formula IX which may be dehydrated to afford a compound of formula (I).

Compounds of Formula (I) may be synthesized by the method outlined in Scheme 2

Scheme 2

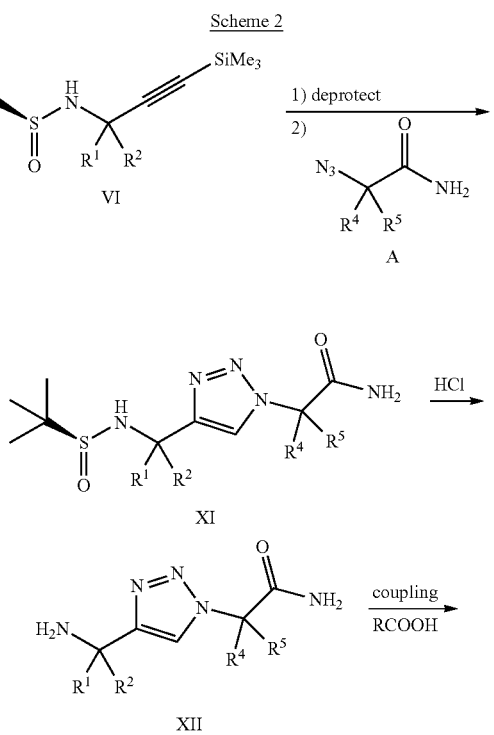

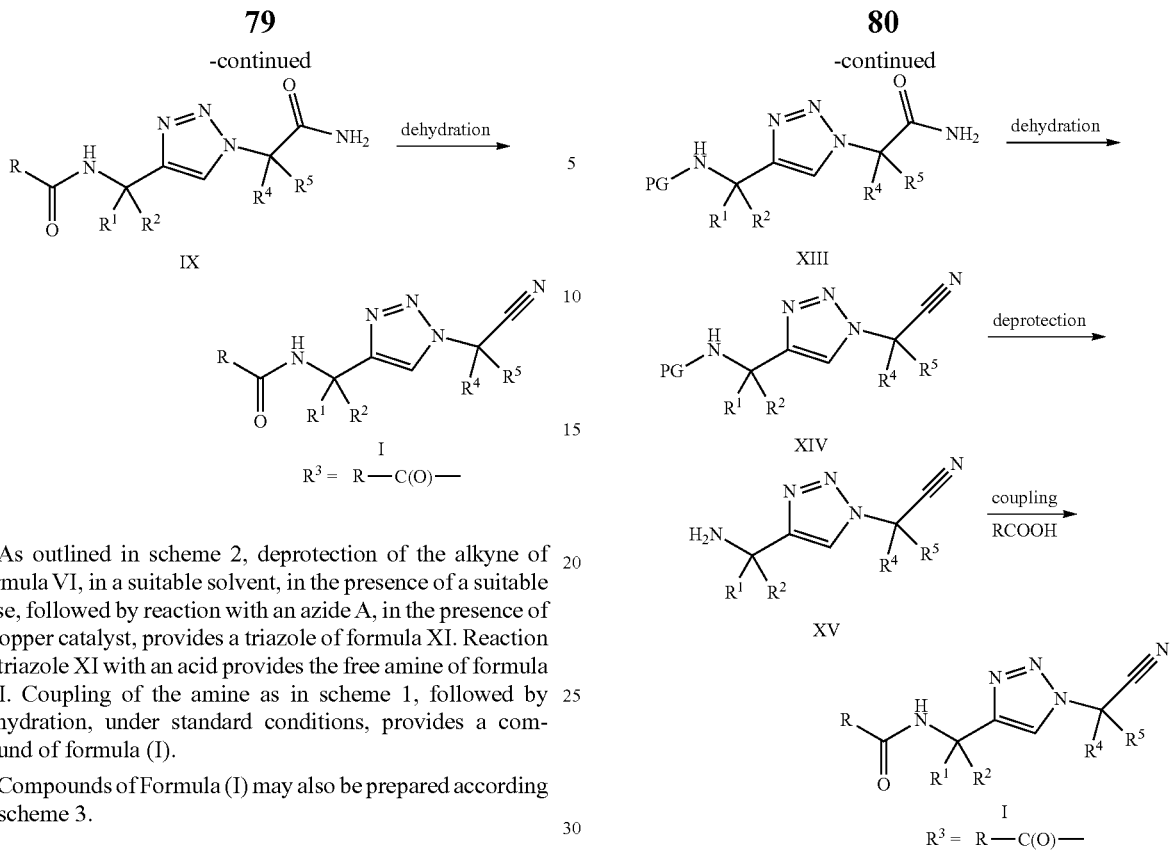

As outlined in scheme 2, deprotection of the alkyne of formula VI, in a suitable solvent, in the presence of a suitable base, followed by reaction with an azide A, in the presence of a copper catalyst, provides a triazole of formula XI. Reaction of triazole XI with an acid provides the free amine of formula XII. Coupling of the amine as in scheme 1, followed by dehydration, under standard conditions, provides a compound of formula (I).

Compounds of Formula (I) may also be prepared according to scheme 3.

As shown in scheme 3, protection of the amino group in a compound of formula XII provides the corresponding protected amine of formula XIII, wherein PG=protecting group such as BOC. Dehydration of the amide in compound XIII, provides the corresponding nitrile of formula XIV. Deprotection of the amino group of compound XIV, under standard conditions, followed by coupling as in scheme 1, provides a compound of formula (I).

Compounds of Formula (I) may be made according to scheme 4

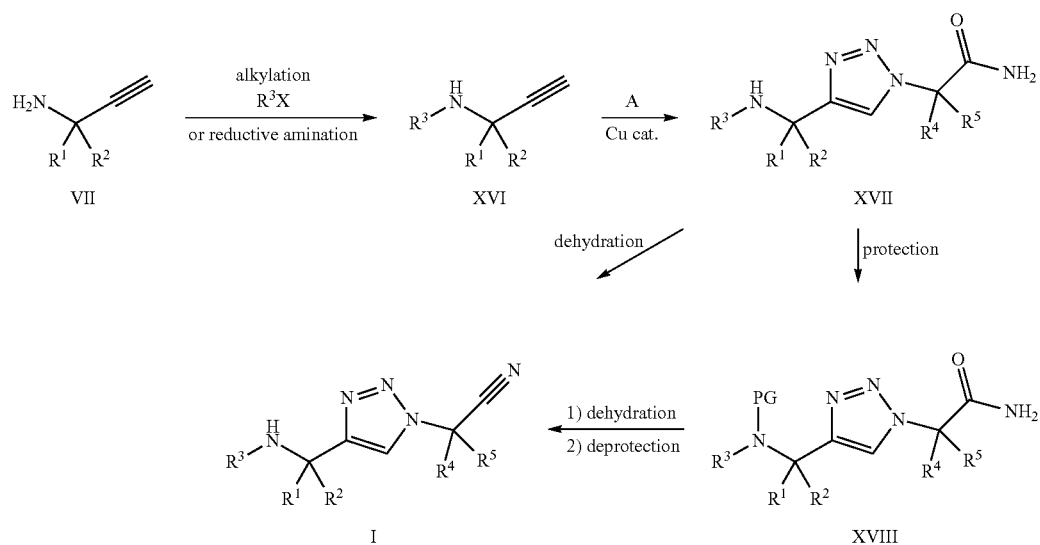

As outlined in scheme 4, reaction of an amine of formula VII with an alkylating agent R³X, in a suitable solvent, provides the corresponding alkylated compound of formula XVI. X=halide or —OTf. Compound XVI can alternatively be prepared by the reaction of the amine VII with a carbonyl compound R³=O under reducing conditions. Reaction of compound XVI with azide A as in scheme 1, provides a triazole of formula XVII. Dehydration of the amide group in compound XVII, under standard conditions, provides a compound of formula (I). Alternatively, the amino group in compound XVII may be protected prior to dehydration as shown in the scheme above.

Compounds of Formula (I) may be synthesized as outlined in scheme 5

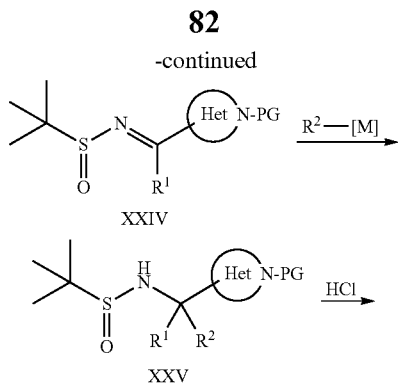

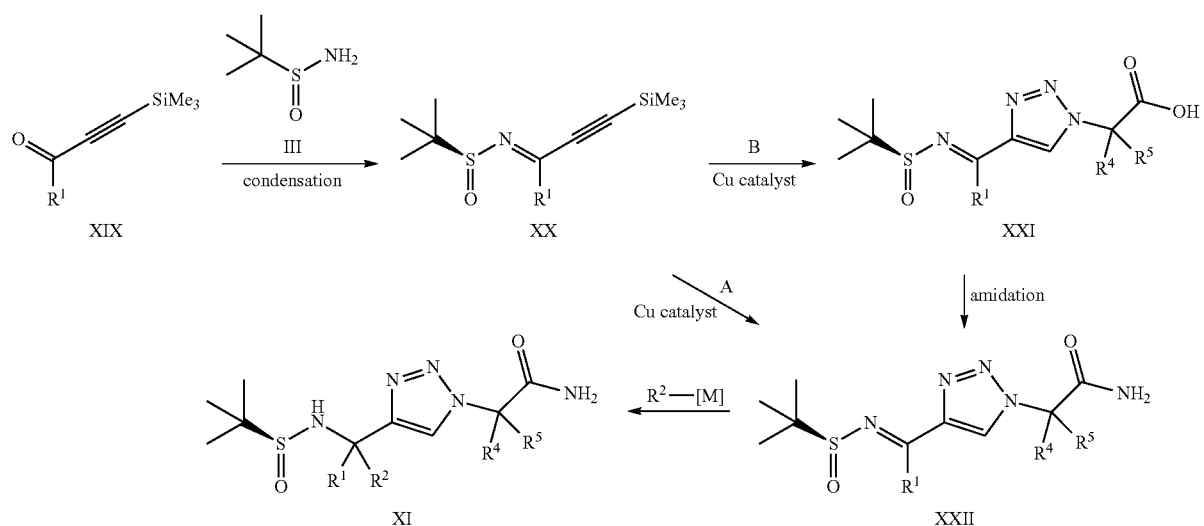

As illustrated in scheme 5, reaction of a compound of formula XIX with compound III, in a suitable solvent, provides a trimethylsilyl alkyne of formula XX. Removal of the silyl group and reaction with azide A or B, in the presence of a copper catalyst, provides the corresponding triazoles XXI or XXII respectively. Compound XXI may be converted to compound XXII under standard amidation conditions known in the literature. Alkylation of compound of formula XXII with R²-M, where M is a metal such as Li or Mg, provides a compound of formula XI which may be converted to a compound of formula (I) as outlined in scheme 2.

Compounds of Formula (I) may be prepared by the method outlined in scheme 6

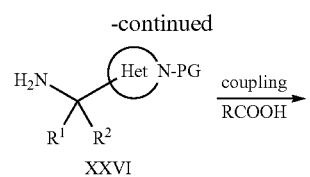

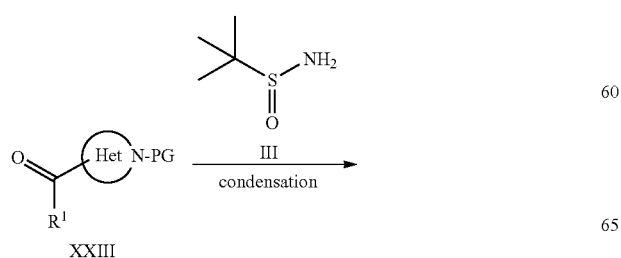

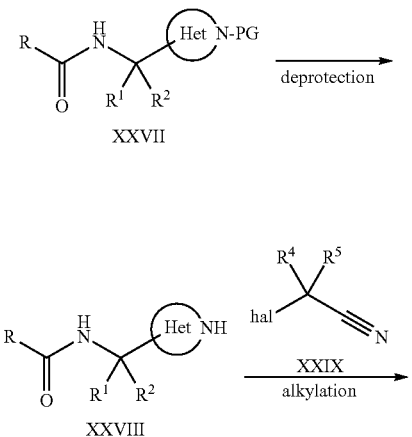

-continued

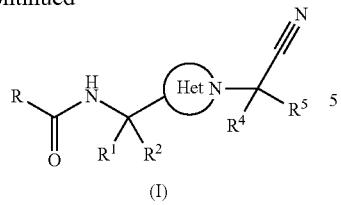

(I)

Het = triazole or imidazole
R³ = R—C(O)—

-continued

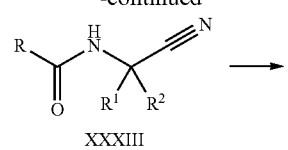

XXXIII

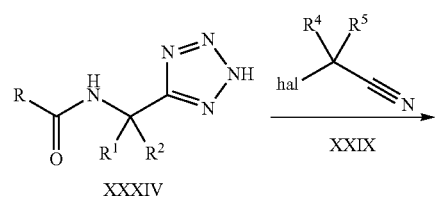

XXXIV

As shown in scheme 6, reaction of a compound of formula XXIII with compound III, in a suitable solvent, provides an imine of formula XXIV. Het=triazole or imidazole and PG=protecting group. Alkylation of compound of formula XXIV with R²-M, where M is a metal such as Li or Mg, provides a compound of formula XXV. Reaction of compound XXV with an acid such as hydrochloric acid, provides the free amine of formula XXVI. Coupling of the free amine XXVI as in scheme 1, provides a compound of formula XXVIII. Deprotection of the amine nitrogen followed by alkylation with an appropriate alkylating agent XXIX, provides a compound of formula (I).

Compounds of Formula (I) may be made by the method shown in scheme 7.

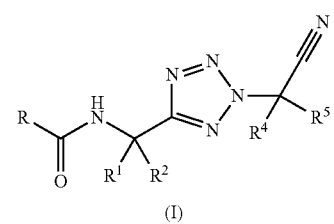

(I)

R³ = R—C(O)—

Scheme 7

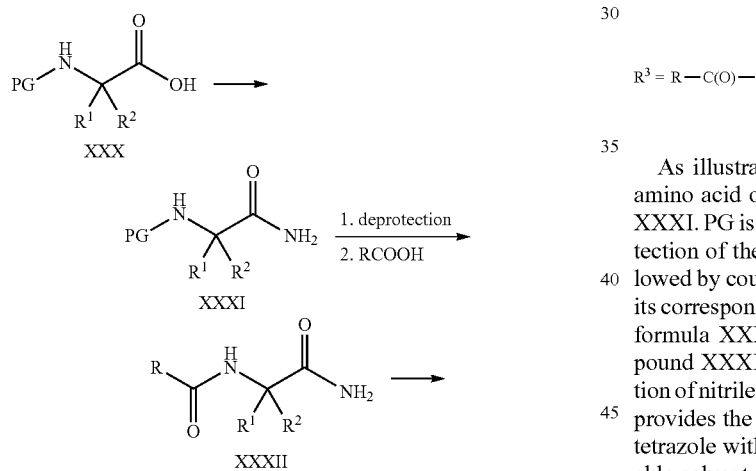

As illustrated in scheme 7, amidation of an N-protected amino acid of formula XXX provides an amide of formula XXXI. PG is an amine protecting group such as BOC. Deprotection of the amine under standard reaction conditions followed by coupling of the free amine with an acid RCOOH or its corresponding acid chloride provides a coupled product of formula XXXII. Dehydration of the amide group of compound XXXII, provides a nitrile of formula XXXIII. Reaction of nitrile XXXIII with sodium azide, in a suitable solvent, provides the tetrazole of formula XXXIV. Alkylation of the tetrazole with an alkylating agent of formula XXIX, in suitable solvent, provides a compound of formula (I)

Compounds of Formula (I) may be made by the method shown in scheme 8.

Scheme 8

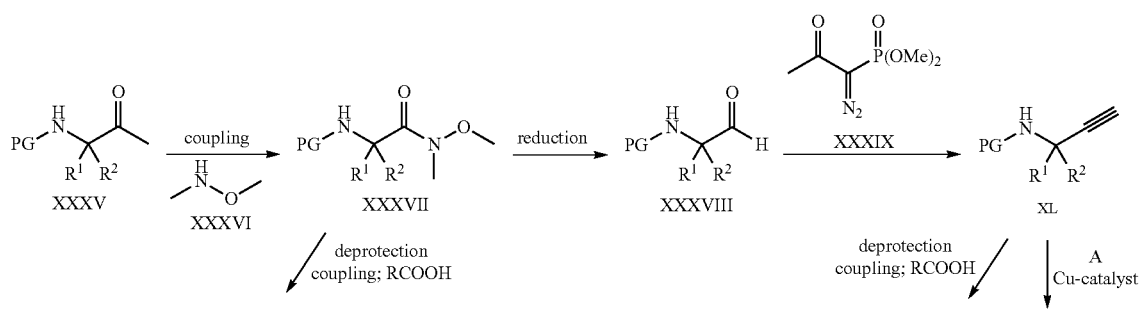

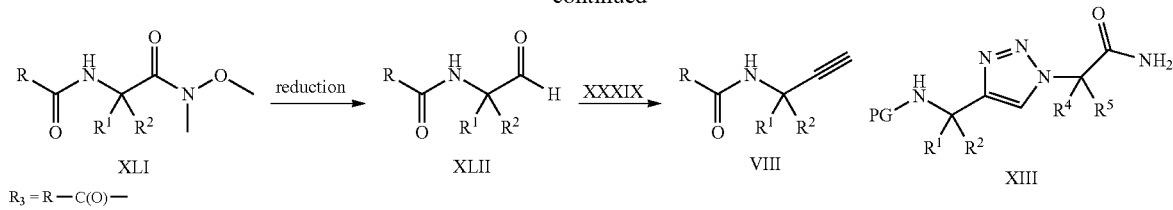

As illustrated in Scheme 8, amino aldehydes of formula XXXVIII can be prepared from protected amino acids of formula XXXV by first coupling with amine XXXVI under standard conditions followed by reduction using a reducing agent such as diisobutylaluminum hydride. Reaction of the aldehyde of formula XXXVIII with the Ohira-Bestman reagent XXXIX in standard solvents and in the presence of a base such as $K_2CO_3$, provides an alkyne of formula XL. Deprotection of the amino group in XL, under standard conditions, followed by standard coupling with an acid RCOOH provides a compound of formula VIII, which can be transformed into a compound of formula (I) as illustrated in Scheme 1. The compound of formula XL can react with an azide A in the presence of a copper catalyst to provide a compound of structure XIII (Scheme 3). Alternatively, the amides of formula XLI may be similarly reduced to XLII and then reacted with XXXIX to provide compounds of formula VIII. Amides of structure XLI can be prepared, for example from XXXVII via standard deprotection followed by coupling with RCOOH.

Further modification of the initial product of formula (I) by methods known in the art and illustrated in the Examples below, may be used to prepare additional compounds of this invention.

EXAMPLES

The following intermediates are used in the preparation of the Examples.

Synthesis of I-001

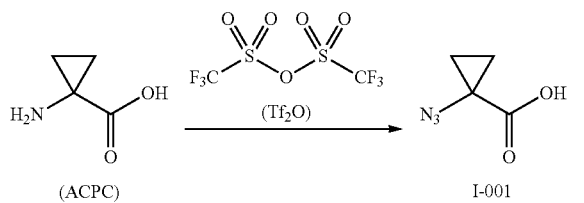 [SMILES: "(Tf2O)" ; NC1(C(=O)O)CC1 ; O=S(=O)(OS(=O)(=O)C(F)(F)F)C(F)(F)F ; [N-]=[N+]=NC1(C(=O)O)CC1]

$Tf_2O$ (3.3 mL, 20 mmol) is added to a mixture of $NaN_3$ (6.33 g, 97.3 mmol), $H_2O$ (16 mL), and $CH_2Cl_2$ (26 mL) at 0 C. The mixture is stirred at 0 C for 2 h, then the layers are separated. The aqueous layer is extracted with $CH_2Cl_2$ (2×15 mL). The combined extracts are washed with saturated aqueous $Na_2CO_3$, then added to a stirring mixture of ACPC (1.0 mg, 9.9 mmol), $K_2CO_3$ (2.05 g, 14.8 mmol), $CuSO_4.5H_2O$ (24 mg), $H_2O$ (30 mL), and methanol (50 mL). The resulting mixture is stirred for 16 h, then evaporated, diluted with $H_2O$ (150 mL), and concentrated HCl is added until the pH reaches 6. Phosphate buffer (pH 7, 150 mL) is added, and the mixture is washed with EtOAc (3×100 mL). Concentrated HCl is added to until the pH reaches 2. The mixture is extracted with EtOAc (3×150 mL). The extracts are combined, dried over $Na_2SO_4$, filtered, and concentrated to provide I-001 as an oil.

Synthesis of I-002

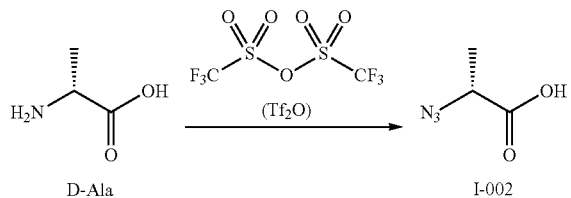

$Tf_2O$ (2.78 mL, 16.7 mmol) is added to a mixture of $NaN_3$ (5.35 g, 82.4 mmol), $H_2O$ (14 mL), and $CH_2Cl_2$ (22 mL) at 0 C. The mixture is stirred at 0 C for 2 h, then the layers are separated. The aqueous layer is extracted with $CH_2Cl_2$ (2×10 mL). The combined extracts are washed with saturated aqueous $Na_2CO_3$, then added to a stirring mixture of D-Ala (745 mg, 8.37 mmol), $K_2CO_3$ (1.74 g, 12.6 mmol), $CuSO_4.5H_2O$ (21 mg), $H_2O$ (27 mL), and MeOHl (45 mL). The resulting mixture is stirred for 16 h, then evaporated, and diluted with $H_2O$ (50 mL). Concentrated HCl is added until the pH is 6. Phosphate buffer (pH 7, 50 mL) is added, and the mixture is washed with EtOAc (3×25 mL). The aqueous layer is acidified to pH 2 with concentrated HCl, and extracted with EtOAc (3×30 mL). The extracts are combined, dried over $Na_2SO_4$, filtered, and concentrated to provide I-002 as an oil.

The following azides are prepared from the appropriate amino acid in the same manner as I-001 and I-002.

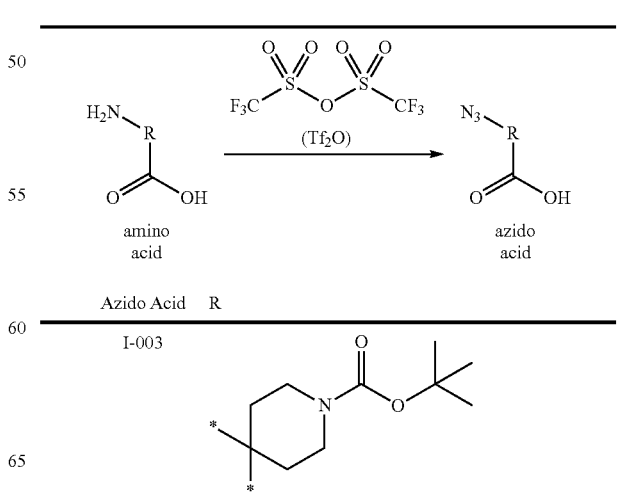

-continued

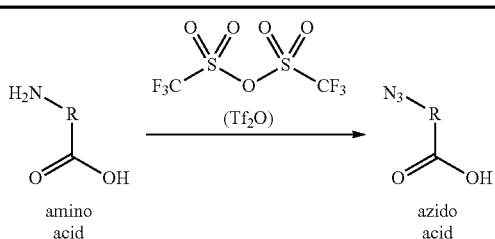

| Azido Acid | R |
|---|---|
| I-004 | 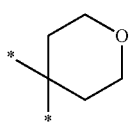 |
| I-006 | 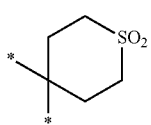 [SMILES: *C1(*)CCS(=O)(=O)CC1] |

Synthesis of I-007

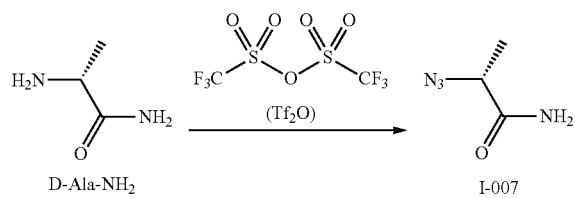

Tf$_2$O (12 mL, 71 mmol) is added to a mixture of NaN$_3$ (23 g, 350 mmol), H$_2$O (100 mL), and CH$_2$Cl$_2$ (200 mL) at 0 C. The mixture is stirred at 0 C for 2 h, then the layers are separated. The aqueous layer is extracted with CH$_2$Cl$_2$ (2×50 mL). The combined extracts are added to a stirring mixture of D-Ala-NH$_2$ (4.4 g, 35 mmol), K$_2$CO$_3$ (7.3 g, 53 mmol), 0.3 M CuSO$_4$.5H$_2$O (1.2 mL, 0.35 mmol), H$_2$O (200 mL), and MeOH (400 mL). The resulting mixture is stirred for 16 h, then evaporated, and diluted with H$_2$O (50 mL). The mixture is concentrated, H$_2$O (100 mL) is added, and the mixture is extracted with EtOAc (3×100 mL). The extracts are combined, washed with brine (100 mL), dried over Na$_2$SO$_4$, filtered, and concentrated to provide I-007 as a solid.

Synthesis of I-009

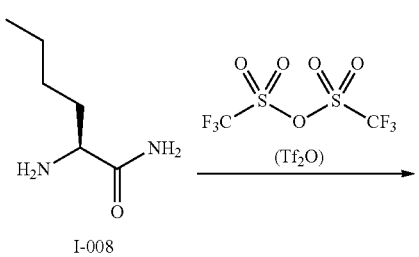

-continued

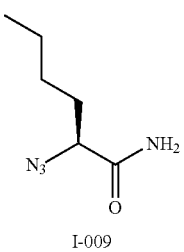

Tf$_2$O (5.0 mL, 30 mmol) is added to a mixture of NaN$_3$ (10 g, 160 mmol), H$_2$O (20 mL), and CH$_2$Cl$_2$ (20 mL) at 0 C. The mixture is stirred at 0 C for 2 h, then the layers are separated. The aqueous layer is extracted with CH$_2$Cl$_2$ (2×20 mL). The combined extracts are washed with saturated Na$_2$CO$_3$, then added to a stirring mixture of I-008 (2.0 g, 15 mmol), K$_2$CO$_3$ (33 g, 240 mmol), CuSO$_4$.5H$_2$O (40 mg, 0.163 mmol), H$_2$O (40 mL), and MeOH (80 mL). The resulting mixture is stirred for 16 h, then evaporated to 60 mL and extracted with EtOAc (2×70 mL). The extracts are combined, washed with brine, dried over Na$_2$SO$_4$, filtered, and concentrated to provide I-009.

Synthesis of I-010

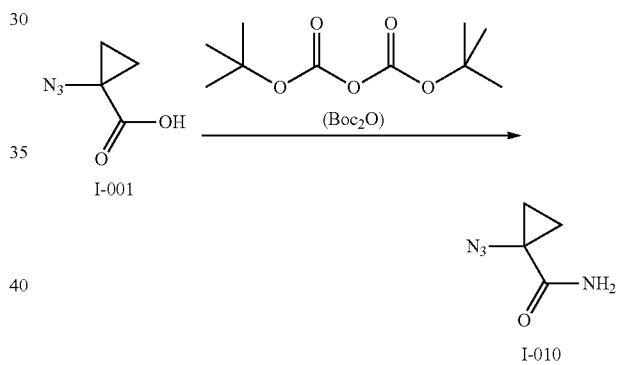

Boc$_2$O (11.5 g, 52.7 mmol) is added to I-001 (7.92 mg, 49.9 mmol), pyridine (2.5 mL, 31 mmol), (NH$_4$)HCO$_3$ (4.75 g, 60.1 mmol), and MeCN (50 mL). The mixture is stirred for 16 h, then concentrated by half, diluted with EtOAc (40 mL), washed with H$_2$O (20 mL), NaHCO$_3$ (20 mL), and brine (20 mL). The washes are extracted with EtOAc (40 mL), the extracts are combined, dried over Na$_2$SO$_4$, filtered, and concentrated. The product is recrystallized from iPrOH to provide I-010 as a solid.

Synthesis of I-012

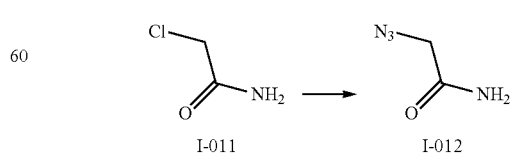

I-011 (2.0 g, 21.4 mmol), NaN$_3$ (7.0 g, 110 mmol), Bu$_4$NI (0.79 g, 2.1 mmol), and DMF (30 mL) are stirred at 50° C. for

Synthesis of I-018

Synthesis of I-022

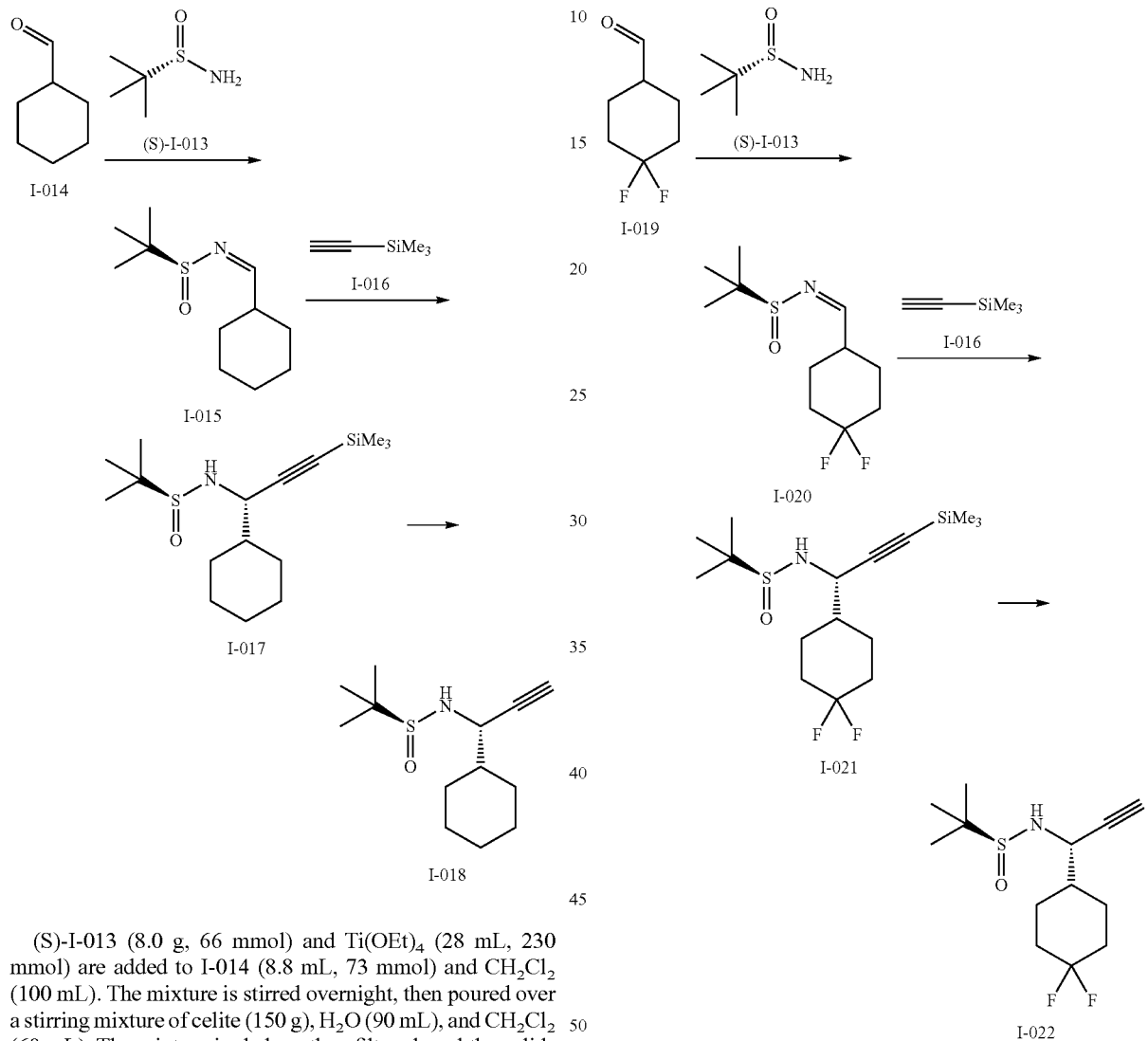

(S)-I-013 (8.0 g, 66 mmol) and Ti(OEt)₄ (28 mL, 230 mmol) are added to I-014 (8.8 mL, 73 mmol) and CH₂Cl₂ (100 mL). The mixture is stirred overnight, then poured over a stirring mixture of celite (150 g), H₂O (90 mL), and CH₂Cl₂ (60 mL). The mixture is shaken, then filtered, and the solids washed with CH₂Cl₂ (600 mL). The filtrate is washed with brine (60 mL), dried over MgSO₄, filtered, and concentrated to provide I-015 as an oil.

1.67 M BuLi in hexane (77 mL, 120 mmol) is added to I-016 (19 mL, 140 mmol) and toluene (100 mL) at −78 C. The mixture is stirred for 15 min, and a −78 C mixture of Me₃Al (34 mL, 67 mmol), I-015 (14 g, 61 mmol), and toluene (100 mL) prepared at −78 C is added. The resulting mixture is stirred at −78 C for 2 h, then is poured over a stirring mixture of celite (30 g), NaHCO₃ (20 mL), H₂O (10 mL), and EtOAc (240 mL). The mixture is stirred for 20 min, dried with MgSO₄, then filtered, washed with EtOAc, concentrated, and purified by silica chromatography (5-50% EtOAc in heptane gradient) to provide I-017 as an oil.

4 M NaOH in H₂O (11 mL, 44 mmol) is added to I-017 (15 g, 42 mmol) and MeOH (50 mL). The resulting mixture is stirred overnight, and EtOAc (40 mL) is added and stirred for 4 h. EtOAc is added (80 mL), and the mixture is washed with half saturated NaHCO₃ (10 mL) and brine (10 mL), dried over Na₂SO₄, filtered, and concentrated to provide I-018 as a solid.

(S)-I-013 (1.1 g, 8.8 mmol), Ti(OiPr)₄ (4.0 mL, 14 mmol), I-019 (1.0 g, 6.8 mmol; Evans, K. et al., US patent application US2007/0249670, 2007) and THF (100 mL) are stirred at 60 C for 12 h. The mixture is poured over stirring saturated aqueous NaHCO₃ (130 mL), and filtered through celite. The filtrate is washed with brine, dried over MgSO₄, and purified by silica chromatography (0-60% MTBE in heptane) to provide I-020 as an oil.

1.67 M BuLi in hexane (0.87 mL, 2.2 mmol) is added to I-016 (0.26 mL, 1.0 mmol) and toluene (30 mL) at −78 C. The mixture is stirred for 15 min, and a −78 C mixture of 2.0 M Me₃Al in toluene (0.57 mL, 1.1 mmol), I-020 (0.26 g, 1.0 mmol), and toluene (30 mL) prepared at −78 C is added. The mixture is stirred for 2 h at −78 C and 4 h at rt. Saturated aqueous Na₂SO₄ (25 mL) is added, and the mixture is extracted by EtOAc (3×75 mL). The extracts are combined, washed with brine, dried over MgSO₄ filtered, and concentrated to provide I-021 as an oil.

4 M NaOH in H₂O (0.26 mL, 1.0 mmol) is added to I-021 (0.36 g, 1.0 mmol) and MeOH (2 mL). The resulting mixture is stirred for 2 h. Saturated aqueous NH₄Cl (20 mL) is added, and the mixture is extracted with EtOAc (2×20 mL). The extracts are combined, washed with brine, dried over MgSO₄, filtered, and concentrated to provide I-022 as an oil.

The following intermediates are prepared from the corresponding aldehydes in the same manner as I-018 and I-022.

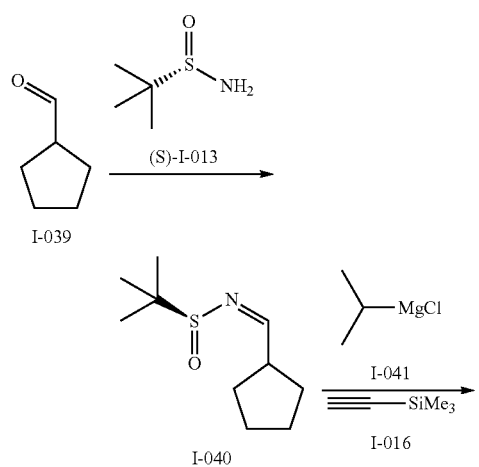

| Intermediate | R |
| --- | --- |
| I-023 | cyclohexylmethyl |
| I-024 | tetrahydropyran-2-yl |
| I-025 | tetrahydropyran-3-yl |
| I-026 | tetrahydropyran-4-yl |
| I-027 | cyclopropyl |
| I-028 | N-Cbz-piperidin-3-yl |
| I-029 | benzyl |
| I-030 | cyclohexan-D11-yl |
| I-031 | 2-phenylethyl |
| I-032 | 3-methoxycyclohexyl |
| I-033 | trans-(4-CF₃)-cyclohexyl |
| I-034 | t-butyl |
| I-035 | isobutyl |
| I-036 | 3-pentyl |
| I-037 | sec-butyl |
| I-038 | thiocyclohexan-4-yl |

Synthesis of I-043

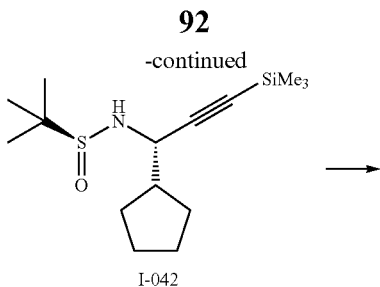

I-042

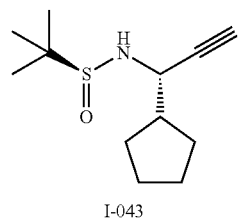

I-043

(S)-I-013 (0.5 g, 4.9 mmol) and Ti(OEt)₄ (1.8 mL, 8.7 mmol) are added to I-039 (0.60 mL, 4.9 mmol) and ClCH₂CH₂Cl (100 mL). The mixture is stirred for 2 h at 60 C, then poured over a stirring mixture of celite (30 mL) and H₂O (10 mL). The mixture is stirred for 30 min, filtered through MgSO₄, and concentrated to provide I-040 as an oil.

I-016 (1.3 mL, 9.3 mmol) is added to 2.0 M I-041 in Et₂O (4.1 mL) at 0 C and stirred for 4 h at rt. The resulting mixture is added to stirring I-040 (0.83 g, 4.1 mmol) and CH₂Cl₂ (20 mL) at −48 C. The mixture warms to rt, and is stirred for 5 days. H₂O (5 mL) and saturated aqueous NH₄Cl (5 mL) are added. The organic phase is separated, washed with brine, dried over MgSO₄, filtered, concentrated, and purified by silica chromatography (5-50% EtOAc in heptane) to provide I-042 as an oil.

4 M NaOH in H₂O (0.56 mL, 2.2 mmol) is added to I-042 (0.64 g, 2.1 mmol) in MeOH (2 mL). The resulting mixture is stirred for 2 h. EtOAc (10 mL) is added and the mixture stirred for 14 h. The mixture is washed with half saturated NaHCO₃ (5 mL) and brine (10 mL), dried over Na₂SO₄, filtered, and concentrated to provide I-043 as an oil.

Synthesis of I-044

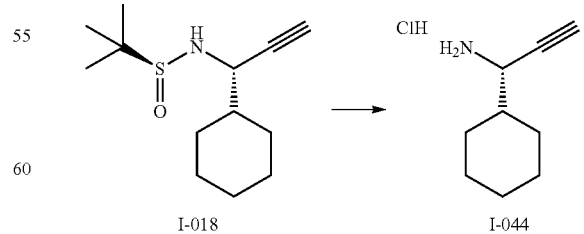

4M HCl in dioxane (11 mL, 44 mmol) is added to I-018 (5.3 g, 20 mmol) and MeOH (44 mL). The mixture is stirred at 0 C for 2 h, then concentrated, and stirred in 10:1 MTBE/

Synthesis of I-045

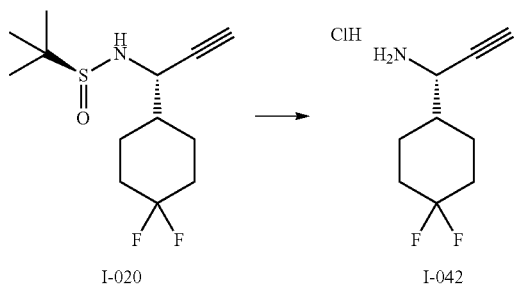 [SMILES: C#C[C@@H](N[S@@](=O)C(C)(C)C)C1CCC(F)(F)CC1 ; Cl ; C#C[C@@H](N)C1CCC(F)(F)CC1]

4M HCl in dioxane (3 mL, 12 mmol) is added to I-022 (0.31 g, 1.1 mmol) and MeOH (10 mL). The mixture is stirred for 2 h, then concentrated, and washed with Et$_2$O to provide I-045 as a solid.

The following intermediates are prepared from the corresponding sulfinamides in the same manner as I-044 and I-045.

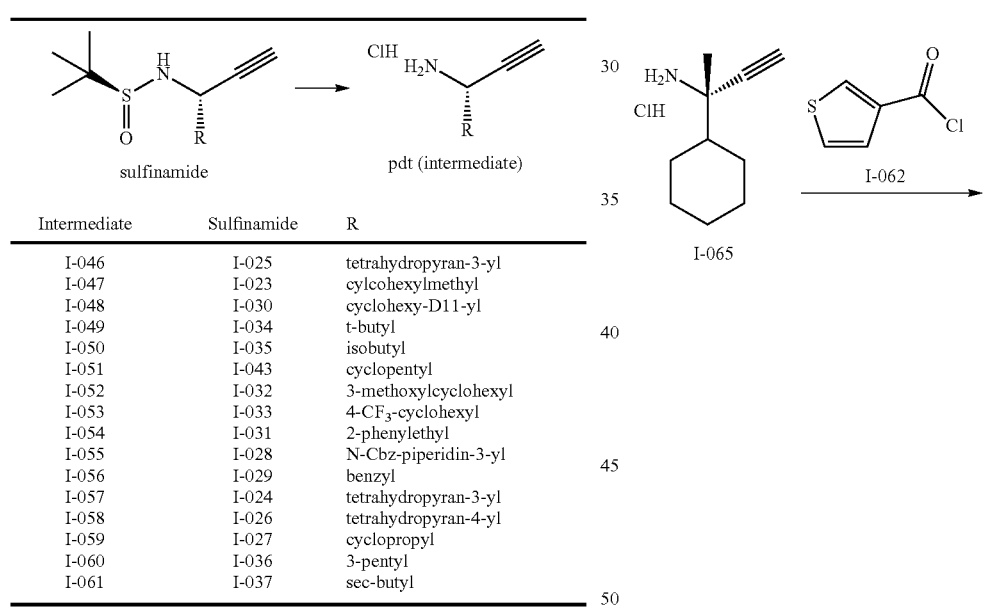

| Intermediate | Sulfinamide | R |
|---|---|---|
| I-046 | I-025 | tetrahydropyran-3-yl |
| I-047 | I-023 | cylcohexylmethyl |
| I-048 | I-030 | cyclohexy-D11-yl |
| I-049 | I-034 | t-butyl |
| I-050 | I-035 | isobutyl |
| I-051 | I-043 | cyclopentyl |
| I-052 | I-032 | 3-methoxylcyclohexyl |
| I-053 | I-033 | 4-CF$_3$-cyclohexyl |
| I-054 | I-031 | 2-phenylethyl |
| I-055 | I-028 | N-Cbz-piperidin-3-yl |
| I-056 | I-029 | benzyl |
| I-057 | I-024 | tetrahydropyran-3-yl |
| I-058 | I-026 | tetrahydropyran-4-yl |
| I-059 | I-027 | cyclopropyl |
| I-060 | I-036 | 3-pentyl |
| I-061 | I-037 | sec-butyl |

Synthesis of I-064

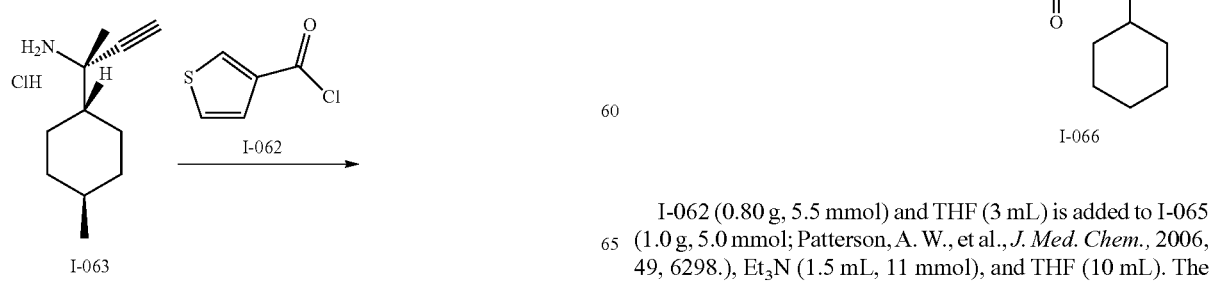

I-062 (0.80 g, 5.5 mmol) and THF (3 mL) is added to I-063 (1.0 g, 5.0 mmol; Patterson, A. W., et al., *J. Med. Chem.*, 2006, 49, 6298.), Et$_3$N (1.5 mL, 11 mmol), and THF (10 mL). The mixture is stirred for 16 h, then filtered through celite, concentrated, and purified by silica chromatography (10-60% EtOAc in heptane gradient) to provide I-064 as a solid.

Synthesis of I-066

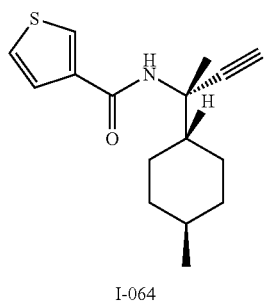

I-062 (0.80 g, 5.5 mmol) and THF (3 mL) is added to I-065 (1.0 g, 5.0 mmol; Patterson, A. W., et al., *J. Med. Chem.*, 2006, 49, 6298.), Et$_3$N (1.5 mL, 11 mmol), and THF (10 mL). The mixture is stirred for 16 h, then filtered through celite, concentrated, and purified by silica chromatography (10-60% EtOAc in heptane gradient) to provide I-066 as a solid.

Synthesis of I-068

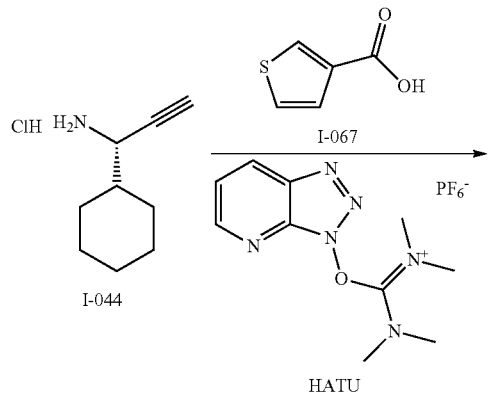

HATU (1.36 g, 3.6 mmol) is added to I-044 (560 mg, 3.3 mmol), I-067 (1.4 g, 3.6 mmol), Et₃N (4.5 mL, 32 mmol), and THF (16 mL). The resulting mixture is stirred for 16 h, then concentrated and purified by silica chromatography (5-60% EtOAc in heptane gradient) to provide I-068 as a solid.

Synthesis of I-069

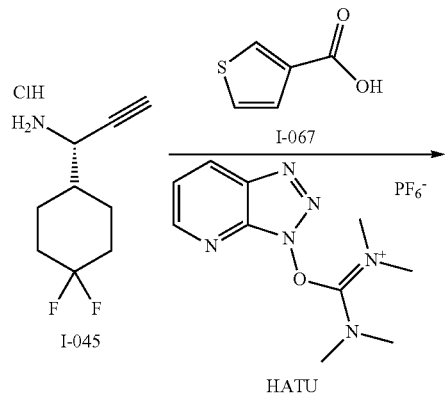

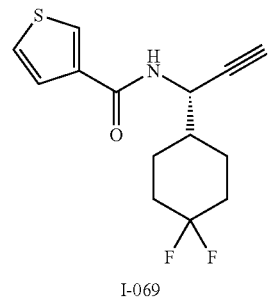

HATU (0.43 g, 1.1 mmol) and I-045 (0.21 g, 1.0 mmol) are added to I-067 (0.14 g, 1.1 mmol), Et₃N (0.71 mL, 5 mmol), and DMF (3 mL). The resulting mixture is stirred for 2 h, then directly purified by C18 semi-preparative HPLC (5-95% MeCN in H₂O gradient with 0.1% TFA) provide I-069 as a solid.

The following intermediates are prepared from the appropriate propargylamine in the same manner as I-068 and I-069.

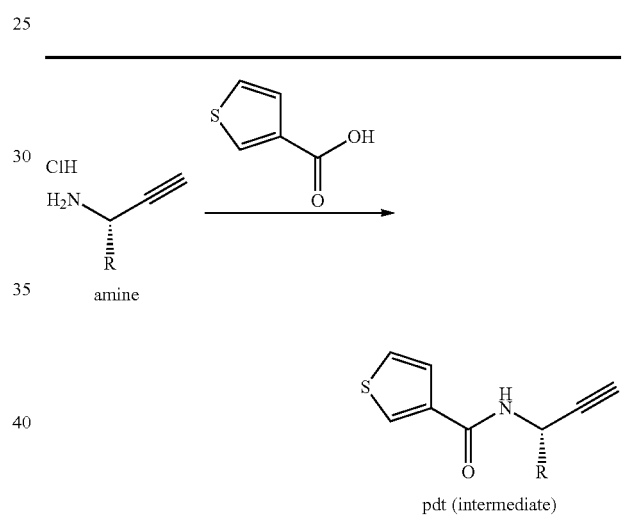

| Intermediate | amine | R |
|---|---|---|
| I-070 | I-047 | cyclohexylmethyl |
| I-071 | I-048 | cyclohexan-D11-yl |
| I-072 | I-049 | t-butyl |
| I-073 | I-051 | cyclopentyl |
| I-074 | I-057 | tetrahydropyran-2-yl |
| I-075 | I-046 | tetrahydropyran-3-y |
| I-076 | I-058 | tetrahydropyran-4-yl |
| I-077 | I-052 | 3-methoxycyclohexyl |
| I-078 | I-050 | isobutyl |
| I-079 | I-054 | 2-phenylethyl |
| I-080 | I-055 | N-Cbz-piperidin-3-yl |
| I-081 | I-056 | benzyl |
| I-082 | I-059 | cyclopropyl |
| I-083 | I-060 | 3-pentyl |
| I-084 | I-061 | sec-butyl |

Synthesis of I-086

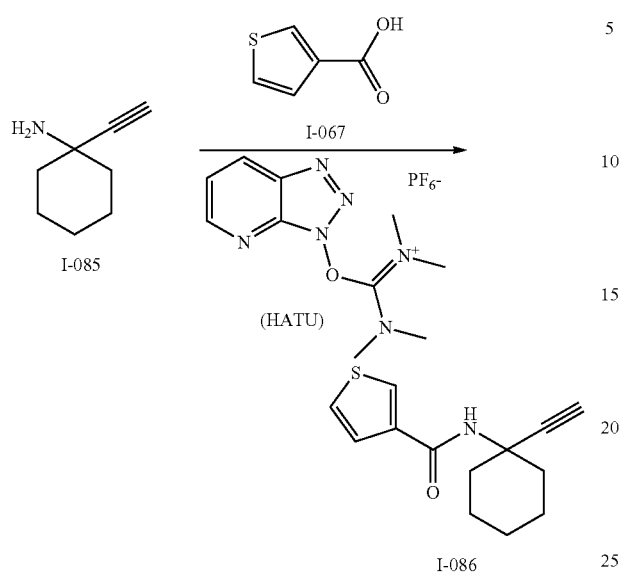

HATU (2.0 g, 5.4 mmol) and Et₃N (2.0 mL, 3.0 mmol) are added to I-085 (0.60 g, 4.9 mmol), I-067 (0.69 g, 5.4 mmol), and THF (24 mL). The mixture is stirred for 16 h, concentrated, and purified by silica chromatography (5-60% EtOAc in heptane gradient) to provide I-086 as a solid.

Synthesis of I-087

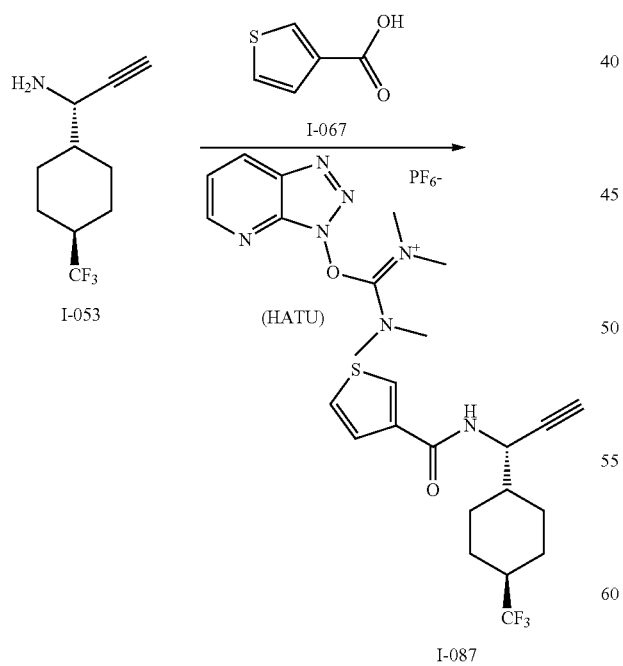

TBTU (0.37 g, 1.1 mmol) and Et₃N (0.43 mL, 3.1 mmol) are added to I-053 (0.25 g, 1.0 mmol), I-067 (0.15 g, 1.1 mmol), and DMF (3 mL). The mixture is stirred for 16 h, mixed with EtOAc, and washed with saturated NaHCO₃, dried over Na₂SO₄, filtered, and concentrated to provide I-087.

Synthesis of I-089

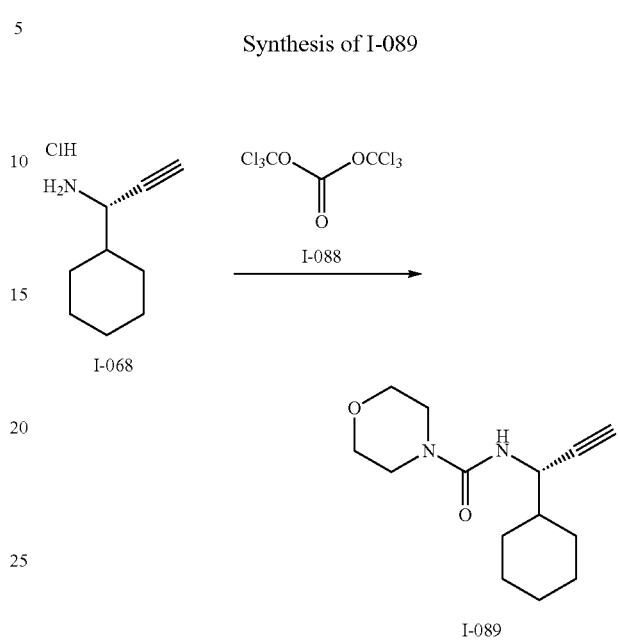

I-088 (0.33 g, 1.1 mmol) and CH₂Cl₂ (10 mL) are added to I-068 (0.50 g, 2.9 mmol), iPr₂NEt (2.0 mL, 12 mmol), and CH₂Cl₂ (5 mL). The mixture is stirred for 10 min and morpholine (0.32 mg, 3.7 mmol) is added. After 12 h, EtOAc (40 mL) is added. The mixture is washed with brine, dried over Na₂SO₄, filtered, concentrated and purified first by silica chromatography (2-10% MeOH in CH₂Cl₂ gradient), then by C18 semi-preparative HPLC (5-95% MeCN in H₂O gradient with 0.1% TFA) provide I-089 as a solid.

Synthesis of I-091

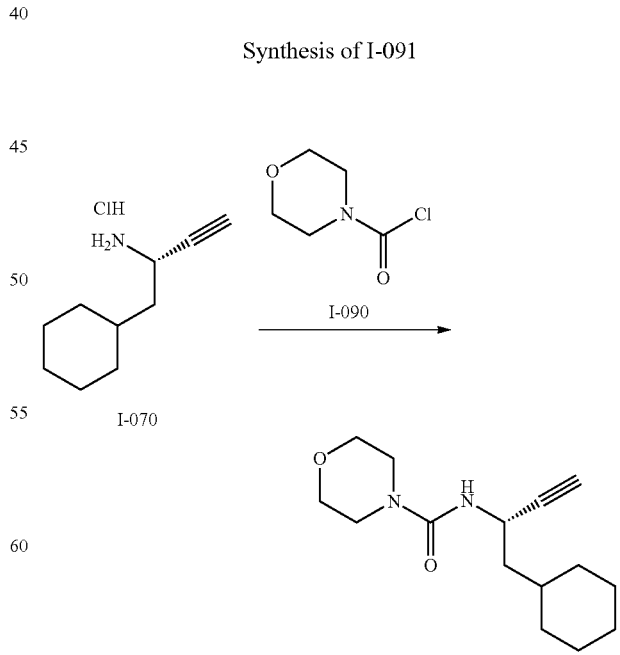

I-090 (87 mg, 0.59 mmol) is added to I-070 (0.10 g, 0.53 mmol), Et$_3$N (0.37 mL, 2.7 mmol), and DMF (3 mL). The mixture is stirred for 2 h and concentrated to provide I-091 as an oil.

Synthesis of I-096

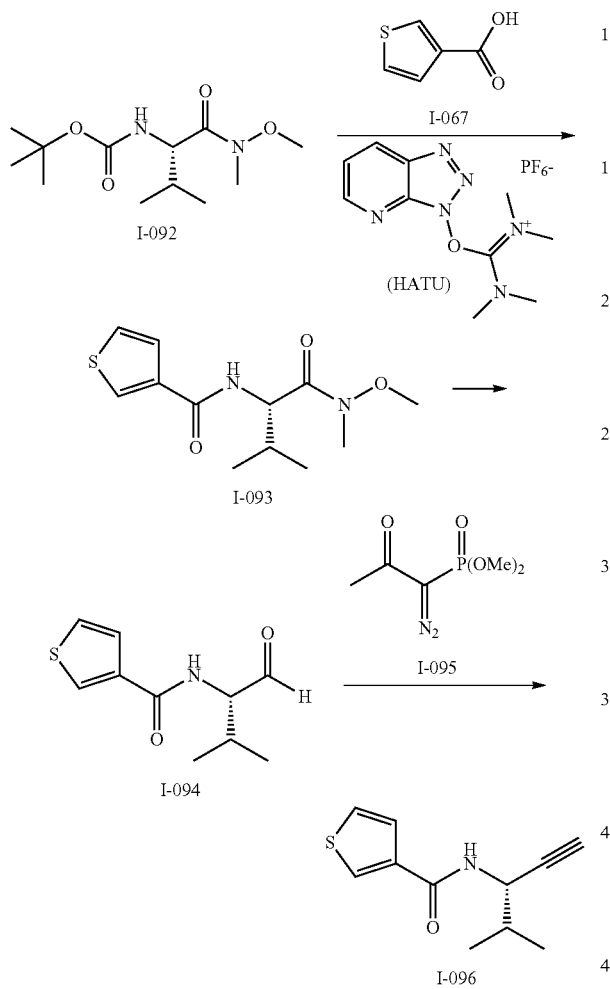

I-095 (0.12 g, 0.63 mmol) is added to I-094 (65 mg, 0.31 mmol), K$_2$CO$_3$ (0.13 g, 0.94 mmol), and MeOH (5 mL) at 0 C. The mixture is stirred for 14 h and concentrated. EtOAc (50 mL) is added, and the mixture is washed with brine, dried over Na$_2$SO$_4$, filtered, concentrated, and purified by silica chromatography (5-50% EtOAc in heptane gradient) to provide I-096 as a solid.

Synthesis of I-098

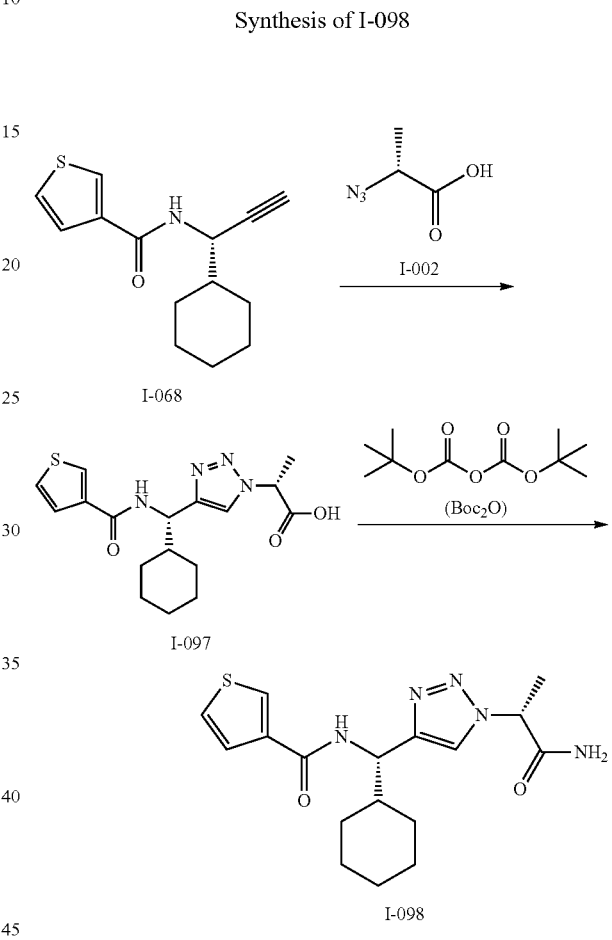

4.0 M HCl in dioxane (5.0 mL, 20 mmol) is added to I-092 (0.84 g, 3.2 mmol). The mixture is stirred for 12 h, then concentrated. THF (12 ml), Et$_3$N (1.8 mL, 13 mmol), I-067 (0.41 g, 3.2 mmol), and HATU (1.8 g, 4.8 mmol) are added. The mixture is stirred for 12 h. EtOAc (20 mL) is added and the mixture is washed with NaHCO$_3$ (10 mL). The wash is extracted with EtOAc (10 mL), and the extracts are combined, washed with NaHCO$_3$ (10 mL) and brine (10 mL), dried with Na$_2$SO$_4$, filtered, concentrated, and purified by silica chromatography (30-70% EtOAc in heptane gradient) to provide I-093 as an oil.

1.0 M (iBu)$_2$AlH (3.3 mL, 3.3 mmol) is added dropwise to I-093 (0.41 g, 1.5 mmol) and CH$_2$Cl$_2$ (10 mL) at −78 C. The mixture is stirred at −78 C for 40 min, MeOH (3.5 mL) is added, and the mixture is warmed to rt. The mixture is stirred for 15 min with celite (0.84 g) wet with water (0.33 mL) and 1 M NaHSO$_4$ (0.33 mL) and additional CH$_2$Cl$_2$ (4 mL). The mixture is filtered, and the filtrate is dried over Na$_2$SO$_4$, filtered, concentrated, and purified by silica chromatography (20-66% EtOAc in heptane gradient) to provide I-094 as an oil.

iPr$_2$NEt (0.33 mL, 1.9 mmol) and CuI (550 mg, 2.9 mmol) are added to I-068 (240 mg, 0.96 mmol), I-002 (130 mg, 1.1 mmol), and THF (30 mL). The mixture is stirred for 72 h, then concentrated, diluted with EtOAc (200 mL), and washed with saturated aqueous NH$_4$Cl (2×100 mL), and H$_2$O (2×100 mL). The organic layer is extracted with saturated aqueous NaHCO$_3$ (3×100 mL), and concentrated HCl is added until the pH reaches 2. The resulting mixture is extracted with EtOAc (3×100 mL). Extracts are combined, dried over MgSO$_4$, filtered, and concentrated to provide I-097 as a solid.

Boc$_2$O (270 mg, 1.2 mmol) and MeCN (0.5 mL) is added to I-097 (350 mg, 0.95 mmol), pyridine (47 μL, 0.57 mmol), (NH$_4$)HCO$_3$ (91 mg, 1.2 mmol), and MeCN (1.5 mL). The mixture is stirred for 16 h, Boc$_2$O (270 mg, 1.2 mmol) is added again, the mixture is stirred for 16 h, then concentrated and purified by silica chromatography (twice by 5-20% MeOH in CH$_2$Cl$_2$ gradient) to provide I-098 as a solid.

The following intermediates are prepared from the appropriate alkynes and azides in the same manner as I-098.

Synthesis of I-104

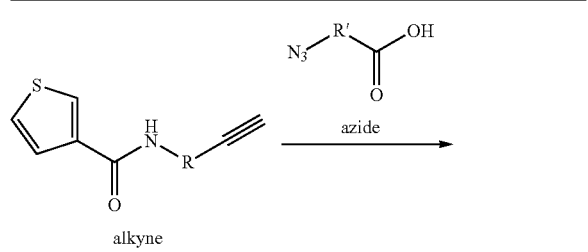

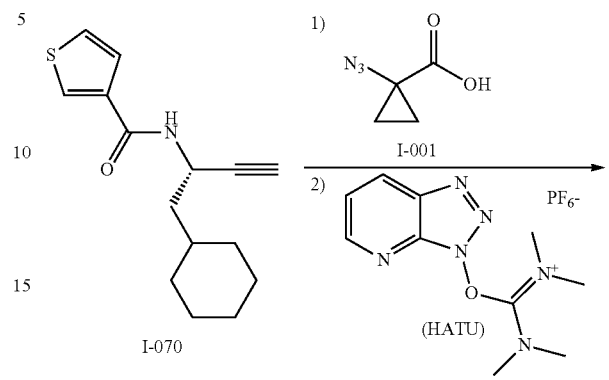

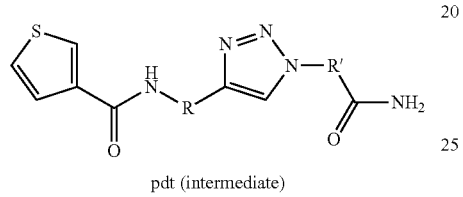

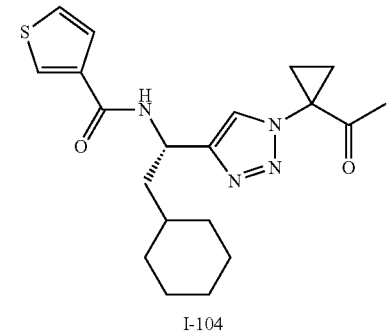

Sodium ascorbate (0.16 g, 0.81 mmol) in $H_2O$ (0.4 mL) is added to a stirring mixture of I-070 (0.21 g, 0.81 mmol), I-001 (0.10 g, 0.79 mmol), 0.5 M $CuSO_4$ (0.16 mL, 0.08 mmol), 2M NaOH (0.20 mL, 0.80 mmol), and EtOH (3 mL). The mixture is stirred for 16 h and diluted with $H_2O$ (10 mL). 2N HCl is added until the pH falls between 4 and 5, and the mixture is extracted with EtOAc (2×15 mL). The extracts are combined, washed with brine, dried over $MgSO_4$, filtered, and concentrated to provide a solid. This solid is combined with HATU (0.33 g, 0.86 mmol), DMF (2 mL), and $NH_3$ is bubbled through for 5 minutes. The resulting mixture is stirred for 1 h, diluted with EtOAc (20 mL), washed with brine. The extract is dried over $MgSO_4$, filtered, concentrated, and purified by C18 semi-preparative HPLC (5-90% MeCN in $H_2O$ gradient with 0.1% TFA) to provide I-104 as a solid.

The following intermediates are is prepared from the appropriate propargylamine in the same manner as I-104.

| Intermediate | Alkyne | Azide | R | R' |
|---|---|---|---|---|
| I-099 | I-064 | I-001 |  | |
| I-100 | I-064 | I-003 | | |
| I-101 | I-068 | I-102 (Patterson, A. W., 2006) |  | |
| I-103 | I-073 | I-001 | 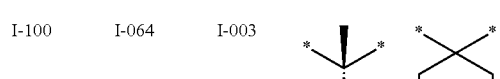 |  |

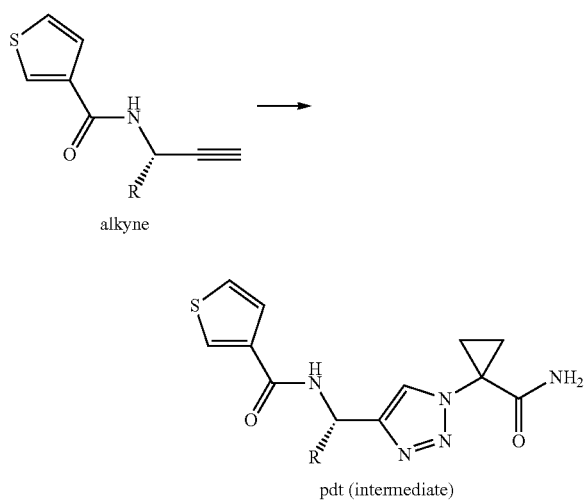

alkyne pdt (intermediate)

| Intermediate | Alkyne | R |
|---|---|---|
| I-105 | I-076 | tetrahydropyran-4-yl |
| I-106 | I-082 | cyclopropyl |

Synthesis of I-107

I-066

I-107

Sodium ascorbate in H$_2$O (1 M; 2.3 mL, 2.3 mmol) is added to a stirring mixture of I-066 (0.30 g, 1.2 mmol), I-010 (0.29 g, 2.3 mmol), CuSO$_4$ (0.3 M; 0.77 mL, 0.23 mmol), and 1:1 H$_2$O/t-BuOH. The mixture is stirred for 16 h, diluted with H$_2$O and saturated NaHCO$_3$, and extracted with EtOAc (3×20 mL). The extracts are combined, washed with brine, dried over MgSO$_4$, filtered, concentrated, and purified by silica chromatography (1-20% MeOH in CH$_2$Cl$_2$ gradient) to provide I-107 as an oil.

Synthesis of I-108

I-069

I-108

Sodium ascorbate in H$_2$O (1 M; 2.05 mL, 2.05 mmol) is added to a stirring mixture of I-069 (0.29 g, 1.0 mmol), I-010 (0.14 g, 1.1 mmol), CuSO$_4$ (0.3 M; 0.35 mL, 0.1 mmol), and 1:1 H$_2$O/t-BuOH (5 mL). The mixture is stirred for 16 h, diluted with EtOAc (60 mL), and washed with saturated NaHCO$_3$. The wash is extracted with EtOAc (20 mL). The extract is washed with brine, dried over Na$_2$SO$_4$, filtered, concentrated, and purified by silica chromatography (1-20% MeOH in CH$_2$Cl$_2$ gradient) to provide I-108 as a solid.

The following intermediates are prepared from the appropriate alkynes and azides in the same manner as I-107 and I-108.

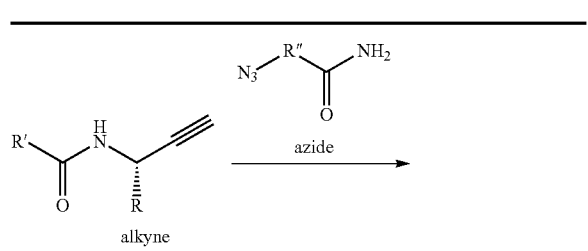

alkyne

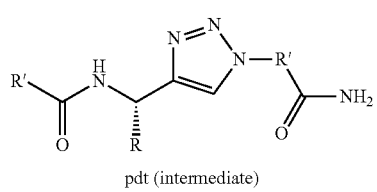

pdt (intermediate)

| Intermediate | alkyne | azide | R | R' | R" |
|---|---|---|---|---|---|
| I-109 | I-091 | I-010 | cyclohexylmethyl | 1-morpholine | 1,1-cPr |
| I-110 | I-080 | I-010 | N-Cbz-piperidin-3-yl | 2-thiophene | 1,1-cPr |
| I-111 | I-096 | I-010 | isopropyl | 2-thiophene | 1,1-cPr |
| I-112 | I-081 | I-010 | benzyl | 2-thiophene | 1,1-cPr |
| I-113 | I-072 | I-010 | t-butyl | 2-thiophene | 1,1-cPr |
| I-114 | I-084 | I-010 | sec-butyl | 2-thiophene | 1,1-cPr |
| I-115 | I-075 | I-010 | tetrahydropyran-3-yl | 2-thiophene | 1,1-cPr |
| I-116 | I-074 | I-007 | tetrahydropyran-2-yl | 2-thiophene | R-CH(Me)— |
| I-117 | I-025 | I-007 | tetrahydropyran-3-yl | 2-thiophene | R-CH(Me)— |
| I-118 | I-077 | I-010 | 3-methoxycyclohexyl | 2-thiophene | 1,1-cPr |
| I-119 | I-077 | I-007 | 3-methoxycyclohexyl | 2-thiophene | R-CH(Me)— |
| I-120 | I-074 | I-010 | tetrahydropyran-2-yl | 2-thiophene | 1,1-cPr |
| I-121 | I-078 | I-010 | isobutyl | 2-thiophene | 1,1-cPr |
| I-122 | I-079 | I-010 | 2-phenylethyl | 2-thiophene | 1,1-cPr |
| I-123 | I-083 | I-010 | 3-pentyl | 2-thiophene | 1,1-cPr |

Synthesis of I-124

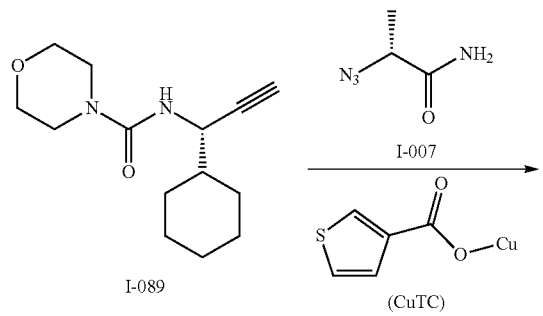

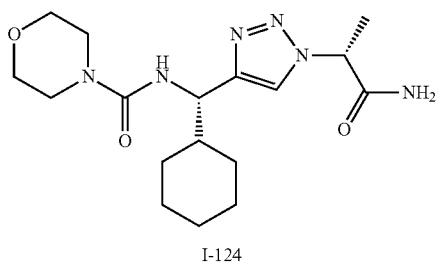

I-124

A mixture of I-089 (0.17 g, 0.68 mmol), I-007 (0.10 g, 0.88 mmol), CuTC (39 mg. 0.20 mmol), 2,6-lutidine (0.16 mL, 1.4 mmol), and CHCl$_3$ (5 mL) is stirred for 2 h at 40 C. MeOH (10 mL) is added, the mixture is cooled to rt, filtered, and the filtrate is concentrated. The resulting residue is washed with MeCN and dried to provide I-124 as a solid.

Synthesis of I-125

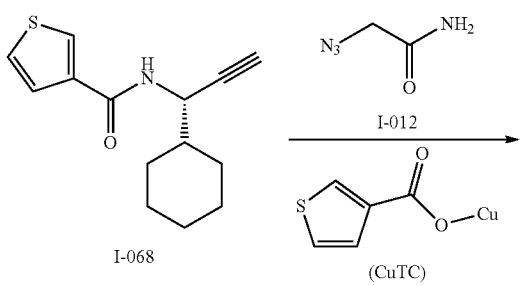

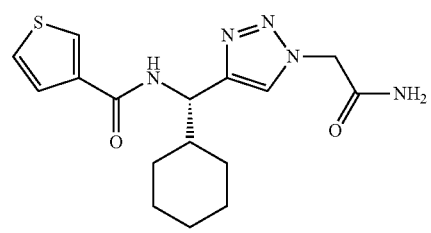

I-125

A mixture of I-068 (0.20 g, 0.81 mmol), I-012 (0.16 g, 1.6 mmol), CuTC (46 mg. 0.24 mmol), 2,6-lutidine (0.19 mL, 1.6 mmol), and CHCl$_3$ (5 mL) is stirred for 4 h at 40 C. MeOH (10 mL) is added, the mixture is cooled to rt, filtered, and the filtrate is concentrated. The resulting residue is washed with MeCN and dried to provide I-125 as a solid.

The following compounds are prepared from the appropriate alkyne in the same manner as I-124 and I-125.

Synthesis of I-133

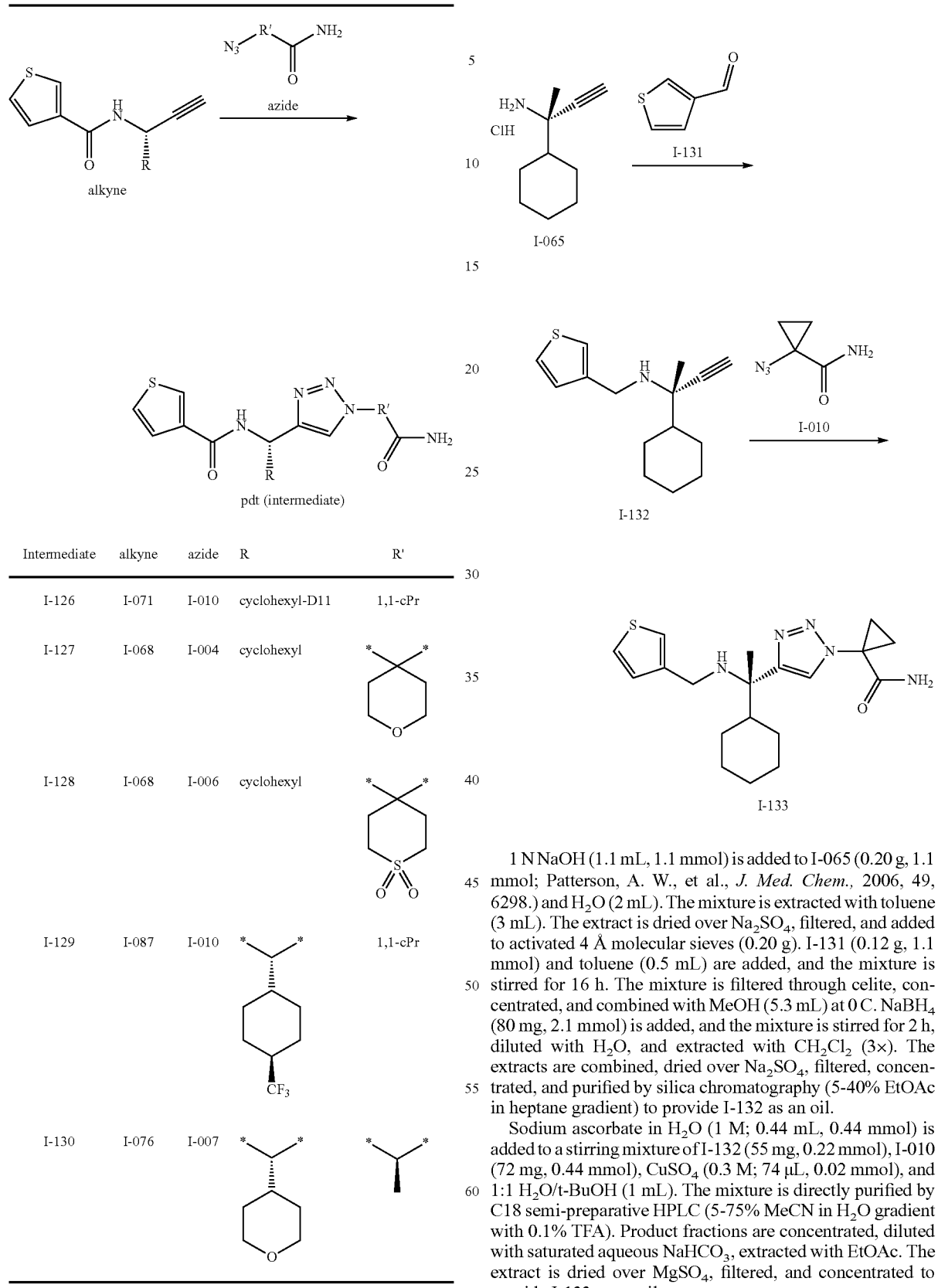

| Intermediate | alkyne | azide | R | R' |
|---|---|---|---|---|
| I-126 | I-071 | I-010 | cyclohexyl-D11 | 1,1-cPr |
| I-127 | I-068 | I-004 | cyclohexyl | 4-tetrahydropyranyl |
| I-128 | I-068 | I-006 | cyclohexyl | 4-tetrahydrothiopyranyl-1,1-dioxide |
| I-129 | I-087 | I-010 | 4-CF3-cyclohexyl | 1,1-cPr |
| I-130 | I-076 | I-007 | 4-tetrahydropyranyl | iPr |

1 N NaOH (1.1 mL, 1.1 mmol) is added to I-065 (0.20 g, 1.1 mmol; Patterson, A. W., et al., *J. Med. Chem.*, 2006, 49, 6298.) and $H_2O$ (2 mL). The mixture is extracted with toluene (3 mL). The extract is dried over $Na_2SO_4$, filtered, and added to activated 4 Å molecular sieves (0.20 g). I-131 (0.12 g, 1.1 mmol) and toluene (0.5 mL) are added, and the mixture is stirred for 16 h. The mixture is filtered through celite, concentrated, and combined with MeOH (5.3 mL) at 0 C. $NaBH_4$ (80 mg, 2.1 mmol) is added, and the mixture is stirred for 2 h, diluted with $H_2O$, and extracted with $CH_2Cl_2$ (3×). The extracts are combined, dried over $Na_2SO_4$, filtered, concentrated, and purified by silica chromatography (5-40% EtOAc in heptane gradient) to provide I-132 as an oil.

Sodium ascorbate in $H_2O$ (1 M; 0.44 mL, 0.44 mmol) is added to a stirring mixture of I-132 (55 mg, 0.22 mmol), I-010 (72 mg, 0.44 mmol), $CuSO_4$ (0.3 M; 74 µL, 0.02 mmol), and 1:1 $H_2O$/t-BuOH (1 mL). The mixture is directly purified by C18 semi-preparative HPLC (5-75% MeCN in $H_2O$ gradient with 0.1% TFA). Product fractions are concentrated, diluted with saturated aqueous $NaHCO_3$, extracted with EtOAc. The extract is dried over $MgSO_4$, filtered, and concentrated to provide I-133 as an oil.

The following intermediates are prepared with the appropriate aldehydes in the same manner as I-133.

Na$_2$SO$_4$, filtered, concentrated, and purified by silica chromatography (5-50% EtOAc in heptane gradient) to provide I-137 as an oil.

Sodium ascorbate in H$_2$O (1 M; 0.86 mL, 0.86 mmol) is added to a stirring mixture of I-137 (100 mg, 0.43 mmol), I-010 (80 mg, 0.63 mmol), CuSO$_4$ (0.3 M; 290 μL, 0.09 mmol), and 1:1 H$_2$O/t-BuOH (2.1 mL). The mixture is stirred for 2 h, diluted with H$_2$O, and extracted with EtOAc (3×20 mL). The extracts are combined, washed with brine, dried over MgSO$_4$, filtered, concentrated, and purified by C18 semi-preparative HPLC (10-95% MeCN in H$_2$O gradient with 0.1% TFA) to provide I-138 as an oil.

The following intermediates are prepared with the appropriate aldehydes and propargyl amines in the same manner as I-138.

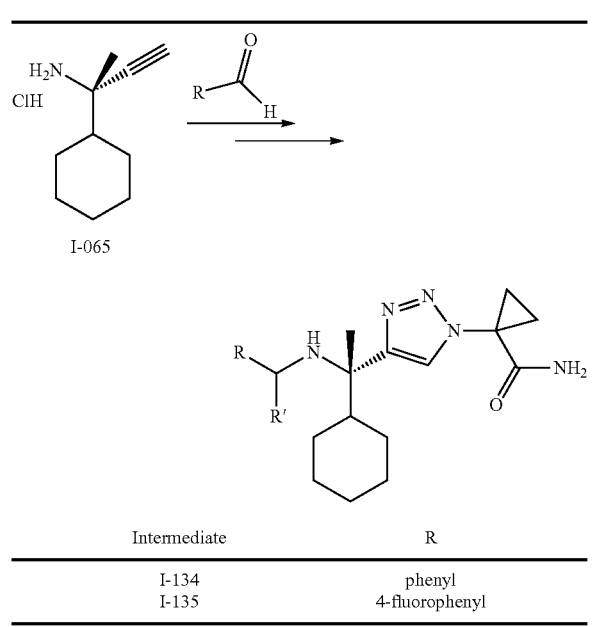

| Intermediate | R |
|---|---|
| I-134 | phenyl |
| I-135 | 4-fluorophenyl |

Synthesis of I-138

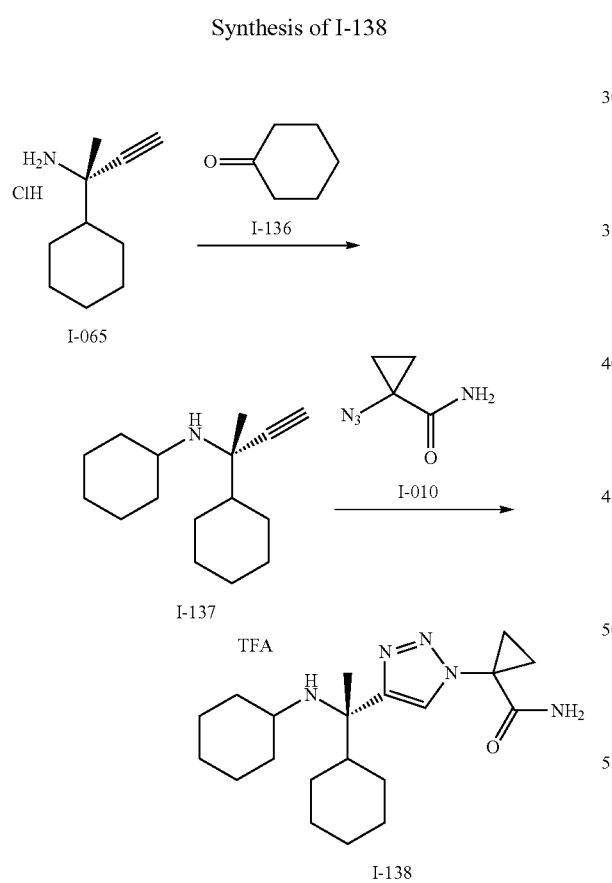

A mixture of I-065 (0.10 g, 0.53 mmol), I-136 (59 mg, 0.60 mmol), NaOAc (49 mg, 0.60 mmol), and ClCH$_2$CH$_2$Cl (3 mL) is stirred for 0.5 h. NaBH(OAc)$_3$ (0.25 g, 1.2 mmol) is added. The mixture is stirred for 16 h, washed with sat NaHCO$_3$, and extracted three times with CH$_2$Cl$_2$. The extracts are combined, washed with brine, dried over

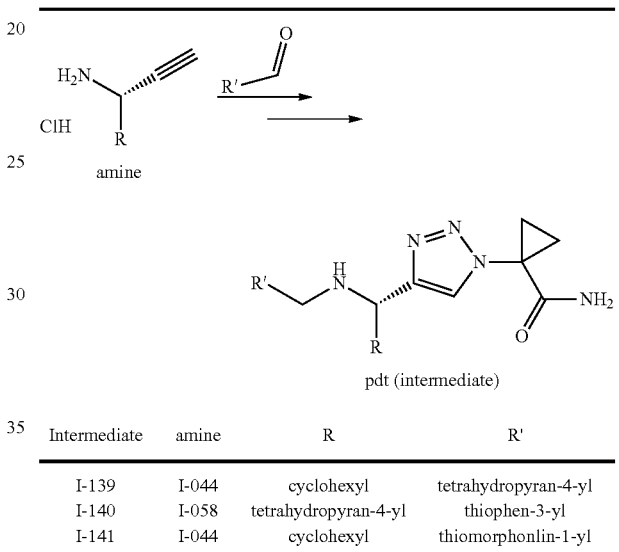

pdt (intermediate)

| Intermediate | amine | R | R' |
|---|---|---|---|
| I-139 | I-044 | cyclohexyl | tetrahydropyran-4-yl |
| I-140 | I-058 | tetrahydropyran-4-yl | thiophen-3-yl |
| I-141 | I-044 | cyclohexyl | thiomorphonlin-1-yl |

Synthesis of I-143

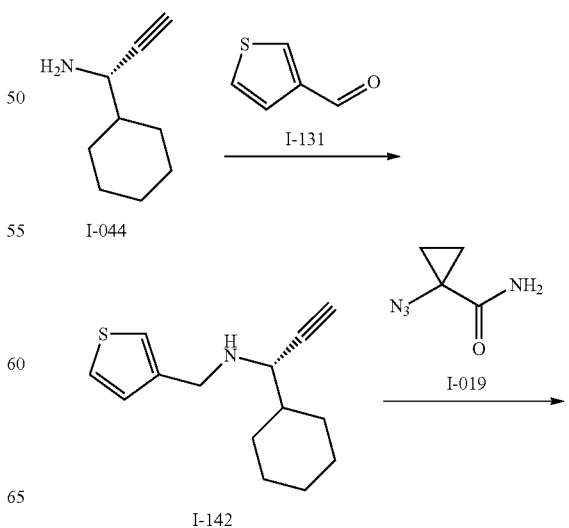

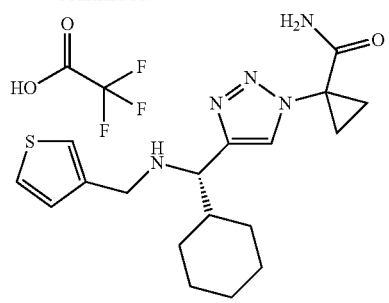

I-143

Activated 4 Å molecular sieves (0.10 g) is added to I-044 (79 mg, 0.57 mmol) and I-131 (70 mg, 0.63 mmol) and toluene (2.4 mL). The mixture is stirred for 16 h, filtered through celite, and concentrated. MeOH (2.6 mL) and then NaBH$_4$ (39 mg, 1.0 mmol) are added at 0 C, and the mixture is stirred for 2 h, diluted with H$_2$O, extracted with CH$_2$Cl$_2$ (3×). The extracts are combined, dried over Na$_2$SO$_4$, filtered, concentrated, and purified by silica chromatography (5-40% EtOAc in heptane gradient) to provide I-142 as an oil.

Sodium ascorbate (1 M; 0.86 mL, 0.86 mmol) is added to a stirring mixture of I-142 (0.10 g, 0.43 mmol), I-010 (80 mg, 0.63 mmol), 0.3 M CuSO$_4$ (0.29 mL, 0.09 mmol), and 1:1 H$_2$O/t-BuOH (2.1 mL). The mixture is stirred for 2 h and diluted with saturated aqueous NaHCO$_3$, then extracted with EtOAC (3×20 mL). The extracts are combined, dried over MgSO$_4$, filtered, concentrated, and purified by C18 semi-preparative HPLC (10-95% MeCN in H$_2$O gradient with 0.1% TFA) to provide I-143 as an oil.

Synthesis of I-145

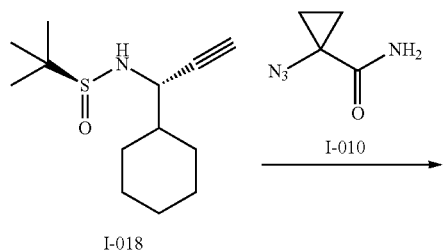

I-018

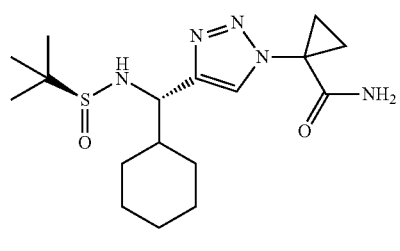

I-144

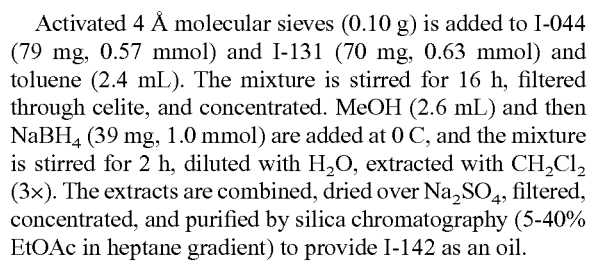

I-145

Sodium ascorbate (5.6 g, 28 mmol) in H$_2$O (39 mL) is added to a stirring mixture of I-018 (3.78 g, 14.1 mmol), I-010 (1.87 g, 14.8 mmol), 0.5 M CuSO$_4$ (2.82 mL, 1.41 mmol), and ethanol (43 mL). The mixture is stirred for 16 h, then concentrated, diluted with EtOAc (120 mL), and washed with aqueous NaHCO$_3$ (30 mL saturated solution diluted with 50 mL of H$_2$O). The EtOAc layer is washed with saturated aqueous NH$_4$Cl (20 mL) and brine (20 mL), dried over MgSO$_4$, filtered, and concentrated to provide I-144.

4M HCl in dioxane (7 mL, 28 mmol) is added to I-144 (5.85 g, 14.0 mmol) and MeOH (25 mL). The mixture is stirred for 1 h, concentrated, and triturated with 95:5 MTBE/iPrOH and MTBE to provide I-145 as a solid.

The following intermediates are prepared in the same manner as I-145.

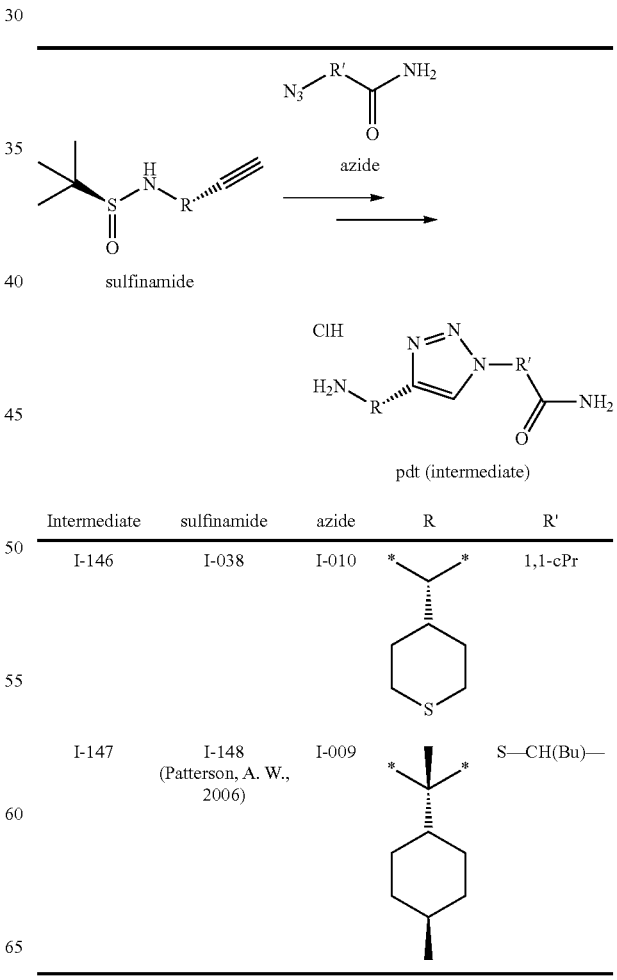

| Intermediate | sulfinamide | azide | R | R' |
|---|---|---|---|---|
| I-146 | I-038 | I-010 | ![tetrahydropyran] | 1,1-cPr |
| I-147 | I-148 (Patterson, A. W., 2006) | I-009 | ![cyclohexyl] | S—CH(Bu)— |

Synthesis of I-151

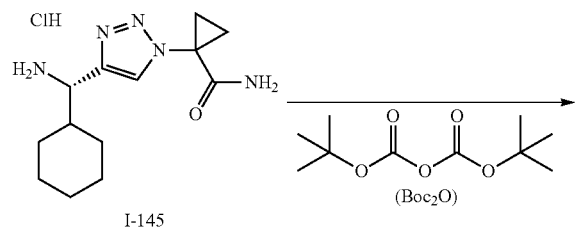

I-145      (Boc₂O)

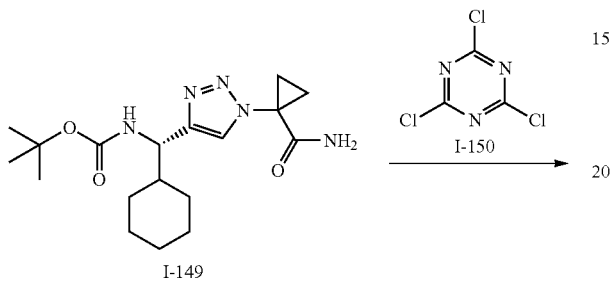

I-149      I-150

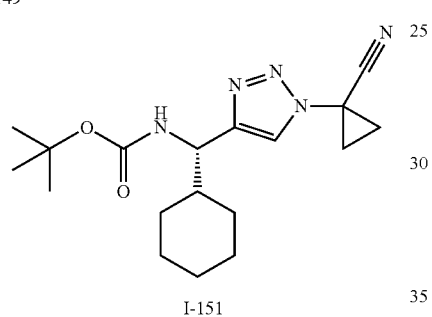

I-151

To I-145 (0.20 g, 0.67 mmol) in CH₂Cl₂ (2.2 mL) is added Et₃N (93 μL, 0.67 mmol) and Boc₂O (0.15 g, 0.67 mmol). The mixture is stirred for 1 h, diluted with CH₂Cl₂, washed with H₂O and brine, dried, and concentrated to provide I-149 as a solid.

I-150 (1.1 g, 6.1 mmol) is added to I-149 (2.2 g, 6.1 mmol) and DMF (20 mL). The mixture is stirred for 1 h, and diluted with saturated NaHCO₃. The aqueous phase is extracted with EtOAc (3×). The extracts are combined, washed with H₂O and brine, dried over Na₂SO₄, filtered, concentrated, and purified by silica chromatography (5-50% EtOAc in heptane gradient) to provide I-151 as a solid.

Synthesis of I-156

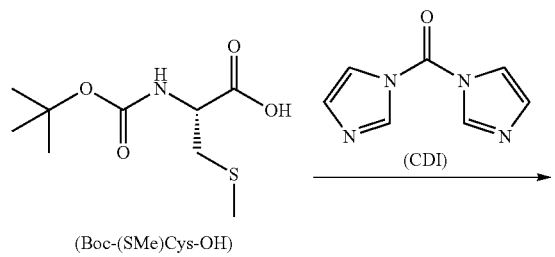

(Boc-(SMe)Cys-OH)      (CDI)

-continued

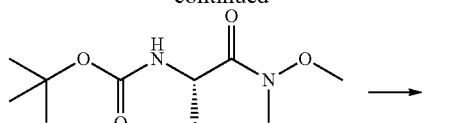

I-152

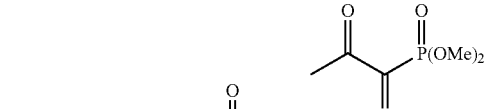

I-153      I-095

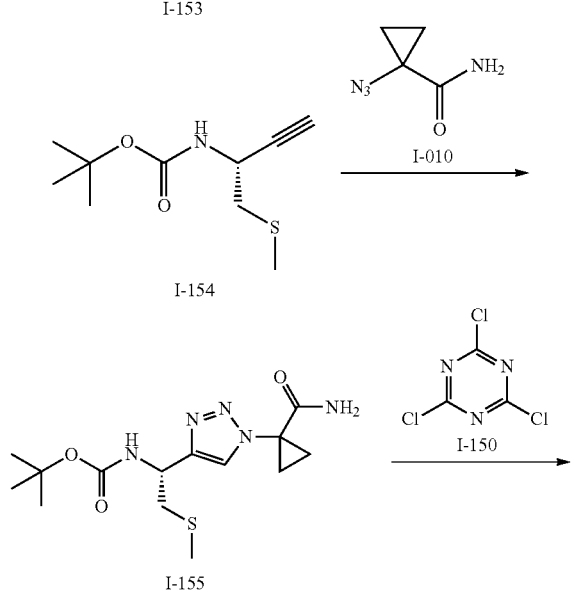

I-154

I-155      I-150

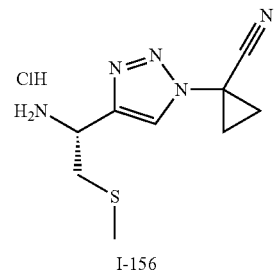

I-156

CDI (0.63 g, 3.9 mmol) is added to a mixture of Boc-(SMe) Cys-OH (0.83 g, 3.5 mmol), MeONHMe-HCl (0.38 g, 3.9 mmol), and CH₂Cl₂ (10 mL). The mixture is stirred overnight, washed with 1M NaHSO₄ and brine, dried over Na₂SO₄, filtered, concentrated and purified by silica chromatography (25-50% EtOAc in heptane gradient) to provide I-152 as an oil.

1M (iBu)₂AlH (5.2 mL, 5.2 mmol) is added slowly to I-152 (0.65 g, 2.3 mmol) and CH₂Cl₂ (10 mL) at -78 C. The mixture is stirred at -78 for 40 min, 1M NaHSO₄ (5 mL) is added, the mixture is warmed to rt, and CH₂Cl₂ (60 mL) and brine (10 mL) are added. The mixture is filtered through celite. The organic phase of the filtrate is dried over Na₂SO₄, filtered, and concentrated to provide I-153 as an oil.

I-095 (0.82 g, 4.3 mmol) is added to I-153 (0.48 g, 2.2 mmol), K$_2$CO$_3$ (0.90 g, 6.5 mmol), and MeOH (5 mL) at 0 C. The mixture is stirred at rt for 14 h and EtOAc (50 mL) is added. The mixture is washed with brine (10 mL), dried over Na$_2$SO$_4$, filtered, concentrated, and purified by silica chromatography (5-50% EtOAc in heptane gradient) to provide I-154 as an oil.

Sodium ascorbate (0.40 g, 2.0 mmol) and H$_2$O (5 mL) is added to a stirring mixture of I-154 (0.21 g, 0.98 mmol), I-010 (0.15 g, 1.2 mmol), 0.3 M CuSO$_4$ (0.35 mL, 0.11 mmol), and EtOH (5 mL). The mixture is stirred for 12 h, concentrated, and diluted with EtOAc (60 mL). The mixture is washed with brine, dried over Na$_2$SO$_4$, filtered, concentrated, and purified by silica chromatography (0-8% MeOH in CH$_2$Cl$_2$ gradient) to provide I-155 as a solid.

I-150 (86 mg, 0.47 mmol) is added to I-155 (0.16 g, 0.47 mmol) and DMF (2 mL) at 0 C. The mixture is stirred for 14 h, and diluted with EtOAc (40 mL). The mixture is washed with brine, dried over Na$_2$SO$_4$, filtered, concentrated, and purified by silica chromatography (2-10% MeOH in CH$_2$Cl$_2$ gradient). The resulting material is stirred in 4.0 M HCl in dioxane (0.5 mL) for 1 h, then concentrated and triturated with MTBE to provide I-156 as a solid.

Synthesis of I-157

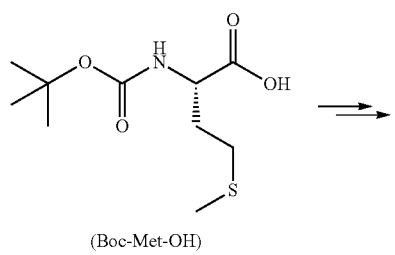

(Boc-Met-OH)

I-157 is prepared from Boc-Met-OH in the same manner as I-156.

Synthesis of I-158

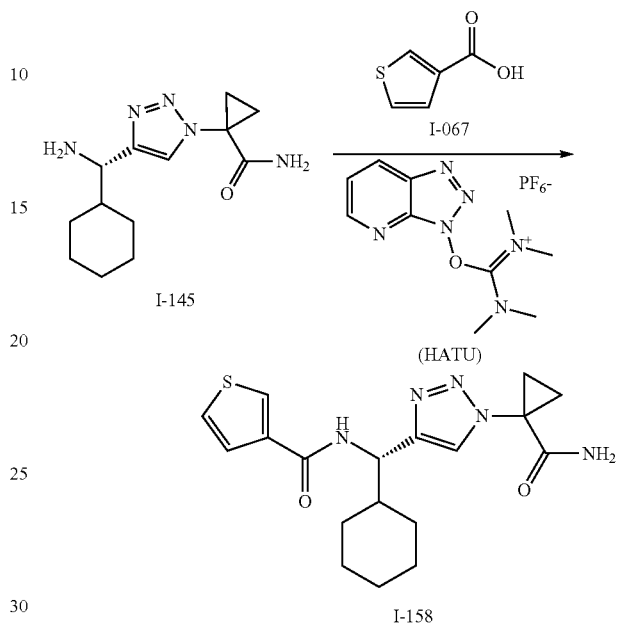

A mixture of I-145 (36 mg, 0.14 mmol), I-067 (20 mg, 0.16 mmol), Et$_3$N (0.05 mL, 0.4 mmol), HATU (75 mg, 0.20 mmol), and DMF (1 mL) is stirred for 3 days, then diluted with EtOAc (30 mL) and washed with H$_2$O (20 mL) and brine (25 mL). The extract is dried over Na$_2$SO$_4$, filtered, concentrated, and purified by silica chromatography (20-100% EtOAc in heptane) to provide I-158.

The following intermediates are prepared in the same manner as I-158.

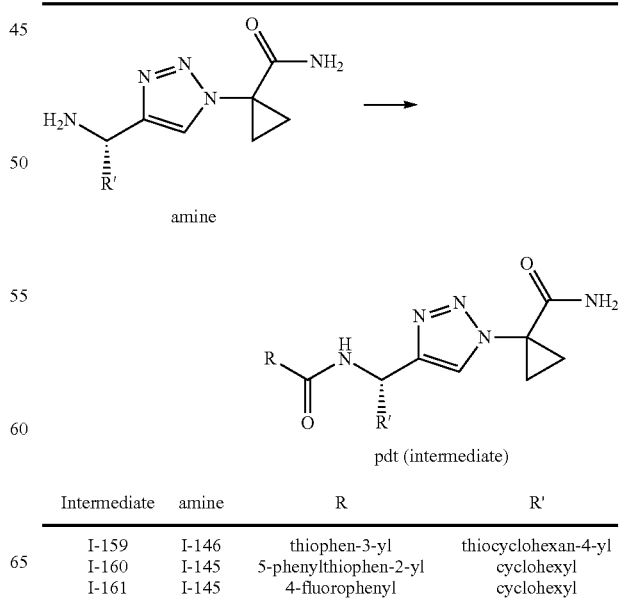

| Intermediate | amine | R | R' |
|---|---|---|---|
| I-159 | I-146 | thiophen-3-yl | thiocyclohexan-4-yl |
| I-160 | I-145 | 5-phenylthiophen-2-yl | cyclohexyl |
| I-161 | I-145 | 4-fluorophenyl | cyclohexyl |

-continued

| | | | |
|---|---|---|---|
| I-162 | I-145 | pyridon-5-yl | cyclohexyl |
| I-163 | I-145 | pyridon-3-yl | cyclohexyl |
| I-164 | I-145 | 6-oxopiperidin-3-yl | cyclohexyl |

Synthesis of I-165

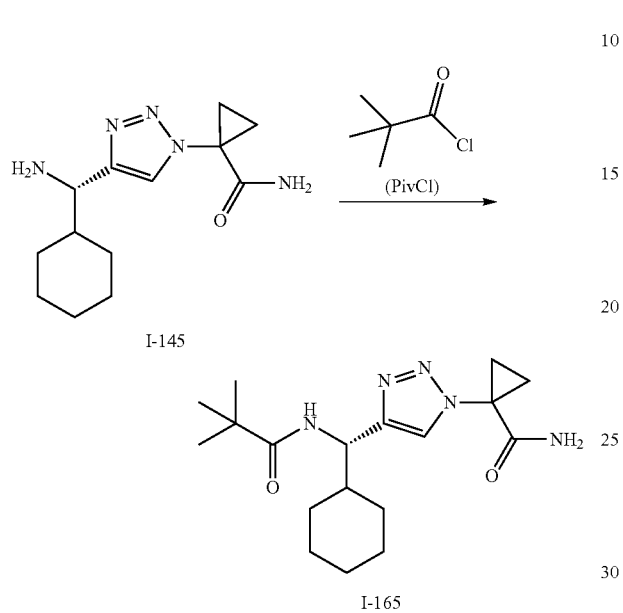

PivCl (45 µL, 0.37 mmol) is added to I-145 (0.10 g, 0.33 mmol), Et₃N (0.14 mL, 1.0 mmol), and THF (1.7 mL). The mixture is stirred for 4 h, concentrated, and purified by C18 semi-preparative HPLC (5-95% MeCN in H₂O gradient with 0.1% TFA) to provide I-165 as a solid.

Synthesis of I-166

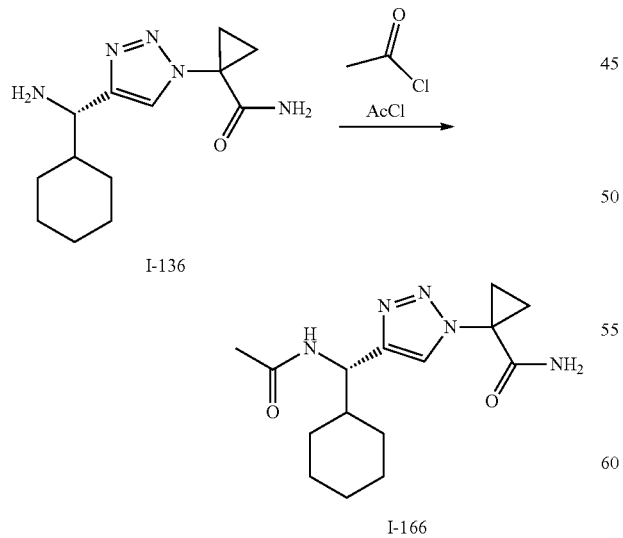

AcCl (30 µL, 0.37 mmol) is added to I-145 (0.10 g, 0.33 mmol), Et₃N (0.14 mL, 1.0 mmol), and THF (1.7 mL). The mixture is stirred for 4 h, concentrated, and purified by C18 semi-preparative HPLC (5-95% MeCN in H₂O gradient with 0.1% TFA) to provide I-166 as a solid.

Synthesis of I-168

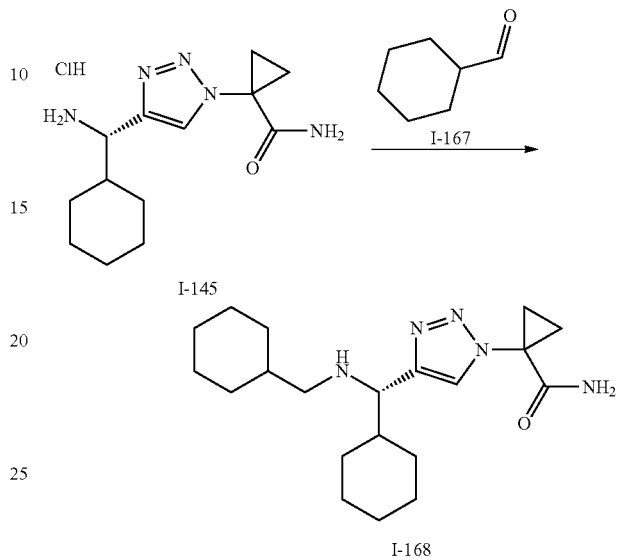

A mixture of I-145 (50 mg, 0.17 mmol), I-167 (19 mg, 0.17 mmol), NaOAc (14 mg, 0.17 mmol), HOAc (50 µL), and ClCH₂CH₂Cl (5 mL) is stirred for 0.5 h. NaBH(OAc)₃ (68 mg, 0.32 mmol) is added. The mixture is stirred for 1 h, washed with sat NaHCO₃, and extracted three times with CH₂Cl₂. The extracts are combined, washed with brine, dried over Na₂SO₄, filtered, concentrated, and purified by silica chromatography (0-30% EtOAc in heptane gradient) to provide I-168 as a solid.

The following intermediates are prepared from the appropriate amines and carbonyl compounds in the same manner as I-168.

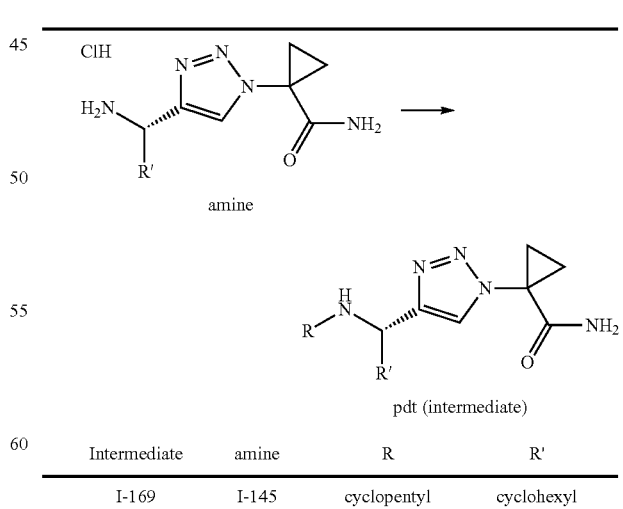

| Intermediate | amine | R | R' |
|---|---|---|---|
| I-169 | I-145 | cyclopentyl | cyclohexyl |
| I-170 | I-145 | cylclohexane | cyclohexyl |
| I-171 | I-145 | cycloheptyl | cyclohexyl |
| I-172 | I-145 | benzyl | cyclohexyl |
| I-173 | I-145 | 4-fluorobenzyl | cyclohexyl |

Synthesis of I-175

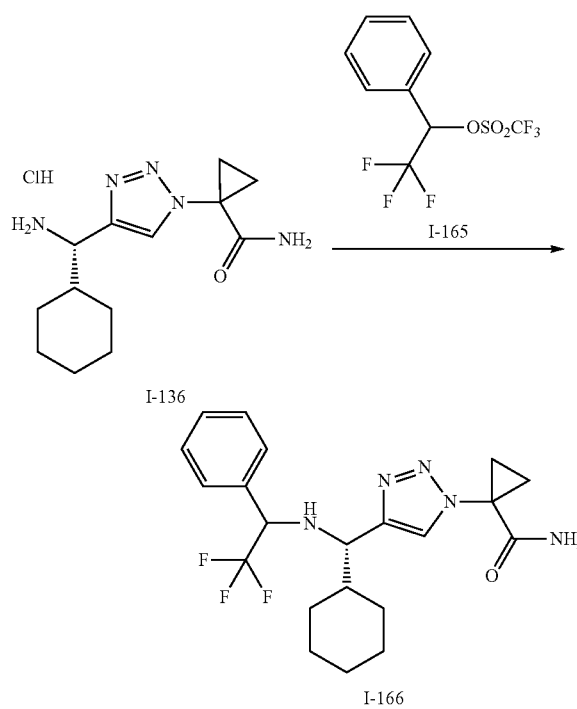

I-174 (0.16 g, 0.50 mmol) is added to I-145 (0.10 g, 0.33 mmol), iPr₂NEt (0.20 mL, 1.2 mmol), and THF (2 mL). The mixture is stirred at 60 C for 4 h. EtOAc (40 mL) is added, and the mixture is washed with 0.5 N HCl (15 mL), saturated aqueous NaHCO₃, and brine. The extract is dried over Na₂SO₄, filtered, concentrated, and purified by silica chromatography (1-10% MeOH in CH₂Cl₂ gradient) to provide I-175 as a mixture of diastereomers.

Synthesis of I-176

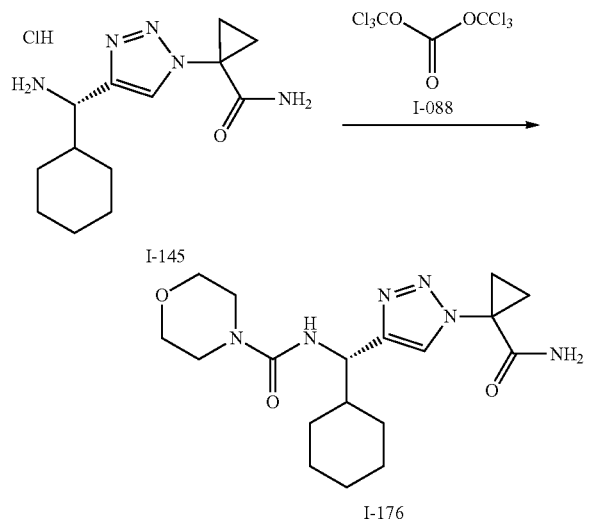

A mixture of I-145 (70 mg, 0.23 mmol) and iPr₂NEt (0.16 mL, 1.0 mmol) is added to I-088 (26 mg, 0.09 mmol) and CH₂Cl₂ (2 mL). The mixture is stirred for 30 min, morpholine (26 mg, 0.30 mmol) is added, and the resulting mixture is stirred overnight, diluted with EtOAc (40 mL), and washed with brine. The extract is dried over Na₂SO₄, filtered, concentrated, and purified by silica chromatography (2-10% MeOH in CH₂Cl₂ gradient) to provide I-176 as a solid.

The following intermediates are prepared from the designated amines and the appropriate amines R in the same manner as I-176.

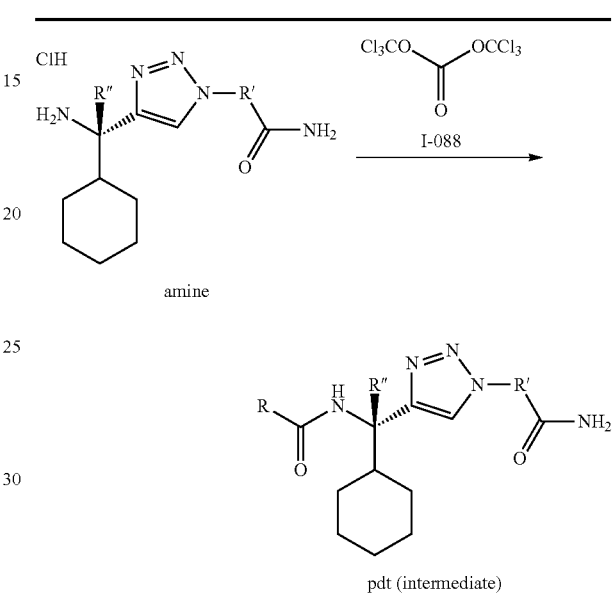

| Intermediate | amine | R | R' | R'' |
|---|---|---|---|---|
| I-177 | I-145 | 1-dioxthiomorpholine | 1,1-cPr | H |
| I-178 | I-145 | 1-piperidine | 1,1-cPr | H |
| I-179 | I-147 | 1-morpholine | S—CH(Bu)— | Me |
| I-180 | I-147 | 1-(4-Me-piperidine) | S—CH(Bu)— | Me |
| I-181 | I-147 | Me₂N— | S—CH(Bu)— | Me |
| I-182 | I-147 | PhNH— | S—CH(Bu)— | Me |

Synthesis of I-183

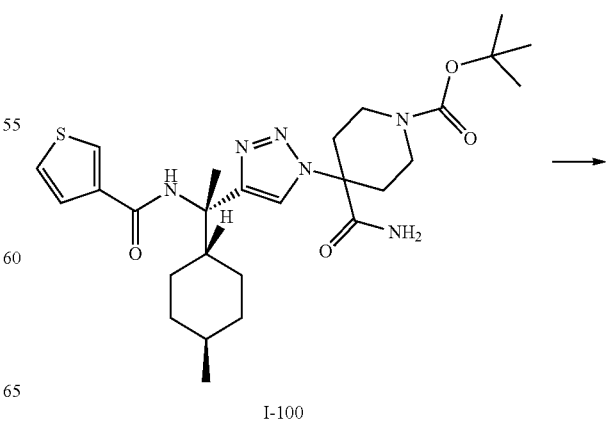

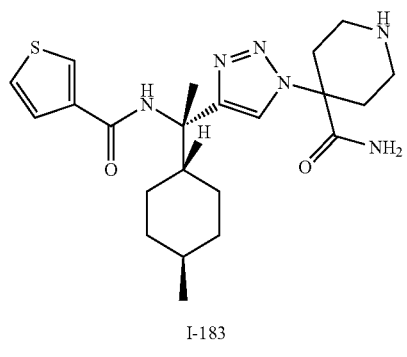

I-183

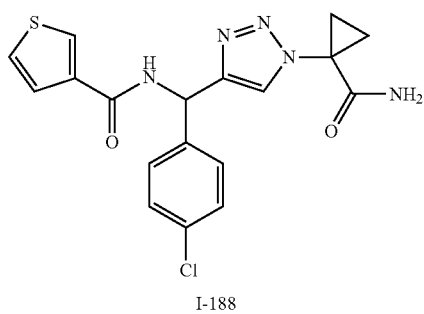

I-188

TFA (0.5 mL, 6.7 mmol) is added to I-100 (240 mg, 0.44 mmol) and CH$_2$Cl$_2$ (2 mL). The mixture is stirred for 72 h, concentrated, and purified directly by C18 semi-preparative HPLC (5-95% MeCN in H$_2$O gradient with 0.1% TFA). Product fractions are diluted with NaHCO$_3$ and extracted with EtOAc (3×30 mL). The extracts are combined, dried over MgSO$_4$, filtered, and concentrated to provide I-183 as a solid.

Synthesis of I-188

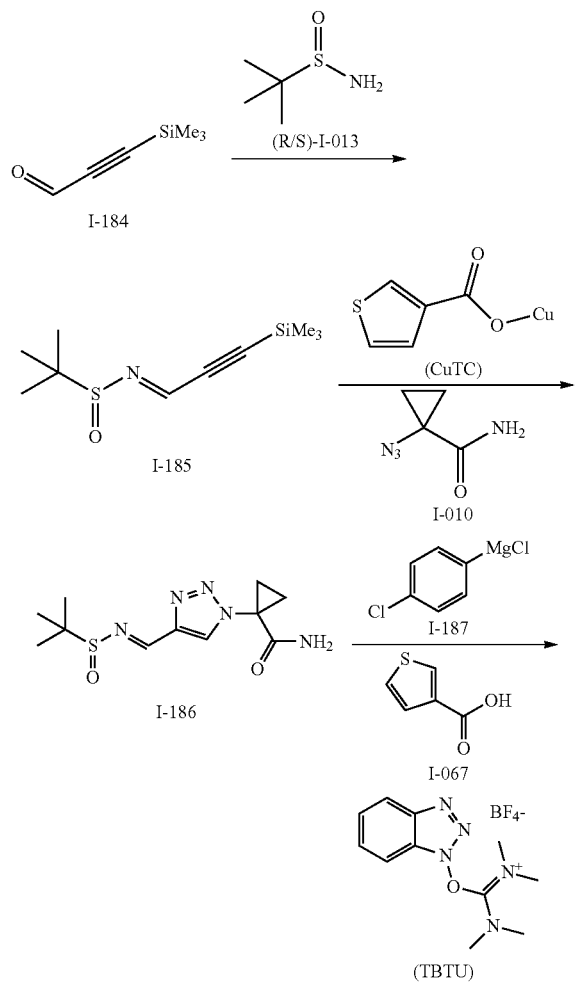

A mixture of I-184 (2.8 g, 22 mmol), Ti(OEt)$_4$ (7.7 mL, 26 mmol), (R/S)-I-013 (4.0 g, 33 mmol), and THF (100 mL) are stirred for 1 h. The mixture is poured into a stirring mixture of H$_2$O (100 mL) and EtOAc (100 mL). The resulting mixture is filtered through celite. The EtOAc phase is separated, dried, filtered, concentrated, mixed with CH$_2$Cl$_2$, filtered, and concentrated to provide I-185 as an oil.

2,6-Lutidine (0.91 mL, 7.9 mmol) is added to CuTC (0.22 g, 1.2 mmol) I-185 (0.90 g, 3.92 mmol), I-010 (0.64 g, 5.1 mmol), and CHCl$_3$ (10 mL). The mixture is stirred for 16 h at 40 C. The mixture is filtered, concentrated, and purified by silica chromatography (50-100% EtOAc in heptane gradient) to provide I-186.

1 M I-187 in THF (2.2 mL, 2.2 mmol) is added to I-186 (0.20 g, 0.72 mmol) and THF (5 mL). After stirring for 1 h, saturated aqueous NH$_4$Cl is added and the mixture is extracted with EtOAc. The extract is dried, filtered, concentrated, dissolved in CH$_2$Cl$_2$, filtered, and concentrated. The resulting residue is combined with MeOH (1 mL) and 4 M HCl in dioxane (1 mL) is added. The resulting mixture is combined with DMF (3 mL) and added to Et$_3$N (0.30 mL, 2.2 mmol), I-067 (0.11 g, 0.86 mmol), and TBTU (0.25 g, 0.79 mmol). The mixture is stirred for 2 h, diluted with MeOH and purified by C18 semi-preparative HPLC (5-100% MeCN in H$_2$O gradient with 0.1% TFA) to provide I-188 as a solid.

The following intermediates are prepared using I-186 and the appropriate Grignard reagent (RMgX) in the same manner as I-188.

| Intermediate | R |
|---|---|
| I-189 | 3,4-difluorophenyl |
| I-190 | phenyl |
| I-191 | 4-fluorophenyl |

Synthesis of I-193

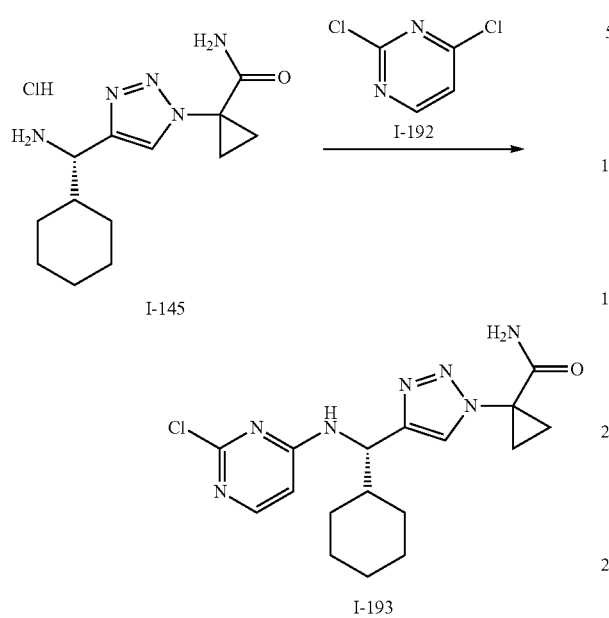

A mixture of I-192 (49 mg, 0.33 mmol), I-145 (99 mg, 0.33 mmol), iPr$_2$NEt (0.2 mL), and DMF (2.0 mL) is stirred at 75 C for 6 h. The mixture is directly purified by C18 semi-preparative HPLC (10-95% MeCN in H$_2$O gradient with 0.1% TFA) to provide I-193 as a solid.

Synthesis of I-195

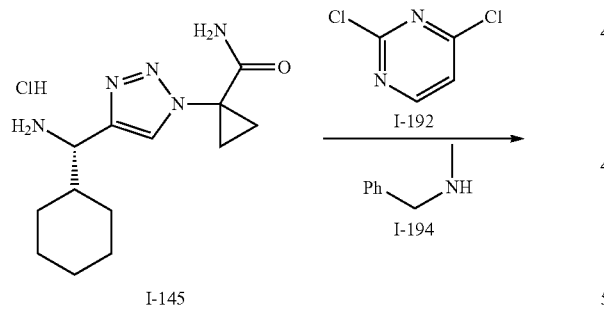

A mixture of I-192 (49 mg, 0.33 mmol), I-145 (99 mg, 0.33 mmol), iPr$_2$NEt (0.2 mL), and DMF (2.0 mL) is stirred at 75 C for 6 h. I-194 (48 mg, 0.40 mmol) is added and the mixture is stirred at 150 C for 4 h. The mixture is directly purified by C18 semi-preparative HPLC (10-95% MeCN in H$_2$O gradient with 0.1% TFA) to provide I-195 as a solid.

The following intermediates are used in the preparation of the Examples.

Example 1

Synthesis of C-001

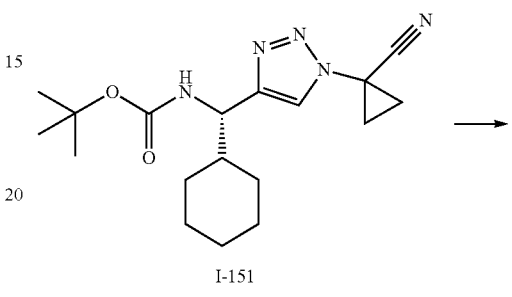

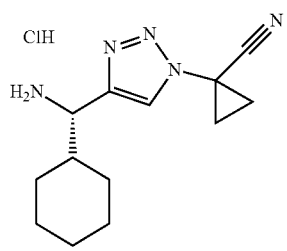

4M HCl in dioxane (3.6 mL, 14 mmol) is added to I-151 (1.7 g, 4.8 mmol) and CH$_2$Cl$_2$ (3.5 mL). The mixture is stirred for 1 h, concentrated, and triturated with MTBE to provide C-001 as a solid.

Example 2

Synthesis of C-002

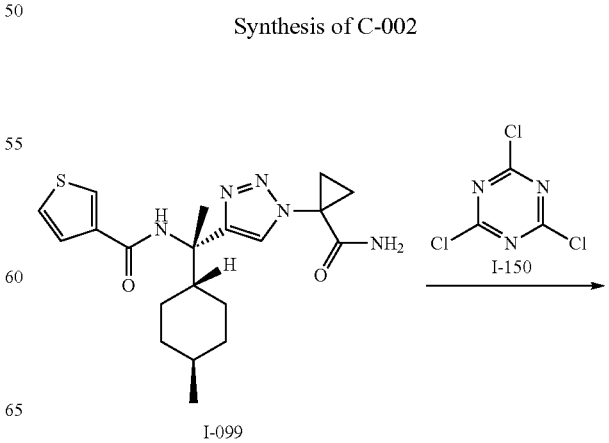

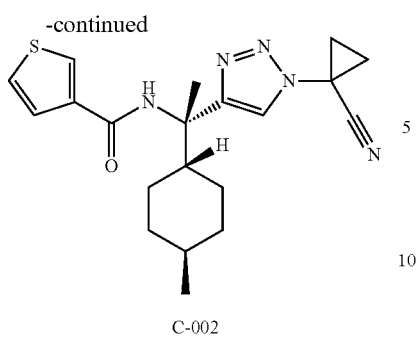

C-002

I-150 (70 mg, 0.38 mmol) is added to I-099 (220 mg, 0.55 mmol) and DMF (2 mL) at 0 C. The mixture is stirred at 0 C for 1 h then at rt for 16 h. I-150 (70 mg, 0.38 mmol) is added and the mixture is stirred for 24 h. I-150 (70 mg, 0.38 mmol) is added and the mixture is stirred overnight, cooled to 5 C, and H$_2$O (5 mL) is added. The mixture is extracted with EtOAc (3×5 mL). The extracts are combined, washed with brine, dried over Na$_2$SO$_4$, filtered, and concentrated, then purified by C18 semi-preparative HPLC (5-95% MeCN in H$_2$O gradient with 0.1% TFA) provide C-002 as a solid.

Example 3

Synthesis of C-003

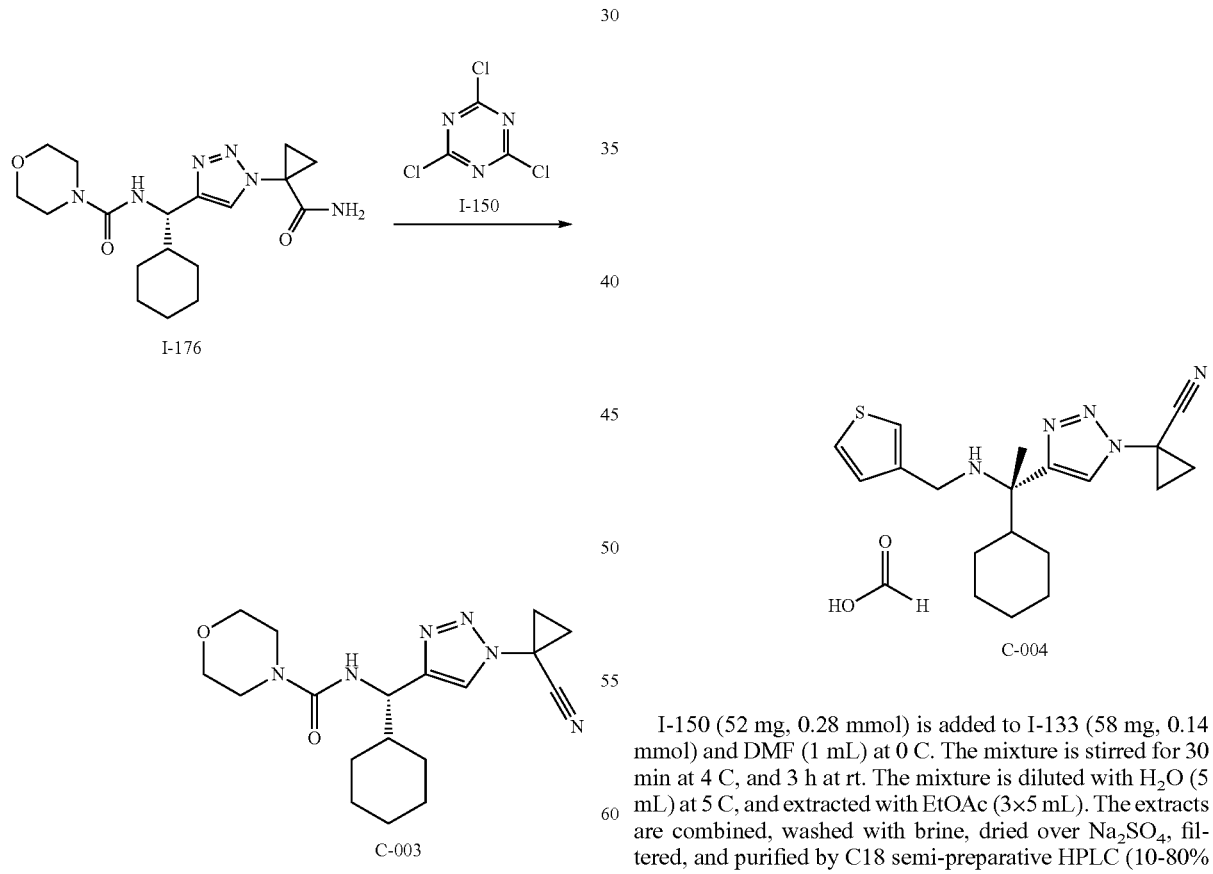

I-150 (16 mg, 0.09 mmol) is added to I-176 (32 mg, 0.09 mmol) and DMF (1 mL). The mixture is stirred for 14 h, diluted with EtOAc (40 mL), washed with saturated aqueous NaHCO$_3$ and brine. The extract is dried over Na$_2$SO$_4$, concentrated, and purified by silica chromatography (2-10% MeOH with 0.5% NH$_4$OH in CH$_2$Cl$_2$ gradient) to provide C-003 as a solid.

Example 4

Synthesis of C-004

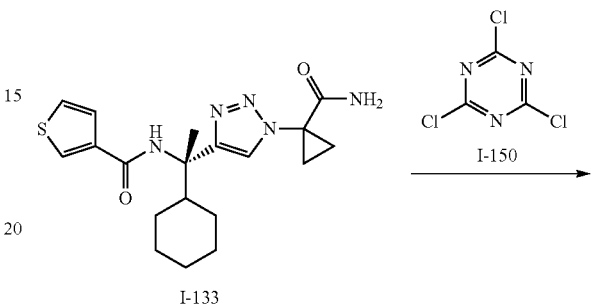

I-150 (52 mg, 0.28 mmol) is added to I-133 (58 mg, 0.14 mmol) and DMF (1 mL) at 0 C. The mixture is stirred for 30 min at 4 C, and 3 h at rt. The mixture is diluted with H$_2$O (5 mL) at 5 C, and extracted with EtOAc (3×5 mL). The extracts are combined, washed with brine, dried over Na$_2$SO$_4$, filtered, and purified by C18 semi-preparative HPLC (10-80% MeCN in H$_2$O gradient with 0.1% HCO$_2$H) to provide C-004 as a solid.

The following Examples are prepared via dehydration of the appropriate amide in the same manner as C-002, C-003, C-004.

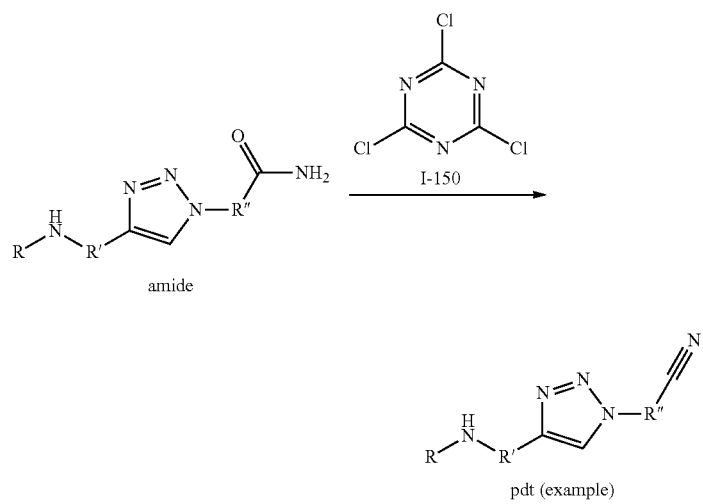
| Example | Amide | R | R' | R" |
|---|---|---|---|---|
| C-005 | I-104 | thiophen-3-yl-C(O)-* | *-CH(CH3)-CH2-cyclohexyl | *-cyclopropyl |
| C-006 | I-161 | 4-F-C6H4-C(O)-* | *-CH(*)-cyclohexyl | *-cyclopropyl |
| C-007 | I-111 | thiophen-3-yl-C(O)-* | *-CH(*)-CH(CH3)2 | *-cyclopropyl |
| C-008 | I-105 | thiophen-3-yl-C(O)-* | *-CH(*)-tetrahydropyran-4-yl | *-cyclopropyl |
| C-009 | I-106 | thiophen-3-yl-C(O)-* | *-CH(*)-cyclopropyl | *-cyclopropyl |
| C-010 | I-101 | thiophen-3-yl-C(O)-* | *-CH(*)-cyclohexyl | *-CH(*)-Bu |

-continued
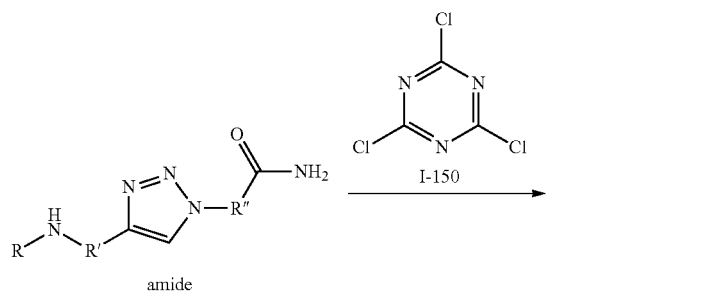
amide
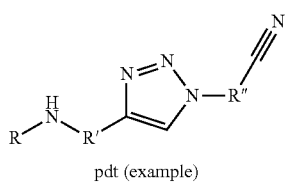
pdt (example)
| Example | Amide | R | R' | R" |
|---|---|---|---|---|
| C-011 | I-179 | morpholine-C(O)-* | *-C(CH₃)₂-cyclohexyl | *-CH(Bu)-* |
| C-012 | I-180 | 4-methylpiperazine-C(O)-* | *-C(CH₃)₂-cyclohexyl | *-CH(Bu)-* |
| C-013 | I-181 | (CH₃)₂N-C(O)-* | *-C(CH₃)₂-cyclohexyl | *-CH(Bu)-* |
| C-014 | I-182 | PhNH-C(O)-* | *-C(CH₃)₂-cyclohexyl | *-CH(Bu)-* |
| C-015 | I-110 | 3-thienyl-C(O)-* | *-CH(CH₃)-(3-NCbz-piperidinyl) | *-cyclopropyl |
| C-016 | I-112 | 3-thienyl-C(O)-* | *-CH(CH₃)-CH₂-Ph | *-cyclopropyl |

-continued
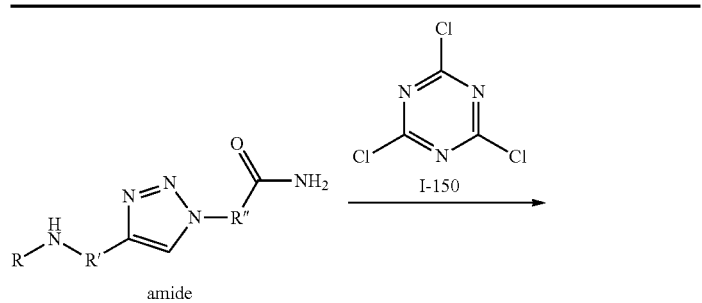
amide
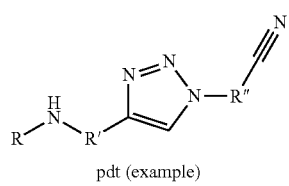
pdt (example)
| Example | Amide | R | R' | R'' |
|---|---|---|---|---|
| C-017 | I-134 | benzyl | 1-cyclohexyl-1-methyl | cyclopropyl |
| C-018 | I-135 | 4-fluorobenzyl | 1-cyclohexyl-1-methyl | cyclopropyl |
| C-019 | I-138 | cyclohexyl | 1-cyclohexyl-1-methyl | cyclopropyl |
Example 5
Synthesis of C-020
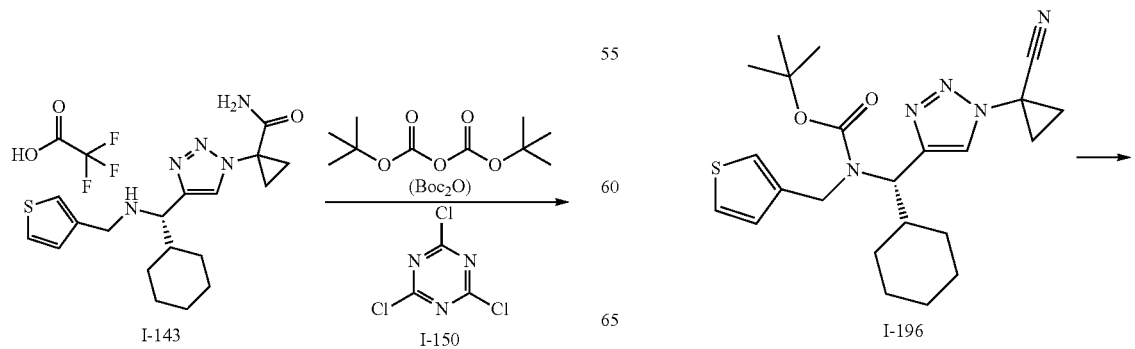

-continued

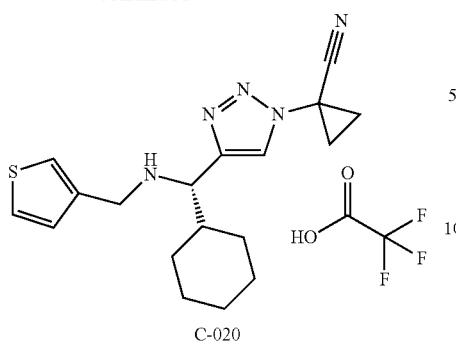

C-020

Boc₂O (33 mg, 0.15 mmol) is added to I-143 (55 mg, 0.12 mmol), Et₃N (27 μL, 0.20 mmol), and CH₂Cl₂ (0.5 mL). The mixture is stirred for 1 h, CH₂Cl₂ is added and the mixture is washed with H₂O and brine, dried, filtered, and concentrated. To this residue and DMF (1 mL) is added I-150 (18 mg, 0.10 mmol). The mixture is stirred for 1 h, and then is diluted with EtOAc and saturated aqueous NaHCO₃ (1 mL). The mixture is stirred for 15 min, then extracted with EtOAc (3×). The extracts are combined, washed with H₂O and brine, dried over Na₂SO₄, filtered, and concentrated to provide I-196 as a solid.

4N HCl in dioxane (0.14 mL, 0.56 mmol) is added to I-196 (43 mg, 0.10 mmol) and CH₂Cl₂ (0.5 mL). The mixture is stirred at rt for 2 h, at 4 C for 60 h, and at rt for 2 h. The mixture is directly purified by C18 semi-preparative HPLC (5-75% MeCN in H₂O gradient with 0.1% TFA) provide C-020 as a solid The following Examples are prepared from the appropriate intermediates in the same manner as C-020.

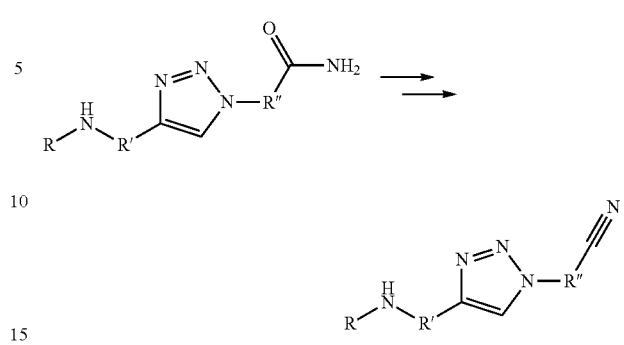

Example 6

Synthesis of C-029

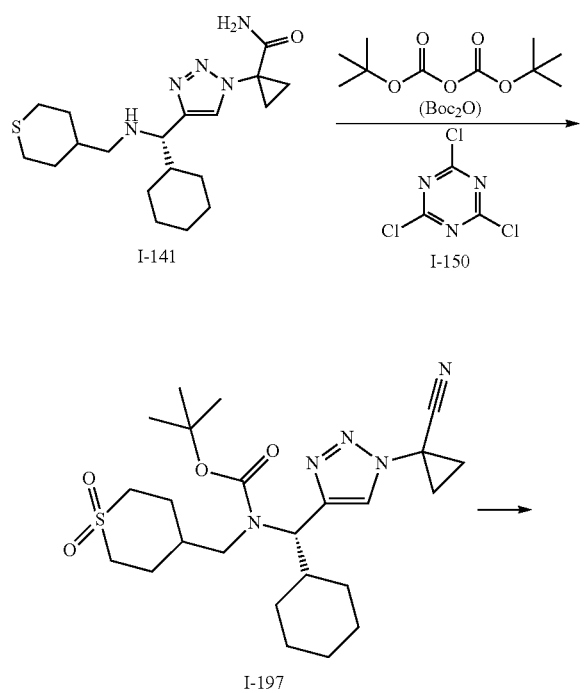

Boc₂O (57 mg, 0.26 mmol) is added to I-141 (97 mg, 0.26 mmol), Et₃N (42 μL, 0.30 mmol), and CH₂Cl₂ (0.9 mL). The mixture is stirred for 1 h, CH₂Cl₂ is added and the mixture is washed with H₂O and brine, dried, filtered, and concentrated. To this residue and THF (1 mL) is added oxone (0.20 g, 0.32 mmol). This mixture is stirred for 1 h and filtered and the solids washed with EtOAc. The filtrate is washed with 10% Na₂S₂O₃, water, and brined, then dried over Na₂SO₄, filtered, and concentrated. To this residue and DMF (1 mL) is added I-150 (22 mg, 0.12 mmol). The mixture is stirred for 1 h, and then is diluted with EtOAc and saturated aqueous NaHCO₃ (1 mL). The mixture is stirred for 15 min, then extracted with EtOAc (3×). The extracts are combined, washed with H₂O and brine, dried over Na₂SO₄, filtered, and concentrated to provide I-197 as a solid.

4N HCl in dioxane (0.090 mL, 0.36 mmol) is added to I-197 (57 mg, 0.10 mmol) and CH₂Cl₂ (0.5 mL). The mixture is stirred at rt for 2 h, at 4 C for 60 h, and at rt for 2 h. The mixture is directly purified by C18 semi-preparative HPLC (5-60% MeCN in H₂O gradient with 0.1% TFA) to provide C-029 as a solid

Example 7

Preparation of C-030

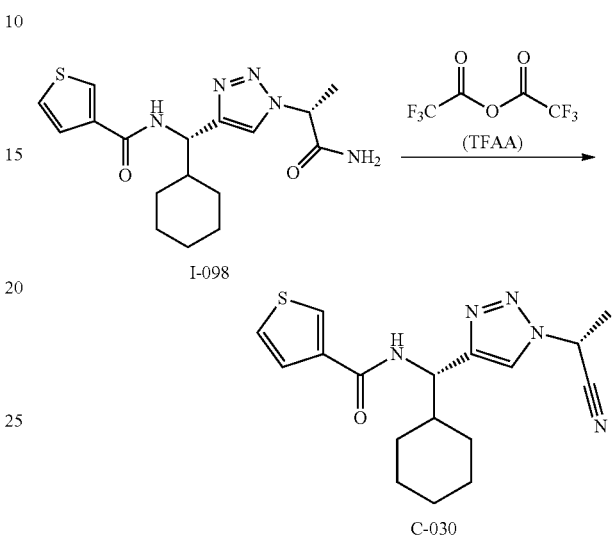

TFAA is added in three portions (each 15 μL; 0.11 mmol) to I-098 (36 mg, 0.10 mmol) and pyridine (0.5 mL). The mixture is stirred for 3.5 h. Direct purification by reverse phase C18 semi-preparative HPLC (5-95% MeCN in H₂O gradient with 0.1% TFA) provides C-030 as a solid.

Example 8

Synthesis of C-031

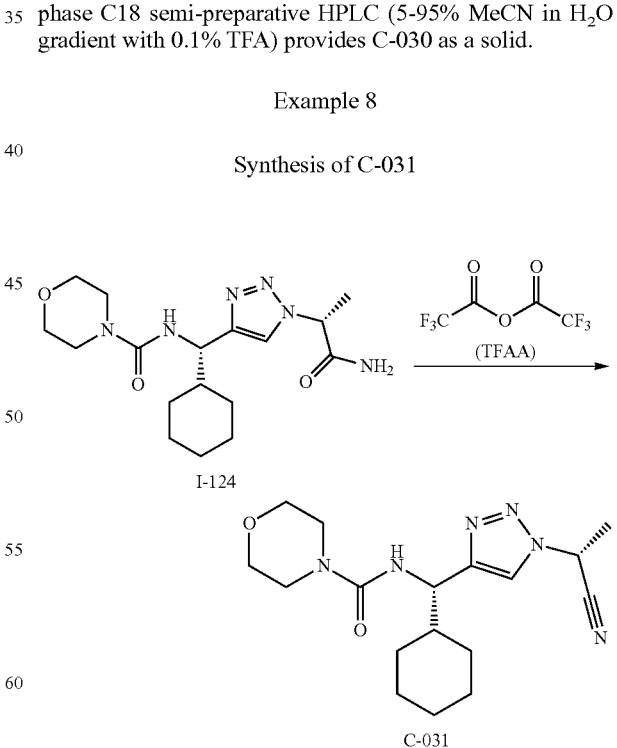

TFAA (42 μL, 0.30 mmol) is added to I-124 (210 mg, 0.52 mmol), and pyridine (1.4 mL). After 1 h, MeOH (1 mL) is added, and the mixture is directly purified by C18 semi-preparative HPLC (5-95% MeCN in H₂O gradient with 0.1% TFA) to provide C-031 as a solid.

Example 9

Synthesis of C-032

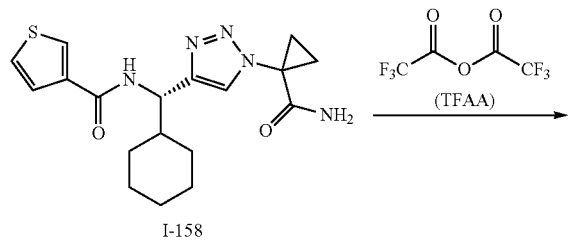

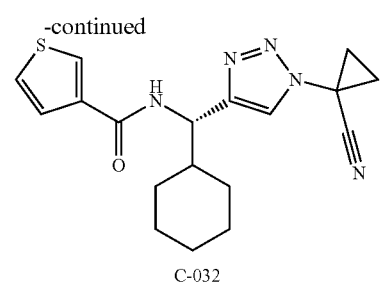

C-032

TFAA (17 μL; 0.12 mmol) is added in portions to a mixture of I-158 (39 mg, 0.10 mmol), THF (1 mL), and Et₃N (30 μL, 0.22 mmol). The mixture is stirred for 1 h. The mixture is diluted with EtOAc (40 mL), and washed with brine. The extract is dried over Na₂SO₄, filtered, concentrated, and purified by silica chromatography (10-70% EtOAc in heptane gradient) to provide C-032 as a solid.

The following Examples are prepared via dehydration of the appropriate amide in the same manner as C-030, C-031, and C-032.

| Example | Amide SM | R | R' | R" |
|---|---|---|---|---|
| C-033 | I-086 | 3-thienyl-C(O)- | cyclohexyl (gem) | cyclopropyl |
| C-034 | I-107 | 3-thienyl-C(O)- | cyclohexyl-CH- | cyclopropyl |
| C-035 | I-125 | 3-thienyl-C(O)- | cyclohexyl-CH- | CH-CH₃ |
| C-036 | I-166 | CH₃-C(O)- | cyclohexyl-CH- | cyclopropyl |
| C-037 | I-177 | 1,1-dioxo-thiomorpholin-4-yl-C(O)- | cyclohexyl-CH- | cyclopropyl |

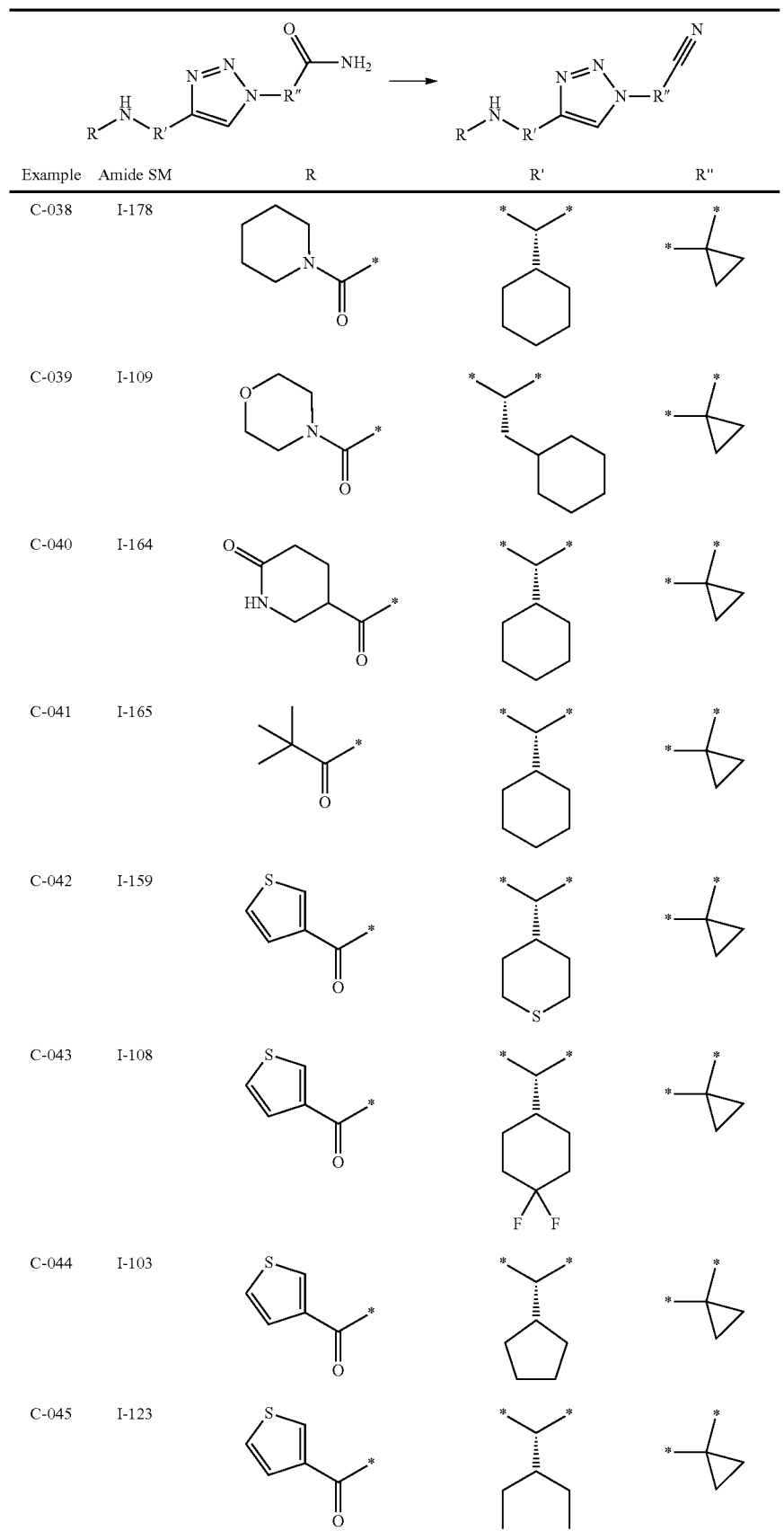

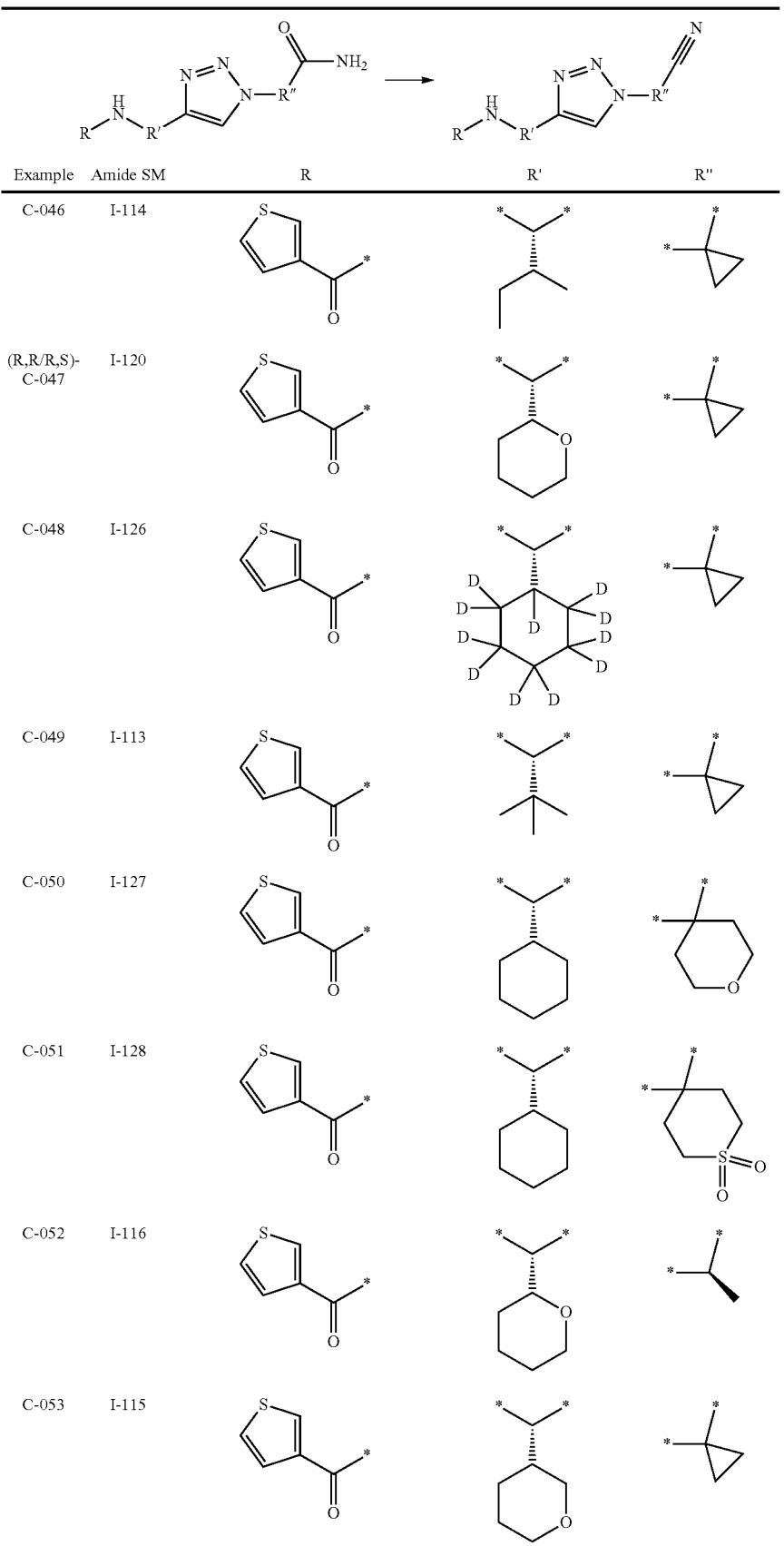

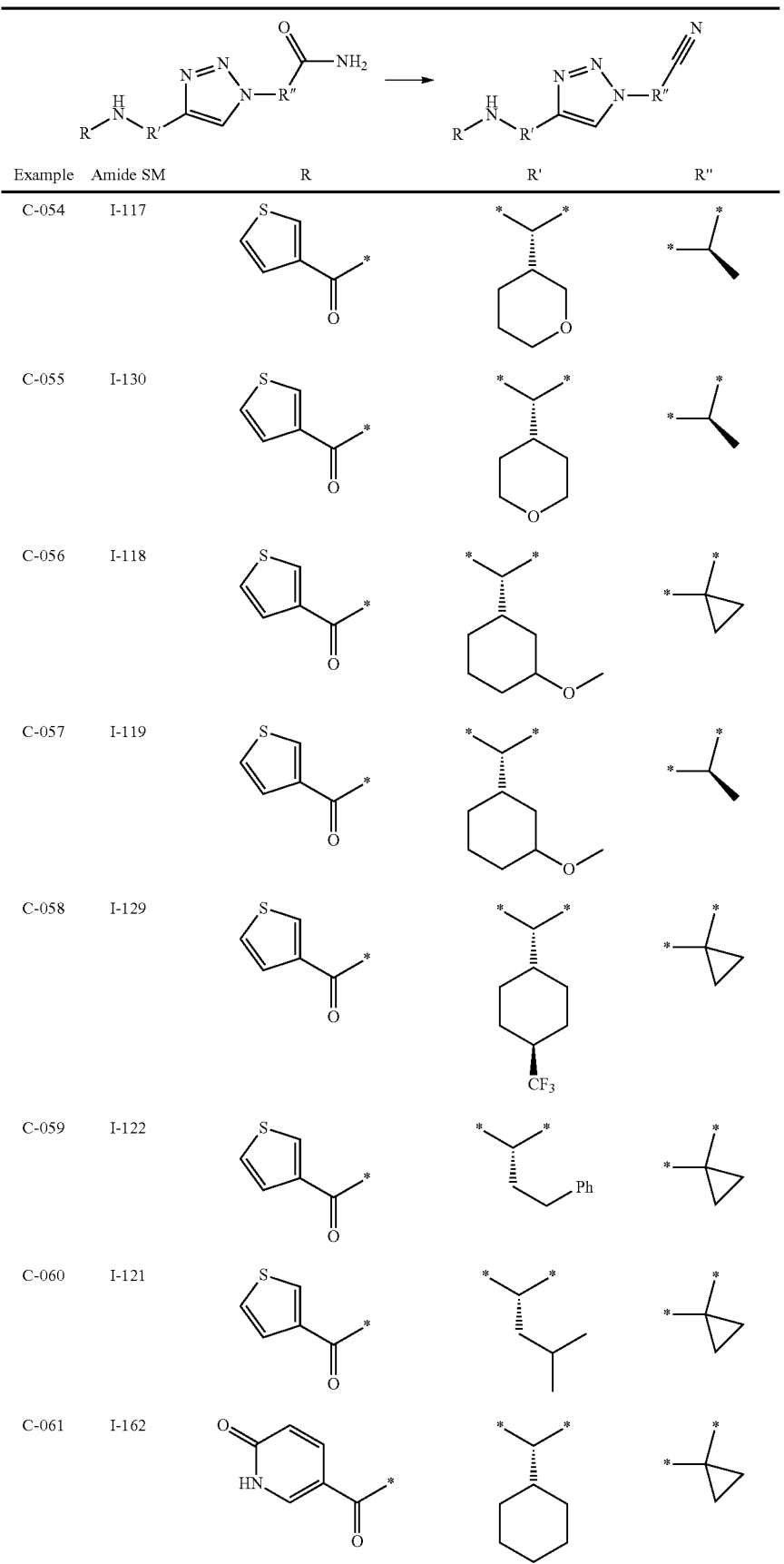

-continued
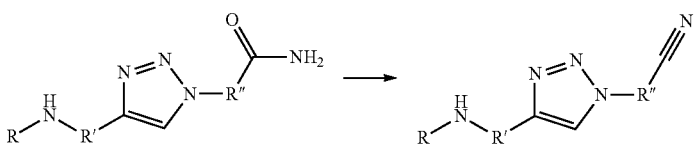
| Example | Amide SM | R | R' | R" |
|---|---|---|---|---|
| C-062 | I-163 | 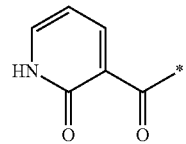 | 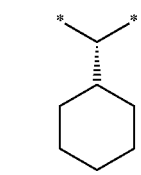 |  |
| C-064 | I-160 | 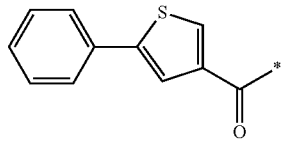 [SMILES: *C(=O)c1csc(-c2ccccc2)c1] | 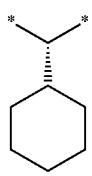 |  |
| C-065 | I-188 | 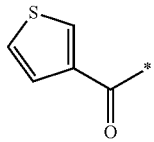 [SMILES: *C(=O)c1ccsc1] | 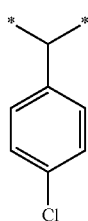 |  |
| C-066 | I-189 | 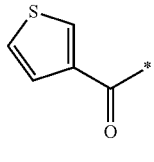 [SMILES: *C(=O)c1ccsc1] | 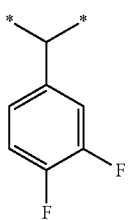 [SMILES: *C(*)c1ccc(F)c(F)c1] |  |
| (R/S)-C-067 | I-190 | 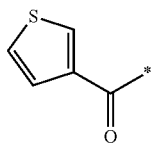 [SMILES: *C(=O)c1ccsc1] | 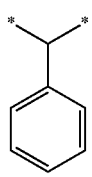 |  |
| (R/S)-C-068 | I-191 | 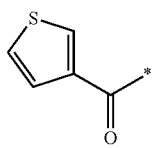 [SMILES: *C(=O)c1ccsc1] | 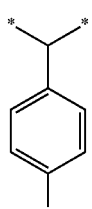 |  |
| C-069 | I-193 | 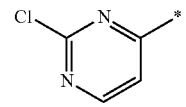 [SMILES: *c1ccnc(Cl)n1] | 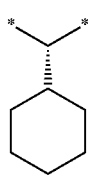 |  |

-continued

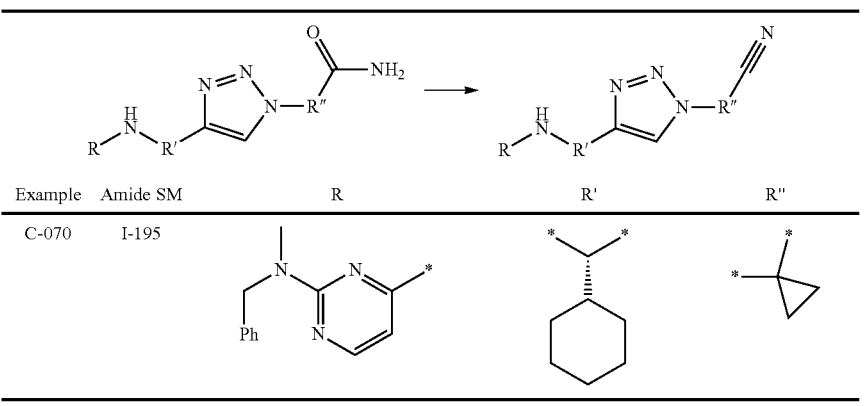

| Example | Amide SM | R | R' | R" |
|---|---|---|---|---|
| C-070 | I-195 | *N(Me)(CH2Ph)-pyrimidin-2-yl-4-* | *CH(cyclohexyl)* | *cyclopropyl-1,1-diyl* |

Example 10

Isolation of (S)-C-067

(R/S)-C-067 is separated by chiral semi-preparative HPLC (Chiralcel AD-H; 40% iPrOH in heptane) to provide (S)-C-067 as a solid.

Example 11

Isolation of (S)-C-068

(R/S)-C-068 is separated by chiral semi-preparative HPLC (Chiralcel AD-H; 40% iPrOH in heptane) to provide (S)-C-068 as a solid.

Example of 12

Isolation of (R,R)- and (R,S)-C-047

(R,R/R,S)-C-047 is separated by chiral semi-preparative HPLC (Luna C18, 33% MeCN in $H_2O$ with 0.1% TFA) to provide its two diastereomers, each as solids.

Example 13

Synthesis of C-071 and C-072

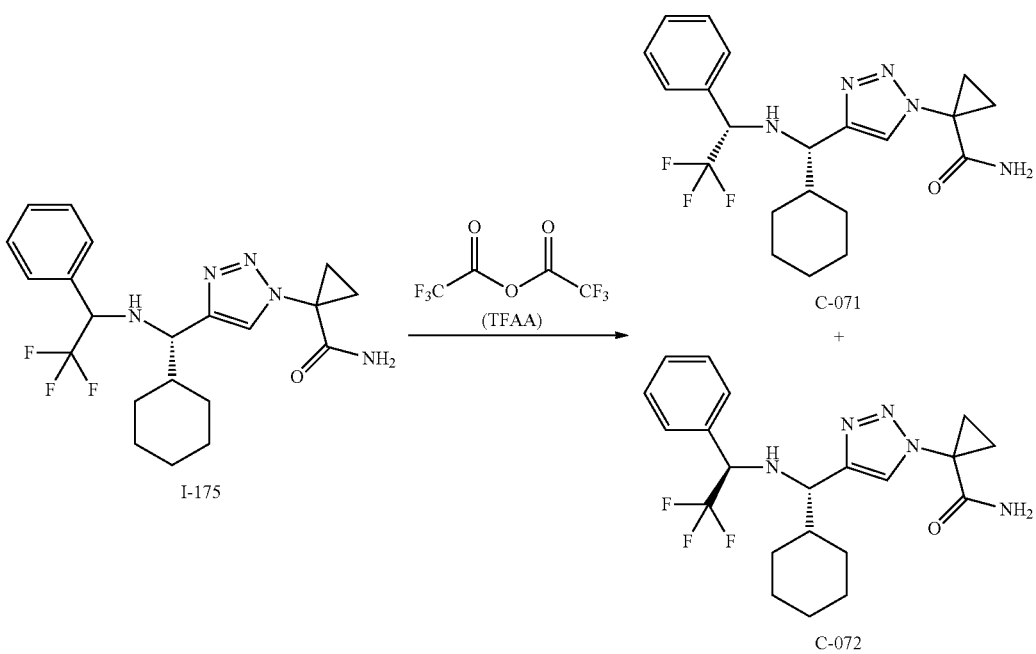

TFAA (0.03 mL, 0.15 mmol) is added to I-175 (30 mg, 0.07 mmol) and pyridine (1 mL). The mixture is stirred for 14 h, concentrated, and purified by C18 semi-preparative HPLC (50-95% MeCN in H₂O gradient with 0.1% HCO₂H) to provide C-071 and C-072 as solids.

Example 14

Synthesis of C-073

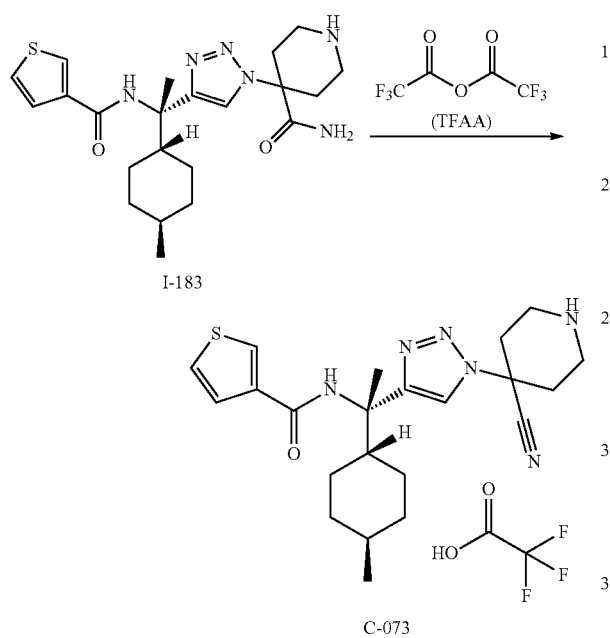

I-183

C-073

TFAA (0.15 mL, 0.11 mmol) is added to I-183 (0.45 g, 0.10 mmol), Et₃N (31 uL, 0.22 mmol), and THF (1 mL). The mixture is stirred for 4 h and concentrated. H₂O (0.5 mL), MeOH (0.5 mL), and K₂CO₃ (50 mg) are added. The resulting mixture is stirred for 16 h, then directly purified by C18 semi-preparative HPLC (5-95% MeCN in H₂O gradient with 0.1% TFA) to provide C-073 as a solid.

Example 15

Synthesis of C-074

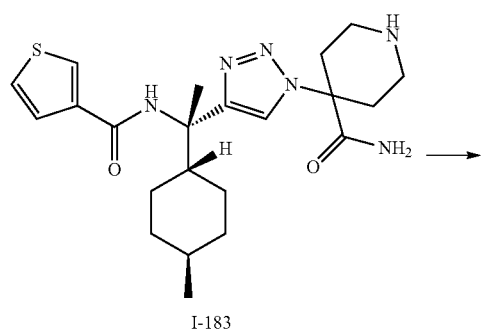

I-183

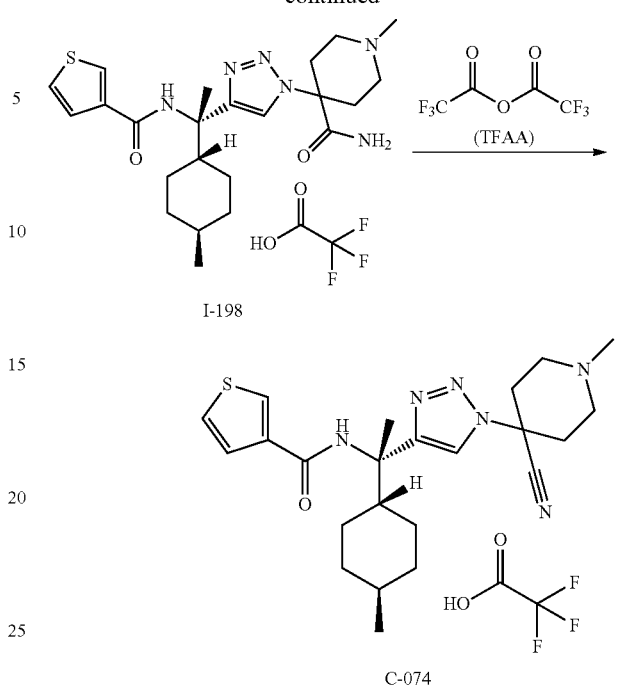

I-198

C-074

NaCNBH₃ (32 mg, 0.51 mmol) is added to a mixture of I-183 (45 mg, 0.10 mmol), 37% aqueous formaldehyde (75 µL, 1.0 mmol), and MeOH (1 mL). The mixture is stirred for 16 h, concentrated, and directly purified by C18 semi-preparative HPLC (5-95% MeCN in H₂O gradient with 0.1% TFA) to provide I-198 as a solid.

TFAA (4 µL, 0.03 mmol) is added to I-198 (12 mg, 0.03 mmol), Et₃N (8 µL, 0.06 mmol), and THF (1 mL). The mixture is stirred for 16 h and concentrated, then directly purified by C18 semi-preparative HPLC (5-95% MeCN in H₂O gradient with 0.1% TFA) to provide C-074 as a solid.

Example 16

Preparation of C-075 and C-076

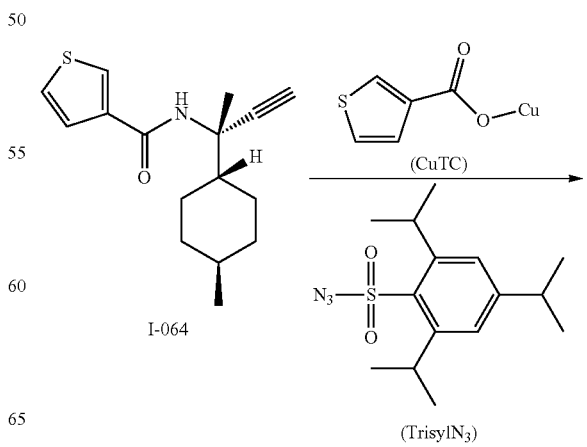

I-064

(TrisylN₃)

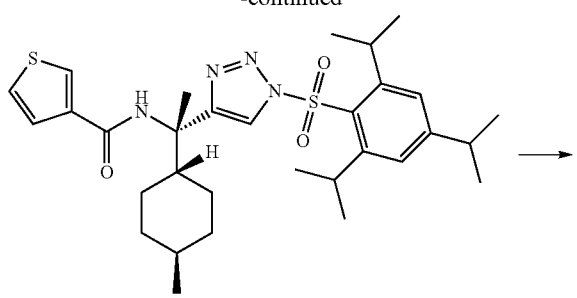

I-199

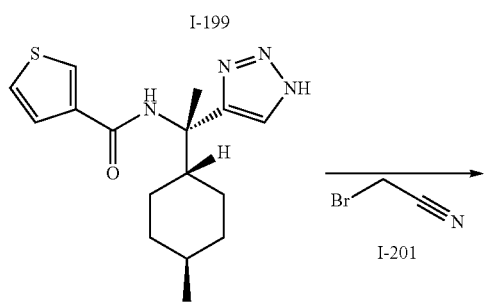

I-200

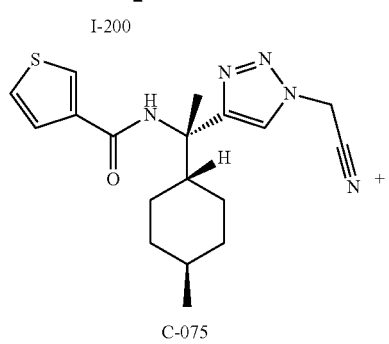

C-075

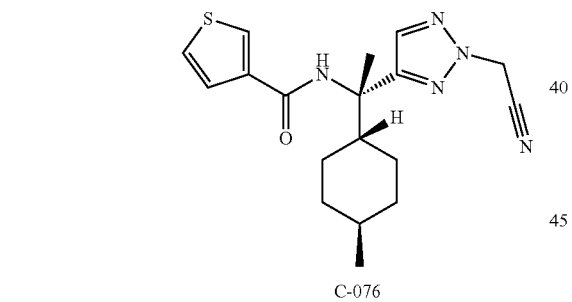

C-076 tion by reverse phase C18 semi-preparative HPLC (5-95% MeCN in H₂O gradient with 0.1% TFA) provides C-075 and C-076 both as solids.

Example 17

Synthesis of C-077

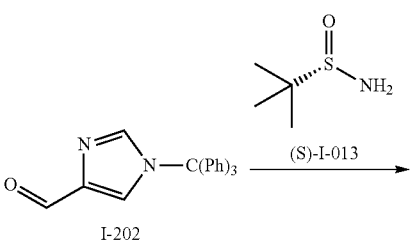

I-202    (S)-I-013

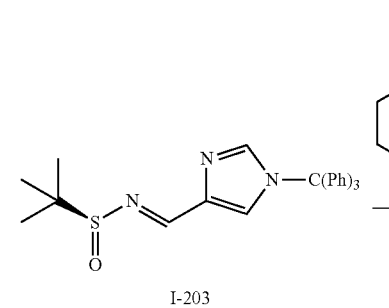

I-203

I-204

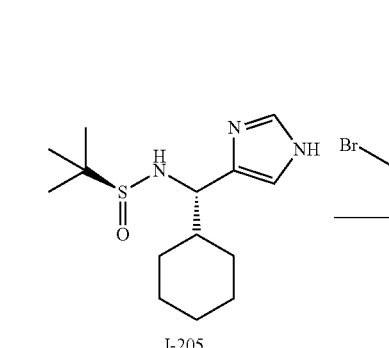

I-205

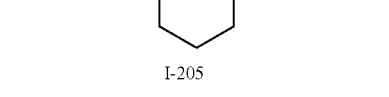

I-206

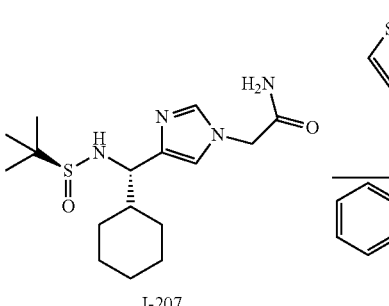

I-207

I-067

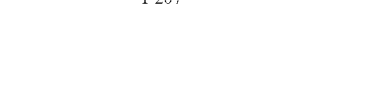

(TBTU)

I-064 (275 mg, 1.00 mmol) and TrisylN₃ (310 mg, 1.00 mmol) are added to CuTC (19 mg, 0.10 mmol) and toluene (5 mL). The mixture is stirred for 2 days, filtered, concentrated, and purified first by silica chromatography (0-25% EtOAc in heptane gradient), and then by C18 semi-preparative HPLC (60-100% MeCN in H₂O gradient with 0.1% TFA) to provide I-199 as a solid.

I-199 (120 mg, 0.21 mmol), Me₃SiCN (0.08 mL, 0.63 mmol), and CHCl₃ (1 mL) are heated in a microwave at 140 C for 20 min, then concentrated, and purified by C18 semi-preparative HPLC (5-100% MeCN in H₂O gradient with 0.1% TFA) to provide I-200.

NaH (60% in mineral oil; 16 mg, 0.41 mmol) is added to I-200 (65 mg, 0.20 mmol) and DMF (1 mL) at 0 C. The mixture is stirred for 30 min, I-201 (15 uL, 0.22 mmol) is added, and the mixture is stirred at rt for 2 h. Direct purifica- -continued

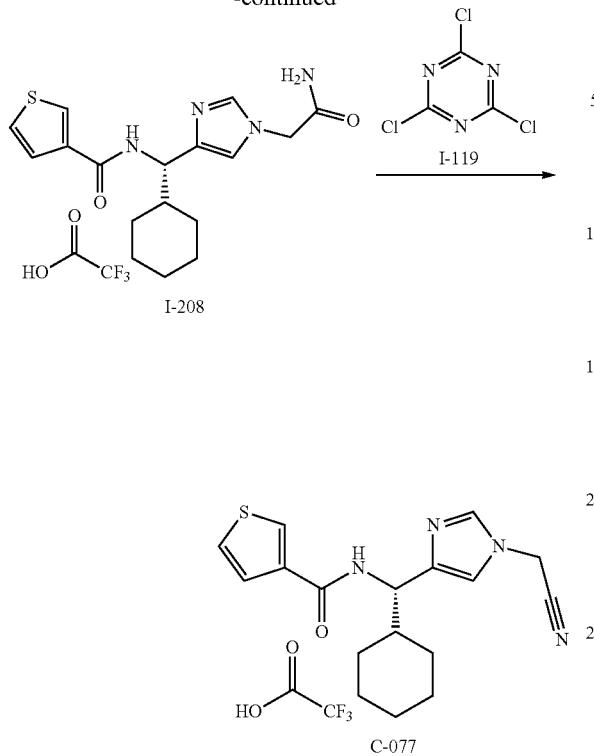

Example 18

Synthesis of C-078

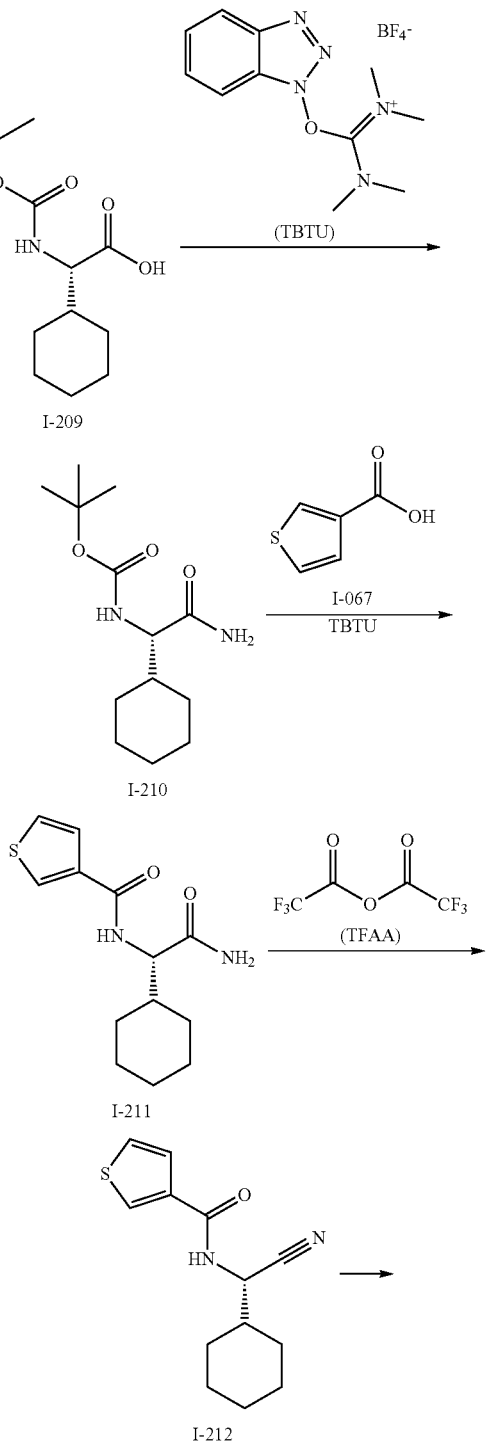

purification by reverse phase C18 semi-preparative HPLC (5-95% MeCN in H₂O gradient with 0.1% TFA) provides C-077 as a solid.

(S)-I-013 (3.2 g, 26 mmol) and Ti(OiPr)₄ (5.8 mL, 20 mmol) are added to I-202 (4.5 mL, 23 mmol) and THF (20 mL). The mixture is stirred for 3 h at 45 C, then poured into stirring EtOAc (300 mL) and H₂O (300 mL). The mixture is filtered, the extract is separated, dried, filtered, concentrated, and purified by silica chromatography (0-70% EtOAc in heptane gradient) to provide I-203 as a solid.

2.0 M I-204 in Et₂O (8.5 mL, 17 mmol) is added slowly to I-203 (3.0 g, 6.8 mmol) and THF (40 mL) at −78 C. The mixture is stirred for 30 min and saturated aqueous NH₄Cl is added. The mixture is extracted with EtOAc. The extract is concentrated to provide a solid. A portion of this material (1.0 g) is stirred with AcOH (12 mL) and H₂O (1 mL) at 60 C for 2 h. The mixture is concentrated and purified by silica chromatography (0-10% MeOH in CH₂Cl₂ gradient) to provide I-205 as a solid.

60% NaH in mineral oil (64 mg, 1.6 mmol) is added to I-205 (0.42 g, 1.5 mmol) in DMF (10 mL). When gas evolution subsides, I-206 (0.22 g, 1.6 mmol) is added. The mixture is stirred for 16 h. EtOAc is added, and the mixture is washed with brine, dried, filtered, concentrated, and purified by silica chromatography (0-15% MeOH in CH₂Cl₂ gradient) to provide I-207 as a solid.

4 M HCl in dioxane (0.5 mL, 2 mmol) is added to I-207 (240 mg, 0.70 mmol) and MeOH (3 mL). The mixture is stirred for 3 h, then concentrated. The resulting mixture is combined with DMF (3 mL), Et₃N (0.39 mL, 2.8 mmol), I-067 (0.11 g, 0.85 mmol), and TBTU (0.27 g, 0.85 mmol). The mixture is stirred for 1 h, concentrated, and purified by C18 semi-preparative HPLC (5-65% MeCN in H₂O gradient with 0.1% TFA) to provide I-208 as a solid.

I-150 (19 mg, 0.10 mmol) is added to I-208 (60 mg, 0.13 mmol) and DMF (1 mL). The mixture is stirred for 3 h. Direct -continued

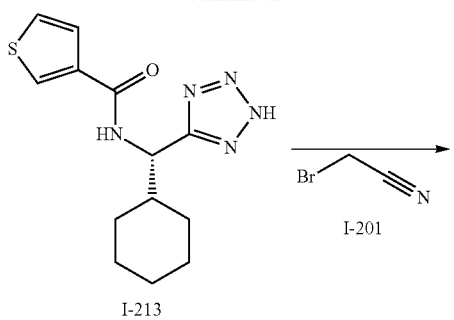

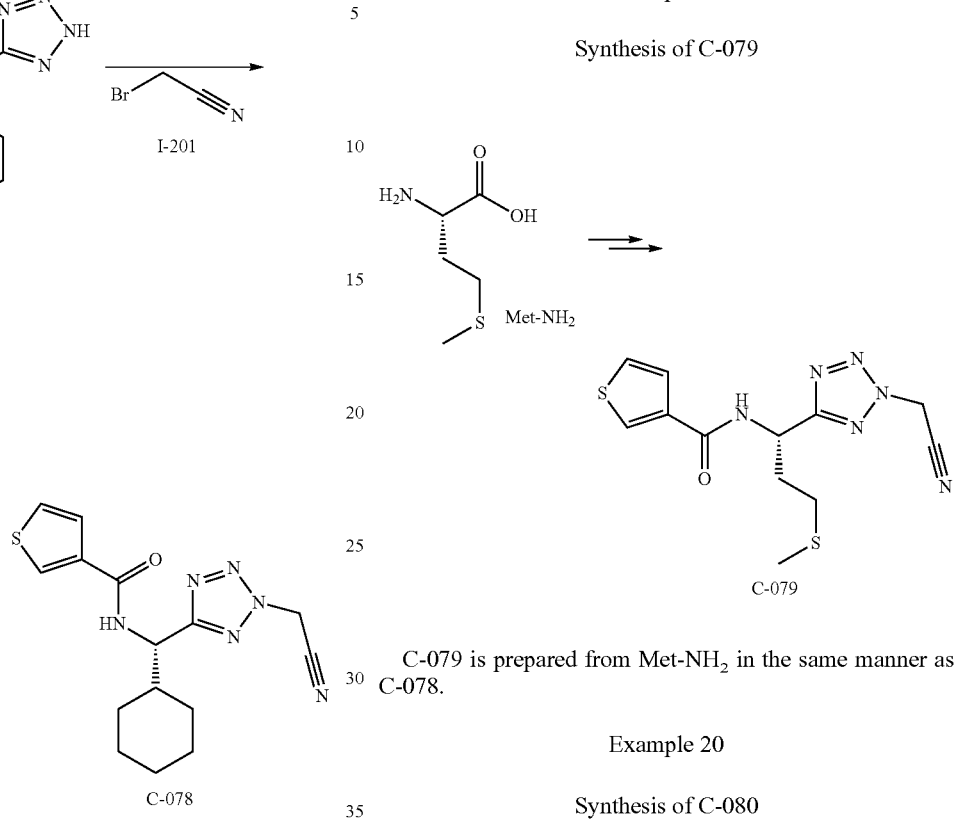

in H₂O gradient with 0.1% TFA), then by silica chromatography (0-50% EtOAc in heptane) to provide C-078 as a solid.

Example 19

Synthesis of C-079

C-079 is prepared from Met-NH₂ in the same manner as C-078.

Example 20

Synthesis of C-080

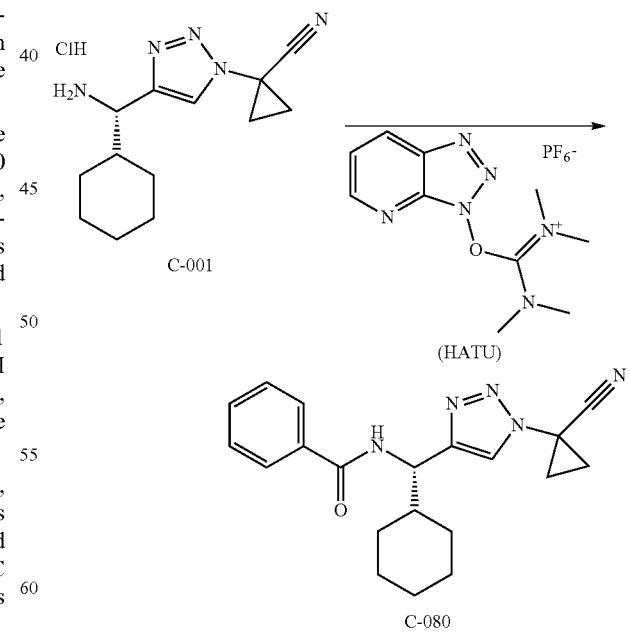

A mixture of I-209 (1.0 g, 3.9 mmol), Et₃N (0.65 mL, 4.7 mmol), TBTU (1.4 g, 4.3 mmol), and DMF (20 mL) is saturated with NH₃ and stirred for 1 h. It is then diluted with saturated aqueous NaHCO₃. The mixture is filtered to provide I-210.

I-210 (480 mg, 1.9 mmol) is stirred in 4N HCl in dioxane (8 mL) for 15 min. The mixture is concentrated and DMF (10 mL), Et₃N (0.79 mL, 5.7 mmol), I-067 (360 mg, 2.8 mmol), and TBTU (0.73 g, 2.3 mmol) are added. The resulting mixture is stirred for 16 h and diluted with saturated aqueous NaHCO₃. The mixture is filtered, and the solids are triturated with MeCN to provide I-211 as a solid.

TFAA (0.26 mL, 1.7 mmol) is added dropwise to I-211 (300 mg, 1.1 mmol) in pyridine (6 ml). After 30 min, MeOH is added and the mixture is concentrated, diluted with EtOAc, washed with brine, dried, filtered, and evaporated to provide I-212.

A mixture of I-212 (230 mg, 0.93 mmol), NaN₃ (240 mg, 3.7 mmol), NH₄Cl (200 mg, 3.7 mmol), and DMF (6 mL) is stirred at 100 C for 16 h. It is cooled to rt, filtered, and purified directly by reverse phase C18 semi-preparative HPLC (5-70% MeCN in H₂O gradient with 0.1% TFA) provides I-213 as a solid.

NaH (60% in mineral oil; 22 mg, 0.54 mmol) is added to I-213 (150 mg, 0.51 mmol) in DMF (3 mL) at 0 C and stirred for 10 min. I-201 (38 µL, 0.54 mmol) is added, and the mixture is stirred overnight. The mixture is directly purified by reverse phase C18 semi-preparative HPLC (5-80% MeCN A mixture of C-001 (20 mg, 0.07 mmol), Et₃N (20 µL, 0.15 mmol), and DMAc (0.5 mL) is added to a stirring mixture of benzoic acid (9 mg, 0.07 mmol), HATU (38 mg, 0.10 mmol), and DMAc (0.5 mL). The resulting mixture is stirred for 16 h, concentrated, and purified by C18 semi-preparative HPLC (5-85% MeCN in H₂O gradient with 0.1% TFA) to provide C-080 as a solid.

Example 21

Synthesis of C-081

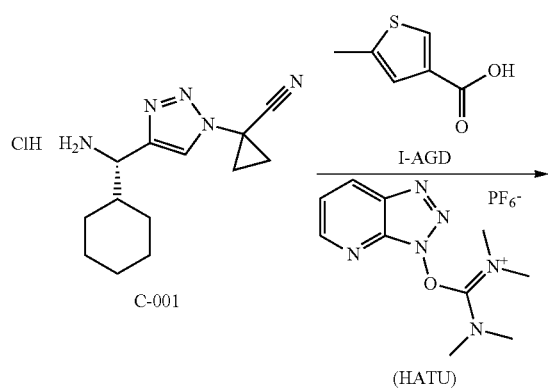

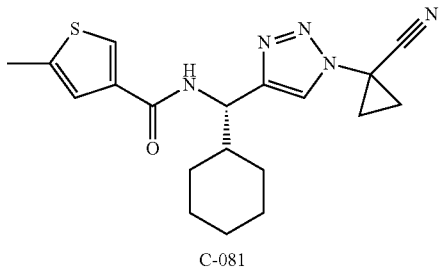

C-081

A mixture of C-001 (38 mg, 0.11 mmol), Et₃N (30 µL, 0.23 mmol), and DMF (0.5 mL) is added to a stirring mixture of 1-AGD (16 mg, 0.11 mmol), HATU (64 mg, 0.17 mmol), and DMF (0.5 mL). The resulting mixture is stirred for 16 h, concentrated, and purified by C18 semi-preparative HPLC (5-85% MeCN in H₂O gradient with 0.1% TFA) to provide C-081 as a solid.

The following Examples are prepared from the appropriate carboxylic acid is the same manner as C-080 and C-081.

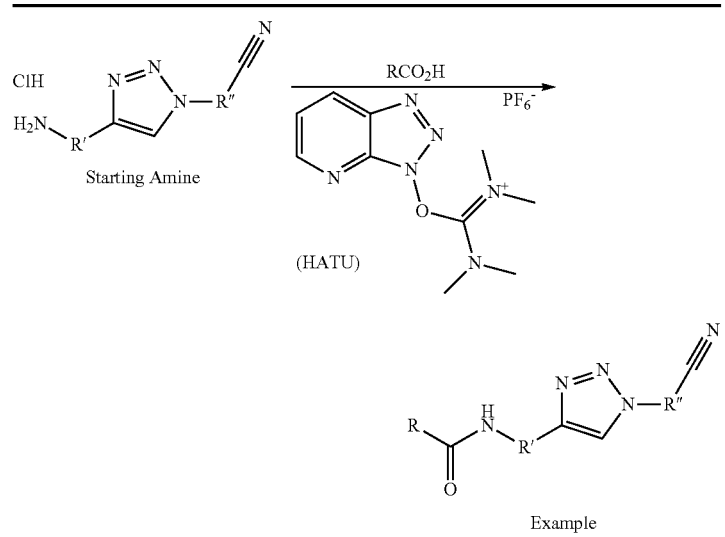

| Example | Starting Amine | R | R' | R" |
|---|---|---|---|---|
| C-082 | C-001 | (1-methylpyrazol-4-yl)carbonyl | cyclohexylmethine | 1-cyanocyclopropyl |
| C-083 | C-001 | 6-(N-methylcarbamoyl)pyridin-3-ylcarbonyl | cyclohexylmethine | 1-cyanocyclopropyl |

-continued
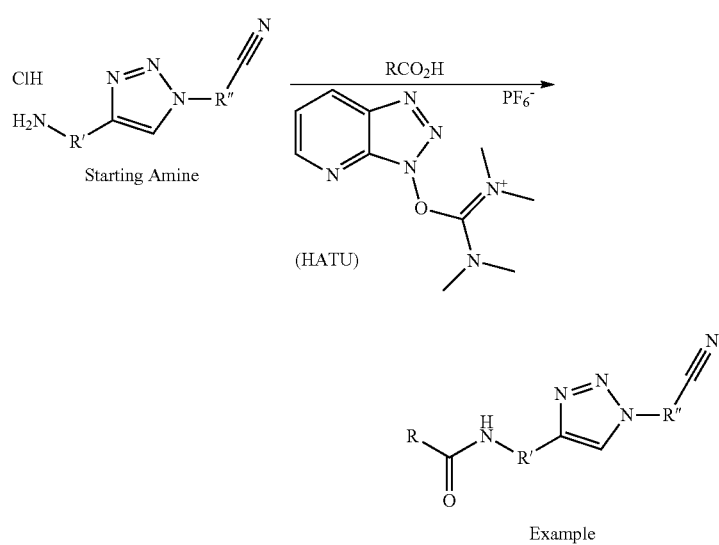
| Example | Starting Amine | R | R' | R" |
|---|---|---|---|---|
| C-084 | C-001 | 6-carbamoylpyridin-3-yl carbonyl | cyclohexyl | cyclopropyl |
| C-085 | C-001 | 4-acetamidobenzoyl | cyclohexyl | cyclopropyl |
| C-086 | C-001 | 4-(trifluoromethyl)benzoyl | cyclohexyl | cyclopropyl |
| C-087 | I-156 | thiophen-3-ylcarbonyl | CH2SMe | cyclopropyl |
| C-088 | I-157 | thiophen-3-ylcarbonyl | CH2CH2SMe | cyclopropyl |

-continued
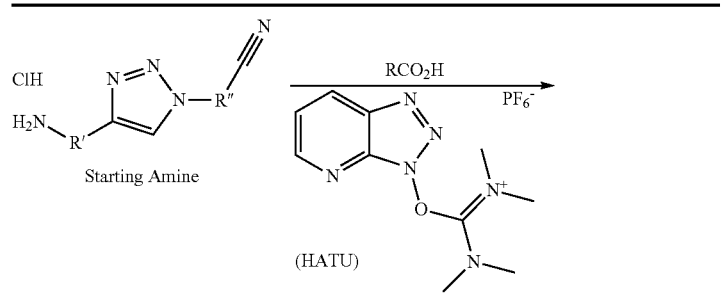
Starting Amine
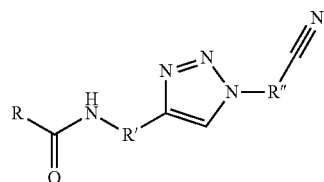
(HATU)
Example
| Example | Starting Amine | R | R' | R" |
|---|---|---|---|---|
| C-089 | C-001 | 2-furanyl-C(=O)- | (cyclohexyl)CH- | cyclopropyl |
| C-090 | C-001 | 3-furanyl-C(=O)- | (cyclohexyl)CH- | cyclopropyl |
| C-091 | C-001 | 1H-pyrazol-4-yl-C(=O)- | (cyclohexyl)CH- | cyclopropyl |
| C-092 | C-001 | 1H-pyrazol-3-yl-C(=O)- | (cyclohexyl)CH- | cyclopropyl |
| C-093 | C-001 | oxazol-5-yl-C(=O)- | (cyclohexyl)CH- | cyclopropyl |
| C-094 | C-001 | isoxazol-5-yl-C(=O)- | (cyclohexyl)CH- | cyclopropyl |

-continued
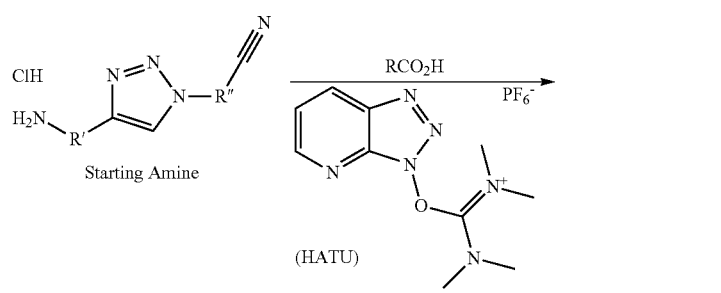
Starting Amine
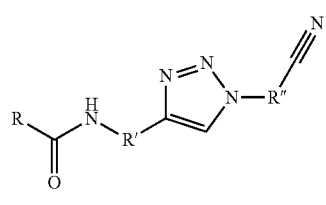
(HATU)
Example
| Example | Starting Amine | R | R' | R" |
|---|---|---|---|---|
| C-095 | C-001 | isoxazol-4-yl-C(=O)- | cyclohexyl | cyclopropyl |
| C-096 | C-001 | oxazol-4-yl-C(=O)- | cyclohexyl | cyclopropyl |
| C-097 | C-001 | isoxazol-3-yl-C(=O)- | cyclohexyl | cyclopropyl |
| C-098 | C-001 | oxazol-2-yl-C(=O)- | cyclohexyl | cyclopropyl |
| C-099 | C-001 | cyclopentyl-C(=O)- | cyclohexyl | cyclopropyl |

-continued
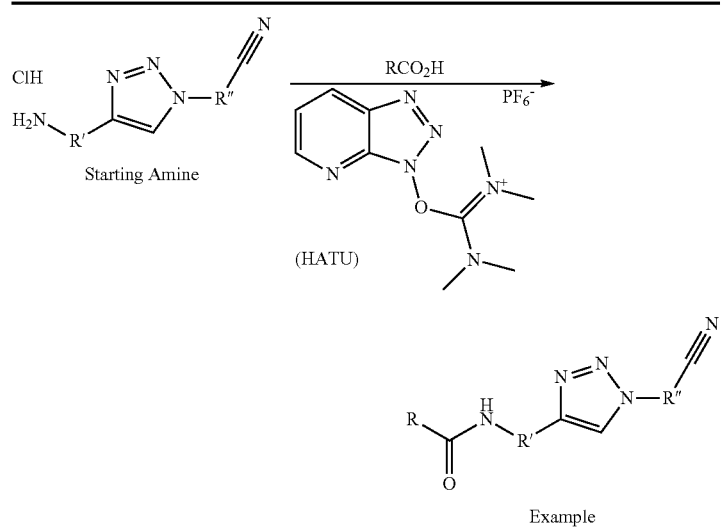
(HATU)
Example
| Example | Starting Amine | R | R' | R'' |
|---|---|---|---|---|
| C-100 | C-001 | tetrahydrofuran-2-yl-C(=O)- | cyclohexyl-CH- | cyclopropyl |
| C-101 | C-001 | tetrahydrofuran-3-yl-C(=O)- | cyclohexyl-CH- | cyclopropyl |
| C-102 | C-001 | pyridin-3-yl-C(=O)- | cyclohexyl-CH- | cyclopropyl |
| C-103 | C-001 | pyridin-4-yl-C(=O)- | cyclohexyl-CH- | cyclopropyl |
| C-104 | C-001 | 1-methyl-1H-pyrazol-5-yl-C(=O)- | cyclohexyl-CH- | cyclopropyl |
| C-105 | C-001 | 1-methyl-1H-pyrazol-4-yl-C(=O)- | cyclohexyl-CH- | cyclopropyl |

-continued
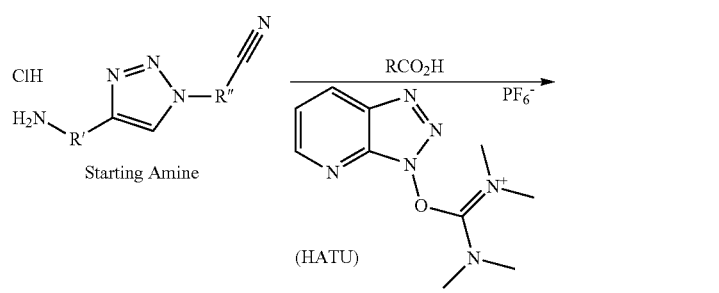
(HATU)
Example
| Example | Starting Amine | R | R' | R'' |
|---|---|---|---|---|
| C-106 | C-001 | 1-methylimidazol-2-yl-C(O)- | cyclohexyl-CH- | cyclopropyl |
| C-107 | C-001 | thiophen-2-yl-C(O)- | cyclohexyl-CH- | cyclopropyl |
| C-108 | C-001 | isothiazol-5-yl-C(O)- | cyclohexyl-CH- | cyclopropyl |
| C-109 | C-001 | thiazol-4-yl-C(O)- | cyclohexyl-CH- | cyclopropyl |
| C-110 | C-001 | thiazol-5-yl-C(O)- | cyclohexyl-CH- | cyclopropyl |

-continued

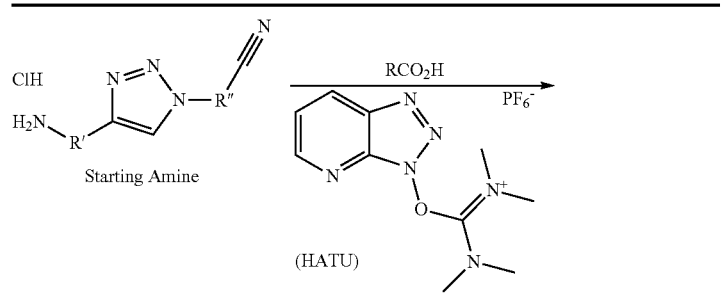

Starting Amine

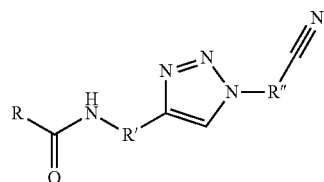

(HATU)

Example

| Example | Starting Amine | R | R' | R'' |
|---|---|---|---|---|
| C-111 | C-001 | tetrahydropyran-4-yl-C(=O)-* | *-cyclohexyl-CH-* | *-cyclopropyl |
| C-112 | C-001 | 3-methylphenyl-C(=O)-* | *-cyclohexyl-CH-* | *-cyclopropyl |
| C-113 | C-001 | 2-methylphenyl-C(=O)-* | *-cyclohexyl-CH-* | *-cyclopropyl |
| C-114 | C-001 | 4-methylphenyl-C(=O)-* | *-cyclohexyl-CH-* | *-cyclopropyl |
| C-115 | C-001 | 3-fluorophenyl-C(=O)-* | *-cyclohexyl-CH-* | *-cyclopropyl |
| C-116 | C-001 | 2-fluorophenyl-C(=O)-* | *-cyclohexyl-CH-* | *-cyclopropyl |

-continued
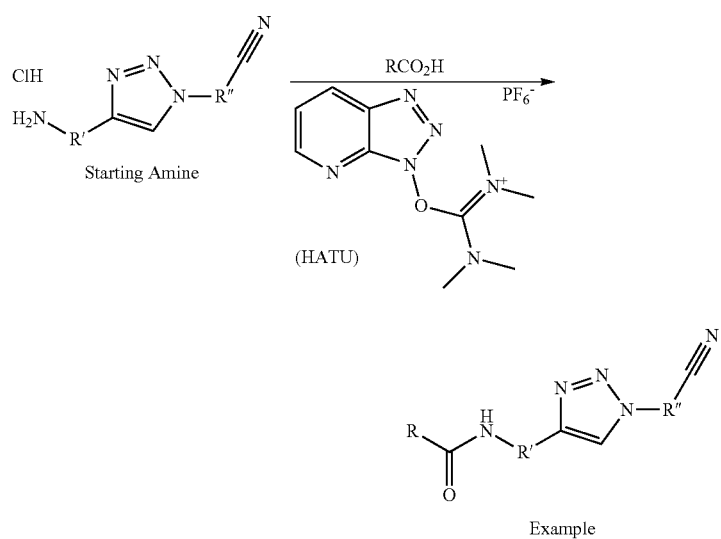
(HATU)
Starting Amine
Example
| Example | Starting Amine | R | R' | R" |
|---|---|---|---|---|
| C-117 | C-001 | 3-cyanobenzoyl | cyclohexyl | cyclopropyl |
| C-118 | C-001 | 4-cyanobenzoyl | cyclohexyl | cyclopropyl |
| C-119 | C-001 | 3-methoxybenzoyl | cyclohexyl | cyclopropyl |
| C-120 | C-001 | 3-chlorobenzoyl | cyclohexyl | cyclopropyl |
| C-121 | C-001 | 4-chlorobenzoyl | cyclohexyl | cyclopropyl |

-continued
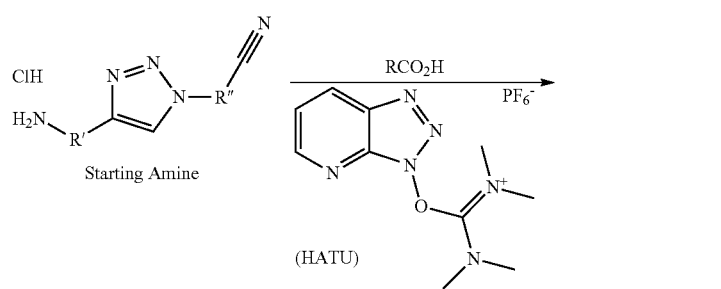
Starting Amine
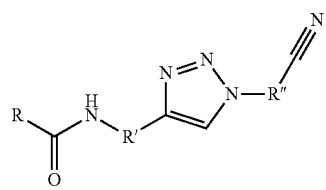
(HATU)
| Example | Starting Amine | R | R' | R" |
|---|---|---|---|---|
| C-122 | C-001 | 3,4-difluorobenzoyl | cyclohexyl-CH | cyclopropyl |
| C-123 | C-001 | benzofuran-2-carbonyl | cyclohexyl-CH | cyclopropyl |
| C-124 | C-001 | pyrazolo[1,5-a]pyridine-2-carbonyl | cyclohexyl-CH | cyclopropyl |
| C-125 | C-001 | pyrazolo[1,5-a]pyridine-3-carbonyl | cyclohexyl-CH | cyclopropyl |
| C-126 | C-001 | imidazo[1,2-a]pyridine-2-carbonyl | cyclohexyl-CH | cyclopropyl |

-continued
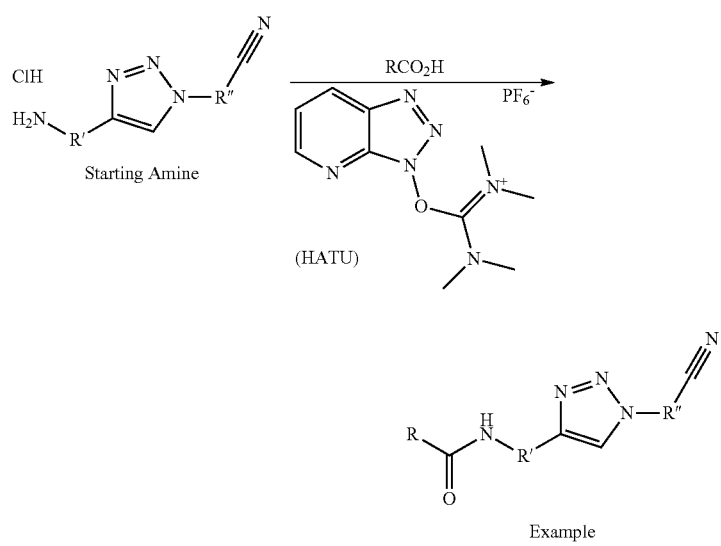
Starting Amine
(HATU)
Example
| Example | Starting Amine | R | R' | R" |
|---|---|---|---|---|
| C-127 | C-001 | imidazo[1,2-a]pyridine-3-carbonyl | cyclohexyl | cyclopropyl |
| C-128 | C-001 | 5-chlorothiophene-2-carbonyl | cyclohexyl | cyclopropyl |
| C-129 | C-001 | imidazo[1,2-a]pyrazine-2-carbonyl | cyclohexyl | cyclopropyl |
| C-130 | C-001 | 1,1-dioxo-tetrahydrothiophene-3-carbonyl | cyclohexyl | cyclopropyl |
| C-131 | C-001 | 4-carbamoylbenzoyl | cyclohexyl | cyclopropyl |

-continued
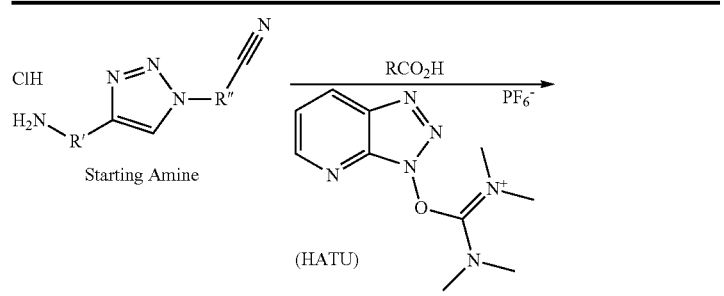
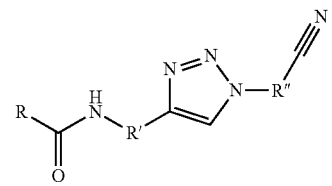
Example
| Example | Starting Amine | R | R' | R" |
|---|---|---|---|---|
| C-132 | C-001 | thiazolo-imidazole-C(O)* | *cyclohexyl* | *cyclopropyl* |
| C-133 | C-001 | 1-acetylpiperidin-4-yl-C(O)* | *cyclohexyl* | *cyclopropyl* |
| C-134 | C-001 | 4-(methylcarbamoyl)phenyl-C(O)* | *cyclohexyl* | *cyclopropyl* |
| C-135 | C-001 | 4-(dimethylcarbamoyl)phenyl-C(O)* | *cyclohexyl* | *cyclopropyl* |
| C-136 | C-001 | 4-(methylsulfonyl)phenyl-C(O)* | *cyclohexyl* | *cyclopropyl* |

-continued
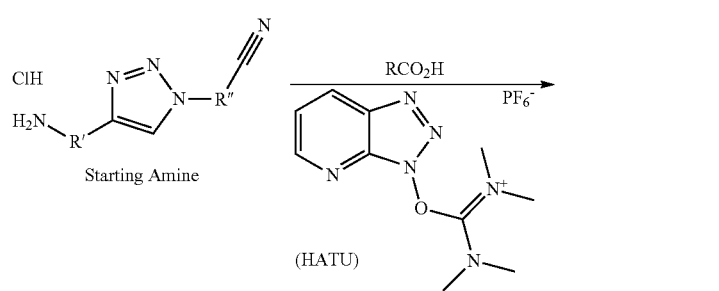
Starting Amine
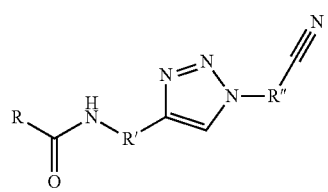
(HATU)
Example
| Example | Starting Amine | R | R' | R" |
|---|---|---|---|---|
| C-137 | C-001 | 3-(methylsulfonyl)benzoyl | cyclohexyl | cyclopropyl |
| C-138 | C-001 | 3-sulfamoylbenzoyl | cyclohexyl | cyclopropyl |
| C-139 | C-001 | 4-(cyclopropanecarboxamido)benzoyl | cyclohexyl | cyclopropyl |
| C-140 | C-001 | 1-(2,2,2-trifluoroethyl)piperidine-3-carbonyl | cyclohexyl | cyclopropyl |
| C-141 | C-001 | 4-(methylsulfonamido)benzoyl | cyclohexyl | cyclopropyl |

-continued
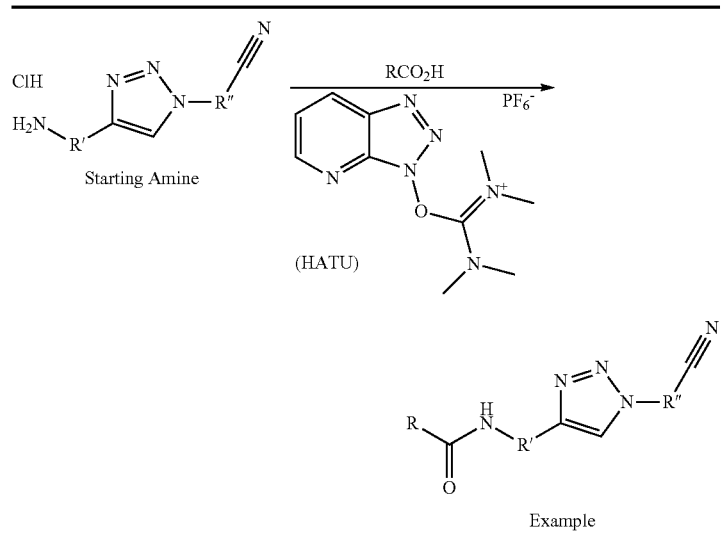
| Example | Starting Amine | R | R' | R'' |
|---|---|---|---|---|
| C-142 | C-001 | | | |
| C-143 | C-001 | | | |
| C-144 | C-001 | | | |
Example 22
Synthesis of C-145 and C-146
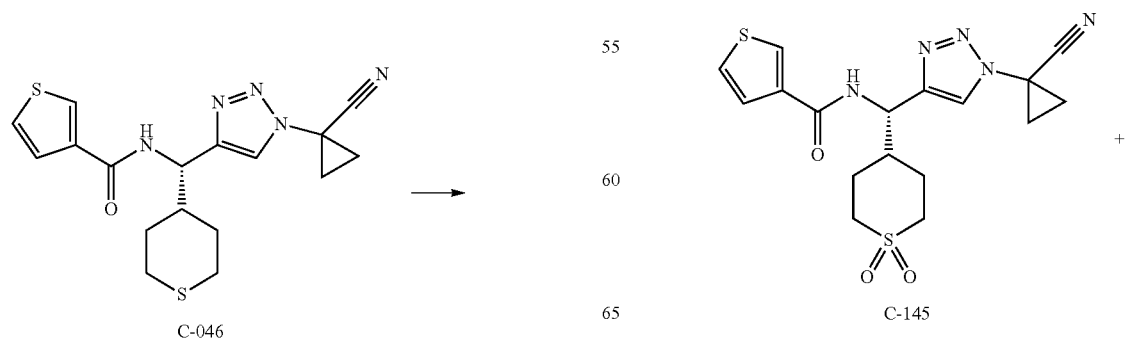
-continued
C-145
+

-continued

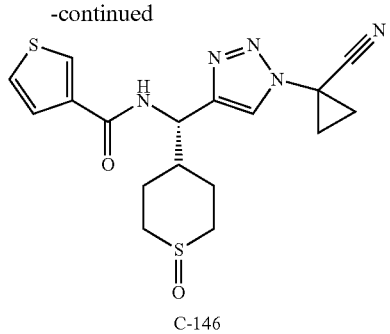

C-146

H₂O₂ (30%; 0.04 mL, 0.4 mmol) is added to C-042 (50 mg, 0.13 mmol), Na₂WO₄.(H₂O)₂ (1 mg), Bu₄N(HSO₄) (3 mg, 0.01 mmol), and EtOAc (5 mL). The mixture is stirred for 3 h, EtOAc (70 mL) is added, and the mixture is stirred with saturated aqueous Na₂SO₃ (10 mL) for 10 min. The organic phase is separated and washed with brine (15 mL), dried over Na₂SO₄, filtered, concentrated, and purified by C18 semi-preparative HPLC (10-85% MeCN in H₂O gradient with 0.1% TFA) to provide C-145 and C-146 both as a solids.

The following sulfones are prepared from their corresponding thiol ethers in the same manner as C-145.

Analytical Methods:

| Method A: Agilent Zorbax C18 SB 3.5 um 4.6 × 30 mm cartridge, 2.5 mL/min | | |
|---|---|---|
| Time (min) | Water 0.1% formic acid (%) | Acetonitrile 0.1% formic acid (%) |
| 0 | 95 | 5 |
| 1.7 | 5 | 95 |
| 2 | 5 | 95 |
| 2.1 | 95 | 5 |
| 2.3 | 95 | 5 |
| 2.5 | 95 | 5 |

| Method B: Agilent Zorbax C18 SB 3.5 um 4.6 × 30 mm cartridge, 1.5 mL/min | | |
|---|---|---|
| Time (min) | Water 0.1% formic acid (%) | Acetonitrile 0.1% formic acid (%) |
| 0 | 95 | 5 |
| 7 | 5 | 95 |

| Thiol Ether | Sulfone Product |
|---|---|

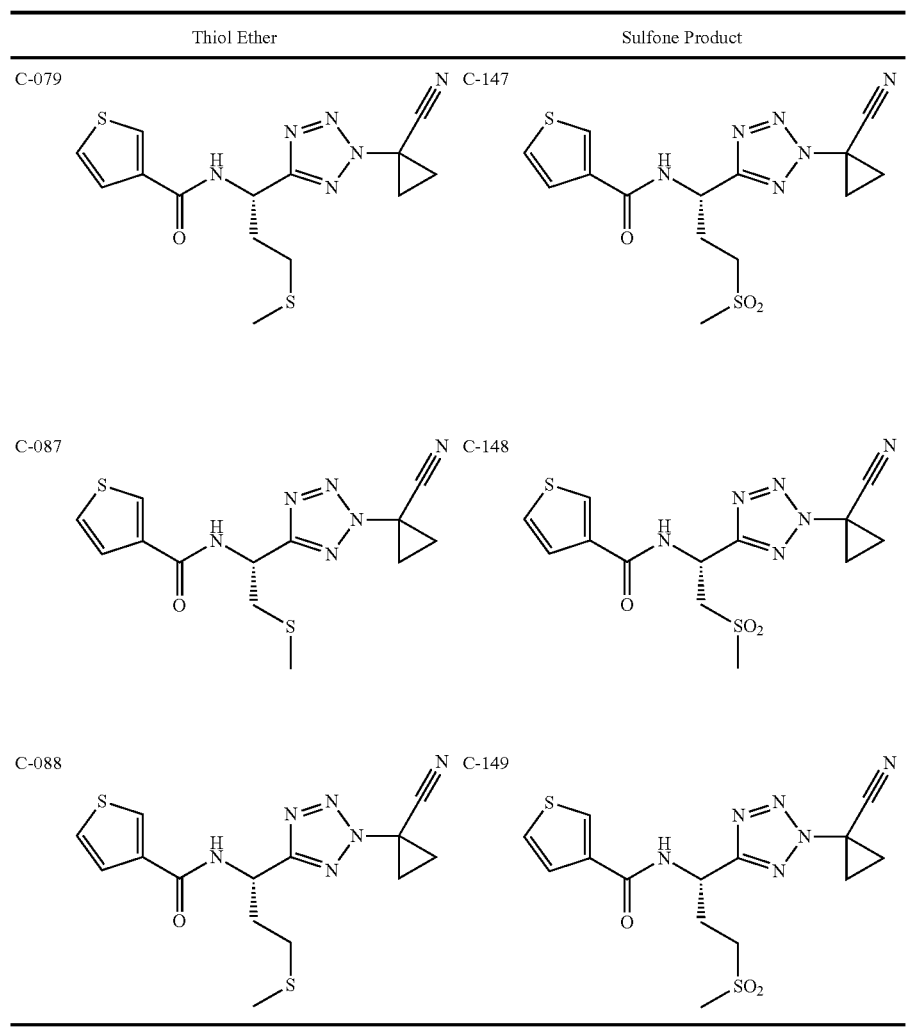

-continued

Method B: Agilent Zorbax C18 SB 3.5 um
4.6 × 30 mm cartridge, 1.5 mL/min

| Time (min) | Water 0.1% formic acid (%) | Acetonitrile 0.1% formic acid (%) |
|---|---|---|
| 9 | 5 | 95 |
| 9.3 | 95 | 5 |
| 10 | 95 | 5 |

Method C: Agilent SB-C18 1.8 um
3 × 50 mm column, 1.5 mL/min

| Time (min) | Water 0.1% formic acid (%) | Acetonitrile 0.1% formic acid (%) |
|---|---|---|
| 0 | 88 | 12 |
| 0.25 | 70 | 30 |
| 0.3 | 60 | 40 |
| 1.19 | 5 | 95 |
| 1.75 | 0 | 100 |
| 2.00 | 0 | 100 |

Method D: Agilent SB-C18 1.8 um
3 × 50 mm column, 1.5 mL/min

| Time (min) | Water 0.1% formic acid (%) | Acetonitrile 0.1% formic acid (%) |
|---|---|---|
| 0 | 95 | 5 |
| 3.8 | 10 | 90 |
| 4.5 | 0 | 100 |
| 5.0 | 0 | 100 |

Method E: Waters BEH 2.1 × 50 mm
C18 1.7 um column, 0.8 mL/min

| Time (min) | Water 0.1% formic acid (%) | Acetonitrile 0.1% formic acid (%) |
|---|---|---|
| 0 | 90 | 10 |
| 1.19 | 5 | 95 |
| 1.7 | 5 | 95 |
| 2.0 | 5 | 95 |

Method F: Waters BEH 2.1 × 50 mm
C18 1.7 um column, 0.8 mL/min

| Time (min) | Water 0.1% formic acid (%) | Acetonitrile 0.1% formic acid (%) |
|---|---|---|
| 0 | 90 | 10 |
| 4.5 | 5 | 95 |
| 4.58 | 5 | 95 |
| 5.0 | 5 | 95 |

Assays:

Cathepsin mediated hydrolysis of FR-Rhodamine 110 substrate (Invitrogen R6502) is measured as the reduction in fluorescence with inhibitor compared to uninhibited controls. The final assay concentrations are 0.5 nM Cat S and 4.2 µM FR-Rhodamine 110 in assay buffer. The assay buffer consists of 50 mM NaOAc, 2.5 mM EDTA, 10 mM MgSO$_4$, 0.1% CHAPS pH 4.8, and 500 µM TCEP. Inhibitors are serially diluted in DMSO, then diluted further with assay buffer, and 2 µL aliquots transferred to assay plates. The reaction takes place at 28 C for 1 hour. Data is plotted as POC vs. inhibitor concentration. The IC$_{50}$ is defined as the concentration necessary to inhibit 50% of Cathepsin S activity. Preferred compound will have an IC$_{50}$ of less than nM.

Method of Treatment

The present invention is directed to compounds of the formula (I) which are useful in the treatment of a disease and condition wherein the activity of inhibiting Cathepsin-S is of therapeutic benefit, including but not limited to the treatment of autoimmune diseases These encompass autoimmune diseases and other diseases involving inappropriate antigen specific immune responses including, but not limited to, rheumatoid arthritis, systemic lupus erythematosus, Crohn's disease, ulcerative colitis, multiple sclerosis, Guillain-Barre syndrome, psoriasis, Grave's disease, myasthenia gravis, scleroderma, glomerulonephritis, dermatitis including contact and atopic dermatitis, insulin-dependent diabetes mellitus, endometriosis, and chronic obstructive pulmonary disease and asthma including allergic asthma. The compounds of the invention can also be used to treat other disorders associated with extracellular proteolysis such as Alzheimer's disease and atherosclerosis. The compounds of the invention can also be used to treat other disorders associated with inappropriate autoimmune responses, T-cell mediated immune responses, or extracellular proteolysis mediated by cathepsin S. Therefore, the invention also provides methods of modulating an autoimmune disease comprising administering to a patient in need of such treatment a pharmaceutically effect amount of a compound according to the invention.

Furthermore, the present invention relates to the use of a compound of the formula (I) for the treatment of multiple sclerosis, rheumatoid arthritis, psoriasis, atherosclerosis, and chronic obstructive pulmonary disease.

In a further aspect of the present invention the present invention relates to methods for the treatment of above mentioned diseases and conditions, which method comprises the administration of an effective amount of a compound of the formula (I) to a human being.

Dosage levels and requirements are well-recognized in the art and may be selected by those of ordinary skill in the art from available methods and techniques suitable for a particular patient. In some embodiments, dosage levels range from about 10-1000 mg/dose for a 70 kg patient. Although one dose per day may be sufficient, up to 5 doses per day may be given. For oral doses, up to 2000 mg/day may be required. As the skilled artisan will appreciate, lower or higher doses may be required depending on particular factors. For instance, specific dosage and treatment regimens will depend on factors such as the patient's general health profile, the severity and course of the patient's disorder or disposition thereto, and the judgment of the treating physician.

The compounds of the formula (I) may be used on their own or in combination with other active substances according to the invention, optionally also in combination with other pharmaceutically active substances.

Pharmaceutical Compositions:

The instant invention provides a bulk composition comprised of a CAT-S inhibitor of the formula (I) having desirable stability and purity wherein the purity is greater than 90%, 95% or 99%. The composition may additionally comprise in varying percentage, salts, solvates, hydrates, polymorphic forms, and the like, is intended to equally apply to the salt, solvate, hydrates, polymorphic forms of enantiomers, diastereomers, tautomers, racemates of the compounds of the formula (I).

The bulk composition comprised of a CAT-S inhibitor of the formula (I) may be a pharmaceutical composition comprising as an effective amount of the active ingredient which is at least one compound of formula (I). The pharmaceutical composition of formula (I) additionally comprising at least one pharmaceutically acceptable carrier and/or adjuvant.

Suitable preparations for administering the compounds of formula will be apparent to those with ordinary skill in the art and include for example tablets, pills, capsules, suppositories, lozenges, troches, solutions, syrups, elixirs, sachets, injectables, inhalatives and powders etc. Methods for preparing such dosage forms are known. The content of the pharmaceutically active compound(s) should be in the range from contain at least about 15%, but more preferably at least about 20%, of a compound of the invention (w/w) or a combination thereof.

Suitable tablets may be obtained, for example, by mixing one or more compounds according to formula (I) with known excipients, for example inert diluents, carriers, disintegrants, adjuvants, surfactants, binders and/or lubricants. The tablets may also consist of several layers.

The invention claimed is:

1. A compound of the formula (I):

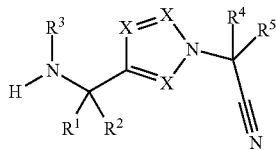
(I)

wherein the

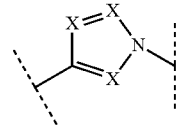

ring is chosen from:

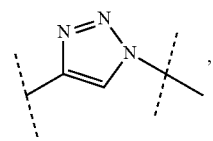
(i)

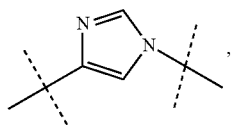
(ii)

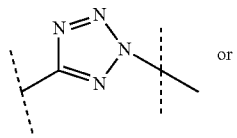
(iii)

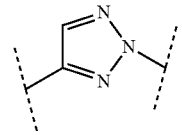
(iv)

each optionally substituted by $C_{1-3}$ alkyl;

$R^1$ is $C_{1-7}$alkyl, $C_{3-7}$cycloalkyl, aryl, heterocyclyl or heteroaryl each optionally substituted by one or more $R^c$;

$R^2$ is hydrogen or $C_{1-7}$alkyl;

or $R^1$ and $R^2$ taken together form a $C_{3-7}$cycloalkyl or $C_{3-7}$heterocyclyl ring optionally substituted by one or more halogen or $C_{1-7}$alkyl;

$R^3$ is —C(O)$C_{1-7}$alkyl, —C(O)$C_{3-7}$cycloalkyl, —C(O) aryl, —C(O)heteroaryl, —C(O)heterocyclyl, —C(O)NR$^a$R$^b$, —C(O)OR$^a$, —CH(R$_f$)-heteroaryl, —CH(R$_f$)-aryl, —CH(R$_f$)-heterocyclyl, aryl, $C_{3-7}$cycloalkyl or heteroaryl, each ring is optionally substituted by one or more $R^d$;

$R^4$ and $R^5$ are each independently hydrogen, $C_{1-7}$alkyl, aryl, or heteroaryl, or $R^4$ and $R^5$ taken together may form a $C_{3-7}$cycloalkyl or $C_{3-7}$ heterocyclyl ring each ring being optionally substituted by $C_{1-5}$alkyl;

$R^a$, $R^b$ each independently are hydrogen, $C_{1-7}$alkyl, aryl or heteroaryl, or may be taken together to form a saturated or unsaturated $C_{3-7}$cycloalkyl or $C_{3-7}$ heterocyclyl ring;

$R^c$ is $C_{1-7}$alkyl, $C_{1-7}$alkoxy, $C_{3-7}$cycloalkyl, aryl, benzyl, halogen or —C(O)—O-benzyl;

$R^d$ each is independently chosen from $C_{1-7}$alkyl, $C_{1-7}$alkoxy, $C_{1-7}$acyl, —C(O)NR$^a$R$^b$, —NH—C(O)—$C_{1-7}$alkyl, halogen, —CN, —S(O)$_m$—R$_e$, —NH—S(O)$_m$—R$_e$;

$R_e$ is chosen from $C_{1-7}$alkyl and amino;

$R^f$ each is independently chosen from hydrogen or $C_{1-7}$alkyl;

m is 0-2;

wherein one or more hydrogens on any one or more of $R^1$, $R^2$, $R^3$, $R^2$, $R^4$, $R^5$, $R^a$, $R^b$ $R^c$, $R^d$, $R^e$, $R^f$ or

may be replaced by a halogen or deuterium atom;
with the proviso that
when

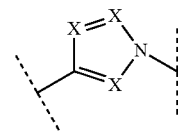

is (i), and neither $R^1$ nor $R^2$ is hydrogen, and $R^3$ is —C(O)$C_{1-7}$alkyl, —C(O)$C_{3-7}$cycloalkyl, —C(O)aryl, —C(O)heteroaryl, —C(O)heterocyclyl, —CH($R^f$)-heteroaryl, —CH($R^f$)-aryl, —CH($R^f$)-heterocyclyl, aryl, $C_{3-7}$cycloalkyl or heteroaryl then $R^4$ and $R^5$ must either both be hydrogen or they must form a ring, or a pharmaceutically acceptable salt thereof.

2. The compound of the formula (I) according claim 1 and wherein $R^2$=hydrogen or $C_{1-7}$alkyl if a)

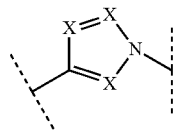

is (i), or b) $R^4$ and $R^5$ are hydrogen, or c) $R^4$ and $R^5$ form a ring, or d) $R^3$ is —C(O)$NR^aR^b$ or —C(O)$OR^a$, or a pharmaceutically acceptable salt thereof.

3. The compound of the formula (I) according claim 2 and wherein $R^1$ is $C_{1-7}$alkyl, $C_{3-7}$cycloalkyl, cyclohexyl-D11, phenyl, oxiranyl, azepanyl, diazepanyl, azetidinyl, pyrrolidinyl, pyrrolinyl, thiomorpholinyl, dioxalanyl, piperazinyl, 1,3-dioxolanone, 1,3-dioxanone, 1,4-dioxanyl, piperidinonyl, tetrahydropyrimidonyl, piperidinyl, tetrahydrofuranyl, tetrahydropyranyl, tetrahydrothiopyranyl, 1,1-dioxo-hexahydro-1λ6-thiopyranyl, 1-oxo-hexahydro-1λ4-thiopyranyl, aziridinyl, thiadiazolyl, tetrazolyl, pyrrolyl, pyrimidinyl, pyrazinyl, pyridazinyl, pyranyl, quinoxalinyl, indolyl, benzimidazolyl, benzoxazolyl, benzothiazolyl, benzothienyl, quinolinyl, quinazolinyl, naphthyridinyl, indazolyl, triazolyl, purinyl, benzofuranyl, thiazolyl, isothiazolyl, imidazolyl, oxazolyl, isoxazolyl, thienyl, furanyl, pyrazolyl and pyridinyl, each optionally substituted by an $R^c$;

$R^2$ is hydrogen or $C_{1-5}$alkyl;

or $R^1$ and $R^2$ taken together form a $C_{3-7}$cycloalkyl;

$R^3$=—C(O)$C_{1-7}$alkyl, —C(O)$C_{3-6}$cycloalkyl, —C(O)phenyl, —C(O)heterocyclyl wherein the heterocyclyl is chosen from oxiranyl, azepanyl, diazepanyl, azetidinyl, pyrrolidinyl, pyrrolinyl, thiomorpholinyl, dioxalanyl, piperazinyl, 1,3-dioxolanone, 1,3-dioxanone, 1,4-dioxanyl, piperidinonyl, tetrahydropyrimidonyl, piperidinyl, tetrahydrothiopyranyl, morpholinyl, piperidinyl, tetrahydrofuranyl and tetrahydropyranyl, —C(O)heteroaryl wherein the heteroaryl is chosen from benzofuranyl, imidazo[2,1-b]thiazolyl, imidazo[1,2-a]pyrazinyl, pyrazolo[1,5-a]pyridinyl, imidazo[1,2-a]pyridinyl, thiazolyl, isothiazolyl, imidazolyl, oxazolyl, isoxazolyl, thienyl, furanyl, pyrazolyl and pyridinyl, —C(O)NH-phenyl, heterocyclyl chosen from oxiranyl, azepanyl, diazepanyl, azetidinyl, pyrrolidinyl, pyrrolinyl, thiomorpholinyl, dioxalanyl, piperazinyl, 1,3-dioxolanone, 1,3-dioxanone, 1,4-dioxanyl, piperidinonyl, tetrahydropyrimidonyl, piperidinyl, tetrahydropyranyl, morpholinyl, piperidinyl, tetrahydropyranyl 1,1-Dioxo-1λ6-thiomorpholine, tetrahydrofuranyl, 1,1-dioxo-hexahydro-1λ6-thiopyranyl, piperidinyl and 2-oxo-imidazolidinyl, phenyl, $C_{3-7}$cycloalkyl, —$CH_2$-2-oxo-imidazolidinyl and —CH($R_f$)-heteroaryl wherein the heteroaryl is chosen from thiazolyl, isothiazolyl, imidazolyl, oxazolyl, isoxazolyl, thienyl, furanyl, pyrazolyl and pyridinyl, each ring is optionally substituted by one or more $R^a$;

$R^4$ and $R^5$ are each independently hydrogen or $C_{1-7}$alkyl, or $R^4$ and $R^5$ taken together may form a $C_{3-6}$cycloalkyl, oxiranyl, azepanyl, diazepanyl, azetidinyl, pyrrolidinyl, pyrrolinyl, thiomorpholinyl, dioxalanyl, piperazinyl, 1,3-dioxolanone, 1,3-dioxanone, 1,4-dioxanyl, piperidinonyl, tetrahydropyrimidonyl, piperidinyl, tetrahydrothiopyranyl, morpholinyl, piperidinyl or tetrahydropyranyl each ring being optionally substituted by $C_{1-3}$alkyl;

$R^a$, $R^b$ are each independently hydrogen, $C_{1-5}$alkyl or phenyl;

$R^c$ is $C_{1-5}$alkyl, $C_{1-5}$alkoxy, $C_{3-6}$cycloalkyl, phenyl, benzyl, fluoro or —C(O)—O-benzyl;

$R^d$ is independently chosen from $C_{1-5}$alkyl, $C_{1-5}$alkoxy, $C_{1-5}$acyl, —C(O)$NR^aR^b$, —NH—C(O)—$C_{1-5}$alkyl, halogen, —CN, —S(O)$_2$—$R_e$, —NH—S(O)$_2$—$R_e$;

$R_e$ is chosen from $C_{1-5}$alkyl and amino;

$R^f$ is independently chosen from hydrogen and $C_{1-5}$alkyl;

wherein one or more hydrogens on any one or more of $R^1$, $R^2$, $R^3$, $R^2$, $R^4$, $R^5$, $R^a$, $R^b$, $R^c$, $R^d$, $R^e$, $R^f$ or

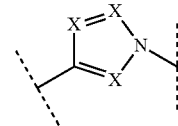

may be replaced by a halogen or deuterium atom;

or a pharmaceutically acceptable salt thereof.

4. The compound of the formula (I) according claim 3 and wherein $R^1$ is t-butyl, sec-butyl, 3-pentyl, cyclohexyl, —$CH_2$-cyclohexyl, cyclopentyl, cyclopropyl, phenyl, cyclohexyl-D11, piperidinyl, tetrahydropyranyl, tetrahydrothiopyranyl, 1,1-dioxo-hexahydro-1λ6-thiopyranyl or 1-oxo-hexahydro-1λ4-thiopyranyl, each optionally substituted by an $R^c$;

$R^2$ is hydrogen or methyl;

or $R^1$ and $R^2$ taken together form a cyclohexyl;

$R^3$ is —C(O)$C_{1-7}$alkyl, —C(O)cyclopropyl, —C(O)cyclopentyl, —C(O)phenyl, —C(O)heterocyclyl wherein the heterocyclyl is chosen from morpholinyl, piperidinyl, tetrahydrofuranyl and tetrahydropyranyl, —C(O)heteroaryl wherein the heteroaryl is chosen from benzofuranyl, imidazo[2,1-b]thiazolyl, imidazo[1,2-a]pyrazinyl, pyrazolo[1,5-a]pyridinyl, imidazo[1,2-a]pyridinyl, thiazolyl, isothiazolyl, imidazolyl, oxazolyl, isoxazolyl, thienyl, furanyl, pyrazolyl and pyridinyl, —C(O)NH-phenyl, heterocyclyl chosen from 1,1-Dioxo-1λ6-thiomorpholine, tetrahydrofuranyl, 1,1-dioxo-hexahydro-1λ6-thiopyranyl, piperidinyl and 2-oxo-imidazolidinyl, phenyl, cyclohexyl and —$CH_2$-thienyl;

$R^4$ and $R^5$ are each independently hydrogen, methyl or n-butyl or $R^4$ and $R^5$ taken together may form cyclopropyl, piperidinyl, tetrahydropyranyl or 1-methyl-piperidinyl;

$R^a$, $R^b$ are each independently hydrogen, methyl or phenyl;

$R^c$ is methyl, methoxy, cyclohexyl, phenyl, benzyl, fluoro or —C(O)—O-benzyl;

$R^d$ is independently chosen from methyl, —$CF_3$, —$CH_2CF_3$, methoxy, acetyl, —$C(O)NH_2$, —$C(O)NHCH_3$, —$C(O)N(CH_3)_2$, —NH—C(O)-methyl, —$S(O)_2$—$CH_3$, —$S(O)_2$—$NH_2$, —NH—$S(O)_2$—$CH_3$, F, Cl and —CN;

$R^f$ is independently chosen from hydrogen, methyl and $CF_3$;

or a pharmaceutically acceptable salt thereof.

5. The compound of the formula (I) according claim 4 and wherein wherein the

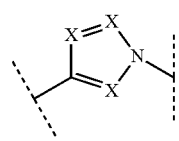

ring is chosen from:

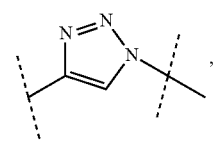  (i)

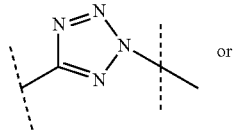  (iii)

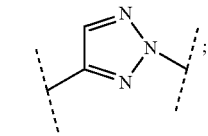  (iv)

or a pharmaceutically acceptable salt thereof.

6. The compound of the formula (I) according claim 5 and wherein wherein the

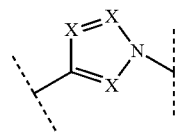

ring is

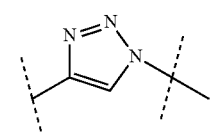  (i)

or a pharmaceutically acceptable salt thereof.

7. The compound of the formula (I) according claim 5 and wherein wherein the

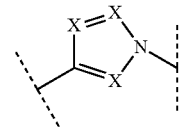

ring is

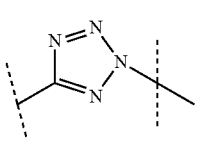  (iii)

or a pharmaceutically acceptable salt thereof.

8. The compound of the formula (I) according claim 5 and wherein wherein the

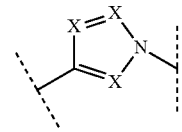

ring is:

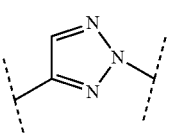  (iv)

or a pharmaceutically acceptable salt thereof.

9. The compound of the formula (I) according claim 5 and wherein $R^1$ is cyclohexyl, —$CH_2$-cyclohexyl, 4,4-difluorocyclohexyl, 3-methoxycyclohexyl, 4-methylcyclohexyl, 4-trifluoromethylcyclohexyl, cyclohexyl-D11, cyclopentyl, 3-pentyl, sec-butyl, tetrahydropyranyl, or tetrahydrothiopyranyl;

or a pharmaceutically acceptable salt thereof.

10. The compound of the formula (I) according claim 9 and wherein $R^2$ is hydrogen or methyl;

or $R^1$ and $R^2$ taken together form a cyclohexyl;

or a pharmaceutically acceptable salt thereof.

11. The compound of the formula (I) according claim 10 and wherein $R^3$ is —C(O)cyclopropyl, —C(O)phenyl, —C(O)heterocyclyl wherein the heterocyclyl is chosen from morpholinyl and piperidinyl, —C(O)heteroaryl wherein the heteroaryl is chosen from imidazo[2,1-b]thiazolyl, thiazolyl, isothiazolyl, oxazolyl, isoxazolyl, thienyl, furanyl, pyrazolyl and pyridinyl, or R³ is
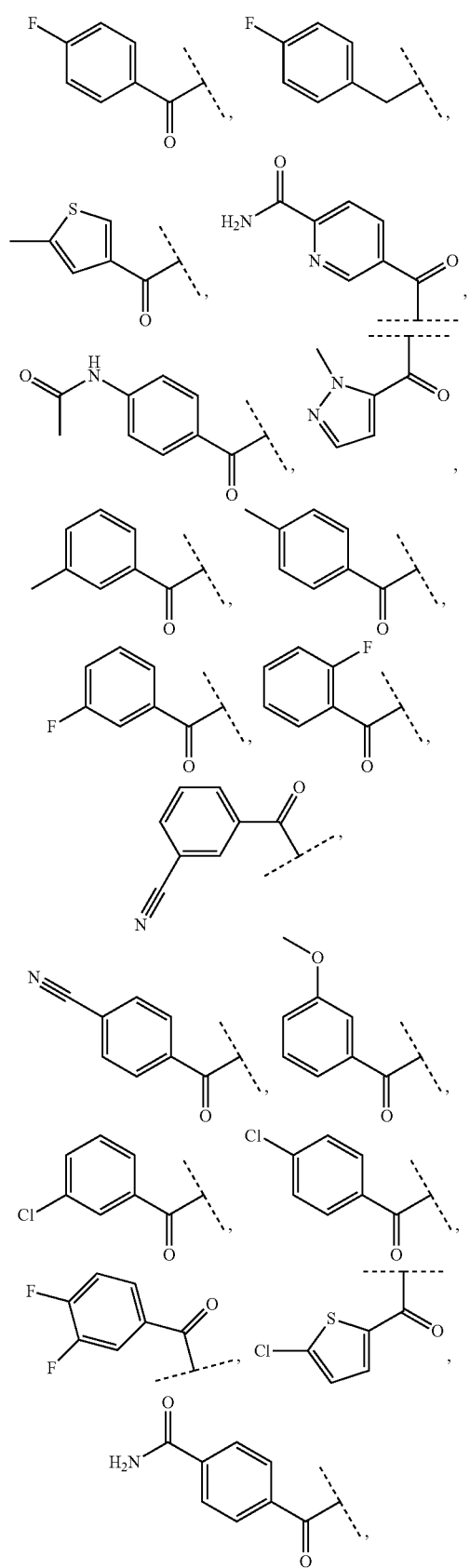
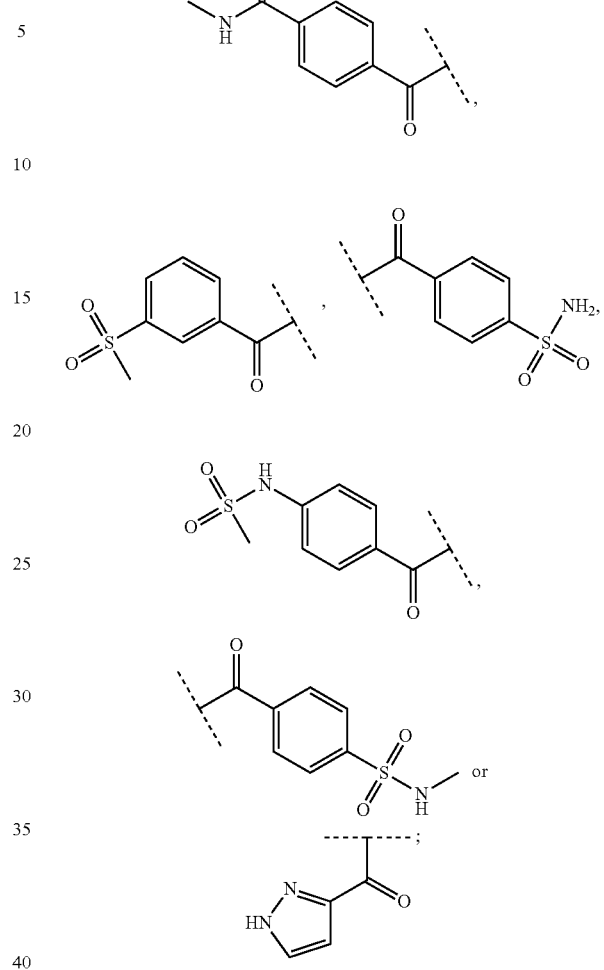
or a pharmaceutically acceptable salt thereof.
12. The compound of the formula (I) according claim 11 and wherein
R⁴ and R⁵ are each independently hydrogen, methyl or n-butyl or
R⁴ and R⁵ taken together may form cyclopropyl, piperidinyl, or tetrahydropyranyl;
or a pharmaceutically acceptable salt thereof.
13. A compound chosen from
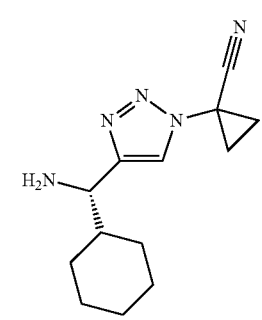

195
-continued
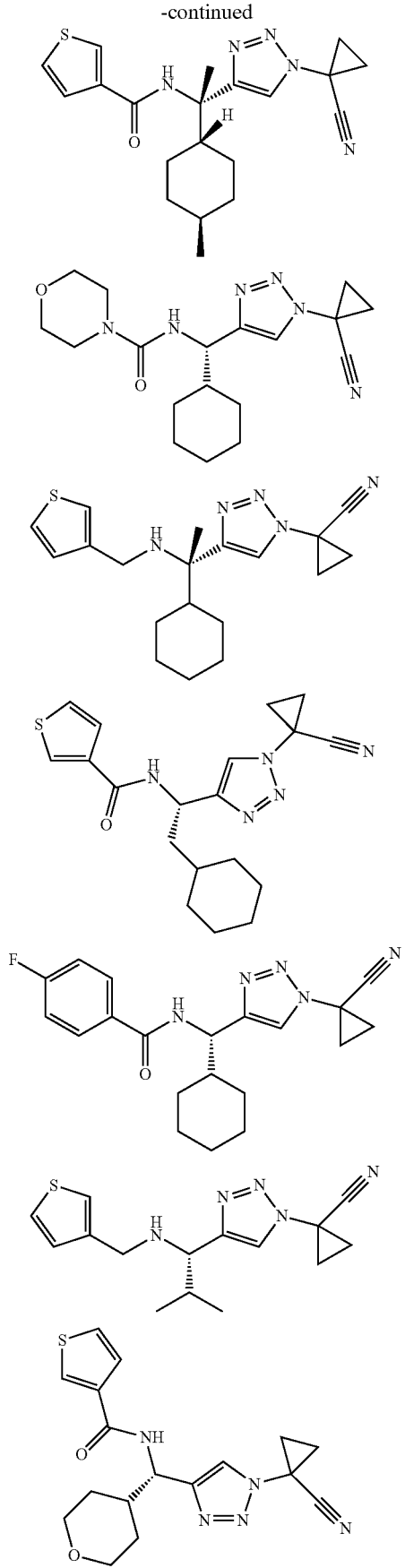
196
-continued
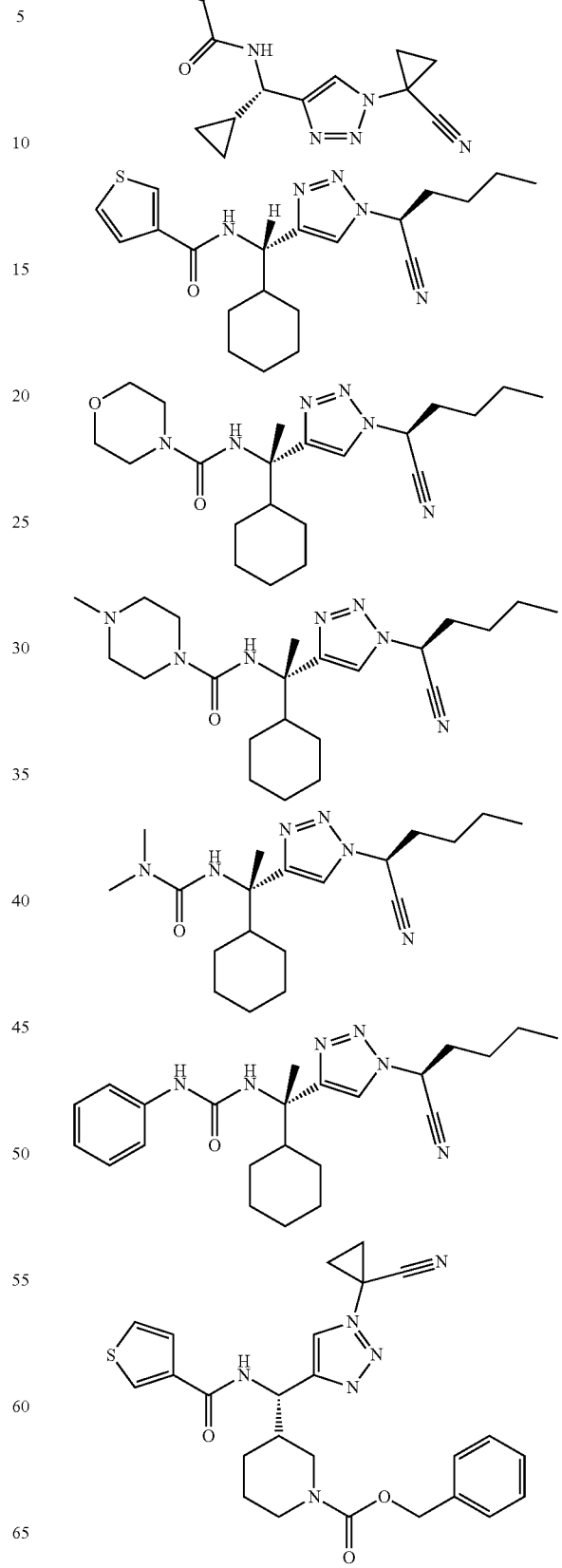

197
-continued
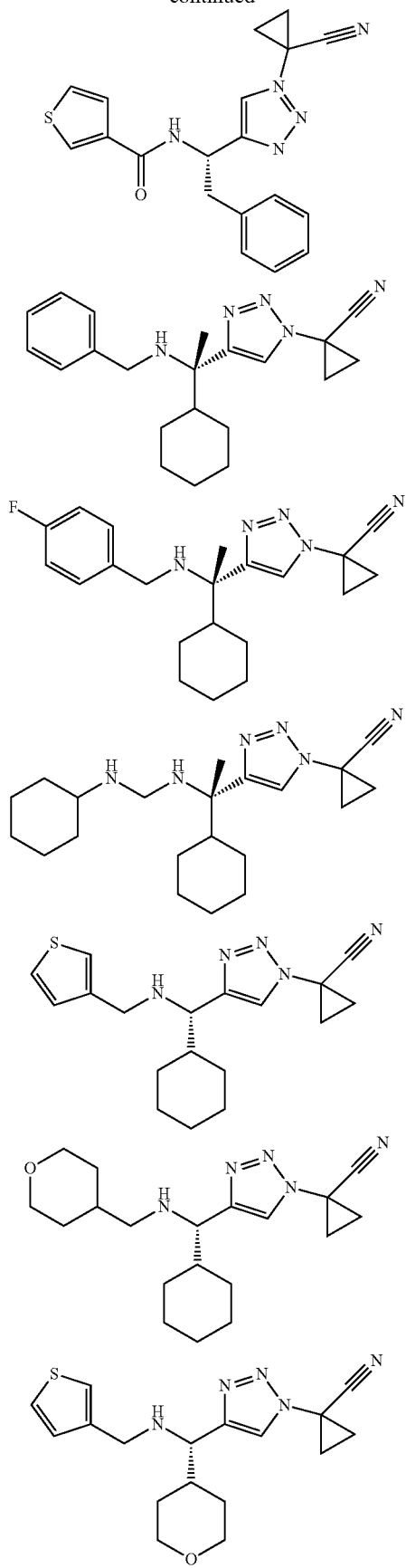
198
-continued
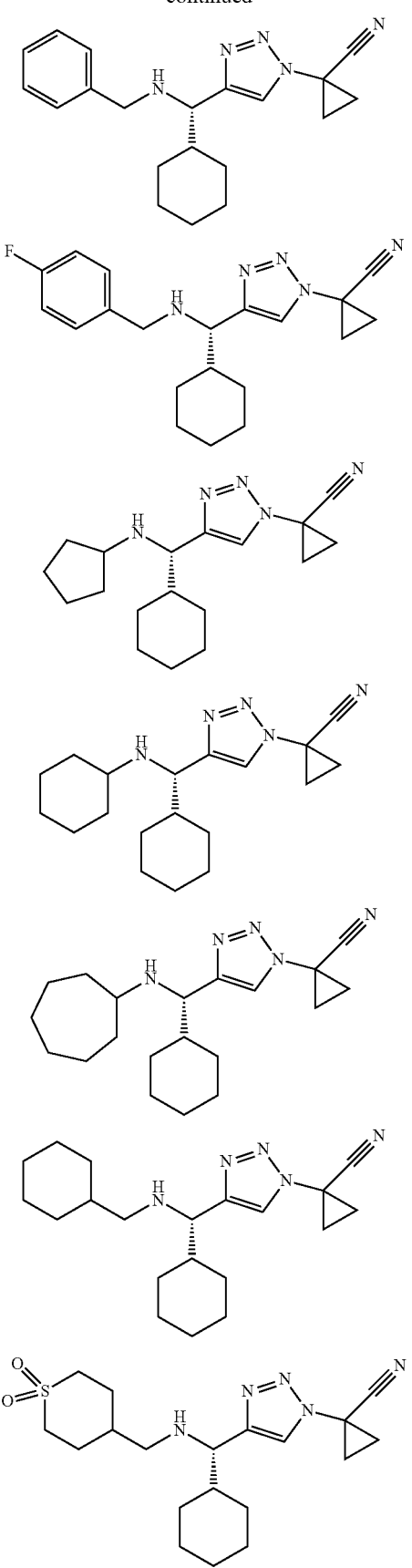

199
-continued
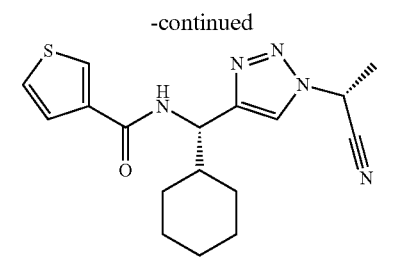
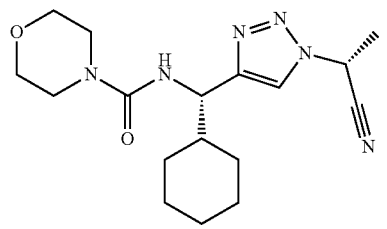
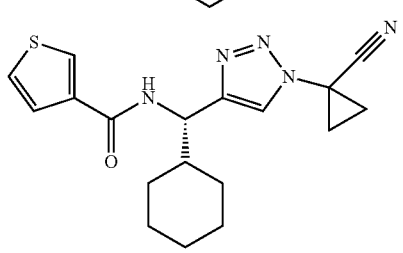
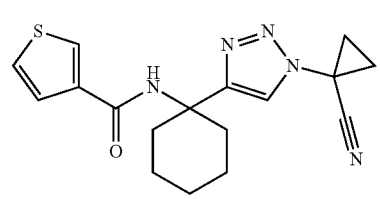
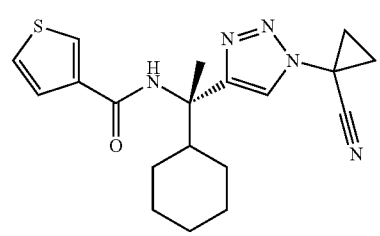
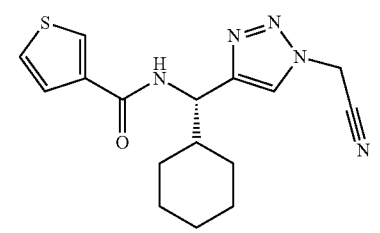
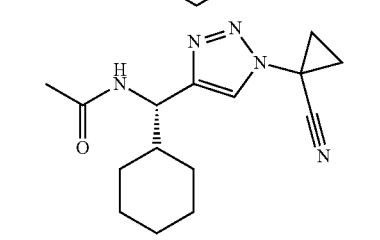
200
-continued
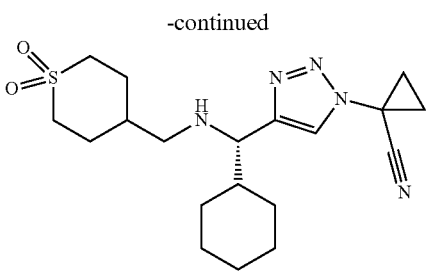
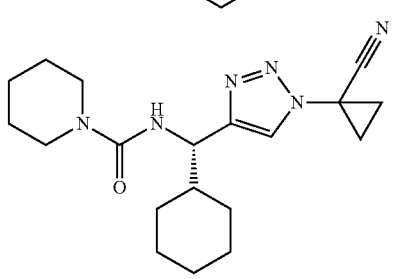
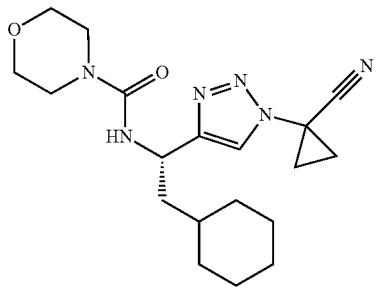
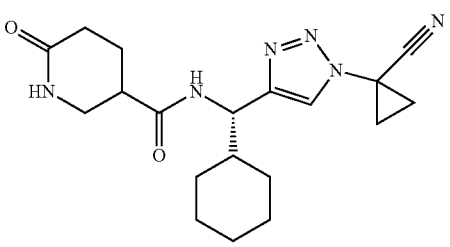
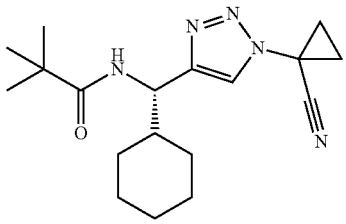
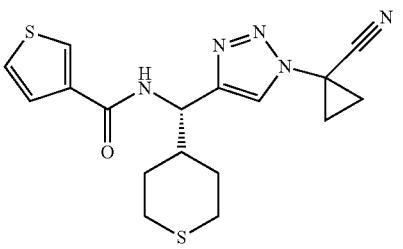

201
-continued
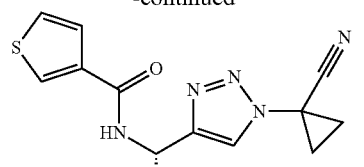
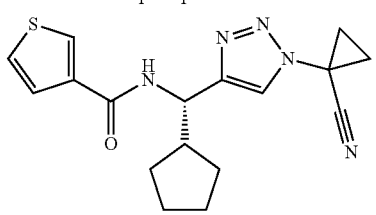
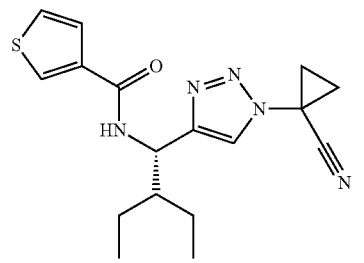
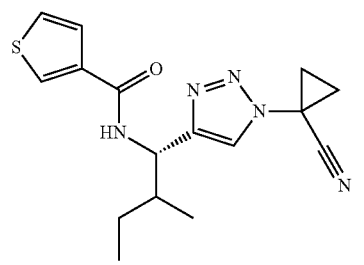
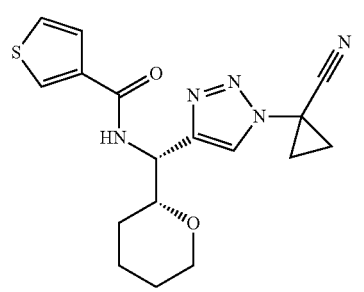
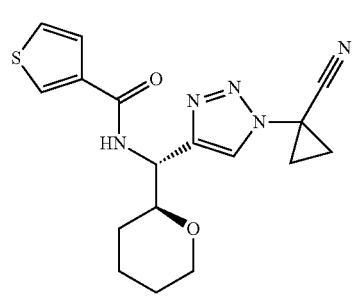
202
-continued
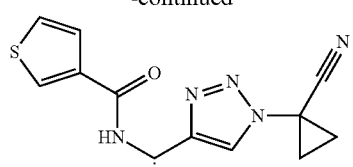
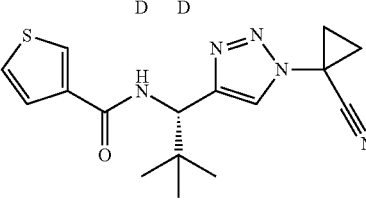
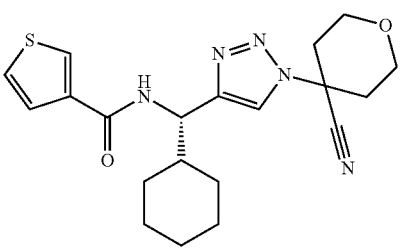
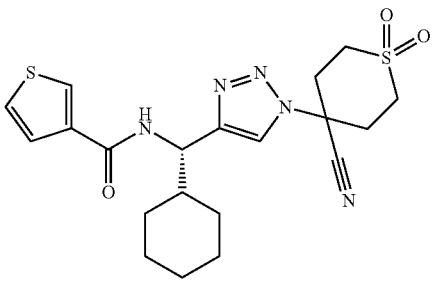
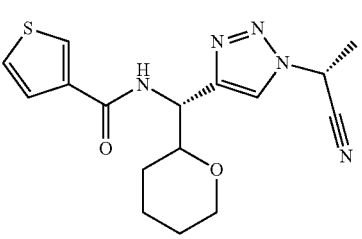
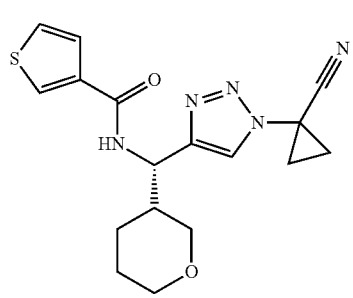

203
-continued
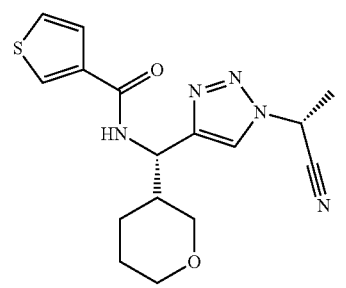
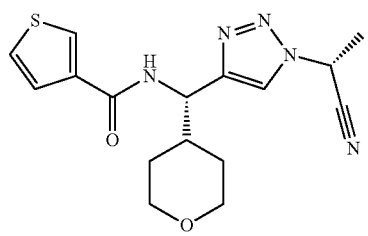
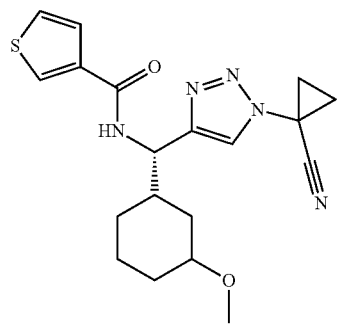
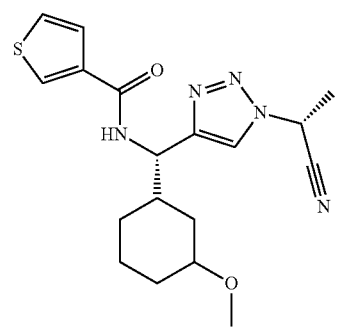
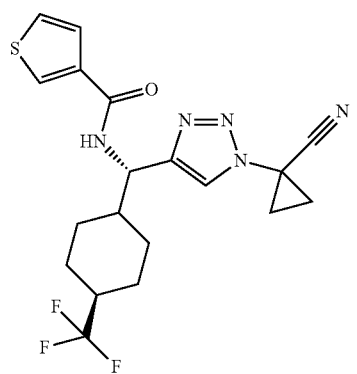
204
-continued
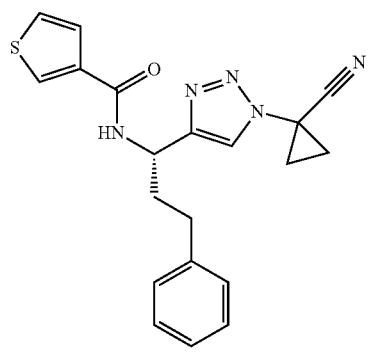
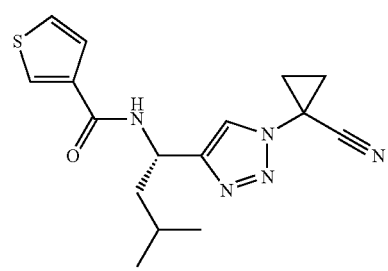
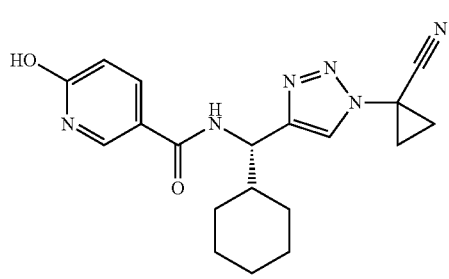
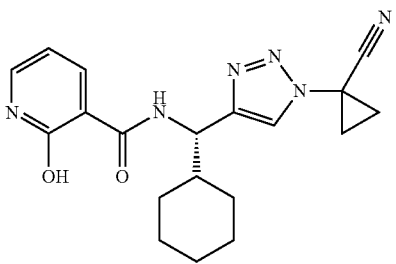
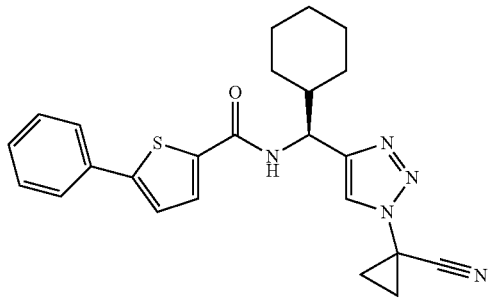

205
-continued
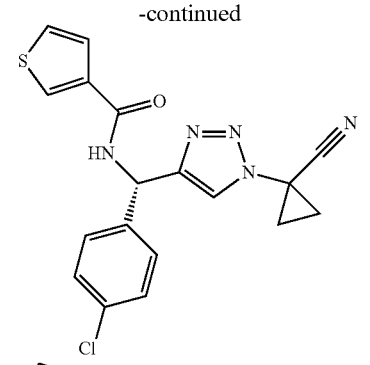
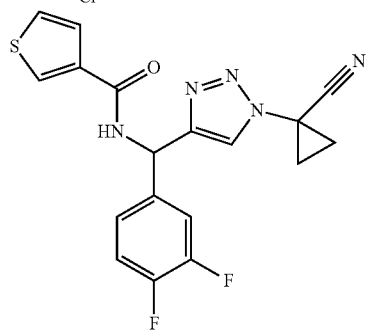
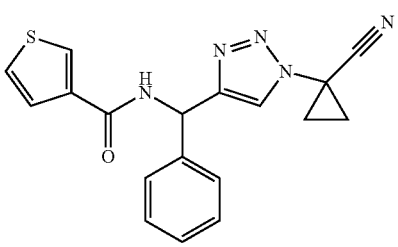
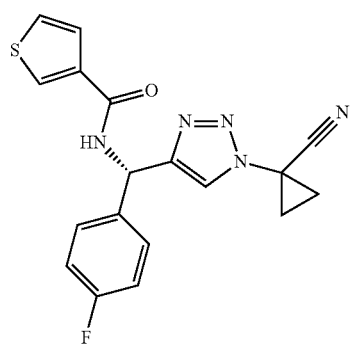
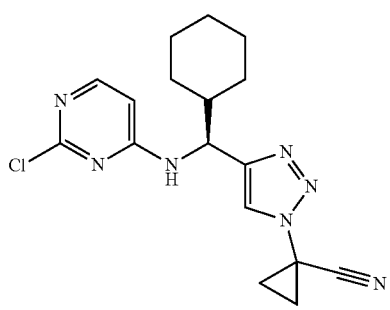
206
-continued
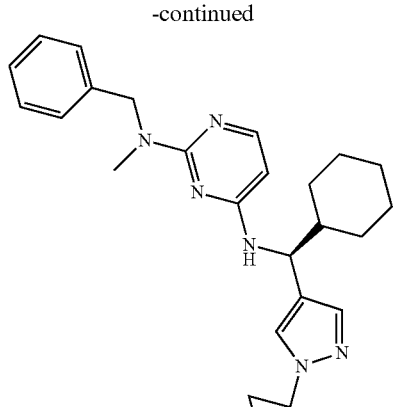
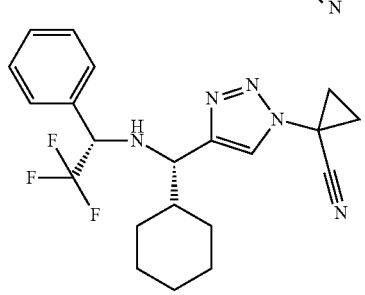
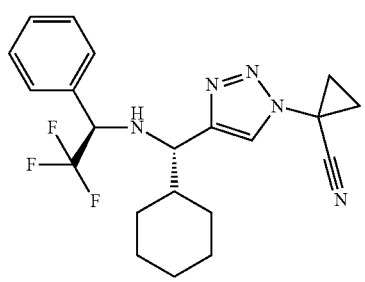
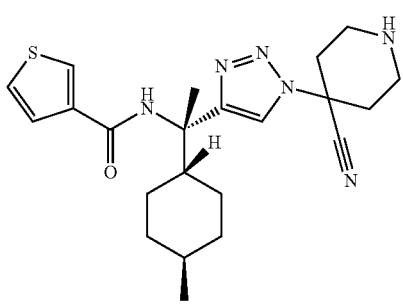
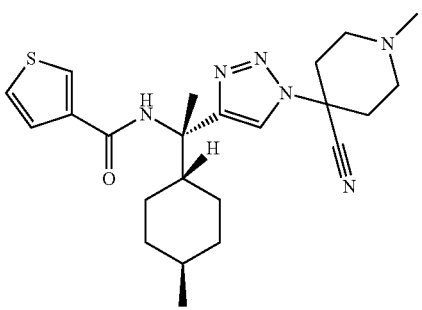

207
-continued
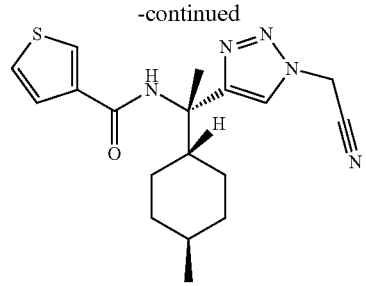
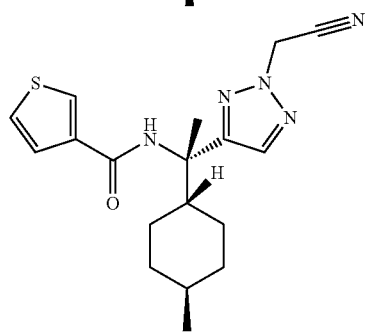
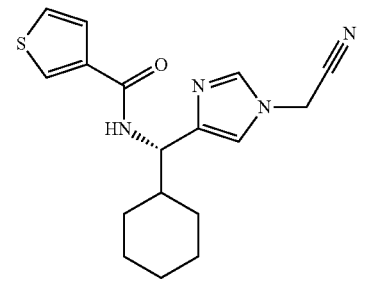
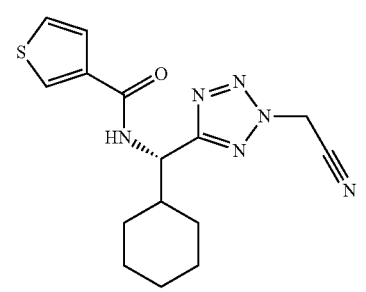
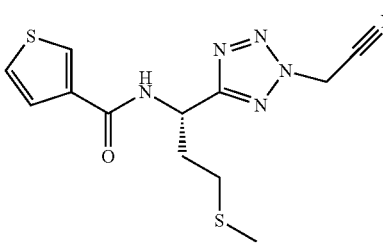
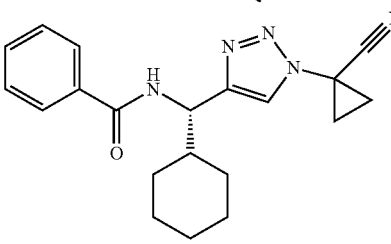
208
-continued
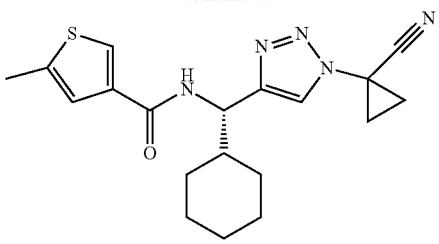
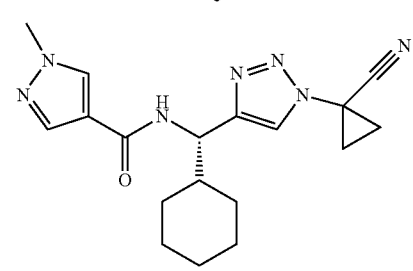
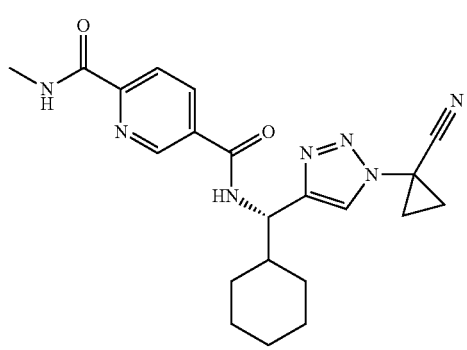
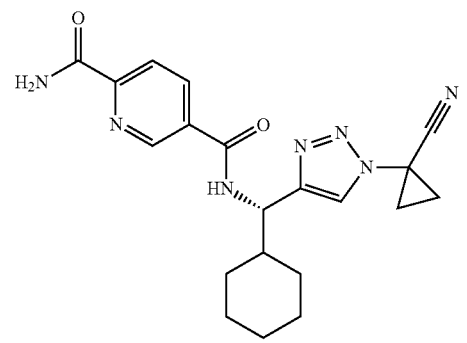
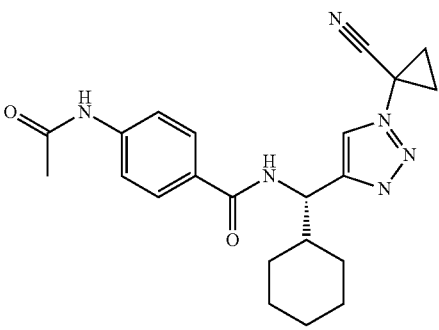

209
-continued
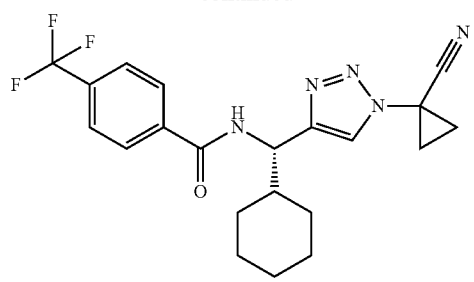
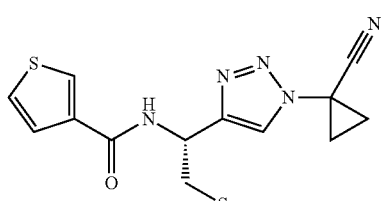
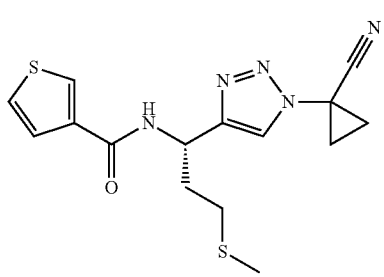
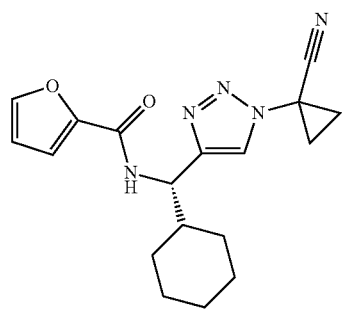
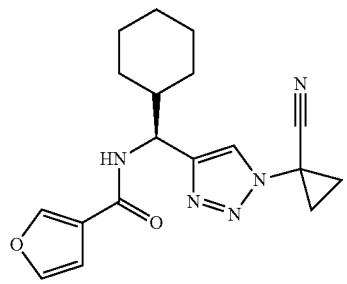
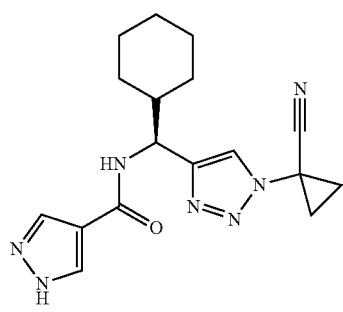
210
-continued
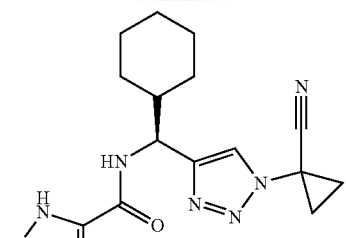
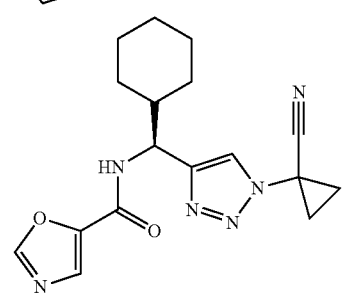
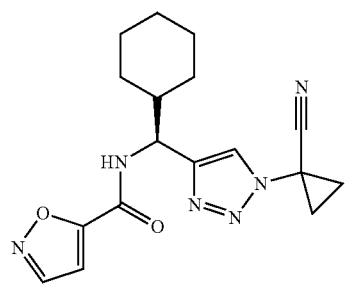
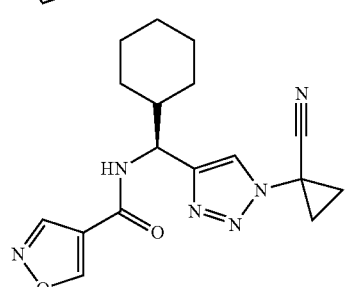
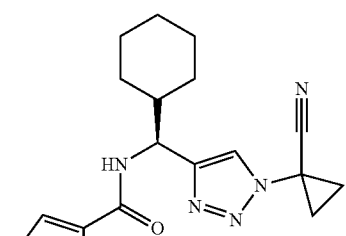
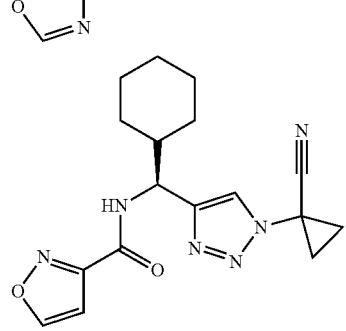

211
-continued
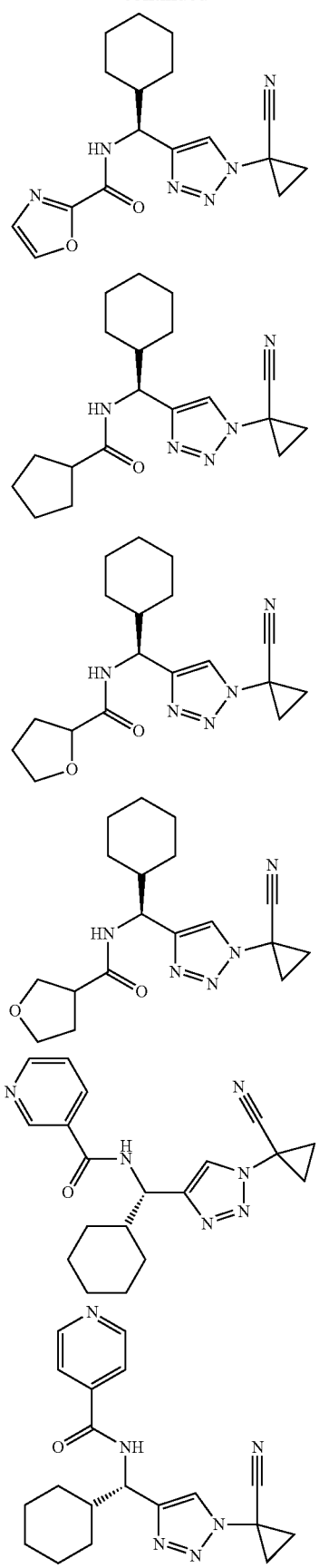
212
-continued
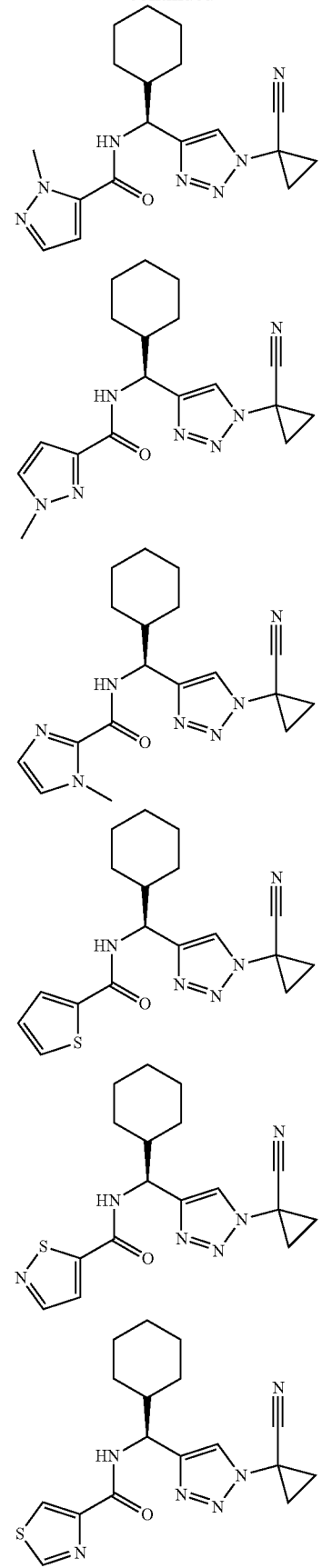

213
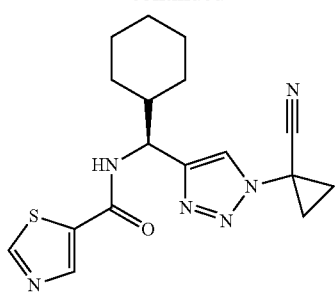
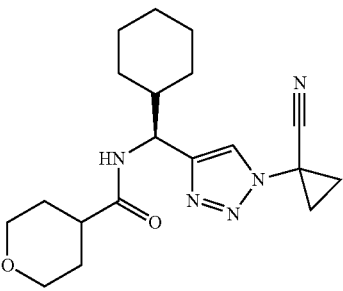
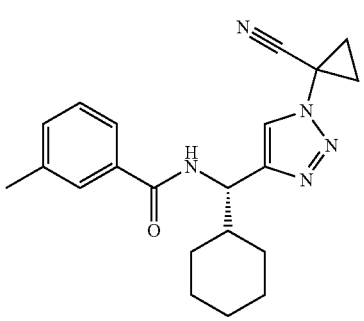
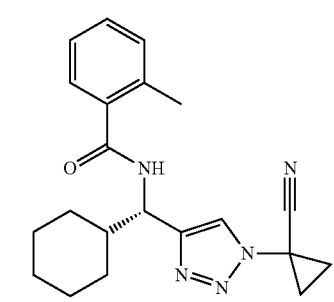
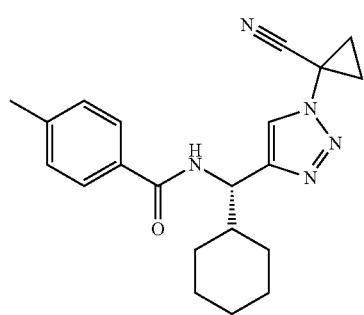
214
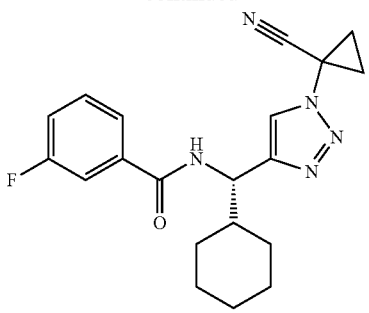
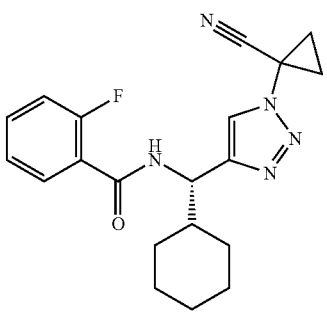
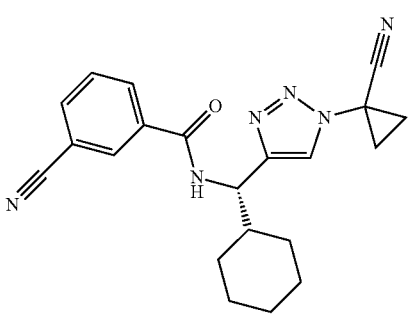
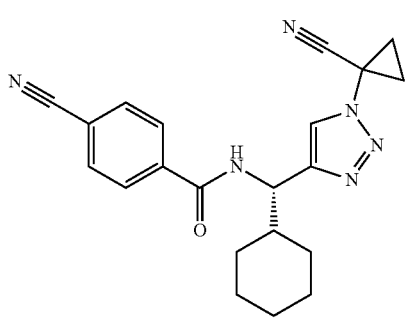
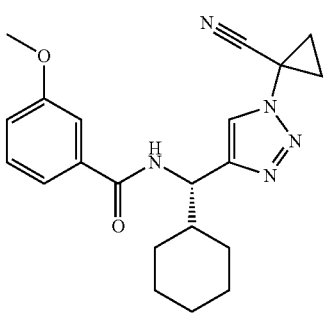

215
-continued
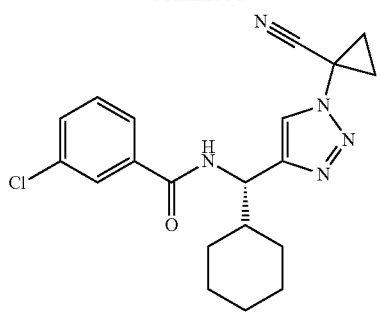
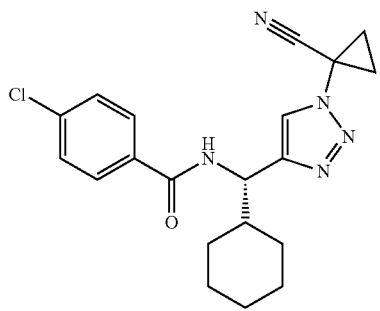
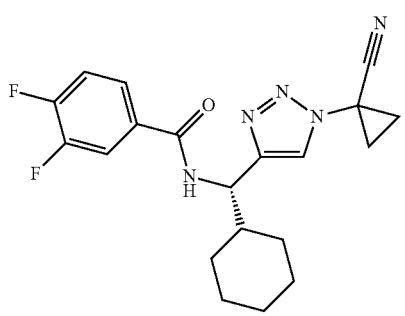
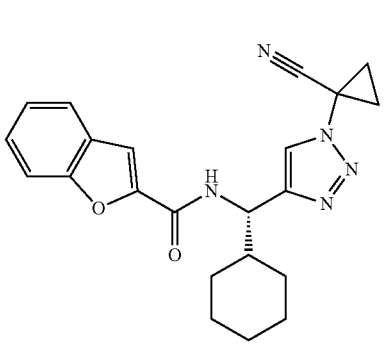
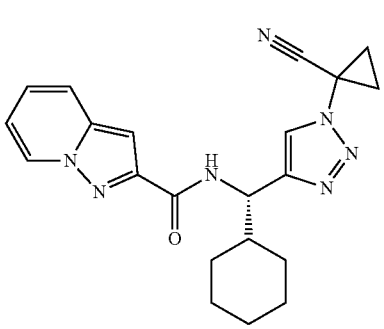
216
-continued
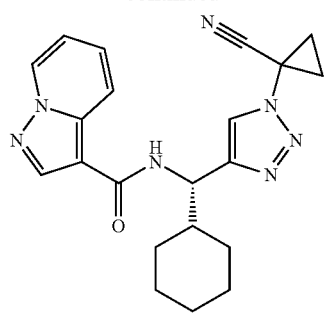
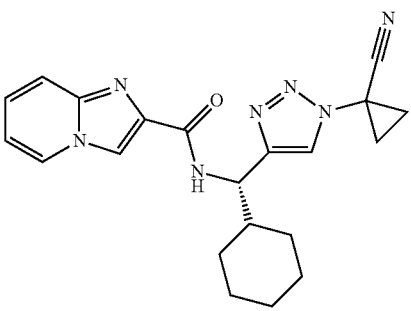
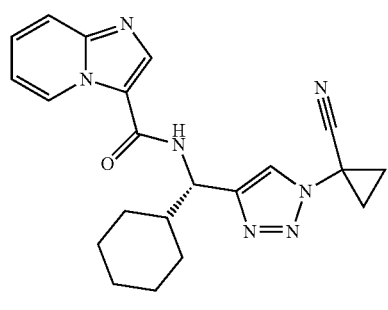
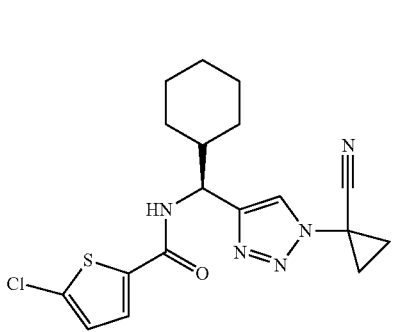
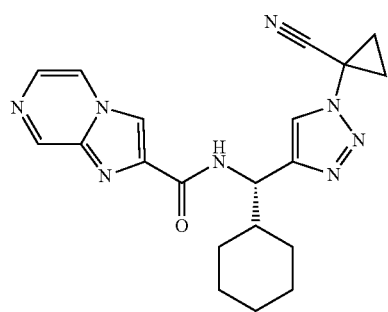

217
-continued
218
-continued
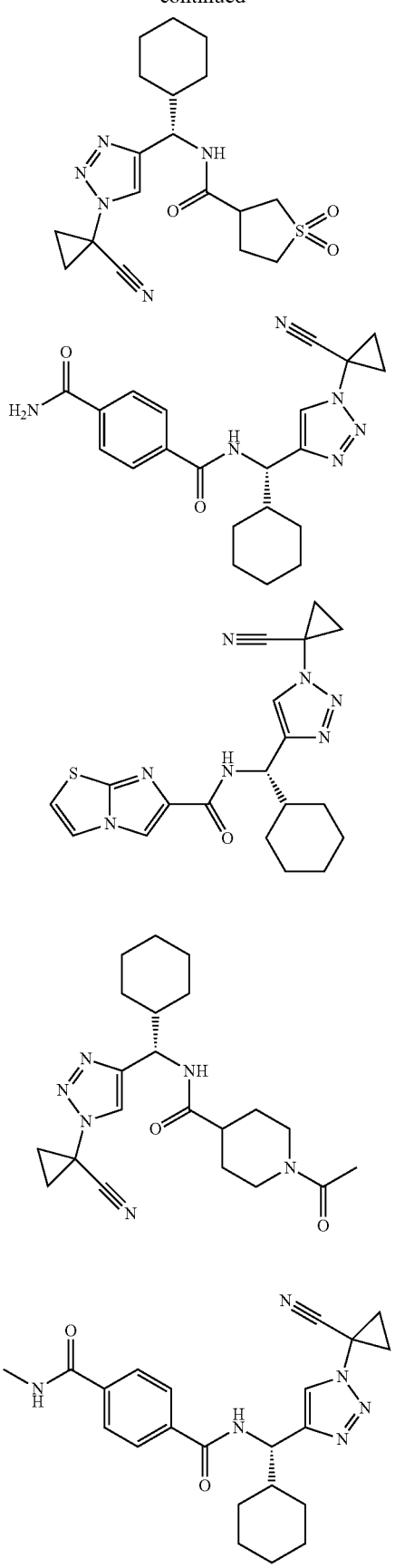
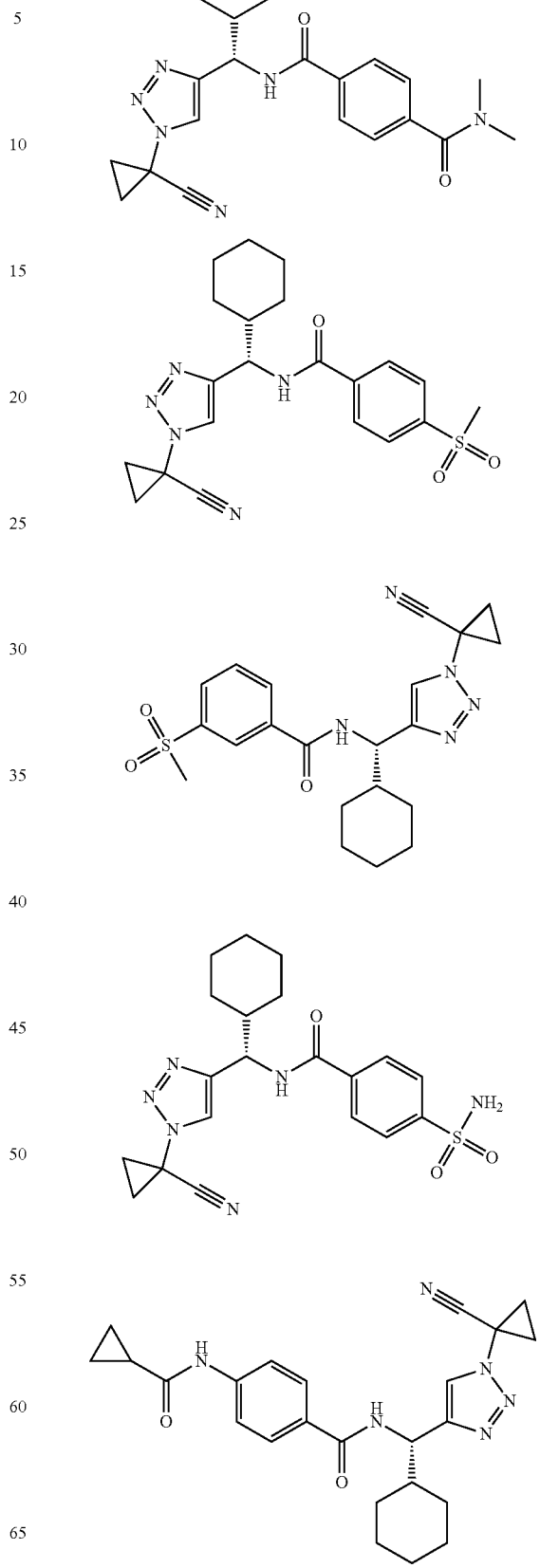

219
-continued

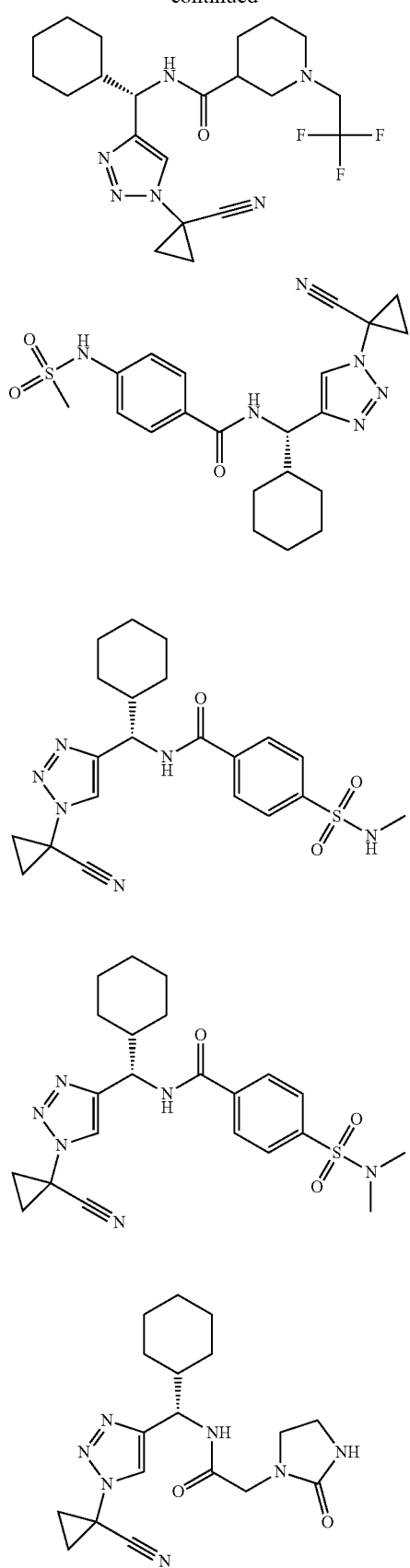

220
-continued

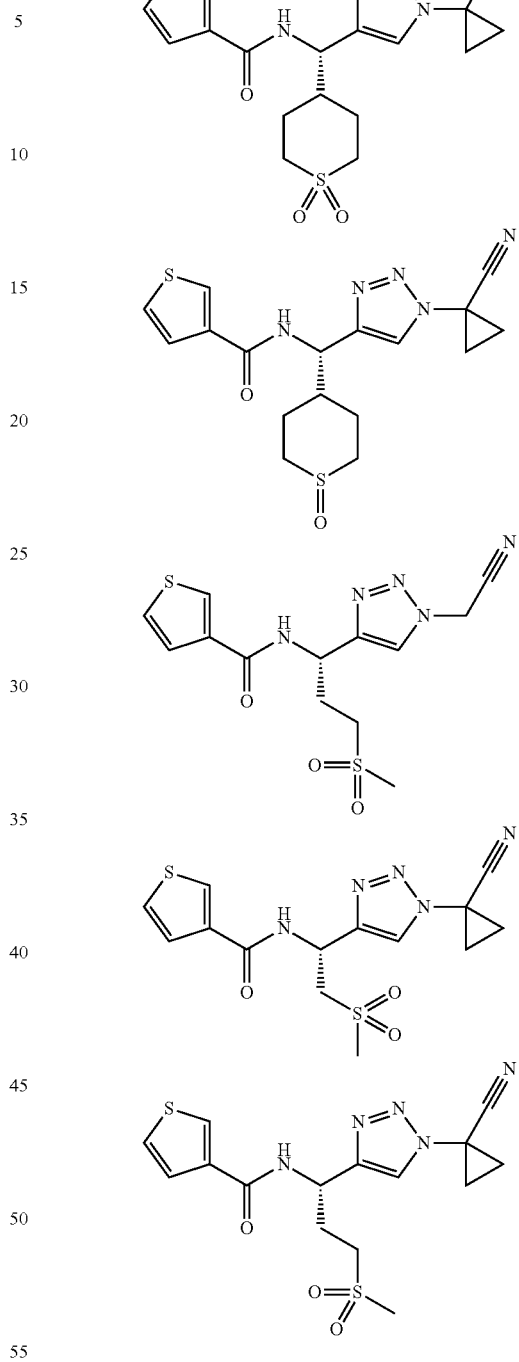

or the pharmaceutically acceptable salts thereof.

14. A pharmaceutical composition comprising a therapeutically effective amount of a compound according to claim 1 and one or more pharmaceutically acceptable carriers and/or adjuvants.

15. A method of treating a disease or condition chosen from rheumatoid arthritis, multiple sclerosis and asthma comprising administering to a patient in need of such treatment a pharmaceutically effect amount of a compound according to claim 1.

* * * * *